(12) United States Patent
Mao et al.

(10) Patent No.: US 11,844,839 B2
(45) Date of Patent: Dec. 19, 2023

(54) PROCESS FOR THE PREPARATION OF PEGYLATED DRUG-LINKERS AND INTERMEDIATES THEREOF

(71) Applicant: SEAGEN INC., Bothell, WA (US)

(72) Inventors: Yunyu Mao, Everett, WA (US); Philip Moquist, Seattle, WA (US); Anusuya Choudhury, Churchhill, PA (US); Wendel Doubleday, Snohomish, WA (US)

(73) Assignee: Seagen Inc., Bothell, WA (US)

( * ) Notice: Subject to any disclaimer, the term of this patent is extended or adjusted under 35 U.S.C. 154(b) by 687 days.

(21) Appl. No.: 16/088,235

(22) PCT Filed: Mar. 24, 2017

(86) PCT No.: PCT/US2017/024148
§ 371 (c)(1),
(2) Date: Sep. 25, 2018

(87) PCT Pub. No.: WO2017/165851
PCT Pub. Date: Sep. 28, 2017

(65) Prior Publication Data
US 2019/0388546 A1  Dec. 26, 2019

Related U.S. Application Data

(60) Provisional application No. 62/313,460, filed on Mar. 25, 2016.

(51) Int. Cl.
*A61K 47/54* (2017.01)
*A61K 47/68* (2017.01)
*A61K 47/60* (2017.01)
*A61K 38/07* (2006.01)

(52) U.S. Cl.
CPC .......... *A61K 47/549* (2017.08); *A61K 38/07* (2013.01); *A61K 47/60* (2017.08); *A61K 47/6811* (2017.08); *A61K 47/6851* (2017.08); *A61K 47/6889* (2017.08)

(58) Field of Classification Search
CPC ...... A61K 47/549; A61K 38/07; A61K 47/60; A61K 47/6811; A61K 47/6851; A61K 47/6889; A61K 47/6883; A61K 47/6817; A61P 35/00; A61P 35/02
See application file for complete search history.

(56) References Cited

U.S. PATENT DOCUMENTS

| | | |
|---|---|---|
| 4,486,414 A | 12/1984 | Pettit |
| 4,816,397 A | 3/1989 | Boss |
| 4,816,444 A | 3/1989 | Pettit |
| 4,816,567 A | 3/1989 | Cabilly |
| 4,879,278 A | 11/1989 | Pettit |
| 4,880,935 A | 11/1989 | Thorpe |
| 4,946,778 A | 8/1990 | Ladner |
| 4,978,744 A | 12/1990 | Pettit |
| 4,986,988 A | 1/1991 | Pettit |
| 5,047,335 A | 9/1991 | Paulson |
| 5,076,973 A | 12/1991 | Pettit |
| 5,122,368 A | 6/1992 | Greenfield |
| 5,138,036 A | 8/1992 | Pettit |
| 5,225,539 A | 7/1993 | Winter |
| 5,278,299 A | 1/1994 | Wong |
| 5,410,024 A | 4/1995 | Pettit |
| 5,504,191 A | 4/1996 | Pettit |
| 5,510,261 A | 4/1996 | Goochee |
| 5,521,284 A | 5/1996 | Pettit |
| 5,530,097 A | 6/1996 | Pettit |
| 5,545,806 A | 8/1996 | Lonberg |
| 5,554,725 A | 9/1996 | Pettit |
| 5,561,119 A | 10/1996 | Jacquesy |
| 5,569,825 A | 10/1996 | Lonberg |
| 5,585,089 A | 12/1996 | Queen |
| 5,591,828 A | 1/1997 | Bosslet |
| 5,599,902 A | 2/1997 | Pettit |
| 5,605,976 A | 2/1997 | Martinez et al. |
| 5,622,929 A | 4/1997 | Willner |
| 5,625,126 A | 4/1997 | Lonberg |
| 5,633,425 A | 5/1997 | Lonberg |
| 5,635,483 A | 6/1997 | Pettit |
| 5,661,016 A | 8/1997 | Lonberg |
| 5,663,149 A | 9/1997 | Pettit |
| 5,665,860 A | 9/1997 | Pettit |
| 5,672,662 A | 9/1997 | Harris |
| 5,681,567 A | 10/1997 | Martinez et al. |
| 5,739,277 A | 4/1998 | Presta |
| 5,756,593 A | 5/1998 | Martinez et al. |

(Continued)

FOREIGN PATENT DOCUMENTS

| | | |
|---|---|---|
| EP | 0105360 A1 | 4/1984 |
| EP | 0171496 A2 | 2/1986 |

(Continued)

OTHER PUBLICATIONS

EP Application No. 17771293.2, European Search Report and Search Opinion dated Oct. 7, 2019, 14 pages.
Amsberry, K.L. et al. (1990) "The Lactonizatin of 2'-Hydroxyhydrocinnamic Acid Amides: A Potential Prodrug For Amines," J. Org. Chem. 55(23):5867-5877.
Beidler, C.B. et al. (Dec. 1, 1988). "Cloning and High Level Expression Of A Chimeric Antibody With Specificity For Human Carcinoembryonic Antigen," J. Immunol. 141(11):4053-4060.
Better, M. et al. (May 20, 1988), "*Escherichia coli* Secretion of An Active Chimerica Antibody Fragment," Science 240:1041-1043.

(Continued)

*Primary Examiner* — Phuong Huynh
(74) *Attorney, Agent, or Firm* — MORRISON & FOERSTER LLP

(57) ABSTRACT

The present invention provides improved processes for the preparation of auristatin drug-linkers with a PEG unit, as well as intermediates thereof.

26 Claims, No Drawings

(56) References Cited

U.S. PATENT DOCUMENTS

| | | |
|---|---|---|
| 5,757,078 A | 5/1998 | Matsuda |
| 5,770,429 A | 6/1998 | Lonberg et al. |
| 5,780,588 A | 7/1998 | Pettit |
| 5,824,805 A | 10/1998 | King |
| 5,851,527 A | 12/1998 | Hansen |
| 5,919,455 A | 7/1999 | Greenwald et al. |
| 5,939,595 A | 8/1999 | Gehrer |
| 5,965,119 A | 10/1999 | Greenwald et al. |
| 6,034,065 A | 3/2000 | Pettit |
| 6,077,499 A | 6/2000 | Griffiths et al. |
| 6,077,939 A | 6/2000 | Wei |
| 6,113,906 A | 9/2000 | Greenwald et al. |
| 6,124,431 A | 9/2000 | Sakakibara |
| 6,130,237 A | 10/2000 | Denny |
| 6,153,655 A | 11/2000 | Martinez et al. |
| 6,214,330 B1 | 4/2001 | Greenwald et al. |
| 6,214,345 B1 | 4/2001 | Firestone et al. |
| 6,239,104 B1 | 5/2001 | Pettit |
| 6,261,537 B1 | 7/2001 | Klaveness et al. |
| 6,303,569 B1 | 10/2001 | Greenwald et al. |
| 6,323,135 B1 | 11/2001 | Ngo |
| 6,323,322 B1 | 11/2001 | Filpula et al. |
| 6,331,289 B1 | 12/2001 | Klaveness et al. |
| 6,361,774 B1 | 3/2002 | Griffiths et al. |
| 6,395,266 B1 | 5/2002 | Martinez et al. |
| 6,556,506 B2 | 5/2003 | Greenwald et al. |
| 6,569,834 B1 | 5/2003 | Petit et al. |
| 6,602,498 B2 | 8/2003 | Shen |
| 6,624,142 B2 | 9/2003 | Greenwald et al. |
| 6,638,499 B2 | 10/2003 | Martinez et al. |
| 6,643,575 B2 | 11/2003 | Ishida et al. |
| 6,680,047 B2 | 1/2004 | Klaveness et al. |
| 6,743,896 B2 | 6/2004 | Filpula et al. |
| 6,743,908 B2 | 6/2004 | Filpula et al. |
| 6,777,387 B2 | 8/2004 | Greenwald et al. |
| 6,824,782 B2 | 11/2004 | Whitlow et al. |
| 6,872,393 B2 | 3/2005 | Whitlow et al. |
| 6,884,869 B2 | 4/2005 | Senter |
| 6,906,182 B2 | 6/2005 | Ts |
| 7,011,812 B1 | 3/2006 | Griffiths et al. |
| 7,026,440 B2 | 4/2006 | Bentley et al. |
| 7,090,843 B1 | 8/2006 | Francisco |
| 7,091,186 B2 | 8/2006 | Senter et al. |
| 7,150,872 B2 | 12/2006 | Whitlow et al. |
| 7,273,845 B2 | 9/2007 | Zhao et al. |
| 7,300,644 B2 | 11/2007 | Griffiths et al. |
| 7,332,164 B2 | 2/2008 | Greenwald et al. |
| 7,374,762 B2 | 5/2008 | Amphlett et al. |
| 7,375,078 B2 | 5/2008 | Feng |
| 7,462,687 B2 | 12/2008 | Greenwald et al. |
| 7,494,649 B2 | 2/2009 | Amphlett et al. |
| 7,498,298 B2 | 3/2009 | Doronina |
| 7,501,120 B2 | 3/2009 | Amphlett et al. |
| 7,514,066 B2 | 4/2009 | Griffiths et al. |
| 7,514,080 B2 | 4/2009 | Amphlett et al. |
| 7,553,816 B2 | 6/2009 | Senter et al. |
| 7,595,304 B2 | 9/2009 | Zhao et al. |
| 7,632,504 B2 | 12/2009 | Whitlow et al. |
| 7,659,241 B2 | 2/2010 | Senter |
| 7,754,681 B2 | 7/2010 | Feng |
| 7,754,885 B2 | 7/2010 | Hoefle et al. |
| 7,767,205 B2 | 8/2010 | Mao et al. |
| 7,785,618 B2 | 8/2010 | Elmaleh et al. |
| 7,872,072 B2 | 1/2011 | Bentley et al. |
| 7,884,869 B2 | 2/2011 | Shurboff et al. |
| 7,888,536 B2 | 2/2011 | Davis et al. |
| 7,931,890 B2 | 4/2011 | Griffiths et al. |
| 7,947,839 B2 | 5/2011 | Gazzard et al. |
| 7,989,434 B2 | 8/2011 | Feng |
| 7,989,598 B2 | 8/2011 | Steeves et al. |
| 7,994,135 B2 | 8/2011 | Doronina et al. |
| 8,012,485 B2 | 9/2011 | Amphlett et al. |
| 8,012,488 B2 | 9/2011 | Sakanoue et al. |
| 8,039,273 B2 | 10/2011 | Jeffrey |
| 8,088,387 B2 | 1/2012 | Steeves et al. |
| 8,163,888 B2 | 4/2012 | Steeves et al. |
| 8,168,605 B2 | 5/2012 | Zhao et al. |
| 8,198,417 B2 | 6/2012 | Steeves et al. |
| 8,257,706 B2 | 9/2012 | Mcdonagh |
| 8,268,317 B2 | 9/2012 | Govindan et al. |
| 8,273,833 B2 | 9/2012 | Bentley et al. |
| 8,367,065 B2 | 2/2013 | Zhao et al. |
| 8,440,816 B2 | 5/2013 | Bentley et al. |
| 8,455,622 B2 | 6/2013 | Mcdonagh et al. |
| 8,563,509 B2 | 10/2013 | Chari et al. |
| 8,568,728 B2 | 10/2013 | Jeffrey |
| 8,609,092 B2 | 12/2013 | Torgov et al. |
| RE45,272 E | 12/2014 | Jeffrey |
| 9,061,074 B2 | 6/2015 | Carter et al. |
| 9,242,013 B2 | 1/2016 | Howard et al. |
| 9,731,030 B2 | 8/2017 | Jeffrey |
| 10,561,739 B2 | 2/2020 | Howard et al. |
| 11,103,593 B2* | 8/2021 | Lyon .................. A61K 47/6885 |
| 2002/0102215 A1 | 8/2002 | Klaveness |
| 2002/0142358 A1 | 10/2002 | Mikayama |
| 2003/0083263 A1 | 5/2003 | Doronina |
| 2003/0211100 A1 | 11/2003 | Bedian |
| 2004/0001820 A1 | 1/2004 | Hahn et al. |
| 2004/0006215 A1 | 1/2004 | Keler |
| 2004/0009166 A1 | 1/2004 | Filpula et al. |
| 2004/0053976 A1 | 3/2004 | Martinez et al. |
| 2004/0141922 A1 | 7/2004 | Klaveness et al. |
| 2005/0002865 A1 | 1/2005 | Klaveness et al. |
| 2005/0009751 A1 | 1/2005 | Senter |
| 2005/0042680 A1 | 2/2005 | Filpula et al. |
| 2005/0238649 A1 | 10/2005 | Doronina |
| 2006/0003412 A1 | 1/2006 | Chamberlain |
| 2006/0008882 A1 | 1/2006 | Wei |
| 2006/0130160 A1 | 6/2006 | Dumas Milne Edwards et al. |
| 2007/0134243 A1 | 6/2007 | Gazzard et al. |
| 2008/0241128 A1 | 10/2008 | Jeffrey |
| 2009/0136526 A1 | 5/2009 | Mcdonagh |
| 2009/0148942 A1 | 6/2009 | Mcdonagh |
| 2009/0202573 A1 | 8/2009 | Zhao et al. |
| 2009/0203706 A1 | 8/2009 | Zhao et al. |
| 2009/0221471 A1 | 9/2009 | Greenwald et al. |
| 2010/0062008 A1 | 3/2010 | Senter |
| 2010/0158909 A1 | 6/2010 | McDonagh et al. |
| 2010/0203007 A1 | 8/2010 | Li et al. |
| 2010/0203066 A1 | 8/2010 | Zhao et al. |
| 2010/0260786 A1 | 10/2010 | Doronina et al. |
| 2010/0278842 A1 | 11/2010 | Mao et al. |
| 2011/0014151 A1 | 1/2011 | Nilsson et al. |
| 2011/0206658 A1 | 8/2011 | Crowley et al. |
| 2011/0243880 A1 | 10/2011 | Yurkovetskiy et al. |
| 2011/0245295 A1 | 10/2011 | Chai et al. |
| 2011/0256157 A1 | 10/2011 | Howard |
| 2011/0263650 A1 | 10/2011 | Ellman et al. |
| 2011/0268751 A1 | 11/2011 | Sievers et al. |
| 2011/0281856 A1 | 11/2011 | Chari et al. |
| 2011/0300162 A1 | 12/2011 | Amphlett et al. |
| 2012/0107332 A1 | 5/2012 | Jeffrey |
| 2012/0226025 A1 | 9/2012 | Chari et al. |
| 2012/0252738 A1 | 10/2012 | Richter |
| 2012/0252739 A1 | 10/2012 | Richter |
| 2012/0328555 A1 | 12/2012 | Patil et al. |
| 2013/0217638 A1 | 8/2013 | Wessjohann et al. |
| 2013/0225789 A1 | 8/2013 | Sun et al. |
| 2013/0259860 A1 | 10/2013 | Smith |
| 2013/0295639 A1 | 11/2013 | Bentley et al. |
| 2013/0309223 A1 | 11/2013 | Sutherland |
| 2013/0309256 A1 | 11/2013 | Lyon et al. |
| 2013/0338231 A1 | 12/2013 | Godwin et al. |
| 2014/0086942 A1 | 3/2014 | Carter et al. |
| 2015/0352224 A1 | 12/2015 | Naito et al. |
| 2016/0030594 A1 | 2/2016 | Abrams |
| 2016/0144052 A1 | 5/2016 | Howard et al. |
| 2016/0310612 A1 | 10/2016 | Lyon et al. |
| 2016/0361424 A1 | 12/2016 | Jeffrey |
| 2017/0031535 A1 | 2/2017 | Greer et al. |
| 2017/0189542 A1 | 7/2017 | Jeffrey |
| 2019/0336614 A1 | 11/2019 | Howard et al. |

(56) References Cited

U.S. PATENT DOCUMENTS

| | | | |
|---|---|---|---|
| 2020/0222553 A1* | 7/2020 | Mao | A61K 47/6889 |
| 2022/0143209 A1 | 5/2022 | Jeffrey | |

FOREIGN PATENT DOCUMENTS

| | | |
|---|---|---|
| EP | 0173494 A2 | 3/1986 |
| EP | 0184187 A2 | 6/1986 |
| EP | 0401384 A1 | 12/1990 |
| EP | 0404097 A2 | 12/1990 |
| EP | 1029551 A2 | 8/2000 |
| EP | 1029551 A3 | 3/2001 |
| JP | 2009501800 A | 1/2009 |
| JP | 2010509315 A | 3/2010 |
| JP | 2015227891 A | 12/2015 |
| SG | 11201807827 A | 10/2018 |
| TW | 201420118 A | 6/2014 |
| WO | 198303679 A1 | 10/1983 |
| WO | 198601533 A1 | 3/1986 |
| WO | 198702671 A1 | 5/1987 |
| WO | 199012874 A2 | 11/1990 |
| WO | 199012874 A3 | 1/1991 |
| WO | 199308829 A1 | 5/1993 |
| WO | 199311161 A1 | 6/1993 |
| WO | 1994004690 A1 | 3/1994 |
| WO | 199734631 A1 | 9/1997 |
| WO | 2002088172 A2 | 11/2002 |
| WO | 2002088172 A3 | 2/2003 |
| WO | WO2003/026577 A2 | 4/2003 |
| WO | 2003086312 A2 | 10/2003 |
| WO | WO2004/010957 A2 | 2/2004 |
| WO | 2003086312 A3 | 9/2004 |
| WO | WO2004/085386 A2 | 10/2004 |
| WO | 2005082023 A2 | 9/2005 |
| WO | WO2005/081711 A3 | 9/2005 |
| WO | 2005099768 A2 | 10/2005 |
| WO | 2005082023 A3 | 12/2005 |
| WO | 2005112919 A2 | 12/2005 |
| WO | 2006066020 A2 | 6/2006 |
| WO | 2005099768 A3 | 8/2006 |
| WO | 2006066020 A3 | 8/2006 |
| WO | 2006132670 A2 | 12/2006 |
| WO | 2007001968 A2 | 1/2007 |
| WO | 2007008848 A2 | 1/2007 |
| WO | WO2007/011968 A2 | 1/2007 |
| WO | 2005112919 A3 | 2/2007 |
| WO | 2006132670 A3 | 7/2007 |
| WO | 2007001968 A3 | 8/2007 |
| WO | 2007085930 A1 | 8/2007 |
| WO | 2007103288 A2 | 9/2007 |
| WO | 2007103288 A3 | 11/2007 |
| WO | WO2008/034124 A2 | 3/2008 |
| WO | WO2008/056346 A2 | 5/2008 |
| WO | 2008070593 A2 | 6/2008 |
| WO | 2009002993 A1 | 12/2008 |
| WO | 2009009712 A1 | 1/2009 |
| WO | 2009009716 A1 | 1/2009 |
| WO | 2009025669 A1 | 2/2009 |
| WO | 2007008848 A3 | 4/2009 |
| WO | 2009117531 A1 | 9/2009 |
| WO | WO2010/048018 A1 | 4/2010 |
| WO | 2010081163 A2 | 7/2010 |
| WO | 2010091150 A1 | 8/2010 |
| WO | WO2010/126551 A1 | 11/2010 |
| WO | 2010081163 A3 | 12/2010 |
| WO | 2011023883 A1 | 3/2011 |
| WO | 2011038159 A2 | 3/2011 |
| WO | 2011038159 A3 | 8/2011 |
| WO | 2011109308 A1 | 9/2011 |
| WO | 2011130613 A1 | 10/2011 |
| WO | WO2011/130599 A1 | 10/2011 |
| WO | WO2011/130616 A1 | 10/2011 |
| WO | 2012078688 A2 | 6/2012 |
| WO | 2012078688 A3 | 8/2012 |
| WO | 2012112708 A1 | 8/2012 |
| WO | WO2012/113847 A1 | 8/2012 |
| WO | 2012166560 A1 | 12/2012 |
| WO | 2013033476 A1 | 3/2013 |
| WO | 2013041606 A1 | 3/2013 |
| WO | WO2013/053873 A1 | 4/2013 |
| WO | WO2013/055990 A1 | 4/2013 |
| WO | WO2013/055993 A1 | 4/2013 |
| WO | 2013123152 A2 | 8/2013 |
| WO | WO2013/170272 A2 | 11/2013 |
| WO | WO2013/173337 A2 | 11/2013 |
| WO | WO2013/173391 A1 | 11/2013 |
| WO | WO2013/173392 A1 | 11/2013 |
| WO | WO2013/173393 A1 | 11/2013 |
| WO | 2014061277 A1 | 4/2014 |
| WO | WO2014/064423 A1 | 5/2014 |
| WO | 2013123152 A3 | 11/2014 |
| WO | WO2015/057699 A2 | 4/2015 |
| WO | WO-2015057699 A2 * | 4/2015 ............ A61P 35/00 |
| WO | WO2015/095755 A1 | 6/2015 |
| WO | 2016040684 A1 | 3/2016 |
| WO | WO2016/046574 A1 | 3/2016 |
| WO | WO2016/149535 A1 | 9/2016 |
| WO | WO2018/031690 A1 | 2/2018 |
| WO | 2018175994 A1 | 9/2018 |

OTHER PUBLICATIONS

Chari, R.V.J. et al. (Jan. 1, 1992). "Immunoconjugates Containing Noveal maytansinoids: Promising Anticancer Drugs," Cancer Res. 52:127-131.

Extended European Search Report, dated Aug. 16, 2017, for European Patent Application No. 14853953.9, 16 pages.

Fridkin, M. et al. (1974). "Peptide Synthesis," Ann. Rev. Biochem. 43:419-443.

Gaertner, H.F. et al. (Mar. 11, 1994). "Chemo-Enzymic Backbone Engineering of Proteins," J. Biol. Chem. 269 (10):7224-7230.

Goodson, R.J. et al. (Apr. 1990). "Site-Directed Pegylation of Recombinatnt Interleukin-2 At Its Glycosylation Site," Bio/Technology 8:343-346.

Hamblett, K.J. et al., (Oct. 15, 2004), "Effects of Drug Loading on the Antitumor Activity of a Monoclonal Antibody Drug Conjugate," Clin. Cancer Res. 10:7063-7070.

Han, S.-Y. et al. (2004). "Recent Development Of Peptide Coupling Agents In Organic Synthesis," Tet. 60:2447-2476.

Hay, M.P. et al. (Aug. 2, 1999), "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.

International Search Report and Written Opinion, dated Jun. 21, 2017, for PCT Application No. PCT/US2017/24148, filed Mar. 24, 2017, 24 pages.

International Union of Pure and Applied Chemistry (Nov. 5, 1960). "Definitive Rules for Nomenclature of Organic Chemistry," J. Am. Chem. Soc. 82:5545-5473, 30 pages.

Jones, P.T. et al. (May 29, 1986). "Replacing the Complementarity-Determining Regions in a Human Antibody With Those From a Mouse," Nature 321:522-525.

Junutula, J.R. et al. (Oct. 1, 2010, e-pub. Aug. 30, 2010). "Engineered Thio-Trastuzumab-DM1 Conjugate With an Improved Therapeutic Index to Target Human Epidermal Growth Factor Receptor 2-Postitive Breast Cancer," Clinical Cancer Res. 16(19):4769-4778.

Kabat, E.A. et al. (1991). Sequences of Proteins of Immunological Interest, Fifth Edition, National Institute of Health, Bethesda, Md., 10 pages.

Kabat, E.A. et al. (Sep. 1980). "Origins of Antibody Complementarity and Specificity-Hypervariable Regions and the Minigene Hypothesis," J Immunology 125(3):961-969.

Kaneko, T. et al. (May-Jun. 1991). "New Hydrazone Derivatives Of Adriamycin and Their Immunoconjugates—A Correlation Between Acid Stability and Cytotoxicity," Bioconjugate Chem. 2(3):133-141.

Khandare, J. et al. (2006). "Polymer-Drug Conjugates: Progress In Polymeric Prodrugs," Prog. Polym. Sci. 31:359-397.

(56) References Cited

OTHER PUBLICATIONS

Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451.
Kotarbinski, T. (2014). "Chapter 20—Hematopietic Cancers," in MAK: Primer To The Immune Response pp. 553-585.
Kozbor, D. et al. (1983). "The Production of Monoclonal Antibodies From Human Lymphocytes," Immunology Today 4(3):72-79.
Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.
Li, W. et al. (2013, e-pub. Aug. 11, 2012). "Current Drug Research On Pegylation With Small Molecular Agents," Progress in Polymer Science 38:421-444.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987), "Production of a Mouse-Human Chimeric Monoclonal Antibody to CD20 With Potent Fc-Dependent Biologic Activity," J. Immunol. 139(10):3521-3526.
Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035.
Morrison, S.L. (Sep. 1985). "Transfectomas Provide Novel Chimeric Antibodies," Science 229 (4719):1202-1207.
Neville, D.M. et al. (Sep. 5, 1989). "Enhancement of Immunotoxin Efficacy by Acid-cleavable Crosslinking Agents Utilizing Diphtheria Toxin and Toxin Mutants," The Journal of Biological Chemistry 264(25):14653-14661.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
Oi, V.T. et al. (1986). "Chimeric Antibodies," Bio Techniques 4(3):214-219.
Olsson, L. et al. (1983). "Human-Human Monoclonal Antibody-Producing Hybridomas: Technical Aspects," Meth Enzymol. 92:3-16.
Page, B. et al. (Sep. 1993). "A New Fluorometric Assay For Cytotoxicity Measurements In-Vitro," Intl. J. of Oncology 3(3):473-476.
Rodrigues, M.L. et al. (Apr. 1995). "Synthesis and B-Lactamase-Mediated Activation Of A Cephalosporine-Taxol Prodrug," Chem. Biol. 2:223-227.
Rose, K. et al. (May-Jun. 1991). "Preparation Of Well-Defined Protein Conjugates Using Enzyme-Assisted Reverse Proteolysis," Bioconjugate Chem. 2(3):154-159.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwartz, A. et al. (1990). "Enzymatic C-Terminal Biotinylation Of Proteins," Methods Enzymol. 184:160-162.
Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.
Skehan, P. et al. (Jul. 4, 1990). "New Colorimetric Cytotoxicity Assay for Anticancer-Drug Screening," J. Nat'l Cancer Inst. 82(13):1107-1112.
Storm, D.R. et al. (Aug. 9, 1972). "Effect of Small Changes in Orientation on Reaction Rate," Journal of the American Chemical Society 94(16):5815-5825.
Sun, L.K. et al. (Jan. 1987), "Chimeric Antibody With Human Constant Regions and Mouse Variable Regions Directed Against Carcinoma-Associated Antigen 17-1A," Proc. Natl. Acad. Sci. USA 84(1):214-218.
Teng, N.N.H. et al. (Dec. 1983). "Construction and Testing of Mouse-Human Heteromyelomas For Human Monoclonal Antibody Production," Proc. Natl. Acad. Sci. USA. 80:7308-7312.
Thorpe, P.E. et al. (Nov. 15, 1987). "New Coupling Agents for the Synthesis of Immunotoxins Containing a Hindered Disulfide Bond with Improved Stability in Vivo," Cancer Research 47:5924-5931.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
Venonese, F.M. et al. (Nov. 2005). "PEGylatlon, Successful Approach to Drug Delivery," Drug Discovery Today 10(21):1451-1458.
Verhoeyan, M. et al. (Mar. 25, 1988). "Reshaping Human Antibodies: Grafting an Antilysozyme Activity," Science 239:1534-1536.
Veronese, F.M. (2001). "Peptide and Protein PEGylatlon: A Review Of Problems and Solutions," Biomaterials 22:405-417.
Veronese, F.M. et al. (Apr. 1985). "Surface Modification Of Proteins: Activation Of Monomethoxy-Polyethylene Glycols By Phenylchloroformates and Modification Of Ribonuclease and Superoxide Dismutase," Appl. Biochem. Bioechnol 11(2):141-152.
Wan, L. et al. (Apr. 24, 2006). "Novel Multi-Component Nanopharmaceuticals Derived From poly (ethylene) glycol, retro-inverso-Tat Nonapeptide and Saquinavir Demostrate Combined Anti-HIV Effects," AIDS Research and Therapy, pp. 1-15.
Wildman, S.A. et al. (1999, e-pub. Aug. 19, 1999). "Prediction of Physiochemical Parameters by Atomic Contributions," J. Chem. Inf. Comput. Sci. 39(5):868-873.
Wood, C.R. et al. (Apr. 4, 1985). "The Synthesis and in vivo Assembly of Functional Antibodies In Yeast," Nature 314 (6010):446-449.
Yokoyama, M. et al. (1989). "Molecular Design for Missile Drug: Synthesis of Adriamycin Conjugate With Immunoglobulin G Using Poly(ethylene glycol)-Block-poly(aspartic acid) As Intermediate Carrier," Makromol. Chem. 190:2041-2054.
Allen, "Ligand-Targeted Therapeutics in Anticancer Therapy," Nature Reviews, 2:750-765, 2002.
Alley et al., "Contribution of Linker Stability to the Activities of Anticancer Immunoconjugates," Bioconjugate Chem. 19:759-765, 2008.
Baldwin et al., "Tunable Degradation of Maleimide—Thiol Adducts in Reducing Environments," Bioconjugate Chem. 22:1946-1953, 2011.
Chen et al., Glucuronides in Anti-Cancer Therapy, Curr. Med. Chem. 3:139-150, 2003.
De Graff et al., "Beta-Glucuronidase-Mediated Drug Release," Current Pharmaceutical Design 8:1391-1403, 2002.
G.M. Dubowchik, M.A. Walker, Pharmacology & Therapeutics 83:67-123, 1999.
Greenwald, et al., "Effective drug delivery by PEGylated drug conjugates", Advanced Drug Delivery Reviews, 55, pp. 217-250, (2003).
Huang et al., "Drug-targeting strategies in cancer therapy," Current Opinion in Genetics & Development 11:104-110, 2001.
Jeffrey et al, "Development and Properties of Beta-Glucuronide Linkers for Monoclonal Antibody-Drug Conjugates," American Chemical Society, 2006.
Jeffrey et al., "Development and Properties of Beta-Glucuronide Linkers for Monoclonal antibody-Drug Conjugates," Bioconjugate Chem. 17:831-840, 2006.
Jeffrey et al., "Expanded Utility of the Beta-Glucuronide Linker: ADCs That Deliver Henolic Cytotoxic Agents," ACS Medicinal Chemistry Letters, 1:277-280, 2010.
Jongkees et al., "Mechanistic Investigations of Unsaturated Glucuronyl Hydrolase from *Clostridium perfringens*", Journal of Biological Chemistry, vol. 289, No. 16, pp. 11385-11395, (Apr. 18, 2014).
King et al., "Monoclonal Antibody Conjugates of Doxorubicin Prepared with Branched Peptide Linkers: Inhibition of Aggregation by Methoxytriethyleneglycol Chains," J. Med. Chem. 45:4336-4343, 2002.
Kirschke, "Lysosomal Cysteine Peptidases and Malignant Tumours," Cellular Peptidases in Immune Functions and Diseases, edited by Ansorge and Langner plenum Press, New York, 1997.
Lyon et al., "Self-hydrolyzing maleimides improve the stability and pharmacological properties of antibody-drug conjugates," Nature Biotechnology, 1-7, 2014.

(56) References Cited

OTHER PUBLICATIONS

Miller et al., "Potent antigen-specific anti-tumor activity observed with antibodydrug conjugates (ADCs) made using a new class of DNA-crosslinking agents," Poster, Nov. 2009.
Molineaux, "Pegylation: engineering improved pharmaceuticals for enhanced therapy," Cancer Treatment Reviews 28(Suppl. A):13-16, 2002.
Papot et al., "Design of Selectively Activated Anticancer Prodrugs: Elimination and Cyclization Strategies," Curr. Med. Chem. Anti-Cancer Agents 2:155-185, 2002.
PCT Application No. PCT/US2014/060477, Search Report and Written Opinion, 22 pages, (dated Jul. 30, 2015).
Sanderson et al., "In Vivo Drug-Linker Stability of an Anti-CD30 Dipeptide-Linked Auristatin Immunoconjugate," Clin. Cancer Res. 11:843-852, 2005.
Sperker et al., "The Role of Beta-Glucuronidase in Drug Disposition and Drug Targeting in Humans," Clin. Pharmocokinet, 33(1):18-31, 1997.
Translation of Taiwan Patent Office Search Report for Appl. Ser. No. 103135737 dated Feb. 11, 2019.
Non-Final Office Action, dated Dec. 7, 2021, for U.S. Appl. No. 16/497,133, filed Sep. 24, 2019, 14 pages.
Final Office Action, dated Apr. 5, 2022, for U.S. Appl. No. 16/497,133, filed Sep. 24, 2019, 9 pages.
Pfeifer, M. et al. (2015). "Anti-CD22 and Anti-CD79B Antibody Drug Conjugates are Active in Different Molecular Diffuse Large B-cell Lymphoma Subtypes," Leukemia 29:1578-1586.
Zhu, G.D. et al. (2013). "Design of Next Generation Antibody Drug Conjugates," Acta Pharmaceutica Sinica 48 (7):1053-1070. With English Abstract, 18 pages.
Final Office Action, dated Oct. 25, 2022, for U.S. Appl. No. 16/497,133, filed Sep. 24, 2019, 12 pages.
Albin, N. et al. (Aug. 1, 1993). Main Drug-metabolizing Enzyme Systems in Human Breast Tumors and Peritumoral Tissues, Cancer Research 53:3541-3546.
Andrianomenjanahary, S. et al. (1992). "Synthesis of Novel Targeted Pro-Prodrugs of Anthracyclines Potentially Activated by a Monoclonal Antibody Galactosidase Conjugate (Part 1)," Bioorganic & Medicinal Chemistry Letters 2(9):1093-1096.
Angenault, S. et al. (2003). "Cancer Chemotherapy: A SN-38 (7-Ethyl-10-hydroxycamptothecin) Glucuronide Prodrug for Treatment by a PMT (Prodrug Mono Therapy) Strategy," Bioorganic & Medicinal Chemistry Letters 13:947-950.
Anonymous. (1999). "Calculation of SlogP Values," 4 pages.
Asai, A. et al. (1999). "Synthesis and Antitumor Activity of Water-Soluble Duocarmycin B1 Prodrugs," Bioorganic & Medicinal Chemistry Letters 9:2995-2998.
Azoulay, M. et al. (1995). "Prodrugs Of Anthracycline Antibiotics Suited For Tumor-Specific Activation," Anti-Cancer Drug Design 10:441-450.
Bakina, E. et al. (1997). "Intensely Cytotoxic Anthracycline Prodrugs: Glucuronides," J. Med. Chem. 40(25):4013-4018.
Banerjee, S.S. et al. (May 7, 2012). "Poly(ethylene glycol)-Prodrug Conjugates: Concepts Design, and Applications," Journal of Drug Delivery 2012(103973):1-17.
Bhattacharya-Chatterjee, M. et al. (Aug. 15, 1988). "Idiotype Vaccines Against Human T Cell Leukemia. II. Generation and Characterization Of A Monoclonal Idiotype Cascade (Ab1, Ab2, and Ab3)," J. Immunol. 141(4):1398-1403.
Bird, R.E. et al. (Oct. 21, 1988). "Single-Chain Antigen-Binding Proteins," Science 242(4877):423-426.
Boons, G-J. ed. (1998). Carbohydrate Chemistry. Blackie Academic & Professional: London, United Kingdom pp. 98-174.
Bosslet, K. et al. (Mar. 15, 1998). "Elucidation of the Mechanism Enabling Tumor Selective Prodrug Monotherapy," Cancer Research 58:1195-1201.
Bouvier et al. (2003). "A New Paclitaxel Prodrug For Use In ADEPT Strategy," Org. Biomol. Chem. 1:3343-3352.

Bouvier et al. (Mar. 1, 2004). "First Enzymatically Activated Taxotere Prodrugs Designed For ADEPT and PMT," Bioorganic & Medicinal Chemistry 12:969-977.
Bowen, M.A. et al. (Dec. 1, 1993). "Functional Effects of CD30 on a Large Granular Lymphoma Cell Line, YT. Inhibition of Cytotoxicity, Regulation of CD28 and IL-2R, and Induction of Homotypic Aggregation," J. Immunol. 151 (11):5896-5906.
Boyd, P.N. et al. (Dec. 1995). "The Effect of the Removal of Sialic Acid, Galactose and Total Carbohydrate on the Functional Activity of Campath-1H," Mol. Immunol. 32(17/18):1311-1318.
Brief Communication (Sep. 24, 2021). Reply to Opposition for European Patent Application No. 14853953.9, 322 pages.
Bross, P.F. et al. (Jun. 2001). "Approval Summary: Gemtuzumab Ozogamicln In Relapsed Acute Myeloid Leukemia," Clinical Cancer Research 7:1490-1496.
Bumol, T.F. (Aug. 1988). "Characterization Of The Human Tumor and Normal Tissue Reactivity Of The KS1/4 Monoclonal Antibody," Hybridoma 7(4):407-415.
Burke, P.J. et al. (Jun. 2009). "Design, Synthesis, and Biological Evaluation Of Antibody-Drug Conjugates Comprised Of Potent Camptothecin Analogues," Bioconj. Chem. 20(6):1242-1250.
Caron, P.C. et al. (Oct. 1, 1992). "Engineering Humanized Dimeric Forms of IgG Are More Effective Antibodies," J. Exp Med. 176:1191-1195.
Carter, P. et al. (Feb. 1992). "High Level *Escherichia Coli* Expression and Production of a Bivalent Humanized Antibody Fragment," Bio/Technology 10:163-167.
Carter, P. et al. (Oct. 1995). Toward The Production Of Bispecific Antibody Fragments For Clinical Applications. J. Hematotherapy 4:463-470.
Cole, S.P.C. et al. (1985). "The EBV-Hybridoma Technique and Its Applicaton to Human Lung Cancer," in Monoclonal Antibodies and Cancer Therapy, Alan R. Liss, p. 77-96.
Communication Pursuant to Rule 114(2) EPC (dated Mar. 9, 2022). Third Party Opposition for European Patent Application No. 14853953.9, 49 pages.
Consolidated List for European Opposition for European Application No. EP14853953.9, 1 page.
Cunningham, B.C. et al. (Jun. 2, 1989). "High-Resolution Epitope Mapping of hGH-Receptor Interactions by Alanine-Scanning Mutagenesis," Science 244:1081-1085.
De Graaf, M. et al. (2003). "Cytosolic ß-glycosidases For Activation Of Glycoside Prodrugs Of Daunorubicin," Biochemical Pharmacology 65:1875-1881.
De Groot, F.M.H., et al. (2001). "Anticancer Prodrugs for Application in Monotherapy: Targeting Hypoxia, Tumor-Associated Enzymes, and Receptors," Current Medicinal Chemistry 8(9):1093-1122.
Desai, A.A. et al. (2003). "UGT Pharmcogenomics: Implications For Cancer Risk and Cancer Therapeutics," Pharmacogenetics 13(8):517-523.
Desbene, S. et al. (1998). "Doxorubicin Prodrugs With Reduced Cytotoxicity Suited For Tumour Specific Activation," Anti-Cancer Dru Design 13:955-968.
Doronina, S.O. et al. (Jul. 2003). "Development of Potent Monoclonal Antibody Auristatin Conjugates for Cancer Therapy," Nat. Biotechnol. 21(7):778-784.
Doronina, S.O. et al. (Jan. 2006). "Enhanced Activity Of Monomethylauristatin F Through Monoclonal Antibody Delivery: Effects Of Linker Technology On Efficacy And Toxicity," Bioconjug. Chem. 17(1):114-124.
Drueckhammer, D.G. et al. (Jul. 1991). "Enzyme Catalysis in Synthetic Carbohydrate Chemistry," Synthesis pp. 499-525.
Eneyskaya, E.V. et al. (2005). "Chemo-Enzymatic Synthesis Of 4-methylumbelliferyl 13-(1-4)-D-2 xylooligosides: New Substrates For 13-D-xylanease assaus," Org. Biomol. Chem. 3:146-151.
Estin, C.D. et al. (Mar. 15, 1989). "Transfected Mouse Melanoma Lines That Express Various Levels Of Human Melanoma-Associated Antigen p. 97," J. Natl. Cancer Instit. 81(6):445-446.
European Notice of Opposition, dated Apr. 30, 2021, for European Application No. 14853953.9, 76 pages.
European Summons to Attend Oral Proceedings, dated Jan. 4, 2022, for European Application No. 14853953.9, 19 pages.

(56) References Cited

OTHER PUBLICATIONS

Extended European Search Report, dated Jun. 10, 2022, for European Patent Application No. 21206543.7, 9 pages.
Extended European Search Report, dated May 11, 2017, for European Patent Application No. 06787774.6, 8 pages.
Extended European Search Report, dated Oct. 20, 2020, for European Patent Application No. 20186727.2, 15 pages.
Extended European Search Report, dated Oct. 26, 2017, for European Patent Application No. 17179428.2, 11 pages.
Farquhar, D. et al. (Mar. 12, 1998). "Intensely Potent Doxorubicin Analogues: Structure-Activity Relationship," J. Med. Chem. 41(6):965-972.
Feizi, T. (Mar. 7-13, 1985). "Demonstration By Monoclonal Antibodies That Carbohydrate Structures Of Glycoproteins and Glycolipids Are Onco-Developmental Antigens," Nature 314(6006):53-57.
Florent, J.C. et al. (Sep. 10, 1998, e-pub. Aug. 21, 1998). "Prodrugs of Anthracyclines For Use in Antibody-Directed Enzyme Prodrug Therapy," J. Med. Chem. 41(19):3572-3581.
Foon, K.A. et al. (1994). "Murine Anti-Idiotype Monoclonal Antibody Induces Specific Humoral Responses To Carcinoembryonic Antigen (CEA) In Colorectal Cancer Patients," Proc. Am. Soc. Clin. Oncol. 13:294, Abstract # 957, 2 pages.
Francisco, J.A. et al. (Aug. 15, 2003). "CAC10-vcMMAE, An Anti-CD30-menomethyl auristatin E-Conjugate With Potent and Selective Antitumor Activity," Blood 102(4):1468-1465.
Francisco, J.A. et al. (Jun. 15, 2000). "Agonistic Properties and in Vivo Antitumor Activity of the Anti-CD40 Anibody SGN-14," Cancer Res. 60:3225-3231.
Frankel, A.E et al. (2000). "Cell Surface Receptor-Targeted Therapy of Acute Myeloid Leukemia: A Review," Cancer Biother. Radiopharm. 15(5):459-476.
Fuselier, J.A. et al. (2003). "An Adjustable Refease Rate Linking Strategy for Cytotoxin-Peptide Conjugates," Bioorganic & Medicinal Chemistry Letters 13:799-803.
Gesson, J.-P. et al. (1994). "Prodrugs Of Anthracyclines For Chemotherapy Via Enzyme-Monoclonal Antibody Conjugates," Anti-Cancer Drug Design 9:409-423.
Ghetie, M.A. et al. (Mar. 1, 1994). "Anti-CD19 Inhibits The Growth Of Human B-Cell Tumor Lines In Vitro And Of Daudi Cells In SCID Mice By Inducing Cell Cycle Arrest," Blood 83(5):1329-1336.
Ghosh, N. et al. (2009). "Chemical and Biological Evaluations Of The Family Of CC-1065 and The Duocarmycin Natural Products," Curr. Topics in Med. Chem. 9(16):1494-1524.
Goodson, J. M. (1984). "Chapter 6: Dental Applications," in Medical Applications of Controlled Release 2:115-138.
Grounds for Opposition, dated Apr. 2021, for European Patent No. EP3057585, 66 pages.
Haisma, H.J. et al. (1992). "A Monoclonal Antibody-B-glucuronidase Conjugate As Activator Of The Prodrug Epirubicin-Glucuronide For Specific Treatment Of Cancer," Br. J. Cancer 66:474-478.
Hellström, I. et al.(Aug. 1986). "Monoclonal Mouse Antibodies Raised Against Human Lung Carcinoma," Cancer Res. 46(8):3917-3923.
Hellstrom, I. et al. (May 1985). "Monoclonal Antibodies To Cell Surface Antigens Shared By Chemically Induced Mouse Bladder Carcinomas," Cancer. Res. 45(5):2210-2218.
Henttu, P. et al. (Apr. 28, 1989). "cDNA Coding For The Entire Human Prostate Specific Antigen Shows High Homologies To The Human Tissue Kallikrein Genes," Biochem. Biophys. Res. Comm. 160(2):903-910.
Herlyn, M. et al. (Apr. 1982). "Monoclonal Antibody Detection Of A Circulating Tumor-Associated Antigen. I. Presence Of Antigen In Sera Of Patients With Colorectal, Gastric, and Pancreatic Carcinoma," J. Clin. Immunol. 2(2):135-140.
Hilkens, J. et al. (Sep. 1992). "Cell Membrane-Associated Mucins and Their Adhesion-Modulating Property," Trends in Bio. Chem. Sci. 17(9):359-363.

Holliger, P. et al. (Jul. 1993). "Diabodies: Small Bivalent And Bispecific Antibody Fragments," Proc. Natl. Acad. Sci. USA 90:6444-6448.
Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.
Hoon, D.S.B. et al. (Nov. 1, 1993). "Molecular Cloning of a Human Monoclonal Antibody Reactive to Ganglioside GM3 Antigen on Human Cancers," Cancer Res. 53:5244-5250.
Houba, P.H.J. et al. (1996). "Characterization of Novel Anthracycline Prodrugs Activated by Human ß-glucuronidase for Use in Antibody-Directed Enzyme Prodrug Therapy," Biochemical Pharmacology 52(3):455-463.
Hsu, T.-A. et al. (Apr. 4, 1997). "Differential N-Glycan Patterns of Secreted and Intracellular IgG Produced in Trichoplusia ni Cells," J. Biol. Chem. 272(14):9062-9070.
Huston, J.S. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
International Preliminary Report on Patentability, dated Apr. 19, 2016, for PCT Application No. PCT/US2014/060477, filed Oct. 14, 2014, 10 pages.
International Preliminary Report on Patentability, dated Jan. 22, 2008, for PCT Application No. PCT/US2006/027925, filed Jul. 18, 2006, 7 pages.
International Preliminary Report on Patentability, dated Sep. 24, 2019, for PCT Application No. PCT/US2018/024191, filed Mar. 23, 2018, 7 pages.
International Preliminary Report on Patentability, dated Sep. 25, 2018, for PCT Application No. PCT/US2017/24148, filed Mar. 24, 2017, 14 pages.
International Search Report and Written Opinion, dated Aug. 8, 2017, for PCT Application No. PCT/US2006/027925, filed Jul. 18, 2006, 8 pages.
International Search Report and Written Opinion, dated Jul. 30, 2015, for PCT Application No. PCT/US2014/060477, filed Oct. 14, 2015, 22 pages.
International Search Report and Written Opinion, dated Jun. 6, 2019, for PCT Application No. PCT/US2018/024191, filed Mar. 23, 2018, 14 pages.
Israeli, R.S. et al. (Jan. 15, 1993). "Molecular Cloning of a Complementary DNA Encoding a Prostate-Specific Membrane Antigen," Cancer Res. 53:227-230.
Jefferis, R. et al. (1997). "Glycosylation Of Antibody Molecules: Structural and Functional Significance," Chem. Immunol. 65:111-128.
Jeffrey, S.C., et al. (Apr. 15, 2007, e-pub. Jan. 27, 2007). "Minor Groove Binder Antibody Conjugates Employing A Water Soluble β-Glucuronide Linker," Bioorg. Med. Chem. Lett. 17(8):2278-2280.
Jespers, L.S. et al. (Sep. 12. 1994). "Guiding the Selection of Human Antibodies From Phage Display Repertoires to a Single Epitope of an Antigen," Bio/Technology 72:898-903.
Kahn, C.R. et al. (1988). "The Insulin Receptor and the Molecular Mechanism of Insulin Action," Insulin Receptor and Insulin Action 82:1151-1156.
Kelly, M.A. et al. (1988). "Preparation Of Some aryl α-arabinofuranosides As Substrates For Arabinofuranosides," Carbohydrate Research 181:262-266.
Kingston, D.G.I. (Jun. 1994)."Taxol: The Chemistry and Structure-Activity Relationships Of A Novel Anticancer Agent,"TIBTECH 12:222-227.
Kohler, G. et al. (Aug. 7, 1975) "Continuous Cultures Of Fused Cells Secreting Antibody Of Predefined Specificity," Nature 256:495-497.
Langer, R. (Sep. 28, 1990). "New Methods Of Drug Delivery," Science 249(4976): 1527-1533.
Leenders, R.G.G. et al. (1995). "Synthesis and Evaluation of Novel Daunomycin-Phosphate-Sulfate-β-Glucuronide and -β-Glucoside Prodrugs for Application in Adept," Bioorganic & Medicinal Chemistry Letters 5(24):2975-2980.

(56) References Cited

OTHER PUBLICATIONS

Leenders, R.G.G. et al. (1995). "β-Glucuronyl Carbamate Based Pro-moieties Designed for Prodrugs in ADEPT," Tetrahedron Letters 36(10):1701-1704.

Leenders, R.G.G et al. (1999). "Novel Anthracycline-Space-β-glucuronide, -β-glucoside, and -β-galactoside Prodrugs for Application in Selective Chemotherapy," Bioorganic & Medicinal Chemistry 7:1597-1610.

Livingston, P.O. et al. (May 1994). "Improved Survival In Stage III Melanoma Patients With GM2 Antibodies: A Randomized Trial Of Adjuvant Vaccination With GM2 Ganglioside," J. Clin. Oncol. 12(5):1036-1044.

Lonberg, N. et al. (1995). "Human Antibodies From Transgenic Mice," Intern. Rev. Immunol. 13:65-93.

Lougerstay-Madec, R. et al. (1998). "Synthesis Of Self-Immolative Glucuronide-Based Prodrugs D Of A Phenol Mustard," Anti-Cancer Drug Design 13:995-1007.

Lyon, R.P. (May 5, 2014). "Novel ADC Chemistry for Improved Stability and Pharmacokinetics," Characterization of Antibody-Drug Conjugates, Seattle Genetics Presentation, PEGS Boston, 25 pages.

Madec-Lougerstay et al. (1999). "Synthesis Of Self-Immolative Glucuronide Spacers Based On Aminomethylcarbamate. Application To 5-Fluorouracil Prodrugs For Antibody-Directed Enzyme Prodrug Therapy," J. Chem. Soc. Perkin Trans pp. 1369-1375.

Malhotra, R. et al. (Mar. 1995). "Glycosylation Changes Of IgG Associated With Rheumatoid Arthritis Can Activate Complement Via The Mannose-Binding Protein," Nature Med. 1(3):237-243.

Marino, C. et al. (1995). "Synthesis of 4-methylcoumarin-7-yl B-D-galactofuranoside, A Fluorogenic Substrate For Galactofuranosidase," Carbohydrate Research 276:209-213.

Marks, J.D. et al. (1991). "By-Passing Immunization: Human Antibodies From V-Genen Libraries Displayed on Phage," J. Mol. Biol. 222:581-597.

Merchant, A. M. et al. (Jul. 1998). "An Efficient Route To Human Bispecific IgG," Nature Biotechnology 16:677-681.

Milstein, C. et al. (Oct. 6, 1983). "Hybrid Hybridomas and Their Use in Immunohistochemistry," Nature 305:537-539.

Minotti, G. et al. (2004). "Anthracyclines: Molecular Advances and Pharmacologic Developments in Antitumor Activity and Cardiotoxicity," Pharmacol. Rev. 56(2):185-229.

Mittelman, A. et al. (1990). Active Specific Immunotherapy in Patients with Melanoma: A Clinical Trial with Mouse Antiidiotypic Monoclonal Antibodies Elicited with Syngeneic Anti-High-Molecular-Weight-Melanoma-Associated Antigen Monoclonal Antibodies J. Clin. Invest. 86:2136-2144.

Murray.J.L. (Dec. 2000). "Monoclonal Antibody Treatment of Solid Tumors: A Coming of Age," Semin. Oncol. 27(Suppl. 1):64-70.

Natali, P.G. et al. (Jan. 1, 1987). "Immunohistochemical Detection Of Antigen In Human Primary and Metastatic Melanomas By The Monoclonal Antibody 140.240 and Its Possible Prognostic Significance," Cancer 59(1):55-63.

Nicolaou, K.C. et al. (1994). "Calicheamicin ϴ[1]: A Rationally Designed Molecule with Extremely Potent and Selective DNA Cleaving Properties and Apoptosis Inducing Activity," Angew. Chem. Intl. Ed. Engl. 33(2):183-186.

Notice of Opposition, dated Apr. 22, 2021, for European Application No. EP14853953.9, 7 pages.

Perez, M.S. et al. (May 15, 1989). "Isolation and Characterization of A cDNA Encoding the KS1/4 Epithelial Carcinoma Marker," J. Immunol. 142(10):3662-3667.

Pluckthün, A. (1994) "Antibodies from *Escherichia Coli*," The Pharmacology of Monoclonal Antibodies pp. 269-315.

Proprietors Submission dated Aug. 19, 2019, European Opposition for European Application No. EP14853953.9, 79 pages.

Proprietors Submission dated Jul. 3, 2018, European Opposition for European Application No. EP14853953.9, 40 pages.

Proprietors Submission dated Mar. 12, 2018, European Opposition for European Application No. EP14853953.9, 43 pages.

Proprietors Submission dated Nov. 15, 2019, European Opposition for European Application No. EP14853953.9, 99 pages.

Quan, et al. (2002). "The Rise Of Monoclonal Antibodies As Therapeutics," in Anti-IgE and Allergic Disease, Jardieu and Fick Jr., eds., Marcel Dekker, New York, NY, Chapter 20, pp. 427-469.

Quiles, S. et al. (2010, e-pub. Dec. 3, 2009). "Synthesis and Preliminary Biological Evaluation of High-Drug-Load Paclitaxel-Antibody Conjugates for Tumor-Targeted Chemotherapy," J. Med. Chem. 53:586-594.

Ragnhammar, P. et al. (Mar. 12, 1993). "Effect Of Monoclonal Antibody 17-1A and GM-CSF In Patients With Advanced Colorectal Carcinoma—Long-Lasting, Complete Remissions Can Be Induced," Int. J. Cancer 53(5):751-758.

Reff, M.E. et al. (Jan. 15, 1994). "Depletion of B Cells In Vivo by a Chimeric Mouse Human Monoclonal Antibody to CD20," Blood 83(2):435-445.

Ritter, J.K. (2000) "Roles Of Glucuronidation and UDP-glucuronosyltransferases in Xenobiotic Bioactivation Reactions," Chemico-Biological Interactions 129:171-193.

Robbins, P. et al. (1996) "Human Tumor Antigens Recognized By T Cells," Curr. Opin. Immunol. 8:628-636.

Rodrigues, M.L. et al. (Dec. 15, 1993). "Engineering Fab' Fragments For Efficient F(ab)2 Formation In Escherichia coli and For Improved In Vivo Stability," J. Immunology 151(12):6954-6961.

Saleh, M.N. et al. (Sep. 15, 1993). "Generation Of A Human Anti-Idiotypic Antibody That Mimics The GD2 Antigen," J. Immunol. 151(6):3390-3398.

Scheltè, P. et al. (2000). "Differential Reactivity of Maleimide and Bromoacetyl Functions with Thiols: Application to the Preparation of Liposomal Diepitope Constructs," Bioconjugate Chem. 11:118-123.

Schmidt, F. et al. (2001). "Cancer Chemotherapy: A Paclitaxel Prodrug for ADEPT (Antibody-Directed Enzyme Prodrug Therapy)," Eur. J. Org. Chem. pp. 2129-2134.

Sgouros. G. et al. (Mar. 1993). "Modeling and Dosimetry of Monoclonal Antibody M195 (Anti-CD33) in Acute Myelogenous Leukemia," J. Nucl. Med. 34(3):422-430.

Shitara, K. et al. (Jun. 1993). "A Mouse/Human Chimeric Anti-(Ganglioside GD3) Antibody With Enhanced Antitumor Activities," Cancer Immunol. Immunother. 36(6):373-380.

Shopes, B. et al. (May 1, 1992). "A Genetically Engineered Human IgG Mutant With Enhanced Cytolytic Activity," J. Imniunol. 148:2918-2922.

Stachulski, A.V. et al. (1998). "The Synthesis Of O-glucuronides," Natural Product Reports pp. 173-186.

Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.

Summons to Attend Oral Proceedings Pursuant to Rule 115(1) EPC (Jan. 4, 2022), 59 pages.

Sun, M.M.C. et al. (Sep./Oct. 2005). "Reduction-Alkylation Strategies for the Modification of Specific Monoclonal Antibody Disulfides," Bioconjug. Chem. 16(5):1282-1290, 22 pages.

Suresh, M.R. et al. (1986). "Bispecific Monoclonal Antibodies From Hybrid Hybridomas," Methods in Enzymology 121:210-228, 19 pages.

Tailor, P.G. et al. (Aug. 25, 1990). "Nucleotide Sequence Of Human Prostatic Acid Phosphatase Determined From A Full-Length cDNA Clone," Nucl. Acids Res. 18(16):4928, 1 pages.

Toshima, K. et al. (1993). "Recent Progress in O-Glycosylation Methods and Its Application to Natural Products Synthesis," Chemical Reviews 93(4):1503-1531.

Trail, P.A. et al. (Jan. 1, 1997). "Effects of Linker Variation on the Stability, Potency, and Efficacy of Carcinoma-Reactive BR64-Doxorubicin Immunoconjugates," Cancer Research 57:100-105.

Trail, P.A. et al. (Jul. 9, 1993). "Cure Of Xenografted Human Carcinomas by BR96-Doxorubicin Immunoconjugates," Science 261(5118):212-215.

Traunecker, A. et al. (1991). "Bispecific Single Chain Molecules (Janusins) Target Cytotoxic Lymphocytes on HIV Infected Cells," Embo J. 10(12):3655-3659.

(56) References Cited

OTHER PUBLICATIONS

Trauth, B.C. et al. (Jul. 21, 1989). "Monoclonal Antibody-Mediated Tumor Regression by Induction of Apoptosis," Science 245(4915):301-305.

Umaña, P. et al. (Feb. 1999). "Engineered Glycoforms of an Antineuro- Blastoma IgG 1 With Optimized Antibody-Dependent Cellular Cytotoxic Activity," Nat. Biotechnol. 17:176-180.

U.S. Appl. No. 61/891,320, Provisional Application, filed Oct. 15, 2013, 254 pages.

U.S. Appl. No. 61/941,904, Provisional Application, filed Feb. 19, 2014, 269 pages.

U.S. Appl. No. 61/947,742, Provisional Application, filed Mar. 4, 2014, 279 pages.

U.S. Appl. No. 61/975,318, Provisional Application, filed Apr. 4, 2014, 280 pages.

Verdier-Pinard, P. et al. (2000). "Sustained Intracellular Retention of Dolastatin 10 Causes Its Potent Antimitotic Activity," Molecular Pharmacology 57:180-187.

Vijayasardahl, S. et al. (Apr. 1, 1990). "The Melanoma Antigen gp75 Is The Human Homologue Of The Mouse B Brown) Locus Gene Product," J. Exp. Med. 171(4)1375-1380.

Wald, A.F. et al. (Jul. 1, 2002). "The Anti-CD30 Monoclonal Antibody SGN-30 Promotes Growth Arrest and DNA Fragmentation in Vitro and Affects Antitumor Activity In Models Of Hodgkin's Disease," Cancer Res. 62(13):3736-3742.

Ward, E.S. et al. (Oct. 12, 1989). "Binding Activities Of A Repertoire Of Single Immunoglobulin Variable Domains Secreted From Escherichia coli," Nature 341:544-554.

Wiels, J. et al. (Feb. 2, 2022). "38.13: A Monoclonal Antibody Directed Against A Burkitt's Lymphoma-Associated Antigen and Its Use as Carrier for Toxins," Laboratoire d'Immuno-Biolgie des Tumeurs, pp. 457-464.

Wilbur, D.S. et al. (2001, e-pub. Jun. 7, 2001). "Biotin Reagents for Antibody Pretargeting. 5. Additional Studies of Biotin Conjugate Design To Provide Biotinidase Stability," Bioconjugate Chem. 12:616-623.

Wittwer, A.J. et al. (May 1, 1990). "Glycosylation at Asn-184 Inhibits the Conversion of Single-Chain to Two-Chain Tissue-Type Plasminogen Activator by Plasmin," Biochemostry 29(17):4175-4180.

Wolff, E.A. et al. (Jun. 1, 1993). "Monoclonal Antibody Homodimers: Enhanced Antitumor Activity in Nude Mice," Can Res 53:2560-2565.

Wright, A. et al. (Jan. 1997). "Effect of Glycosylation on Antibody Function: Implications for Genetics Engineering," Trends Biotechnol. 15:26-32.

Wyss, D.F. et al. (1996). "The Structural Role of Sugars in Glycoproteins," Current Opin. Biotech. 7:409-416.

Yokata, T. et al. (Jun. 15, 1992). "Rapid Tumor Penetration Of A Single-Chain Fv and Comparison With Other Immunoglobulin Forms," Cancer Res. 52(12):3402-3408.

Yu, Y.H. et al. (Jan. 15, 1991). "Coexpression Of Different Antigenic Markers On Moieties That Bear CA 125 Determinants," Cancer Res. 51(2):468-475.

\* cited by examiner

PROCESS FOR THE PREPARATION OF PEGYLATED DRUG-LINKERS AND INTERMEDIATES THEREOF

CROSS REFERENCE TO RELATED APPLICATIONS

This application is a U.S. national stage filing under 35 USC § 371 of International Application No. PCT/US2017/024148, filed Mar. 24, 2017, which claims priority to U.S. Appl. Ser. No. 62/313,460, filed Mar. 25, 2016, the contents of which are incorporated by reference herein in their entireties.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

A great deal of interest has surrounded the use of monoclonal antibodies (mAbs) for the targeted delivery of cytotoxic agents to cancer cells. The design of antibody drug conjugates, by attaching a cytotoxic agent to an antibody, typically via a linker, involves consideration of a variety of factors. These factors include the identity and location of the chemical group for conjugation of the cytotoxic agent, the mechanism of agent release, the structural element(s) (if any) providing release of the cytotoxic agent, and structural modification of the released free agent, if any. In addition, if the cytotoxic agent is to be released after antibody internalization, the structural elements and mechanism of agent release must be consonant with the intracellular trafficking of the conjugate.

While a number of different drug classes have been evaluated for delivery via antibodies, only a few drug classes have proved sufficiently active as antibody drug conjugates, while having a suitable toxicity profile, to warrant clinical development. One such class is the auristatins, related to the natural product dolastatin 10. Representative auristatins include MMAE (N-methylvaline-valine-dolaisoleuine-dolaproine-norephedrine) and MMAF (N-methylvaline-valine-dolaisoleuine-dolaproine-phenylalanine).

MMAE is an example of a cytotoxic agent that is active as a free drug, and is highly potent when conjugated to a monoclonal antibody (mAb) and is released after internalization into cells. MMAE has been successfully conjugated to a mAb at the N-terminal amino acid of MMAE via a cathepsin B cleavable peptide-based linker containing maleimidocaproyl-valine-citrulline (mc-vc-) and a self-immolative group p-aminobenzyl-carbamoyl (PABC) to produce antibody drug conjugates of the following structure, mAb-(mc-vc-PABC-MMAE)$_p$, wherein p refers to the number of (mc-vc-PABC-MMAE) units per antibody. Upon cleavage of the bond between the vc peptide and the self-immolative PABC group, the PABC group releases itself from MMAE, liberating free MMAE.

Another auristatin, MMAF, is relatively less active as a free drug (compared to MMAE), yet is highly potent when conjugated to an antibody and internalized into cells. MMAF has been successfully conjugated to a monoclonal antibody (mAb) at the N-terminal amino acid of MMAF via a cathepsin B cleavable peptide-based linker containing maleimidocaproyl-valine-citrulline (mc-vc-) and a self-immolative group p-aminobenzyl-carbamoyl (PABC) to produce antibody-drug conjugates of the structure, mAb-(mc-vc-PABC-MMAF)$_p$, wherein p refers to the number of (mc-vc-PABC-MMAF) units per antibody. Upon cleavage of the peptide linker, the self-immolative PABC group releases itself from MMAF, liberating free MMAF.

MMAF was also found to be active as a non-cleavable conjugate, containing the drug-linker maleimidocaproyl MMAF (mcMMAF). When this conjugate, mAb-(mcMMAF)$_p$, is internalized into cells, the active species released is cys-mcMMAF. Because the linker is non-cleavable, the maleimidocaproyl and a cysteine residue of the antibody remain attached to the N-terminus of MMAF. MMAF was also reported to be active as a C-terminal conjugate, attached at its C-terminal amino acid, phenylalanine, to a peptide-maleimidocaproyl linker. When this conjugate, (MMAF-peptide-mc)$_p$-mAb is internalized into cells, the active species, MMAF, is released following cleavage of the MMAF (phenylalanine)-peptide bond.

WO 2015/057699 describes preparation of mDPR-(maleimido-diaminopropanoic) glucuronide-MMAE Drug Linker compounds having a PEG unit, which are exemplary PEGylated Auristatin Drug Linker compounds, as well as improved pharmacokinetics of ADCs prepared from such compounds. Prior methods for producing such compounds can result in loss of material during deprotection of the Glucuronide Unit, and that impurities from that loss can be difficult to remove without further reduction in yield. Therefore, there is a need for improved methods for preparing such Drug Linker compounds with reduced amounts of contaminating impurities, so as to improve purity and yields.

BRIEF SUMMARY OF THE INVENTION

The invention provides inter alia, improved processes in producing PEGylated Drug Linker compounds containing a Glucuronide Unit, as well as the intermediates thereof. Principal embodiments of the invention include methods for preparing Drug Linker intermediates of Formula IE:

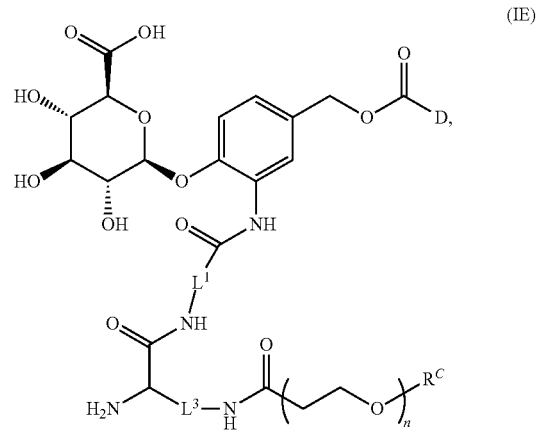

or a salt thereof, wherein D is an auristatin Drug Unit; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_5$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $R^C$ is hydrogen or a PEG Capping Unit; and subscript n ranges from 2 to 24, the method comprising step (c) contacting a Drug Linker intermediate compound of Formula IC with either a Grignard reagent or an alkoxy magnesium halide in a suitable alcohol-containing solvent, wherein the Formula IC Drug Linker intermediate compound has the structure of:

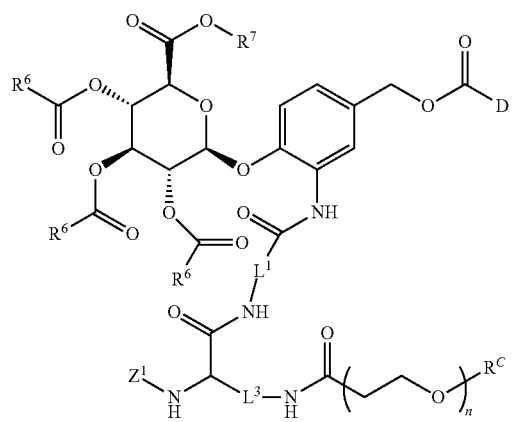

(IC)

(d) contacting the product of step (c) with a first deprotecting agent, wherein said first deprotecting agent contacting removes the $Z^1$ amino and carboxylic acid protecting groups to provide the Formula IE Drug Linker intermediate compound.

Other principle embodiments include Antibody Drug Conjugates compositions comprised of Antibody Drug Conjugate of Formula 12 and Formula 12A, optionally in pharmaceutically acceptable salt form, having the structures of:

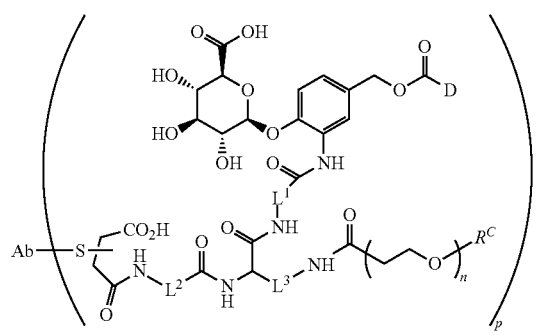

(12)

and

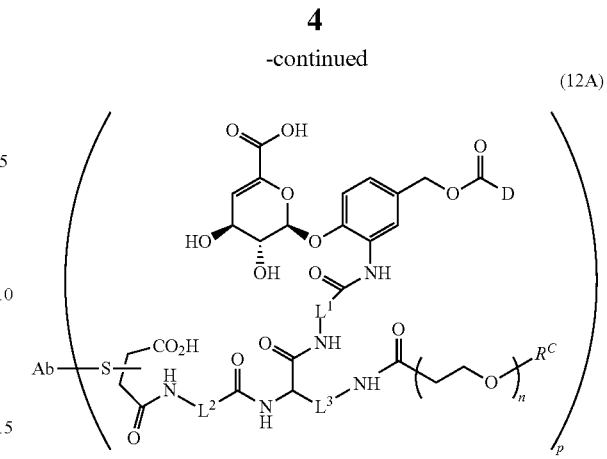

(12A)

wherein Ab is an antibody; S is a sulfur atom from the antibody; the Ab-S— moeity is attached to the carbon atom α or β to the carboxylic acid functional group; D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is a hydrogen or a PEG Capping Unit; subscript n ranges from 2 to 24; and subscript p ranges from about 1 to about 16; and wherein the composition contains no more than 10 wt. % or no more than 5 wt. % Formula 12A Antibody Drug Conjugate,

DESCRIPTION OF THE INVENTION

General

The present invention is based, in part, on the surprising discovery that the method of deprotection of a Glucuronide Unit in the synthesis of certain PEGylated Auristatin Drug Linker compounds can have a profound effect on the purity and yield of the desired product. Specifically, the present inventors have discovered that using an alkoxymagnesium halide in a solvent comprising an alcohol for removal of acyl protecting groups in the carbohydrate moeity of the Glucuronide Unit, instead of conventionally used reagents such as LiOH, leads to significant reduction of in an undesirable β-eliminated impurity (to below about 5% from about 20%). In some aspects, the alkoxymagnesium halide reagent is prepared in situ by contacting a Gringard reagent with the alcohol-containing solvent. Thus, the present invention provides improved processes for preparing certain PEGylated Auristatin Drug Linkers.

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques, and pharmacology are employed.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, typically by 10% to 0.5%, more typically by 5% to 1%, while still describing the particular property.

"Essentially retains", "essentially retaining" and like terms as used herein refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms as used herein refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is essentially retained). Thus the phrase "substantially retains" is made in reference to the effect that a physical property or characteristic of a compound or composition has on a physiochemical or pharmacological property or biological activity that is explicitly associated with that physical property or characteristic.

"Negligibly" or "negligible" as used herein is an amount of an impurity below the level of quantification by HPLC analysis and if present represents from about 0.5% to about 0.1 w/w % of the composition that it contaminates. Depending on context, those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms as used herein refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

"Electron-withdrawing group" as the term is used herein refers to a functional group or electronegative atom that draws electron density away from an atom to which it is bonded either inductively and/or through resonance, whichever is more dominant (i.e. a functional group or atom may be electron-donating through resonance but may overall be electron withdrawing inductively), and tends to stabilize anions or electron-rich moieties. The electron-withdrawing effect is typically transmitted inductively, albeit in attenuated form, to other atoms attached to the bonded atom that has been made electron-deficient by the electron-withdrawing group (EWG), thus affecting the electrophilicity of a more remote reactive center.

An electron-withdrawing group (EWG) is typically selected from the group consisting of —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^{op}$)$_2$, —NO, —NH$_2$, —N(R')(R$^{op}$), —N(R$^{op}$)$_3^+$, and salts thereof, wherein X is —F, —Br, —Cl, or —I, and R$^{op}$ is, at each occurrence, independently selected from a grouping previously described for optional substituents and in some aspects is independently selected from the group consisting of C$_1$-C$_6$ alkyl and phenyl, and wherein R' is hydrogen and R$^{op}$ is selected from a grouping as described elsewhere for optional substituents and in some aspects is a C$_1$-C$_{12}$ alkyl, C$_1$-C$_5$ alkyl, C$_1$-C$_6$ alkyl or C$_1$-C$_4$ alkyl. An EWG can also be an aryl (e.g., phenyl) or heteroaryl depending on its substitution and certain electron deficient heteroaryl groups (e.g., pyridine). Thus, in some aspects, an "electron-withdrawing group" further encompasses electron-deficient C$_5$-C$_{24}$ heteroaryls and C$_6$-C$_{24}$ aryls that are further substituted with electron-withdrawing substituents. More typically, an electron-withdrawing group is selected from the group consisting of —C(=O), —CN, —NO$_2$, —CX$_3$, and —X, wherein X is halogen, independently selected typically from the group consisting of —F and —Cl. Depending on its substituents, an optionally substituted alkyl moiety may also be an electron-withdrawing group and thus in such cases aspects would be encompassed by the term for an electron-withdrawing group.

"Electron-donating group" as the term is used herein refers to a functional group or electropositive atom that increases electron density of an atom to which it is bonded either inductively and/or through resonance, whichever is more dominant (i.e., a functional group or atom may be electron-withdrawing inductively but may overall be electron-donating through resonance), and tends to stabilize cations or electron poor systems. The electron-donating effect is typically transmitted through resonance to other atoms attached to the bonded atom that has been made electron rich by the electron-donating group (EDG) thus affecting the nucleophilicity of a more remote reactive center. Typically, an electron-donating group is selected from the group consisting of —OH, —OR', —NH$_2$, —NHR', and N(R')$_2$, wherein each R' is an independently selected from $C_1$-$C_{12}$ alkyl, typically $C_1$-$C_6$ alkyl. Depending on their substituents, a $C_6$-$C_{24}$ aryl, $C_5$-$C_{24}$ heteroaryl, or unsaturated $C_1$-$C_{12}$ alkyl moiety may also be an electron-donating group and in some aspects such moieties are encompassed by the term for an electron-donating group.

"Moiety" as used herein means a specified segment, fragment, or functional group of a molecule or compound. Chemical moieties are sometimes indicated as chemical entities that are embedded in or appended to (i.e., a substituent or variable group) a molecule, compound or chemical Formula.

Unless indicated otherwise, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents of that base moiety. For esters, carbonates, carbamates, and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more sp$^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls as defined herein.

When referring to an alkyl moiety or group as an alkyl substituent, that alkyl substituent to a Markush structure or another organic moiety with which it is associated is methyl or a chain of contiguous carbon atoms that is covalently attached to the structure or moiety through a sp$^3$ carbon of the alkyl substituent. An alkyl substituent, as used herein, therefore contains at least one saturated moiety and may also contain one or more unsaturated moieties or groups. Thus, an alkyl substituent may additionally contain one, two, three or more independently selected double and/or triple bonds to define an unsaturated alkyl substituent, and may be substituted (i.e., optionally substituted) by other moieties that include optional substituents as described herein. A saturated, unsubstituted alkyl substituent contains saturated carbon atoms (i.e., sp$^3$ carbons) and no sp$^2$ or sp carbon atoms. An unsaturated alkyl substituent contains at least one saturated carbon atom that is monovalent for its site of attachment to the Markush structure or other organic moiety with which it is associated and at least two sp$^2$ or sp carbon atoms that are in conjugation with each other.

Unless otherwise indicated or implied by context, the term "alkyl" will indicate a saturated, non-cyclic hydrocarbon radical, wherein the hydrocarbon radical is methyl or has the indicated number of covalently linked saturated carbon atoms, e.g., "$C_1$-$C_6$ alkyl" or "$C_1$-$C_6$ alkyl" means a saturated alkyl moiety or group containing 1 saturated carbon atom (i.e., is methyl) or 2, 3, 4, 5 or 6 contiguous, non-cyclic saturated carbon atoms and "$C_1$-$C_5$ alkyl" refers to a saturated alkyl moiety or group having 1 saturated carbon atom or 2, 3, 4, 5, 6, 7 or 8 contiguous saturated, non-cyclic carbon atoms. The number of saturated carbon atoms in an alkyl moiety or group can vary and typically is 1 to 50, 1 to 30 or 1 to 20, or 1 to 12, and more typically is 1 to 8, 1 to 6 or 1 to 4. In some aspects, alkyl refers to a saturated $C_1$-$C_{12}$ or a $C_1$-$C_8$ alkyl moiety and more typically is a saturated $C_1$-$C_6$ or $C_1$-$C_4$ alkyl moiety with the latter sometimes referred to as lower alkyl. When the number of carbon atoms is not indicated, an alkyl moiety, group or substituent has from 1 to 8 saturated carbon atoms. In some aspects an alkyl moeity, group or substituent is unsubstituted. When an alkyl substituent is unsaturated such moieties typically are unsaturated $C_3$-$C_{12}$ alkyl or $C_3$-$C_8$ moieties, more typically unsaturated $C_1$-$C_6$ alkyl moieties.

In some aspects when an alkyl substituent, moiety or group is specified, species are those derived from removing a hydrogen atom from a parent alkane (i.e., is monovalent) and are exemplified by methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, and sec-amyl and in other aspects an alkyl substituent, moiety or group are or are additionally exemplified by other linear and branch chain alkyl moieties.

"Alkylene," as used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more sp$^3$ carbons), of the stated number of carbon atoms, typically 1 to 10 carbon atoms, and having two radical centers (i.e., is divalent) derived by the removal of two hydrogen atoms from the same or two different saturated (i.e., sp$^3$) carbon atoms of a parent alkane. An alkylene moiety in some aspects is an alkyl radical as described herein in which a hydrogen atom has been removed from another of its saturated carbons or from the radical carbon of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—$CH_2$—), 1,2-ethylene (—$CH_2CH_2$—), 1,3-propylene (—$CH_2CH_2CH_2$—), 1,4-butylene (—$CH_2CH_2CH_2CH_2$—), and like diradicals. Typically, an alkylene is a branched or straight chain hydrocarbon containing only $sp^3$ carbons (i.e., is fully saturated notwithstanding the radical carbon atoms) and in some aspects is unsubstituted.

"Carbocyclyl" as used herein, by itself of as part of another term, unless otherwise stated or implied by context, refers to a radical of a monocyclic, bicyclic, or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic ring system, wherein the points of fusion to the carbocyclic and aromatic ring systems are to adjacent carbons of each of these ring systems.

When carbocyclyl is used as a Markush group (i.e., a substituent) the carbocyclyl is attached to a Markush formula or another organic moiety with which it is associated through a carbon atom that is involved in the carbocyclic ring system of the carbocyclyl moiety provided that carbon atom is not aromatic. When an unsaturated carbon of an alkene moiety comprising the carbocyclyl substituent is attached to a Markush formula with which it is associated that carbocyclyl is sometimes referred to as a cycloalkenyl substituent. The number of carbon atoms in a carbocyclyl moeity group or substituent is defined by the total number of skeletal atoms of its carbocyclic ring system. That number can vary and typically ranges from 3 to 50, 3 to 30, 3 to 20 or 3 to 12, and more typically from 3 to 8 or 3 to 6 skeletal carbon atoms unless otherwise specified, e.g., $C_3$-$C_8$ carbocyclyl means an carbocyclyl substituent, moiety or group containing 3, 4, 5, 6, 7, or 8 carbocyclic carbon atoms and $C_3$-$C_6$ carbocyclyl means a carbocyclyl substituent, moiety or group containing 3, 4, 5, or 6 carbocyclic carbon atoms. A carbocyclyl in some aspects is unsubstituted and in other aspects is derived by the removal of one hydrogen atom from a skeletal ring atom of a parent cycloalkane or cycloalkene. Representative $C_3$-$C_8$ carbocyclyls are cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3, or 4 carbon atoms, typically 2 or 3. Thus, otherwise specified, a carbocyclyl is typically a $C_3$-$C_8$ carbocyclyl that may be substituted (i.e. optionally substituted) with moieties described herein for alkyl, alkenyl, alkynyl, aryl, arylalkyl, and alkylaryl and in some aspects is unsubstituted. In other aspects, a $C_3$-$C_8$ cycloalkyl moiety, group or substituent is selected from the group consisting of cyclopropyl, cyclopentyl and cyclohexyl, or is encompassed or further encompassed by other cyclic moieties that have no more than 8 carbon atoms in their cyclic ring systems. When the number of carbon atoms is not indicated, a carbocyclyl moiety, group or substituent has from 3 to 8 carbon atoms in its carboxcylic ring system.

"Carbocyclo," by itself or as part of another term, unless otherwise stated or implied by context, refers to an optionally substituted carbocyclyl as defined above wherein another hydrogen atom of its cycloalkyl ring system has been removed (i.e., it is divalent) and typically is a $C_3$-$C_{20}$ or $C_3$-$C_{12}$ carbocyclo, more typically a $C_3$-$C_8$ or $C_3$-$C_6$ carbocyclo and in some aspects is unsubstituted. When the number of carbon atoms is not indicated, a carbocyclo moiety, group or substituent has from 3 to 8 carbon atoms in its carboxcylic ring system.

"Alkenyl" as the terms are used herein, by itself or as part of another term, unless otherwise stated or implied by context, refers to an organic moiety, substituent or group that comprises one or more double bond functional groups (e.g., a —CH═CH— moiety) or 1, 2, 3, 4, 5, or 6 or more, typically 1, 2, or 3 of such functional groups, more typically one such functional group, and in some aspects may be substituted (i.e., is optionally substituted) with an aryl moiety or group such as phenyl, or linked normal, secondary, tertiary or cyclic carbon atoms, i.e., linear, branched, cyclic or any combination thereof unless the alkenyl substituent, moiety or group is a vinyl moiety (e.g., a —CH═$CH_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one $sp^2$ carbon atom in which that carbon atom is doubly, or contains at least two $sp^2$ carbon atoms in conjugation to each other in which one of the $sp^2$ carbon atoms is singly bonded, to another organic moiety or Markush structure to which it is associated. Typically, when alkenyl is used as a Markush group (i.e., is a substituent) the alkenyl is singly bonded to a Markush formula or another organic moiety with which it is associated through a double-bonded carbon (i.e., a $sp^2$ carbon) of one of its alkene functional groups. In some aspects when an alkenyl moiety, group or substituent is specified, species encompasses are any of the optionally substituted alkyl or carbocyclyl, groups moieties or substituents described herein that has one or more endo double bonds and monovalent moieties derived from removal of a hydrogen atom from a $sp^2$ carbon of a parent alkene compound. Such monovalent moieties are exemplified without limitation by vinyl (—CH═$CH_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, and cyclohexenyl. In some aspects the term alkenyl encompasses those and/or other linear, cyclic and branched chained, all carbon-containing moieties containing at least one double bond functional group. The number of carbon atoms in an alkenyl substituent is defined by the number of $sp^2$ carbon atoms of the alkene functional group that defines it as an alkenyl substituent and the total number of contiguous non-aromatic carbon atoms appended to each of these $sp^2$ carbons not including any carbon atom of the other moiety or Markush structure for which the alkenyl moiety is a variable group. That number can vary ranging from 1 to 50, e.g., typically 1 to 30, 1 to 20, or 1 to 12, more typically, 1 to 8, 1 to 6, or 1 to 4 carbon atoms when the double bond functional group is doubly bonded to a Markush structure (e.g. =CH$_2$), or can vary ranging from 2 to 50, typically 2 to 30, 2 to 20, or 2 to 12, more typically 2 to 8, 2 to 6, or 2 to 4 carbon atoms, when the double bond functional group is singly bonded to the Markush structure (e.g., —CH=CH$_2$). For example, C$_2$-C$_5$ alkenyl or C$_2$-C$_8$ alkenyl means an alkenyl moiety containing 2, 3, 4, 5, 6, 7, or 8 carbon atoms in which at least two are sp$^2$ carbon atoms in conjugation with each other with one of these carbon atoms being monovalent, and C$_2$-C$_6$ alkenyl or C$_2$-C$_6$ alkenyl means an alkenyl moiety containing 2, 3, 4, 5, or 6 carbon atoms in which at least two are sp$^2$ carbons that are in conjugation with each other with one of these carbon atoms being monovalent. In some aspects, an alkenyl substituent or group is a C$_2$-C$_6$ or C$_2$-C$_4$ alkenyl moiety having two sp$^2$ carbons that are in conjugation with each other with one of these carbon atoms being monovalent, and in other aspects that alkenyl moiety is unsubstituted. When the number of carbon atoms is not indicated, an alkenyl moiety, group or substituent has from 2 to 8 carbon atoms.

"Alkenylene" as used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different sp$^2$ carbon atoms of an alkene functional group in a parent alkene. In some aspects an alkenylene moiety is that of an alkenyl radical as described herein in which a hydrogen atom has been removed from the same or different sp$^2$ carbon atom of a double bond functional group of the alkenyl radical, or from a sp$^2$ carbon from a different double bonded moiety to provide a diradical. Typically, alkenylene moieties encompass diradicals containing the structure of —C=C— or —C=C—X$^1$—C=C— wherein X$^1$ is absent or is an optionally substituted saturated alkylene as defined herein, which is typically a C$_1$-C$_6$ alkylene, which is more typically unsubstituted. The number of carbon atoms in an alkenylene moiety is defined by the number of sp$^2$ carbon atoms of its alkene functional group(s) that defines it as an alkenylene moiety and the total number of contiguous non-aromatic carbon atoms appended to each of its sp$^2$ carbons not including any carbon atoms of the other moiety or Markush structure in which the alkenyl moiety is a present as a variable group. That number can vary and unless otherwise specified ranges from 2 to 50, typically 2 to 30, 2 to 20, or 2 to 12, more typically 2 to 8, 2 to 6, or 2 to 4. For example, C$_2$-C$_5$ alkenylene or C$_2$-C$_8$ alkenylene means an alkenylene moiety containing 2, 3, 4, 5, 6, 7, or 8 carbon atoms in which at least two are sp$^2$ carbons in conjugation with each other and C$_2$-C$_6$ alkenylene or C$_2$-C$_6$ alkenylene means an alkenyl moiety containing 2, 3, 4, 5, or 6 carbon atoms in which at least two are sp$^2$ carbons that are in conjugation with each other. Typically, an alkenylene substituent is a C$_2$-C$_6$ or C$_2$-C$_4$ alkenylene having two sp$^2$ carbons that are in conjugation with each other, which in some aspects is unsubstituted. When the number of carbon atoms is not indicated, an alkenylene moiety, group or substituent has from 2 to 8 carbon atoms.

"Alkynyl" as the terms are used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, typically 1, 2, or 3 of such functional groups, more typically one such functional group, and in some aspects may be substituted (i.e., is optionally substituted) with an aryl moiety such as phenyl, or by an alkenyl moeity or linked normal, secondary, tertiary or cyclic carbon atoms, i.e., linear, branched, cyclic or any combination thereof unless the alkynyl substituent, moiety or group is —C≡CH). An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

An alkynyl moiety, group or substituent contains at least two sp carbon atom in which the carbon atoms are conjugation to each other and in which one of the sp carbon atoms is singly bonded, to another organic moiety or Markush structure to which it is associated. When alkynyl is used as a Markush group (i.e., is a substituent) the alkynyl is singly bonded to a Markush formula or another organic moiety with which it is associated through a triple-bonded carbon (i.e., a sp carbon) of one of its alkyne functional groups. In some aspects when an alkynyl moiety, group or substituent is specified, species encompasses are any of the optionally substituted alkyl or carbocyclyl, groups moieties or substituents described herein that has one or more endo triple bonds and monovalent moieties derived from removal of a hydrogen atom from a sp carbon of a parent alkyne compound. Such monovalent moieties are exemplified without limitation by —C≡CH, and —C≡C—CH$_3$, and —C≡C-Ph.

The number of carbon atoms in an alkenyl substituent is defined by the number of sp$^2$ carbon atoms of the alkene functional group that defines it as an alkenyl substituent and the total number of contiguous non-aromatic carbon atoms appended to each of these sp$^2$ carbons not including any carbon atom of the other moiety or Markush structure for which the alkenyl moiety is a variable group. That number can vary ranging from 2 to 50, typically 2 to 30, 2 to 20, or 2 to 12, more typically 2 to 8, 2 to 6, or 2 to 4 carbon atoms, when the triple bond functional group is singly bonded to the Markush structure (e.g., —CH—CH). For example, C$_2$-C$_5$ alkynyl or C$_2$-C$_8$ alkynyl means an alkynyl moiety containing 2, 3, 4, 5, 6, 7, or 8 carbon atoms in which at least two are sp carbon atoms in conjugation with each other with one of these carbon atoms being monovalent, and C$_2$-C$_6$ alkynyl or C$_2$-C$_6$ alkynyl means an alkynyl moiety containing 2, 3, 4, 5, or 6 carbon atoms in which at least two are sp carbons that are in conjugation with each other with one of these carbon atoms being monovalent. In some aspects, an alkynyl substituent or group is a C$_2$-C$_6$ or C$_2$-C$_4$ alkynyl moiety having two sp carbons that are in conjugation with each other with one of these carbon atoms being monovalent, and in other aspects that alkynyl moeity is unsubstituted. When the number of carbon atoms is not indicated, an alkynyl moiety, group or substituent has from 2 to 8 carbon atoms.

"Aryl" as the terms are used herein, by itself or as part of another term, unless otherwise stated or implied by context, refers to an organic moiety, substituent or group having an aromatic or fused aromatic ring system with no ring heteroatoms comprising 1, 2, 3, or 4 to 6 aromatic rings, typically 1 to 3 aromatic rings, more typically 1 or 2 aromatic rings, wherein the rings are composed of only carbon atoms that participate in a cyclically conjugated system of 4n+2 electrons (Hickel rule), typically 6, 10, or 14 electrons, some of which may additionally participate in exocyclic conjugation with a heteroatom (cross-conjugated, e.g., quinone). Aryl substituents, moieties or groups are typically formed by six, eight, ten, or more aromatic carbon atoms up to 24 to include $C_6$-$C_{24}$ aryl. Aryl substituents, moieties or groups are optionally substituted and in some aspects are unsubstituted or are substituted with 1 or 2 independently selected substituents as defined herein for optional substituents. Exemplary aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Arylene," or "heteroarylene" as used herein, by itself or as part of another term, unless otherwise stated or implied by context, is an aromatic or heteroaromatic diradical moiety that forms two covalent bonds (i.e., it is divalent) within another moiety, which can be in the ortho, meta, or para configurations. Arylene and heteroarylenes include divalent species by removal of a hydrogen atom from a parent aryl or heteroaryl moiety, group or substituent as defined herein. Heteroarylene further include those in which heteroatom(s) replaces one or more but not all of the aromatic carbon atoms of a parent arylene. Exemplary arylenes are, but not limited to, phenyl-1,2-ene, phenyl-1,3-ene, and phenyl-1,4-ene as shown in the following structures:

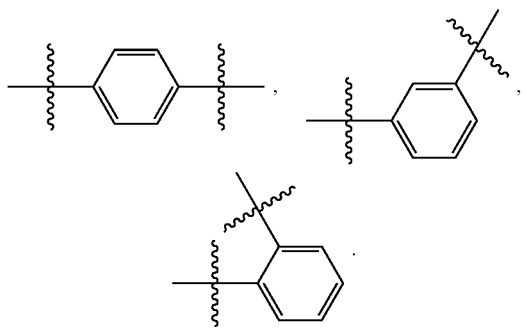

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically an arylalkyl is a ($C_6$-$C_{24}$ aryl)-$C_1$-$C_{12}$ alkyl moeity, group or substituent, and heteroarylalkyl is a ($C_5$-$C_{24}$ heteroaryl)-$C_1$-$C_{12}$ alkyl moeity, group or substituent. When (hetero)arylalkyl is used as a Markush group (i.e., a substituent) the alkyl moiety of the (hetero)arylalkyl is attached to a Markush formula with which it is associated through a sp$^3$ carbon of its alkyl moiety. In some aspects an arylalkyl is a ($C_6$-$C_{10}$ aryl)-$C_1$-$C_{12}$ alkyl, more typically a ($C_6$-$C_{10}$ aryl)-$C_1$-$C_6$ exemplified without limitation, by $C_6H_5$—$CH_2$—, $C_6H_5$—$CH(CH_3)CH_2$— and $C_6H_5$—$CH_2$—$CH(CH_2CH_2CH_3)$—.

"Alkylaryl" or "alkylheteroaryl," as the terms are used herein, by itself or as part of another term, unless otherwise stated or implied by context, refers to an alkyl moiety bonded to an aryl or heteroaryl moiety, i.e., -(hetero)arylalkyl, where (hetero)aryl and alkyl groups are as described above. Typically, an alkylaryl is a ($C_1$-$C_{12}$ alkyl)-$C_6$-$C_{24}$ aryl- moeity, group or substituent, and alkylheteroaryl is a ($C_1$-$C_{12}$ alkyl)-$C_5$-$C_{24}$ heteroaryl- moeity, group or substituent. When alkyl(hetero)aryl is used as a Markush group (i.e., a substituent) the (hetero)aryl moiety of the alkyl(hetero)aryl is attached to a Markush formula with which it is associated through an aromatic carbon atom or heteroatom of its aryl or heteroaryl moiety. In some aspects, an alkylaryl is a ($C_1$-$C_{12}$ alkyl)-$C_6$-$C_{10}$ aryl- or a ($C_1$-$C_6$ alkyl)-$C_6$-$C_{10}$ aryl-exemplified without limitation, for example, by —$C_6H_4$—$CH_3$ or —$C_6H_4$—$CH_2CH(CH_3)_2$.

"Heterocyclyl," as the term is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms, optionally substituted where permitted, including without limitation N/NH, O, S, Se, B, Si, and P, wherein two or more heteroatoms may be adjacent to each other or separated by one or more carbon atoms within the same ring system, typically by 1 to 3 atoms. Those heteroatoms typically are N/NH, O, and S. A heterocyclyl typically contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of N/NH, O, and S, with the proviso that any one ring does not contain two adjacent O or S atoms. Exemplary heterocyclyls and heteroaryls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., a substituent), a saturated or partially unsaturated heterocyclic ring of the heterocyclyl is attached to a Markush structure or other moiety with which it is associated through a carbon atom or a heteroatom of that heterocyclic ring, where such attachment does not result in an unstable or disallowed formal oxidation state of that carbon or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

Typically, a heterocyclyl is a $C_3$-$C_{20}$ carbocyclyl wherein 1, 2 or 3 carbons of its cycloalkyl ring system is replaced along with its attached hydrogens with a heteroatom selected from the group consisting of optionally substituted N/NH, O, and S and thus is a $C_3$-$C_{20}$ heterocyclyl, more typically a $C_3$-$C_{12}$ heterocyclyl, or a $C_5$-$C_{12}$, $C_3$-$C_6$, or $C_5$-$C_6$ heterocyclyl in which the subscript indicates the total number of skeletal atoms (inclusive of its carbon atoms and heteroatoms) of the heterocyclic ring system of the heterocyclyl. In some aspects a heterocyclyl contains 0 to 2 N atoms, 0 to 2 O atoms, or 0 to 1 S atoms or some combination thereof provided at least one of said heteroatoms is present in the cyclic ring system, which may be substituted at a carbon atom with an oxo (=O) moiety, as in pyrrolidin-2-one, or at a heteroatom with one or two oxo moieties so as to contain an oxidized heteroatom as exemplified, but not limited to, —N(=O), —S(=O)—, or —S(=O)$_2$—. More typically, heterocyclyl is selected from the group consisting of pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of the aryl is replaced by a heteroatom. A heteroaryl typically contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms, or 0 to 3 N atoms, typically 0 to 1 O atoms and/or 0 to 1 S atoms, provided that at least one heteroatom is present. A heteroaryl may be monocyclic, bicyclic or polycyclic. A monocyclic heteroaryl typically is a $C_5$-$C_{24}$ heteroaryl, more typically a $C_5$-$C_{12}$ or $C_5$-$C_6$ heteroaryl, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2, or 3 of the carbon atoms of the aromatic ring(s) and their attached hydrogen atoms of a parent aryl moiety are replaced by a heteroatom, optionally substituted where permitted, including N/NH, O and S, provided that not all of the skeletal atoms of any one aromatic ring system in the aryl moiety are replaced by heteroatoms and more typically are replaced by oxygen (—O—), sulfur (—S—) nitrogen (═N—) or —NR—, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a biaryl. In other aspects one 1, 2, or 3 of the carbon atoms of the aromatic ring(s) and their attached hydrogen atoms of a parent aryl moiety are replaced by nitrogen substituted with another organic moiety in a manner which retains the cyclic conjugated system. In aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

Typically, a heteroaryl is monocyclic, which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two, or one aromatic heteroatom(s), and heteroaryls that are 6-membered include heteroaryls having five, four, three, two, or one aromatic heteroatom(s). $C_5$-heteroaryls are monovalent moieties derived from removing a hydrogen atom from a skeletal aromatic carbon or an electron from a skeletal aromatic heteroatom, where permitted, from a parent aromatic heterocycle compound, which is some aspects is selected from the group consisting of pyrrole, furan, thiophene, oxazole, isoxazole, thiazole, isothiazole, imidazole, pyrazole, triazole and tetrazole. $C_6$ heteroaryls, which are 6-membered, are monovalent moieties derived from removing a hydrogen atom from an aromatic carbon or an electron from an aromatic heteroatom, where permitted, from a parent aromatic heterocycle compound, which is some aspects is selected from the group consisting of pyridine, pyridazine, pyrimidine, and triazine.

A "5-membered nitrogen-containing heteroaryl" as the terms are used herein, by itself or as part of another term, unless otherwise stated or implied by context, refers to an optionally substituted heteroaryl that is monovalent and contains a skeletal aromatic nitrogen atom in a 5-membered heteroaromatic ring and is typically a monocyclic heteroaryl or is fused to an aryl or another heteroaryl ring system to typically form a 6,5-fused ring system in which the 5-membered heteroaromatic ring is some aspects contain one or more other independently selected heteroatoms selected from the group consisting of N/NH, O, and S, optionally substituted where permitted. Exemplary 5-membered nitrogen-containing heteroaryls without limitation are thiazole, pyrrole, imidazole, oxazole, and triazole.

A "6-membered nitrogen-containing heteroaryl" as the terms are used herein, by itself or as part of another term, unless otherwise stated or implied by context, refers to a heteroaryl containing an optionally substituted 6-membered heteroaromatic ring that is monovalent and contains a skeletal aromatic nitrogen atom. In some aspects a 6-membered nitrogen-containing heteroaryl is monocyclic heteroaryl and in other aspects is fused to an aryl or another heteroaryl ring to typically form a 6,5- or 6,6-fused ring system in which the 6-membered heteroaromatic ring may contain one or more other independently selected heteroatoms selected from the group consisting of N/NH, O, and S, optionally substituted where permitted. Exemplary 6-membered nitrogen-containing heteroaryls without limitation are pyridine, pyrimidine and pyrazine.

"Heterocyclo", as the term is used herein, by itself or as part of another term, unless otherwise stated or implied by context, refers to a heterocyclyl moiety, group or substituent as defined above wherein a hydrogen atom or an electron, where permitted, from a different carbon atom or an electron from a nitrogen ring atom, if present, is removed to provide a divalent moiety.

"Heteroarylene", as the term is used herein, by itself or as part of another term, unless otherwise stated or implied by context refers to heteroaryl moiety, group or substituent as defined above wherein a hydrogen atom or an electron, where permitted, from a different aromatic carbon atom or an electron from an aromatic nitrogen ring atom if present is removed to provide a divalent moiety. A "5-membered nitrogen-containing heteroarylene contains at least one aromatic nitrogen atom in its heteroaromatic ring system and is divalent and is similarly related in structure to a 5-membered nitrogen-containing heteroaryl as described above. Likewise, a "6-membered nitrogen-containing heteroarylene is divalent and is similarly related in structure to a 6-membered nitrogen heteroaryl as described above.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation and consisting of 1 to 12 carbon atom and 1 to 6 heteroatoms, typically 1 to 5 heteroatoms, more typically one or two heteroatoms, selected from the group consisting of O, N, Si and S, optionally substituted where permitted, and includes each nitrogen and sulfur atom independently optionally oxidized to an N-oxide, a sulfoxide or sulfone, or wherein one of the nitrogen atoms is optionally quaternized. The heteroatom(s) O, N, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and consists of 1 to 6 carbon atoms and 1 to 2 heteroatoms, and in other aspects that heteroalkyl is unsubstituted. Non-limiting examples are —$CH_2$—$CH_2$—O—$CH_3$, —$CH_2$—$CH_2$—NH—$CH_3$, —$CH_2$—

$CH_2-N(CH_3)-CH_3$, $-CH_2-S-CH_2-CH_3$, $-CH_2-CH_2-S(O)-CH_3$, $-NH-CH_2-CH_2-NH-C(O)-CH_2-CH_3$, $-CH_2-CH_2-S(O)_2-CH_3$, $-CH=CH-O-CH_3$, $-Si(CH_3)_3$, $-CH_2-CH=N-O-CH_3$, and $-CH=CH-N(CH_3)-CH_3$. Up to two heteroatoms may be consecutive, as exemplified by $-CH_2-NH-OCH_3$ and $-CH_2-O-Si(CH_3)_3$. A heteroalkyl is typically denoted by the number of its contiguous heteroatom(s) and non-aromatic carbon atoms of its alkyl moeity unless indicated otherwise or by context. Thus, $-CH_2-CH_2-O-CH_3$ and $-CH_2-CH_2-S(O)-CH_3$ are both $C_4$-heteroalkyls and $-CH_2-CH=N-O-CH_3$, and $-CH=CH-N(CH_3)-CH_3$ are both $C_5$ heteroalkyls.

"Heteroalkylene" as used herein by itself or in combination with another term, unless otherwise stated or implied by context, means a divalent group derived from heteroalkyl (as discussed above), by removal of a hydrogen atom or an heteroatom electron form a parent heteroalkyl to provide a divalent moeity exemplified by, but not limited to $-CH_2-CH_2-S-CH_2-CH_2-$ and $-CH_2-S-CH_2-CH_2-NH-CH_2-$. For a heteroalkylene, heteroatom(s) thereof may be interior to or may occupy either or both termini of its optionally substituted alkylene chain.

"Aminoalkyl" as used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two independent selected optional substituted $C_1$-$C_{12}$ alkyl moieties, respectively, as described above. In some aspects the optionally substituted alkyl is a $C_1$-$C_8$ alkyl or $C_1$-$C_6$ alkyl and in other aspects that alkyl is unsubstituted. In still other aspects, the basic nitrogen together with its substituents defines a $C_3$-$C_8$ heterocyclyl containing the basic nitrogen as a skeletal atom, typically in the form of a nitrogen-containing $C_3$-$C_6$ or $C_5$-$C_6$ heterocyclyl. When aminoalkyl is used as a variable group to a Markush structure, the alkylene moiety of the aminoalkyl is attached to a Markush formula with which it is associated through a $sp^3$ carbon of that moiety, which in some aspects is the other radical terminus of the aforementioned alkylene. An aminoalkyl is typically denoted by the number of contiguous carbon atoms of its alkylene moiety. Thus, a $C_1$ aminoalkyl is exemplified without limitation by $-CH_2NH_2$, $-CH_2NHCH_3$ and $-CH_2N(CH_3)_2$ and a $C_2$ amino alkyl is exemplified without limitation by $-CH_2CH_2NH_2$, $-CH_2CH_2NHCH_3$ and $-CH_2CH_2N(CH_3)_2$.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects an alkene functional group replaces two contiguous $sp^3$ carbon atoms of an alkyl substituent, provided that the radical carbon of the alkyl moiety is not replaced, so that the optionally substituted alkyl becomes an unsaturated alkyl substituent.

Optional substituent replacing hydrogen(s) in any one of the foregoing substituents, moieties, or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses $-NH_2$ and mono-, di-, and tri-substituted amino groups, and the protected derivatives thereof, or is selected from the group consisting of $-X$, $-OR'$, $-SR'$, $-NH_2$, $-N(R')(R^{op})$, $-N(R^{op})_3$, $=NR$, $-CX_3$, $-CN$, $-NO_2$, $-NR'C(=O)H$, $-NR'C(=O)R^{op}$, $-NR'C(=O)R^{op}$, $-C(=O)R'$, $-C(=O)NH_2$, $-C(=O)N(R')R^{op}$, $-S(=O)R^{op}$, $-S(=O)_2NH_2$, $-S(=O)_2N(R')R^{op}$, $-S(=O)_2NH_2$, $-S(=O)_2N(R')R^{op}$, $-S(=O)_2OR'$, $-S(=O)R^{op}$, $-OP(=O)(OR')(OR^{op})$, $-OP(OH)_3$, $-P(=O)(OR')(OR^{op})$, $-PO_3H_2$, $-C(=O)R'$, $-C(=S)R^{op}$, $-CO_2R$, $-C(=S)OR^{op}$, $-C(=O)SR$, $-C(=S)SR$, $-C(=S)NH_2$, $-C(=S)N(R')(R^{op})_2$, $-C(=NR)NH_2$, $-C(=NR)N(R')R^{op}$, and salts thereof, wherein each X is independently selected from the group consisting of halogens: $-F$, $-Cl$, $-Br$, and $-I$; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which they are attached defines a $C_3$-$C_{24}$ heterocyclyl; and R' is hydrogen or $R^{op}$, wherein $R^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

Typically, optional substituents that are present are selected from the group consisting of $-X$, $-OH$, $-OR^{op}$, $-SH$, $-SR^{op}$, $-NH_2$, $-NH(R^{op})$, $-NR'(R^{op})_2$, $-N(R^{op})_3$, $=NH$, $=NR^{op}$, $-CX_3$, $-CN$, $-NO_2$, $-NR'C(=O)H$, $NR'C(=O)R^{op}$, $-CO_2H$, $-C(=O)H$, $-C(=O)R^{op}$, $-C(=O)NH_2$, $-C(=O)NR^{op}$, $-S(=O)_2R^{op}$, $-S(=O)_2NH_2$, $-S(=O)_2N(R')R^{op}$, $-S(=O)_2NH_2$, $-S(=O)_2N(R')(R^{op})$, $-S(=O)_2OR'$, $-S(=O)R^{op}$, $-C(=S)R^{op}$, $-C(=S)NH_2$, $-C(=S)N(R')R^{op}$, $-C(=NR')N(R^{op})_2$, and salts thereof, wherein each X is independently selected from the group consisting of $-F$ and $-Cl$, $R^{op}$ is typically selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group typically consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$.

More typically, optional substituents that are present are selected from the group consisting of $-X$, $-R^{op}$, $-OH$, $-OR^{op}$, $-NH_2$, $-NH(R^{op})$, $-N(R^{op})_2$, $-N(R^{op})_3$, $-CX_3$, $-NO_2$, $-NHC(=O)H$, $-NHC(=O)R^{op}$, $-C(=O)NH_2$, $-C(=O)NHR^{op}$, $-C(=O)N(R^{op})_2$, $-CO_2H$, $-CO_2R^{op}$, $-C(=O)H$, $-C(=O)R^{op}$, $-C(=O)NH_2$, $-C(=O)NH(R^{op})$, $-C(=O)N(R^{op})_2$, $-C(=NR')NH_2$, $-C(=NR')NH(R^{op})$, $-C(=NR')N(R^{op})_2$, a protecting group and salts thereof, wherein each X is $-F$; $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

In some aspects, an optional alkyl substituent that is present is selected from the group consisting $-NH_2$, $-NH(R^{op})$, $-N(R^{op})_2$, $-N(R^{op})_3$, $-C(=NR)NH_2$, $-C(=NR')NH(R^{op})$, and $-C(=NR')N(R^{op})_2$, wherein R' and $R^{op}$ is as defined for any one of the R' or $R^{op}$ groups above. In some of those aspects, the R' and/or $R^{op}$ substituents together with the nitrogen atom to which they are attached provide for the basic functional group of a Basic Unit (BU), as when $R^{op}$ is independently selected from the group consisting of hydrogen and $C_1$-$C_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted.

"Optionally substituted heteroatom" as used herein, unless otherwise stated or implied by context, refers to a heteroatom within a functional group or other organic moiety in which the heteroatom is not further substituted or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two =O substituents or refers to an —NH— moiety within a functional group or other organic moiety in which its hydrogen atom is optionally replaced by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is replaced by a =O moiety to form an N-oxide.

Therefore, in some aspects, an optional substituent of a nitrogen atom that is present is selected from the group consisting of optionally substituted $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, ($C_6$-$C_{24}$ aryl)-$C_1$-$C_{20}$ alkyl-, and ($C_5$-$C_{24}$ heteroaryl)-$C_1$-$C_{20}$ alkyl-, as those terms are defined herein. In other aspects optional substituents of a nitrogen atom that is present is selected from the group consisting of optionally substituted $C_1$-$C_{12}$ alkyl, $C_2$-$C_{12}$ alkenyl, $C_2$-$C_{12}$ alkynyl, $C_6$-$C_{24}$ aryl, $C_5$-$C_{24}$ heteroaryl, ($C_6$-$C_{24}$ aryl)-$C_1$-$C_{12}$ alkyl-, and ($C_5$-$C_{24}$ heteroaryl)-$C_1$-$C_{12}$ alkyl-, from the group consisting of $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, ($C_6$-$C_{10}$ aryl)-$C_1$-$C_8$ alkyl-, and ($C_5$-$C_{10}$ heteroaryl)-$C_1$-$C_8$ alkyl-, or from the group consisting of $C_1$-$C_6$ alkyl, $C_2$-$C_6$ alkenyl, $C_2$-$C_6$ alkynyl, $C_6$-$C_{10}$ aryl, $C_5$-$C_{10}$ heteroaryl, ($C_6$-$C_{10}$ aryl)-$C_1$-$C_6$ alkyl-, and ($C_5$-$C_{10}$ heteroaryl)-$C_1$-$C_6$ alkyl-.

In some aspects, an optional substituent that is present replaces a carbon atom in the acyclic carbon chain of an alkyl or alkylene moeity, group or substituent to provide for a $C_3$-$C_{12}$ heteroalkyl or $C_3$-$C_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, in which —NH— is an optionally substituted heteroatom by replacement of its hydrogen atom by an independently selected substituent from a group previously described for an —NH-optional substituent.

"O-linked moiety", "O-linked substituent" and like terms as used herein, unless otherwise stated or implied by context, refers to a moeity, group or substituent that is attached to a Markush structure or other organic moiety with which it is associated directly through an oxygen atom of the O-linked moiety or substituent. A monovalent 0-linked moeity or substituent is typically —OH, —OC(=O)$R^b$ (acyloxy), wherein $R^b$ is —H, optionally substituted $C_1$-$C_{20}$ alkyl, optionally substituted $C_3$-$C_{20}$ cycloalkyl, optionally substituted $C_3$-$C_{20}$ alkenyl, optionally substituted $C_2$-$C_{20}$ alkynyl, optionally substituted $C_6$-$C_{24}$ aryl, optionally substituted $C_5$-$C_{24}$ heteroaryl or optionally substituted $C_3$-$C_{24}$ heterocyclyl, or $R^b$ is optionally substituted $C_1$-$C_{12}$ alkyl, optionally substituted $C_3$-$C_{12}$ cycloalkyl, optionally substituted $C_3$-$C_{12}$ alkenyl or optionally substituted $C_2$-$C_{12}$ alkynyl, and wherein an monovalent O-linked moeity further encompasses ether groups which are $C_1$-$C_{12}$ alkyloxy (i.e., $C_1$-$C_{12}$ aliphatic ether), optionally substituted, wherein the alkyl moiety is saturated or unsaturated.

In other aspects, a monovalent O-linked moeity, group or substituent is selected from the group consisting of optionally substituted phenoxy, optionally substituted $C_1$-$C_8$ alkyloxy (i.e., $C_1$-$C_8$ aliphatic ether) and —OC(=O)$R^b$, wherein $R^b$ is optionally substituted $C_1$-$C_8$ alkyl, which is typically saturated or is an unsaturated $C_3$-$C_8$ alkyl.

In other aspects, a O-linked substituent is a monovalent moiety selected from the group consisting of —OH, saturated $C_1$-$C_6$ alkyl ether, unsaturated $C_3$-$C_6$ alkyl ether, phenoxy and —OC(=O)$R^b$, wherein $R^b$ is typically $C_1$-$C_6$ saturated alkyl, $C_3$-$C_6$ unsaturated alkyl, $C_3$-$C_6$ cycloalkyl, $C_2$-$C_6$ alkenyl, or phenyl, optionally substituted, or is selected from that group excluding —OH and/or wherein saturated $C_1$-$C_6$ alkyl ether and phenoxy are unsubstituted and $R^b$ is saturated $C_1$-$C_6$ alkyl or unsaturated $C_3$-$C_6$ alkyl.

Other exemplary O-linked substituents are provided by definitions for carbamate, ether and carbonate as disclosed herein in which the monovalent oxygen atom of the carbamate, ether and carbonate functional group is bonded to the Markush structure or other organic moiety with which it is associated.

In other aspects, an O-linked moeity to carbon is divalent and encompasses =O and —X—(CH$_2$)$_n$—Y—, wherein X and Y independently are S and O and subscript n is 2 or 3, to form a spiro ring system with the carbon to which X and Y are both attached.

"Halogen" as used herein, unless otherwise stated or implied by context, refers to fluorine, chlorine, bromine, or iodine and is typically —F or —Cl.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein least one of R$^{PR}$ is a nitrogen atom protecting group or both R$^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic basic group is an acid-labile carbamate protecting group such as t-butyloxycarbonyl (BOC).

"Ester" as used herein, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to some other organic moiety. Typically, esters in addition to the ester functional group comprise or consist of an organic moiety containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but usually O, S and N), typically 0 to 2 heteroatoms where the organic moieties are bonded through the —C(=O)—O— structure (i.e., through the ester functional group).

When an ester is a substituent or variable group of a Markush structure or other organic moeity with which it is associated, that substituent is bonded to the structure or other organic moiety through the monovalent oxygen atom of the ester functional group so that it is an monovalent O-linked substituent, which sometimes referred to as an acyloxy. In such instances, the organic moiety attached to the carbonyl carbon of the ester functional group typically is a $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, $C_3$-$C_{24}$ heterocyclyl or is a substituted derivative of any one of these, e.g., having 1, 2, 3 or 4 substituent, more typically is $C_1$-$C_{12}$ alkyl, $C_2$-$C_{12}$ alkenyl, $C_2$-$C_{12}$ alkynyl, $C_6$-$C_{10}$ aryl, $C_5$-$C_{10}$ heteroaryl, $C_3$-$C_{10}$ heterocyclyl or a substituted derivative of one any of these, e.g., having 1, 2, or 3 substituents or is $C_1$-$C_8$ alkyl, $C_2$-$C_8$ alkenyl, $C_2$-$C_8$ alkynyl, or phenyl or a substituted derivative of any one of these, e.g., having 1 or 2 substituents, wherein each independently selected substituent is as defined herein for optional alkyl substituents, or is unsubstituted $C_1$-$C_6$ alkyl or unsubstituted $C_2$-$C_6$ alkenyl.

Exemplary esters, by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)$R^b$ in which $R^b$ is as defined for acyloxy O-linked substituents and is typically selected from the group consisting of methyl, ethyl, propyl, iso-propyl, 3-methyl-prop-1-yl, 3,3-dimethyl-prop-1-yl, prop-2-ene-1-yl, and vinyl.

"Ether" as used herein, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O-moieties are immediately adjacent (i.e., directly attached) to each other. Typically, an ether contains the formula of —O-organic moiety wherein organic moiety is as described for an organic moiety bonded to an ester functional group or is as described herein for an optionally substituted alkyl group. When ether is recited as a substituent or variable group of a Markush structure or other organic moeity with which it is associated, the oxygen of the ether functional group is attached to a Markush formula with which it is associated and is sometimes designated as an "alkoxy" group, which is an exemplary O-linked substituent. In some aspects an ether O-linked substituent is a $C_1$-$C_{20}$ alkoxy or a $C_1$-$C_{12}$ alkoxy, optionally substituted with 1, 2, 3 or 4 substituents, typically 1, 2 or 3, and in other aspects is a $C_1$-$C_8$ alkoxy or $C_1$-$C_6$ alkoxy, optionally substituted with 1 or 2 substituents, wherein each independently selected substituent is as defined herein for optional alkyl substituents, and in still other aspects an ether O-linked substituent is an unsubstituted, saturated or unsaturated $C_1$-$C_4$ alkoxy such as, by way of example and not limitation, methoxy, ethoxy, propoxy, iso-propoxy, butoxy and allyloxy (i.e., —OCH$_2$CH=CH$_2$).

"Amide" as used herein, unless otherwise stated or implied by context, refers to a moiety having an optionally substituted functional group having the structure of R—C(=O)N($R^c$)— or —C(=O)N($R^c$)$_2$ to which no other heteroatom is directly attached to the carbonyl carbon and wherein each $R^c$ is independently hydrogen, a protecting group or an organic moiety and R is hydrogen or an organic moiety wherein organic moiety, independently selected, is as described herein for an organic moiety bonded to an ester functional group or is as described herein for an optionally substituted alkyl group. When an amide is recited as a substituent or variable group of a Markush structure or other organic moeity with which it is associated, the amide nitrogen atom or carbonyl carbon atom of the amide functional group is bonded to that structure or other organic moeity. Amides are typically prepared by condensing an acid halide, such an acid chloride, with a molecule containing a primary or secondary amine. Alternatively, amide coupling reactions well-known in the art of peptide synthesis, which oftentimes proceed through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a functional group having the structure —O—C(=O)—O— which defines a carbonate functional group. Typically, carbonate groups as used herein are comprised of an organic moiety bonded to the —O—C(=O)—O— structure, wherein the organic moiety is as described herein for an organic moiety bonded to an ester functional group, e.g., organic moiety-O—C(=O)—O—. When carbonate is recited as a substituent or variable group of a Markush structure or other organic moeity with which it is associated, one of the monovalent oxygen atoms of the carbonate functional group is attached to that structure or organic moeity and the other is bonded to a carbon atom of another organic moiety as previously described for an organic moiety bonded to an ester functional group or is as described herein for an optionally substituted alkyl group. In such instances, carbonate is an exemplary O-linked substituent.

"Carbamate" as used here means a substituent, moiety or group that contains a optionally substituted carbamate functional group structure represented by —O—C(=O)N(R$^c$)— or —O—C(=O)N(R$^c$)$_2$, or —O—C(=O)NH(optionally substituted alkyl) or —O—C(=O)N(optionally substituted alkyl)$_2$ in which the optionally substituted alkyl(s) are exemplary carbamate functional group substituents, wherein R$^c$ and optionally substituted alkyl are independently selected wherein independently selected R$^c$, is hydrogen, a protecting group or an organic moiety, wherein the organic moiety is as described herein for an organic moiety bonded to an ester functional group or is as described herein for an optionally substituted alkyl group. Typically, carbamate groups are additionally comprised of an organic moiety, independently selected from R$^c$, wherein the organic moiety is as described herein for an organic moiety bonded to an ester functional group, bonded through the —O—C(=O)—N(R$^c$)— structure, wherein the resulting structure has the formula of organic moiety-O—C(=O)—N(R$^c$)— or —O—C(=O)—N(R$^c$)-organic moiety. When carbamate is recited as a substituent or variable group of a Markush structure or other organic moeity with which it is associated, the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents.

"Pharmaceutically acceptable salt" as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions. Typically, a quaternized tubulysin Drug Unit is in pharmaceutically acceptable salt form.

Typically, a pharmaceutically acceptable salt is selected from those described in P. H. Stahl and C. G. Wermuth, editors, *Handbook of Pharmaceutical Salts: Properties, Selection and Use*, Weinheim/Zürich: Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

"PEG Unit" as used herein refers to a group comprising a polyethylene glycol moiety (PEG) having a repetition of ethylene glycol subunits having the formula of

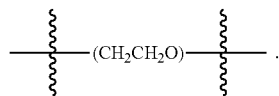

A PEG Unit can comprise at least 2 subunits, at least 3 subunits, at least 4 subunits, at least 5 subunits, least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. Some PEG Units comprise up to 72 subunit.

"PEG Capping Unit" as used herein is an organic moiety or functional group that terminates the free and untethered end of a PEG Unit and is other than hydrogen, and in some aspects is methoxy, ethoxy, or other $C_1$-$C_6$ ether, or is —$CH_2$—$CO_2H$, or other suitable moeity. The ether, —$CH_2$—$CO_2H$, —$CH_2CH_2CO_2H$, or other suitable organic moiety thus acts as a cap for the terminal PEG subunit of the PEG Unit.

PEGs include polydisperse PEGs, monodisperse PEGs and discrete PEGs. Polydisperse PEGs are a heterogeneous mixture of sizes and molecular weights whereas monodisperse PEGs are typically purified from heterogeneous mixtures and are therefore provide a single chain length and molecular weight. Discrete PEGs are compounds that are synthesized in step-wise fashion and not via a polymerization process. Discrete PEGs provide a single molecule with defined and specified chain length.

"Antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., 2001, *Immunol. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. An antibody can be, for example, human, humanized or chimeric. An antibody or antibody fragment thereof, is an exemplary targeting agent that corresponds to or is incorporated into an LDC of the present invention as an antibody Ligand Unit.

In some aspects an antibody selectively and specifically binds to an epitope on hyper-proliferating cells or hyper-stimulated mammalian cells (i.e., abnormal cells), wherein the epitope is preferentially displayed by or is more characteristic the abnormal cells in contrast to normal cells, or is preferentially displayed by or is more characteristic of normal cells in the vicinity of abnormal cells in contrast to normal cells not localized to the abnormal cells. In those aspects the mammalian cells are typically human cells. Other aspects of antibodies incorporated into Ligand Units are described by embodiments for Ligand-Drug Conjugates "Monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

"Antigen" is an entity that is capable of selective binding to an unconjugated antibody or a fragment thereof or to an ADC comprising an antibody Ligand Unit corresponding to or incorporating that antibody or fragment thereof. In some aspects, the antigen is an extracellularly-accessible cell-surface protein, glycoprotein, or carbohydrate preferentially displayed by abnormal or other unwanted cells in comparison to normal cells. In some instances the unwanted cells having the antigen are hyper-proliferating cells in a mammal. In other instances, the unwanted cells having the antigen are hyper-activated immune cells in a mammal. In other aspects, the specifically bound antigen is present in the particular environment of hyper-proliferating cells or hyper-activated immune cells in a mammal in contrast to the environment typically experienced by normal cells in the absence of such abnormal cells. In still other aspects the cell-surface antigen is capable of internalization upon selective binding of an ADC compound and is associated with cells that are particular to the environment in which hyper-proliferating or hyper-stimulated immune cells are found in the absence of such abnormal cells. An antigen is an exemplary targeted moiety of an Antibody Drug Conjugate, wherein its targeting antibody Ligand Unit corresponds to or incorporates an antibody to a targeted antigen and is capable of preferentially recognizing that antigen through selective binding.

Antigens associated with cancer cells that are cell-surface accessible to an ADC include by way of example and not limitation CD19, CD70, CD30, CD33, CD48, NTB-A, $\alpha v \beta 6$, and CD123.

"Antibody-drug conjugate" or "ADC" as the term is used herein refers to a antibody residue, referred to in some aspects as an antibody Ligant Unit, covalently attached to Drug Unit through an intervening Linker Unit. Oftentimes the term refers to a collection (i.e., population or plurality) of Conjugate compounds having the same antibody Ligand Unit, Drug Unit, and Linker Unit that in some aspect have variable loading and/or distribution of the linker-drug moieties attached to each antibody (as, for example, when the number of Drug Units (D) of any two ADC compounds in a plurality of such compounds is the same but the location of their sites of attachment to the targeting moiety differ). In those instances an ADC is described by the averaged drug loading of the Conjugate compounds. The average number Drug Units per antibody Ligand Unit, or fragment thereof, in an ADC composition (i.e., an averaged number for a population of ADC conjugate compounds that in some aspects differ primarily by the number of conjugated Drug Units on the antibody Ligand Unit in each of the ADC compounds that are present in that population and/or by their location). In that context p is a number ranging from about 2 to about 24 or about 2 to about 20 and is typically about 2, about 4, or about 8. In other contexts p represents the number of Drug Units that are covalently bonded to a single antibody Ligand Unit of an ADC within a population of antibody-drug conjugate compounds in which the compounds of that population in some aspects primarily differ by the number and/or location of the conjugated Drug Units. In that context p is designated as p' and is an integer ranging from 1 to 24 or from 1 to 20, typically from 1 to 12 or 1 to 10, and more typically from 1 to 8.

The average number of Drugs Units per antibody Ligand Unit in a preparation from a conjugation reaction may be characterized by conventional means such as mass spectroscopy, ELISA assay, HIC and/or HPLC. The quantitative distribution of conjugate compounds in terms of p' may also be determined. In some instances, separation, purification, and characterization of homogeneous Ligand-Drug Conjugate compounds in which p' is a certain value from a Ligand-Drug Conjugate composition from those with other drug loadings may be achieved by means such as reverse phase HPLC or electrophoresis.

The term "therapeutically effective amount" refers to an amount of a drug effective or an antibody conjugate of the drug to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

"Treat", "treatment," and like terms, unless otherwise indicated by context, refer to therapeutic treatment and prophylactic measures to prevent relapse, wherein the object is to inhibit or slow down (lessen) an undesired physiological change or disorder, such as the development or spread of cancer or tissue damage from chronic inflammation. Typically, beneficial or desired clinical results of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival or quality of like as compared to expected survival or quality of life if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, or ameliorating one or more symptoms associated with cancer.

"Pharmaceutically acceptable salt" as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions. Typically, an Antibody Drug conjugate is in pharmaceutically acceptable salt form.

Typically, a pharmaceutically acceptable salt is selected from those described in P. H. Stahl and C. G. Wermuth, editors, *Handbook of Pharmaceutical Salts: Properties, Selection and Use*, Weinheim/Zürich: Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

EMBODIMENTS

A number of embodiments of the invention are described below followed by a more detailed discussion of the components, e.g., groups, reagents, and steps that are useful in the processes of the present invention. Any of the selected embodiments for the components of the processes can apply to each and every aspect of the invention as described herein or they may relate to a single aspect. The selected embodiments may be combined together in any combination appropriate for preparing a Drug Linker compound or Intermediate thereof.

In one group of embodiments, provided herein are methods for preparing a Drug Linker intermediate compound of Formula ID:

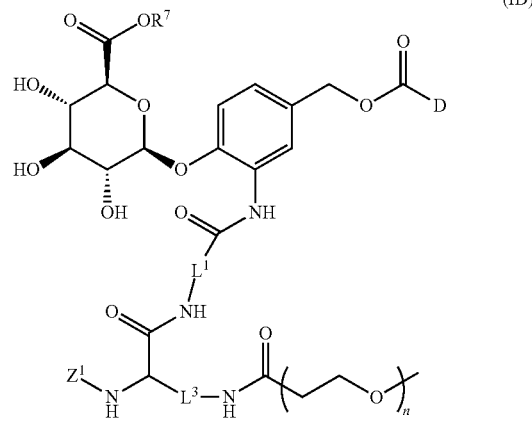

or a salt thereof, wherein
D is an auristatin Drug Unit;
$Z^1$ is a first suitable amine protecting group;
$R^7$ is $C_1$-$C_8$ alkyl or optionally substituted phenyl so that —$OR^7$ provides for an ester functional group that is a suitable carboxylic acid protecting group,
each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n ranges from 2 to 24 or is an integer ranging from 2 to 24,
the method comprising the step of:
contacting a Drug Linker intermediate compound of Formula IC with either a Grignard reagent or an alkoxy magnesium halide in a suitable alcohol-containing solvent, wherein the Formula IC Drug Linker intermediate compound has the structure of:

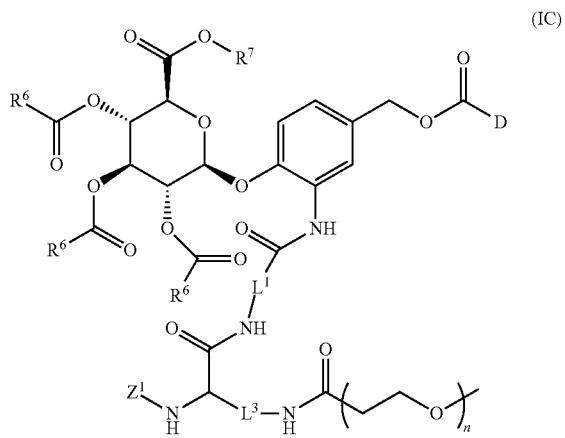

or a salt thereof, wherein
each of $R^6$ is independently $C_1$-$C_8$ alkyl or optionally substituted phenyl so that $R^6C(=O)$— provides for an ester functional group that is a suitable hydroxyl protecting group; and the remaining variable groups are as previously defined, wherein said Grignard reagent or alkoxy magnesium halide contacting selectively removes the hydroxyl protecting groups whereby the Formula ID compound or its salt is obtained.

In another group of embodiments, provided herein are methods for preparing a Drug Linker intermediate compound of Formula IE:

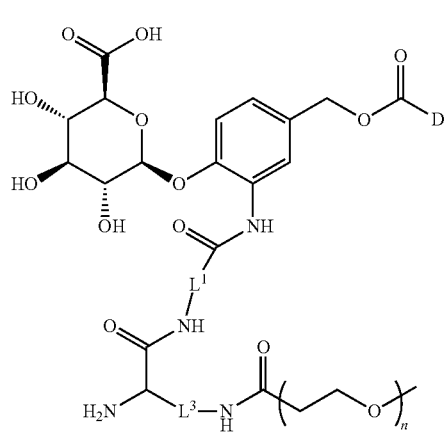

(IE)

or a salt thereof, wherein

D is an auristatin Drug Unit;

each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n ranges from 2 to 24 or is an integer ranging from 2 to 24;

the method comprising the steps of:

(c) contacting a Drug Linker intermediate compound of Formula IC with either a Grignard reagent or an alkoxy magnesium halide in a suitable an alcohol-containing solvent, wherein the Formula IC Drug Linker intermediate compound has the structure of:

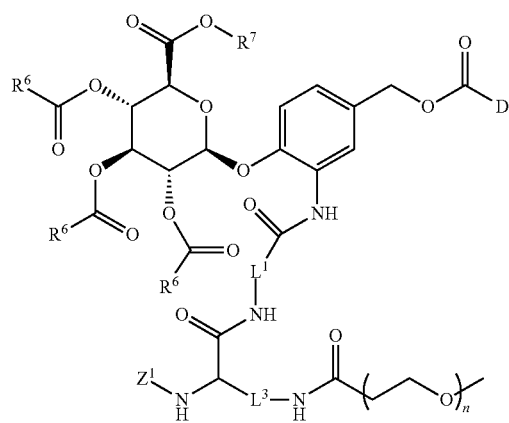

(IC)

or a salt thereof, wherein $Z^1$ is a first suitable amine protecting group; and each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined, wherein said Grignard reagent or alkoxy magnesium halide contacting selectively removes the hydroxyl protecting groups to provide a Drug Linker intermediate compound of Formula ID:

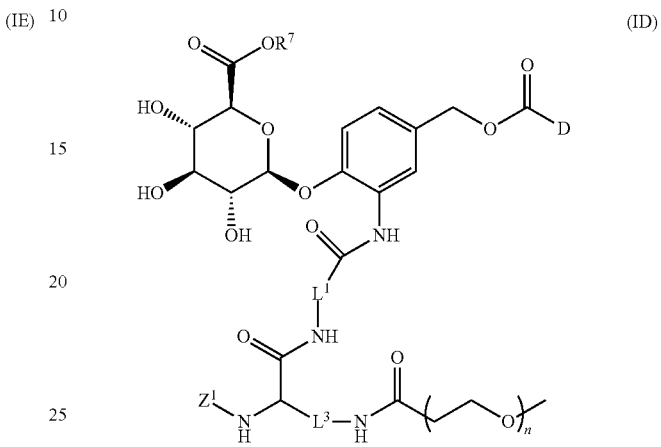

(ID)

or a salt thereof, wherein the variable groups are as previously defined; and (d) contacting the Formula ID Drug Linker intermediate compound with a first deprotecting agent, wherein said first deprotecting agent contacting removes the amine and carboxylic acid protecting groups whereby the Formula IE Drug Linker intermediate compound or its salt is obtained.

In another group of embodiments, provided herein are methods for preparing a Drug Linker intermediate compound of Formula ID:

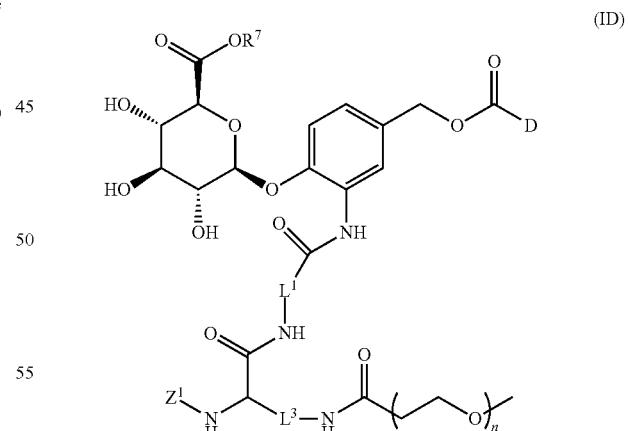

(ID)

or a salt thereof, wherein

D is an auristatin Drug Unit;

$Z^1$ is a first suitable amine protecting group;

each of $L^1$ and $L^3$ is independently a group selected from optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo;

$R^7$ is $C_1$-$C_5$ alkyl or optionally substituted phenyl so that —$OR^7$ provides for an ester functional group that is a suitable carboxylic acid protecting group; and subscript n ranges from 2 to 24 or is an integer ranging from 2 to 24, the method comprising the steps of:

(a) contacting a Drug Linker intermediate compound of Formula IA with a second deprotecting agent, wherein the Formula IA compound has the structure of:

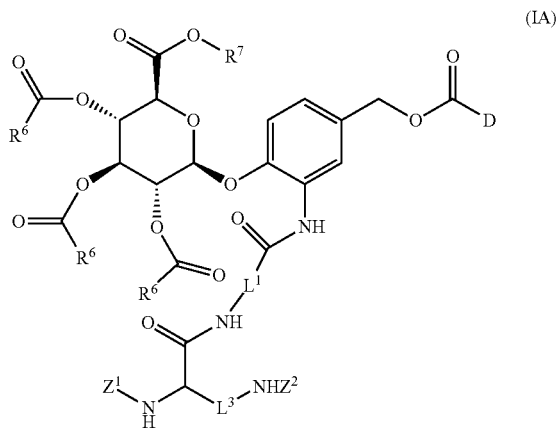

(IA)

or a salt thereof, wherein $Z^2$ is a second suitable amino protecting group;

each of $R^6$ is independently $C_1$-$C_8$ alkyl or optionally substituted phenyl so that $R^6C(=O)$— provides for an ester functional group that is a suitable hydroxyl protecting group;

wherein said second deprotecting agent contacting selectively removes the $Z^2$ amino protecting group to provide a Drug Linker intermediate compound of Formula IB:

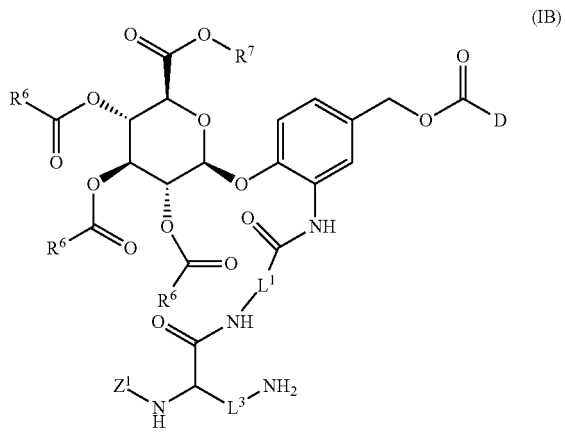

(IB)

or a salt thereof, wherein the variable groups are as previously defined;

(b) contacting the Formula IB Drug Linker intermediate compound in a suitable solvent with a compound of Formula iv:

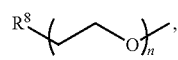

(iv)

wherein $R^8$ is an activated ester; and subscript n is a integer ranging from 2 to 24, or (b') contacting the Formula IB Drug Linker intermediate compound in a suitable solvent with a Formula iv compound in which $R^8$ is —COOH in the presence of a first activating agent; and n ranges from 2 to 24 or is an integer ranging from 2 to 24, wherein said contacting of step (b) or (b') provides a Drug Linker intermediate compound of Formula IC:

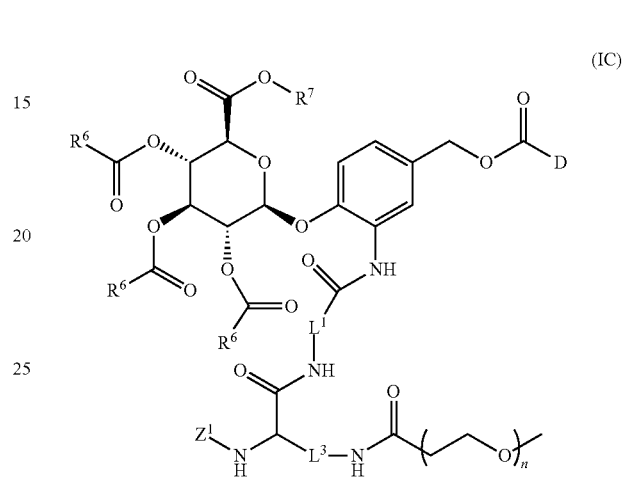

(IC)

or a salt thereof, wherein the variable groups are as previously defined; and (c) contacting the Formula IC Drug Linker intermediate compound with either a Grignard reagent or an alkoxy magnesium halide in a suitable alcohol-containing solvent, wherein said Grignard reagent or alkoxy magnesium halide contacting selectively removes the hydroxyl protecting groups to provide the Formula ID Drug Linker intermediate compound or its salt.

In another group of embodiments is provided herein are methods for preparing a Drug Linker intermediate compound of Formula IE:

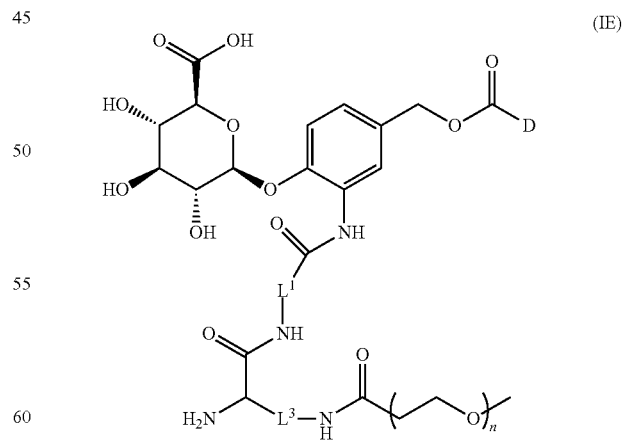

(IE)

or a salt thereof, wherein

D is an auristatin Drug Unit;

each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n ranges from 2 to 24 or is an integer ranging from 2 to 24;

the method comprising the steps of:

(a) contacting a Drug Linker intermediate compound of Formula IA with a second deprotecting agent, wherein the Formula IA Drug Linker intermediate compound has the structure of:

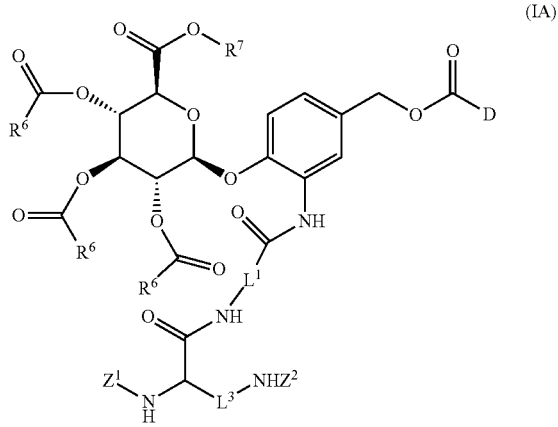

(IA)

or a salt thereof, wherein each of $R^6$ is independently $C_1$-$C_8$ alkyl or optionally substituted phenyl so that $R^6C(=O)-$ provides for an ester functional group that is a suitable hydroxyl protecting group;

each of $Z^1$ and $Z^2$ is independently a first and second suitable amino protecting group, respectively; and the remaining variable groups are as previously defined, wherein said second deprotecting agent contacting selectively removes the $Z^2$ amino protecting group to provide a Drug Linker intermediate compound of Formula IB:

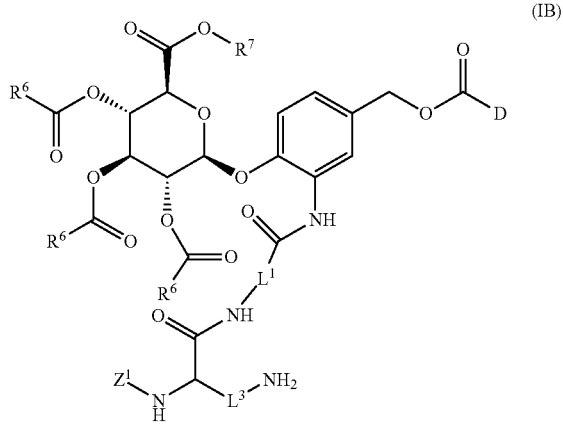

(IB)

or a salt thereof, wherein the variable groups are as previously described;

(b) contacting the Formula IB Drug Linker intermediate compound in a suitable solvent with a compound of Formula iv:

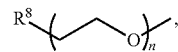

(iv)

wherein $R^8$ is an activated ester; and subscript n ranges from 2 to 24 or is an integer ranging from 2 to 24, or (b') contacting the Formula IB Drug Linker intermediate compound with a Formula iv compound in which $R^8$ is —COOH and subscript n is an integer ranging from 2 to 24 in the presence of a first activating agent in a suitable solvent; and wherein said contacting of step (b) or (b') provides a Drug Linker intermediate compound of Formula IC:

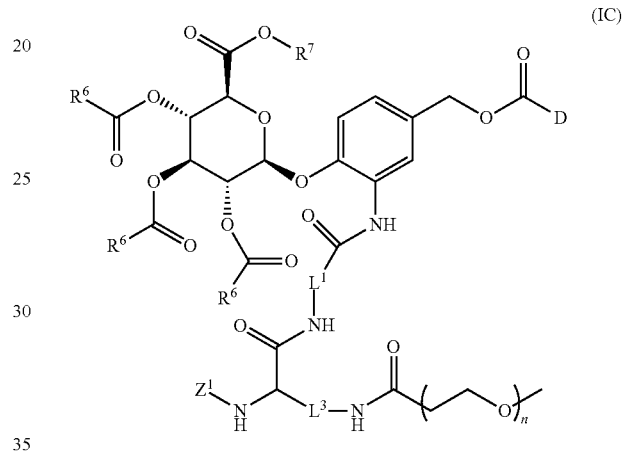

(IC)

or a salt thereof, wherein the variable groups are as previously defined;

(c) contacting the Formula IC Drug Linker intermediate compound with either a Grignard reagent or an alkoxy magnesium halide in a suitable alcohol-containing solvent, wherein said Grignard reagent or alkoxy magnesium halide contacting selectively removes the hydroxyl protecting groups to provide a Drug Linker intermediate compound of Formula ID:

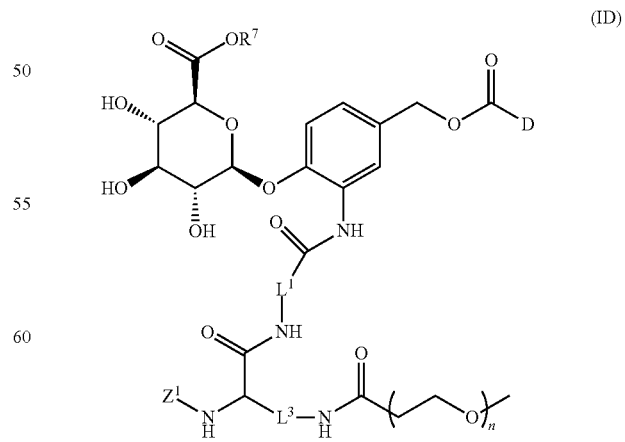

(ID)

or a salt thereof, wherein the variable groups are as previously defined; and (d) contacting the Formula ID Drug Linker intermediate compound with a first deprotection agent, wherein said first deprotection agent contacting removes the $Z^1$ amino and carboxylic acid protecting groups, whereby the Formula IE Drug Linker intermediate compound or its salt is obtained.

In another group of embodiments, provided herein are methods for preparing a Drug Linker intermediate or Drug linker compound of Formula I:

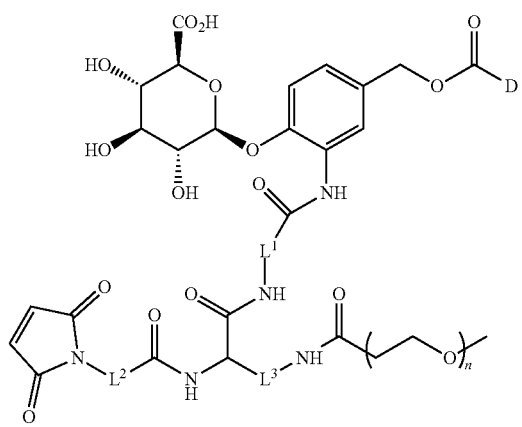

(I)

or a salt thereof, wherein

D is an auristatin Drug Unit;

each of $L^1$, $L^2$, and $L^3$ is independently a group selected from optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n ranges from 2 to 24 or is an integer ranging from 2 to 24, the method comprising the steps of:

(c) contacting a Drug Linker intermediate compound of Formula IC with either a Grignard reagent or an alkoxy magnesium halide in a suitable alcohol-containing solvent, wherein the Formula IC compound has the structure of:

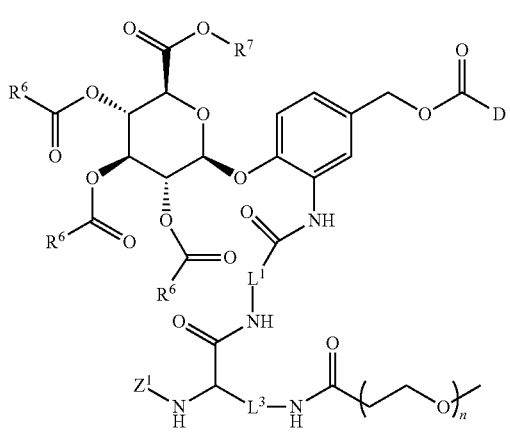

(IC)

or a salt thereof, wherein $Z^1$ is a first suitable amino protecting group; and the remaining variable groups are as previously defined, wherein said Grignard reagent or alkoxy magnesium halide contacting selectively removes the hydroxyl protecting groups to provide a Drug Linker intermediate compound of Formula ID:

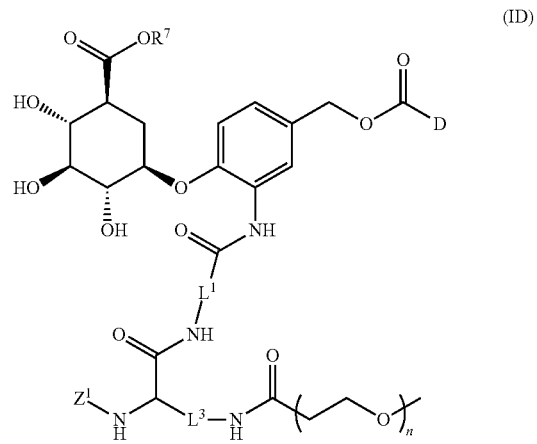

(ID)

or a salt thereof, wherein the variable groups are as previously defined;

(d) contacting the Formula ID Drug Linker intermediate compound with a first deprotecting agent, wherein said deprotecting agent contacting removes the $Z^1$ amino and carboxylic acid protecting groups to provide a Drug Linker intermediate compound of Formula IE:

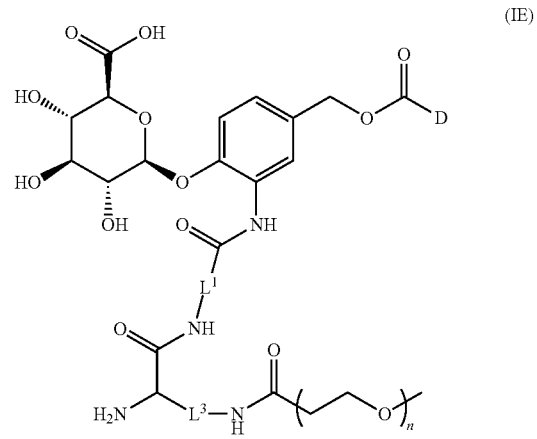

(IE)

or a salt thereof, wherein the variable groups are as previously defined;

(e) contacting the Formula IE Drug Linker intermediate compound in a suitable solvent with a compound of Formula v:

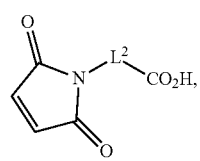

(v)

or a salt thereof, wherein $L^2$ is as previously defined, in the presence of a second activating agent, wherein said Formula v contacting provides the Formula I Drug Linker intermediate or Drug Linker compound.

In another group of embodiments, provided herein are methods for preparing a Drug Linker intermediate or Drug Linker compound of Formula I:

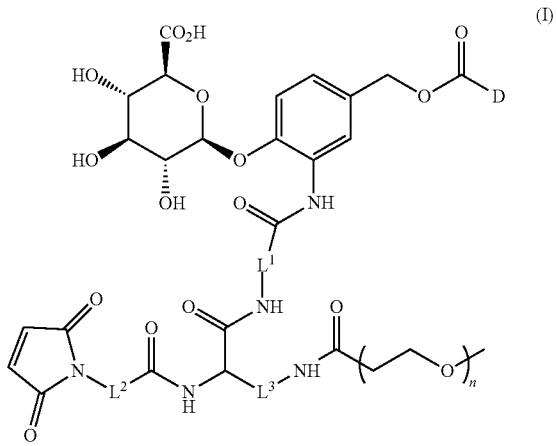

or a salt thereof, wherein

D is an auristatin Drug Unit;

each of $L^1$, $L^2$, and $L^3$ is independently a group selected from optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n ranges from 2 to 24 or is an integer ranging from 2 to 24, the method comprising the steps of:

(a) contacting a Drug Linker intermediate compound of Formula IA with a second deprotecting agent, wherein the Formula IA Drug Linker intermediate compound has the structure of:

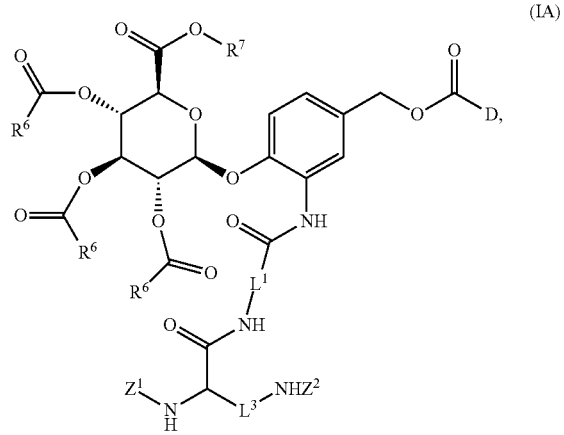

or a salt thereof, wherein each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group, each of $Z^1$ and $Z^2$ is independently a first and second suitable amino protecting group, respectively;

subscript n ranges from 2 to 24 or is an integer ranging from 2 to 24; and the remaining variable groups are as previously defined, wherein said second deprotecting agent contacting selectively removes the $Z^2$ amino protecting group to provide a Drug Linker intermediate compound of Formula IB:

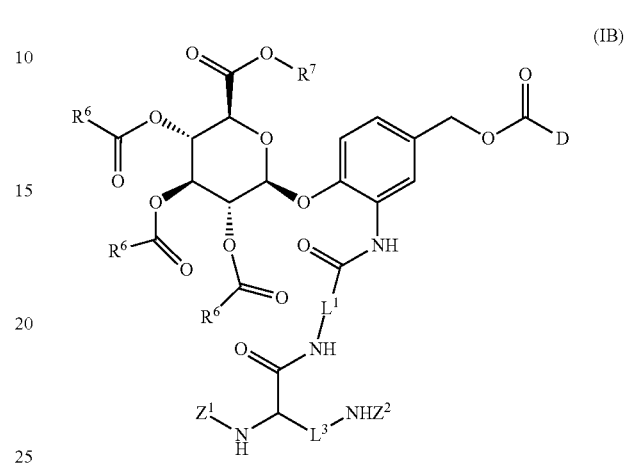

or a salt thereof, wherein the variable groups are as previously defined;

(b) contacting the Formula IB Drug Linker intermediate compound in a suitable solvent with a compound of Formula iv:

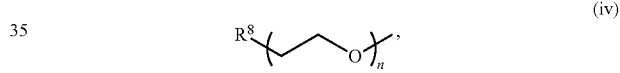

wherein $R^8$ is an activated ester; and subscript n ranges from 2 to 24 or is an integer ranging from 2 to 24, or (b') contacting the Formula IB Drug Linker intermediate compound with a compound of Formula iv in which $R^8$ is —COOH in the presence of a first activating agent, and n ranges from 2 to 24 or is an integer ranging from 2 to 24, wherein said contacting of step (b) or (b') provides a Drug Linker intermediate compound of Formula IC:

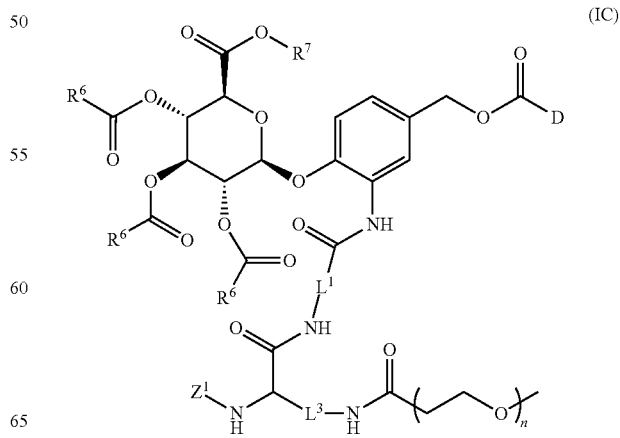

or a salt thereof, wherein the variable groups are as previously defined;

(c) contacting the Formula IC Drug Linker intermediate compound with either a Grignard reagent or an alkoxy magnesium halide in a suitable alcohol-containing solvent, wherein said Grignard reagent or alkoxy magnesium halide contacting selectively removes the hydroxyl protecting groups to provide a Drug Linker intermediate compound of Formula ID:

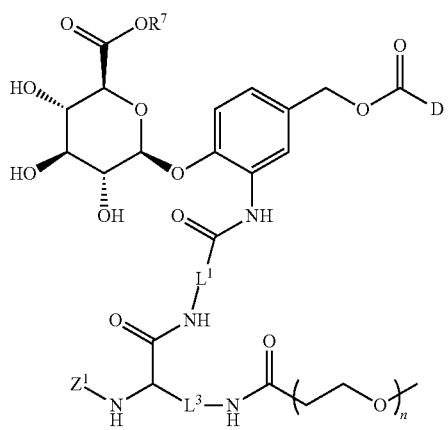

(ID)

or a salt thereof, wherein the variable groups are as previously defined;

(d) contacting the Formula ID Drug Linker intermediate compound with a first deprotecting agent, wherein said first deprotecting agent contacting removes the $Z^1$ amino and carboxylic acid protecting groups to provide a Drug Linker intermediate compound of Formula IE:

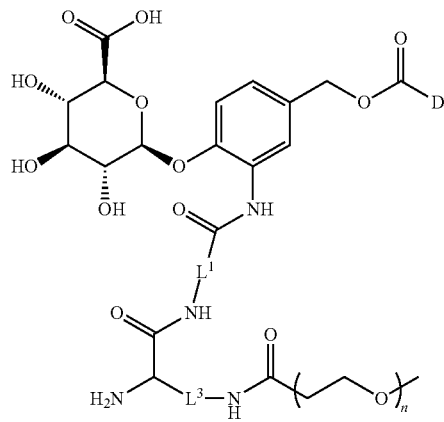

(IE)

or a salt thereof, wherein the variable groups are as previously defined; and (e) contacting the Formula IE Drug Linker intermediate compound with a compound of Formula v:

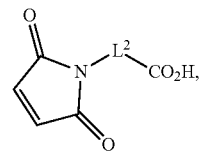

(v)

or a salt thereof, wherein $L^2$ is as previously defined, in the presence of a second activating agent, wherein said Formula v contacting provides the Formula I Drug Linker intermediate or Drug Linker compound.

In another group of embodiments, provided herein are methods for preparing a Drug Linker intermediate or Drug Linker compound of Formula I:

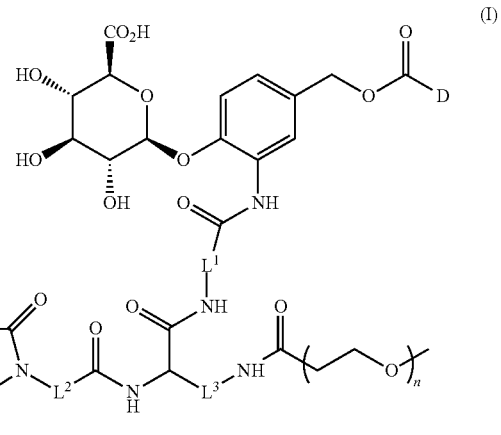

(I)

or a salt thereof, wherein
D is an auristatin Drug Unit;
each of $L^1$, $L^2$, and $L^3$ is independently a group selected from optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and
subscript n ranges from 2 to 24 or is an integer ranging from 2 to 24,
the method comprising the steps of:
(b) contacting a Drug Linker intermediate compound of Formula IB in a suitable solvent with a compound of Formula iv:

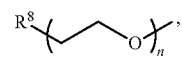

(iv)

wherein $R^8$ is an activated ester; and
subscript n ranges from 2 to 24 or is an integer ranging from 2 to 24, or
(b') contacting a Drug Linker intermediate compound of Formula IB in a suitable solvent with a compound of Formula iv in which $R^8$ is —COOH in the presence of a first activating agent, and n ranges from 2 to 24 or is an integer ranging from 2 to 24, wherein the Formula IB Drug Linker intermediate compound has the structure of:

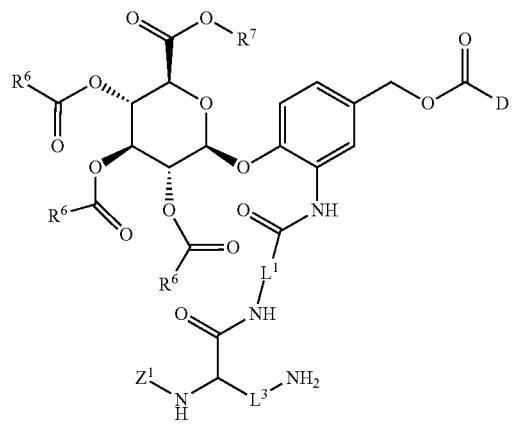

or a salt thereof, wherein $Z^1$ is a first suitable amino protecting group;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group;

subscript n ranges from 2 to 24 or is an integer ranging from 2 to 24; and the remaining variable groups are as previously defined, wherein said contacting of step (b) or (b') provides a Drug Linker intermediate compound of Formula IC:

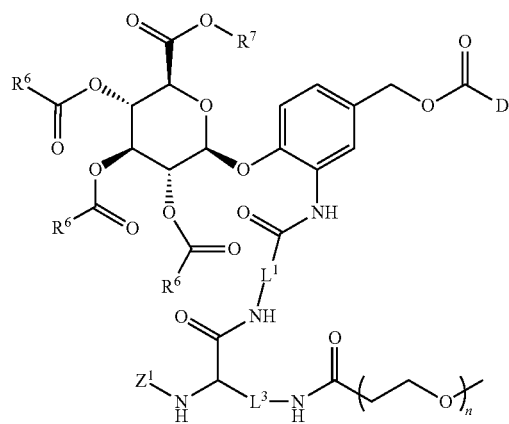

or a salt thereof, wherein the variable groups are as previously defined;

(c) contacting the Formula IC Drug Linker intermediate compound with either a Grignard reagent or an alkoxy magnesium halide in a suitable alcohol-containing solvent, wherein said Grignard reagent or alkoxy magnesium halide contacting selectively removes the hydroxyl protecting groups to provide a Drug Linker intermediate compound of Formula ID:

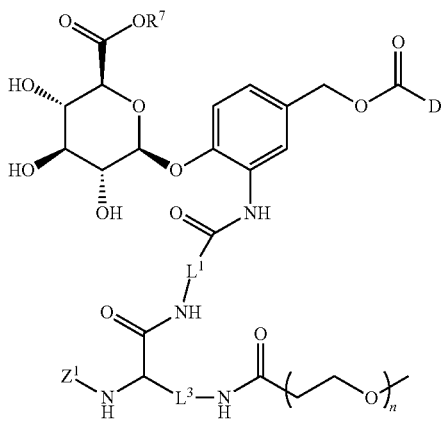

or a salt thereof, wherein the variable groups are as previously defined;

(d) contacting the Formula ID Drug Linker intermediate compound with a first deprotecting agent, wherein said second deprotecting agent contacting removes the $Z^1$ amino and carboxylic acid protecting groups to provide a Drug Linker intermediate compound of Formula IE:

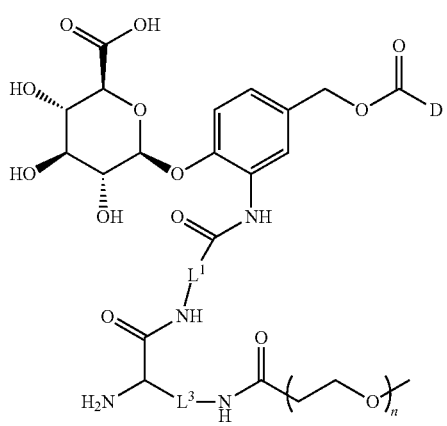

or a salt thereof, wherein the variable groups are as previously defined; and (e) contacting the Formula IE Drug Linker intermediate compound with a compound of Formula v:

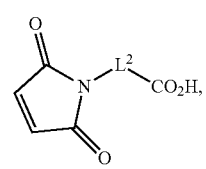

or a salt thereof, wherein $L^2$ is as previously defined, in the presence of a second activating agent, wherein said Formula v contacting provides the Formula I Drug Linker intermediate or Drug Linker compound or its salt.

In other embodiments, provided herein are methods for preparing Drug Linker intermediate compounds of Formula IID:

(IID)

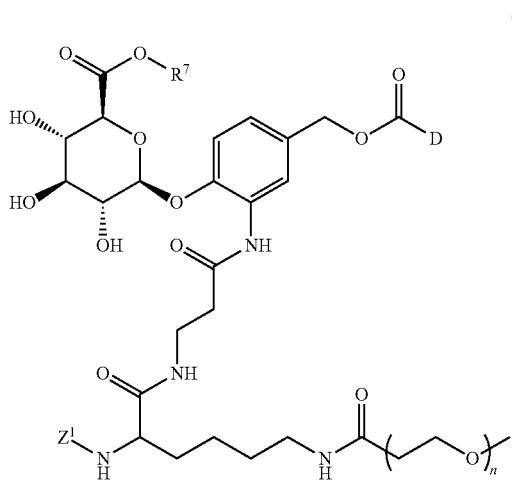

or a salt thereof, wherein

D is an auristatin Drug Unit;

$Z^1$ is a first suitable amino protecting group;

$R^7$ is $C_1$-$C_8$ alkyl or optionally substituted phenyl so that —$OR^7$ provides for an ester functional group that is a suitable carboxylic acid protecting group; and subscript n ranges from 2 to 24 or is an integer ranging from 2 to 24, the method comprising the step of:

(c) contacting a Drug Linker intermediate compound of Formula IIC with either a Grignard reagent or an alkoxy magnesium halide in a suitable alcohol-containing solvent, wherein the Formula IIC Drug Linker intermediate compound has the structure of:

(IIC)

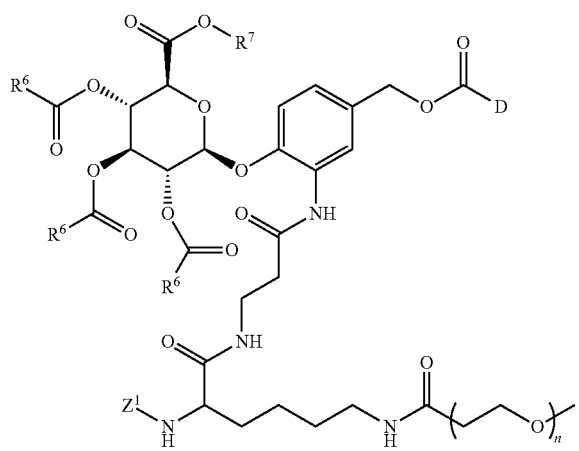

or a salt thereof, wherein each of $R^6$ is independently $C_1$-$C_8$ alkyl or optionally substituted phenyl so that $R^6C(=O)$— provides for an ester functional group that is a suitable hydroxyl protecting group;

and the remaining variable groups are as previously defined, wherein said Grignard reagent or an alkoxy magnesium halide contacting provides the Drug Linker intermediate Formula IIC compound or its salt.

In other embodiments, provided herein are methods for preparing Drug Linker intermediate compounds of Formula IID:

(IID)

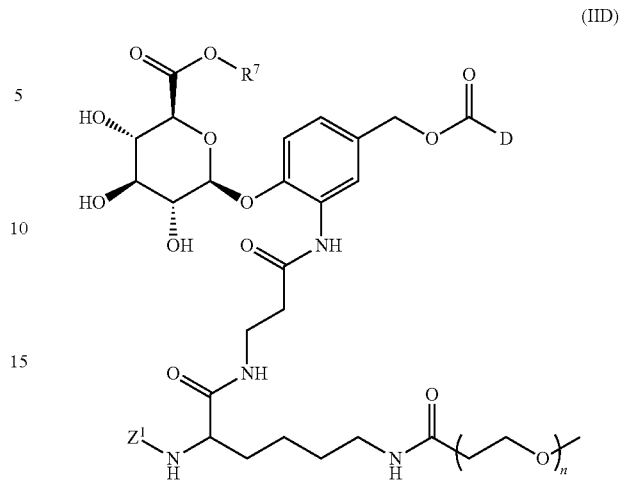

or a salt thereof, wherein

D is an auristatin Drug Unit;

$Z^1$ is a first suitable amino protecting group;

$R^7$ is $C_1$-$C_8$ alkyl or optionally substituted phenyl so that-$OR^7$ provides for an ester functional group that is a suitable carboxylic acid protecting group; and subscript n ranges from 2 to 24 or is an integer ranging from 2 to 24, the method comprising the steps of:

a) contacting a Drug Linker intermediate compound of Formula IIA with a second deprotecting agent, wherein the Formula IIA Drug Linker intermediate compound has the structure of:

(IIA)

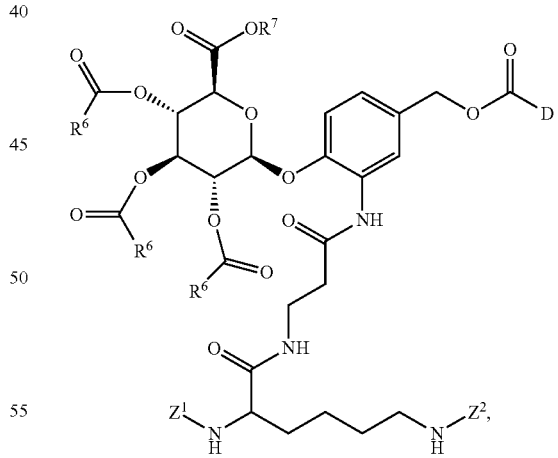

or a salt thereof, wherein $Z^2$ is a second suitable amino protecting group, each of $R_6$ is independently $C_1$-$C_8$ alkyl or optionally substituted phenyl so that $R^6C(=O)$— provides for an ester functional group that is a suitable hydroxyl protecting group, wherein said second deprotecting agent contacting selectively removes the $Z^2$ amino protecting group to provide a Drug Linker intermediate compound of Formula IIB:

(IIB)

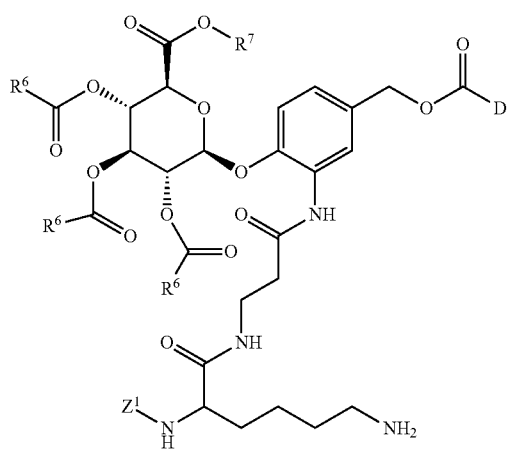

or a salt thereof, wherein the variable groups are as previously defined;

(b) contacting the Formula IIB Drug Linker intermediate in a suitable solvent with a compound of Formula iv:

(iv)

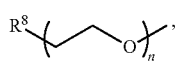

wherein $R^8$ is an activated ester; and n ranges from 2 to 24 or is an integer ranging from 2 to 24, or (b') contacting the Formula IB Drug Linker intermediate compound with a compound of Formula iv in which $R^8$ is —COOH and n ranges from 2 to 24 or is an integer ranging from 2 to 24 in the presence of a first activating agent; and wherein said contacting of step (b) or (b') provides a Drug Linker intermediate compound of Formula IIC:

(IIC)

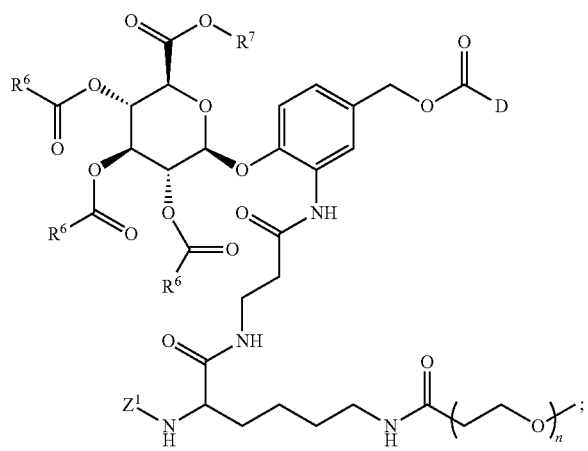

(c) contacting the Formula IIC Drug Linker intermediate compound with either a Grignard reagent or an alkoxy magnesium halide in a suitable alcohol-containing solvent, wherein said Grignard reagent or an alkoxy magnesium halide contacting provides the Formula IID Drug Linker intermediate compound or its salt.

In other embodiments, provided herein are methods for preparing Drug Linker intermediate compounds of Formula IID:

(IID)

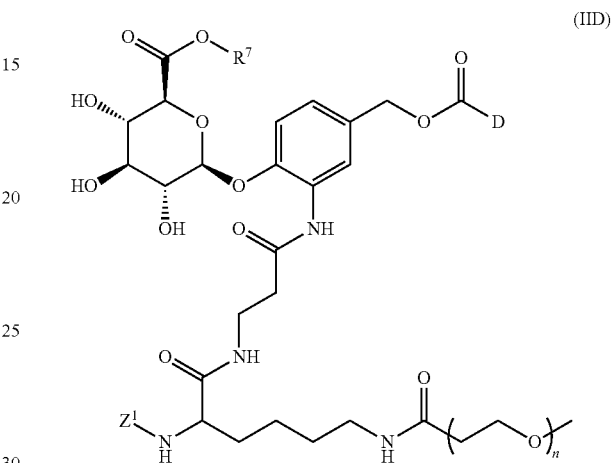

or a salt thereof, wherein

D is an auristatin Drug Unit;

$Z^1$ is a first suitable amino protecting group;

$R^7$ is $C_1$-$C_8$ alkyl or optionally substituted phenyl so that-$OR^7$ provides for an ester functional group that is a suitable carboxylic acid protecting group; and subscript n ranges from 2 to 24 or is an integer ranging from 2 to 24, the method comprising the steps of:

(b) contacting a Drug Linker intermediate compound of Formula IIB in a suitable solvent with a compound of Formula iv:

(iv)

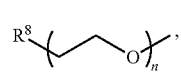

wherein $R^8$ is an activated ester; and n ranges from 2 to 24 or is an integer ranging from 2 to 24, or (b') contacting a Drug Linker intermediate compound of Formula IB with a compound of Formula iv in which $R^8$ is —COOH and n ranges from 2 to 24 or is an integer ranging from 2 to 24 in the presence of a first activating agent, wherein the Formula IIB Drug Linker intermediate compound has the structure of:

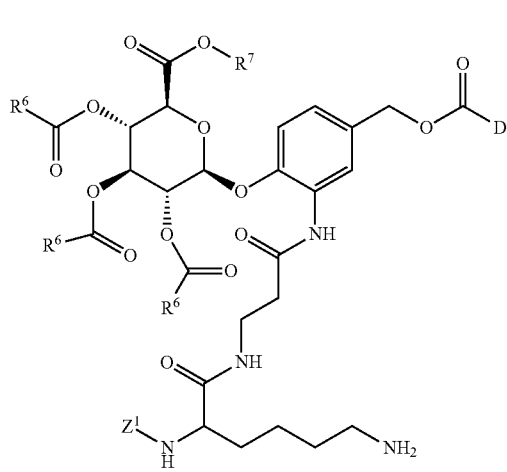

(IIB)

or a salt thereof, wherein each of $R_6$ is independently $C_1$-$C_8$ alkyl or optionally substituted phenyl so that $R^6C(=O)$— provides for an ester functional group that is a suitable hydroxyl protecting group; and the remaining variable groups are as previously defined; and wherein said contacting of step (b) or (b') provides a Drug Linker intermediate compound of Formula IIC:

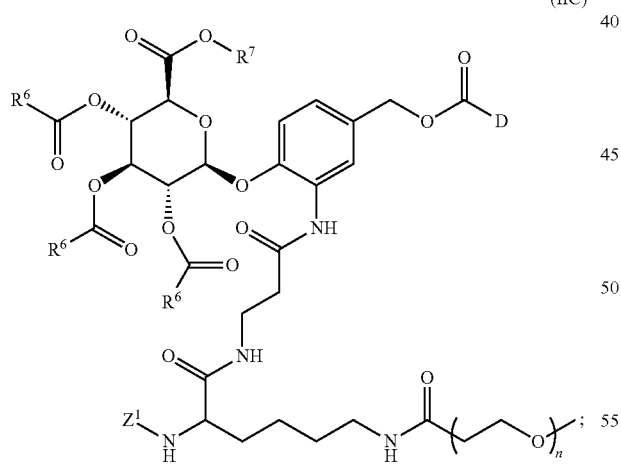

(IIC)

or a salt thereof, wherein the variable groups are as previously defined; and (c) contacting the Formula IIC Drug Linker intermediate compound with either a Grignard reagent or an alkoxy magnesium halide in a suitable alcohol-containing solvent, wherein said Grignard reagent or an alkoxy magnesium halide contacting provides the Formula IID Drug Linker intermediate compound or its salt.

In other embodiments, provided herein are methods for preparing Drug Linker intermediate compounds of Formula IIE:

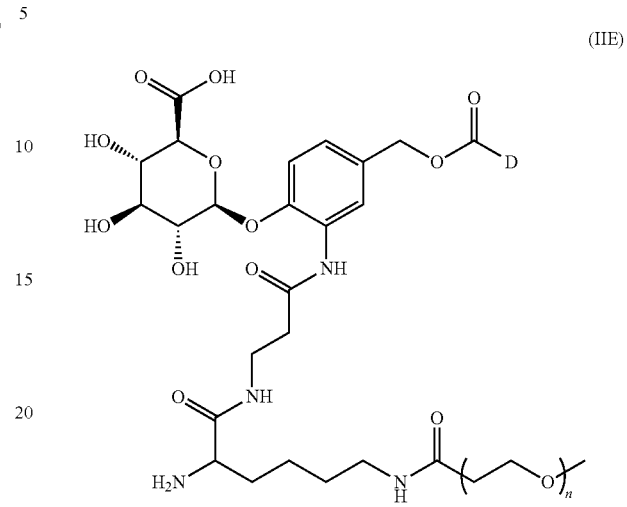

(IIE)

or a salt thereof, wherein
D is an auristatin Drug Unit; and
subscript n ranges from 2 to 24 or is an integer ranging from 2 to 24;

the method comprising the step of:

(c) contacting a Drug Linker intermediate compound of Formula IIC with either a Grignard reagent or an alkoxy magnesium halide in a suitable alcohol-containing solvent; and (d) contacting the product of step (c) with a deprotecting agent wherein the deprotecting agent is an aqueous-containing solution of a suitable base, wherein the Formula IIC Drug Linker intermediate compound has the structure of:

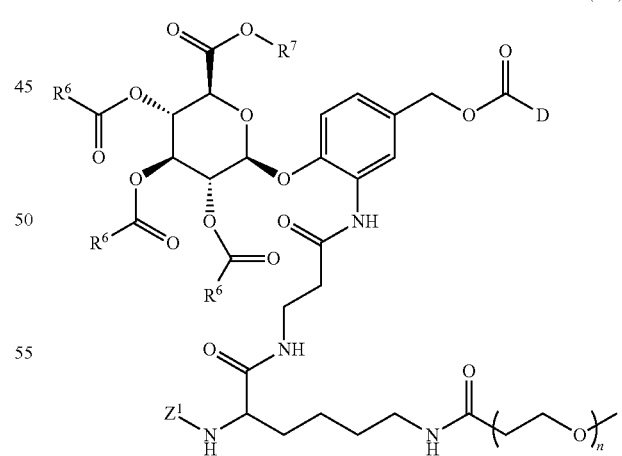

(IIC)

or a salt thereof, wherein
$Z^1$ is a first suitable amino protecting group;
each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined, and wherein said contacting of steps (c) and (d) provide the Formula IIE Drug Linker intermediate compound.

In other embodiments, provided herein are methods for preparing Drug Linker intermediate compounds of Formula IIE:

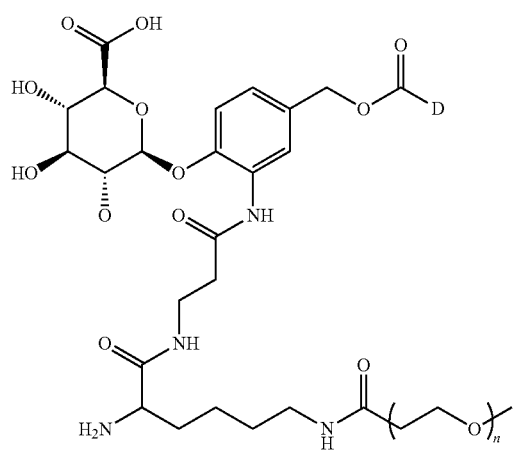
(IIE)

or a salt thereof, wherein

D is an auristatin Drug Unit; and subscript n ranges from 2 to 24 or is an integer ranging from 2 to 24, the method comprising the steps of:

(b) contacting a Drug Linker intermediate compound of Formula IIB in a suitable solvent with a compound of Formula iv:

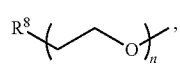
(iv)

wherein $R^8$ is an activated ester; and n ranges from 2 to 24 or is an integer ranging from 2 to 24, or (b') contacting a Drug Linker intermediate compound of Formula IB with a compound of Formula iv in which $R^8$ is —COOH and n is an integer ranging from 2 to 24 in the presence of a first activating agent, wherein the Formula IIB Drug Linker intermediate compound has the structure of:

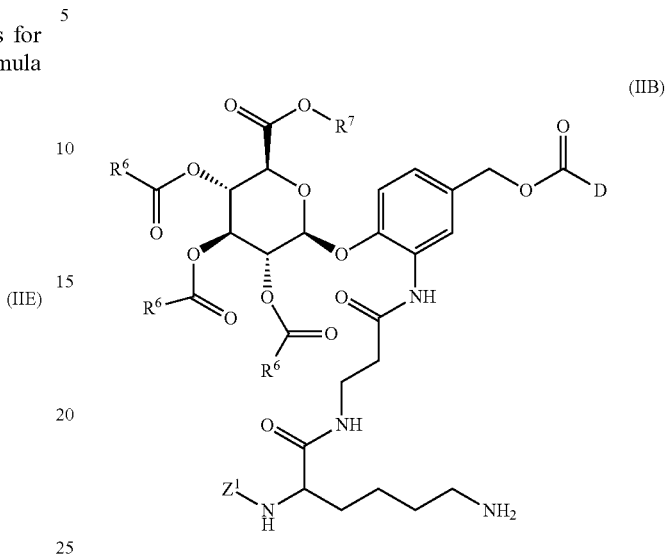
(IIB)

said contacting of step (b) or (b') provides a Drug Linker intermediate compound of Formula IC:

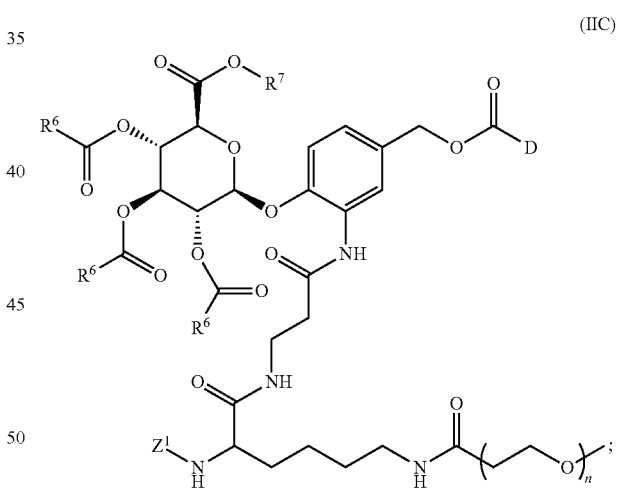
(IIC)

(c) contacting the Formula IIC Drug Linker intermediate compound with either a Grignard reagent or an alkoxy magnesium halide in a suitable alcohol-containing solvent; and (d) contacting the product of step (c) with a second deprotecting agent wherein the second deprotecting agent is an aqueous-containing solution of a suitable base, wherein said contacting of steps (c) and (d) provide the Formula IIE Drug Linker intermediate compound.

In other embodiments, provided herein are methods for preparing Drug Linker intermediate compounds of Formula IIE:

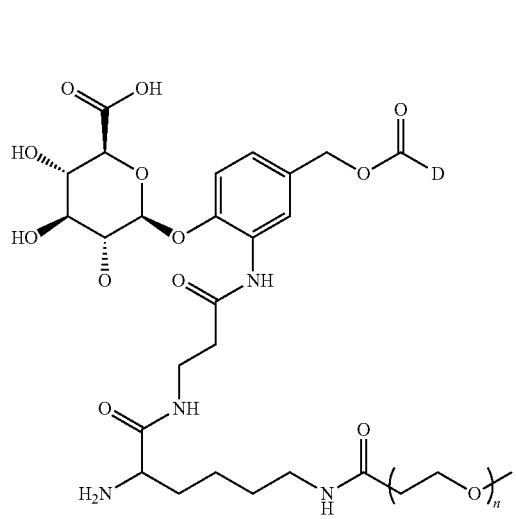

(IIE)

or a salt thereof, wherein

D is an auristatin Drug Unit; and subscript n ranges from 2 to 24 or is an integer ranging from 2 to 24, the method comprising the steps of:

(a) contacting a Drug Linker intermediate compound of Formula IIA with a second deprotecting agent, wherein the Formula IIA Drug Linker intermediate compound has the structure of:

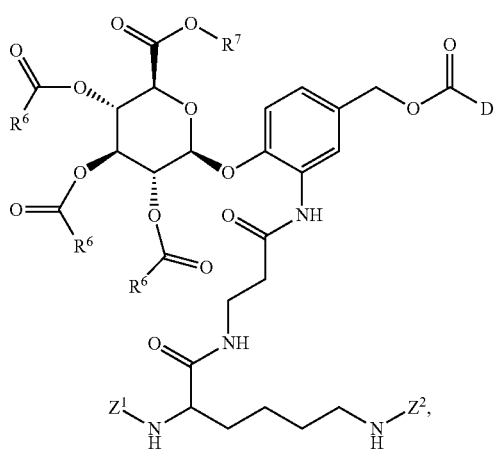

(IIA)

or a salt thereof, wherein each of $Z^1$ and $Z^2$ is independently a first and second suitable amino protecting group, respectively;

each of $R^6$ and $R^7$ is independently $C_1$-$C_8$ alkyl or optionally substituted phenyl so that $R^6C(\!=\!O)$— provides for an ester functional group that is a suitable hydroxyl protecting group and —$OR^7$ provides for an ester functional group that is a suitable carboxylic acid protecting group; and wherein said second deprotecting agent contacting selectively removes the $Z^2$ amino protecting group to provide a Drug Linker intermediate compound of Formula IIB:

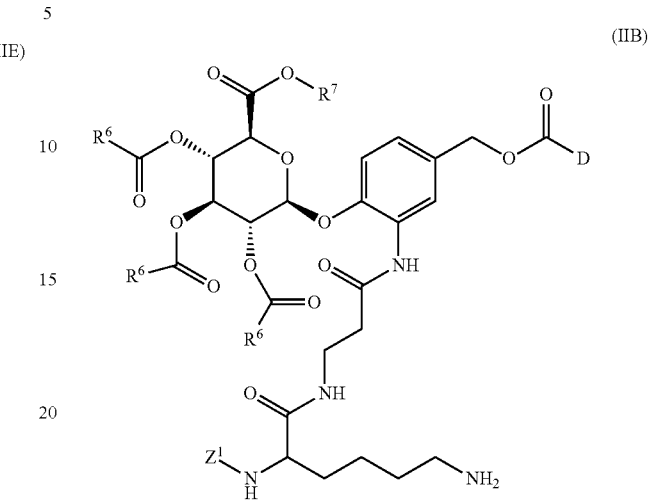

(IIB)

or a salt thereof, wherein the variable groups are as previously defined;

(b) contacting the Formula IIB Drug Linker intermediate compound in a suitable solvent with a compound of Formula iv:

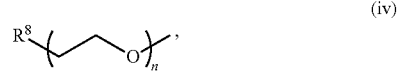

(iv)

wherein $R^8$ is an activated ester; and n ranges from 2 to 24 or is an integer ranging from 2 to 24, or (b') contacting the Formula IB Drug Linker intermediate compound with a compound of Formula iv in which $R^8$ is —COOH and n ranges from 2 to 24 or is an integer ranging from 2 to 24 in the presence of a first activating agent; and wherein said contacting of step (b) or (b') provides a Drug Linker intermediate compound of Formula IIC:

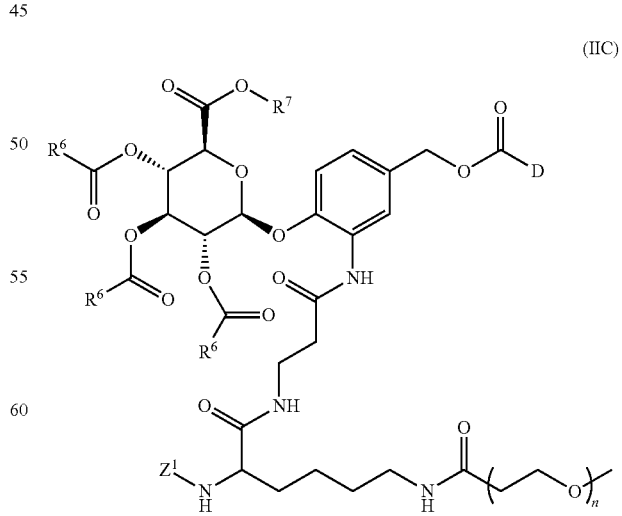

(IIC)

or a salt thereof, wherein the variable groups are as previously defined;

(c) contacting the Formula IIC Drug Linker intermediate compound with either a Grignard reagent or an alkoxy magnesium halide in a suitable alcohol-containing solvent; and (d) contacting the product of step (c) with a first deprotecting agent, wherein the first deprotecting agent is an aqueous-containing solution of a suitable base, wherein said contacting of steps (c) and (d) provide the Formula IIE Drug Linker intermediate compound or its salt.

In other embodiments, provided herein are methods for preparing Drug Linker intermediate compounds of Formula IIF:

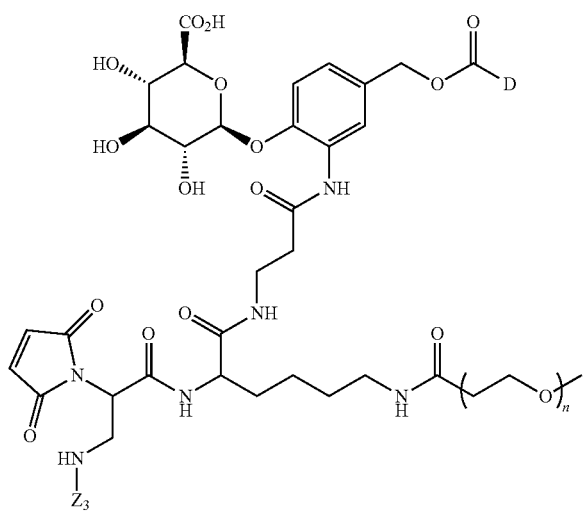

(IIF)

or a salt thereof, wherein

D is an auristatin Drug Unit;

$Z^3$ is a third suitable amino protecting group that is acid-labile; and subscript n ranges from 2 to 24 or is an integer ranging from 2 to 24, the method comprising the steps of:

(c) contacting a Drug Linker intermediate compound of Formula IIC with either a Grignard reagent or an alkoxy magnesium halide in a suitable alcohol-containing solvent; and (d) contacting the product of step (c) with a first deprotecting agent that is an aqueous-containing solution of a suitable base, wherein the Formula IIC Drug Linker intermediate compound has the structure of:

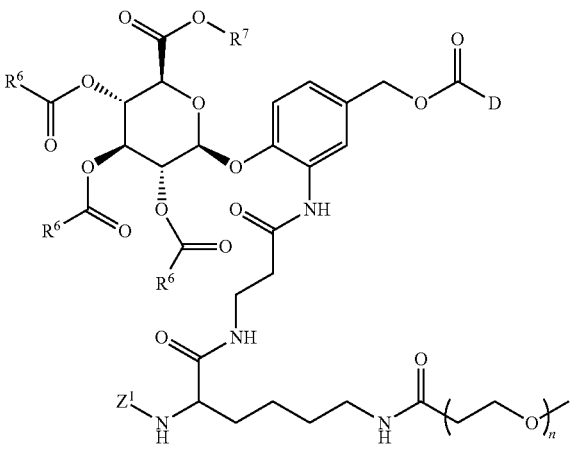

(IIC)

or a salt thereof, wherein $Z^1$ is a first suitable amino protecting group;

each of $R^6$ and $R^7$ is independently $C_1$-$C_5$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and and the remaining variable groups are as previously defined, wherein said contacting of steps (c) and (d) provide a Drug Linker intermediate compound of Formula IIE, wherein the Formula IIE Drug Linker intermediate compound has the structure of:

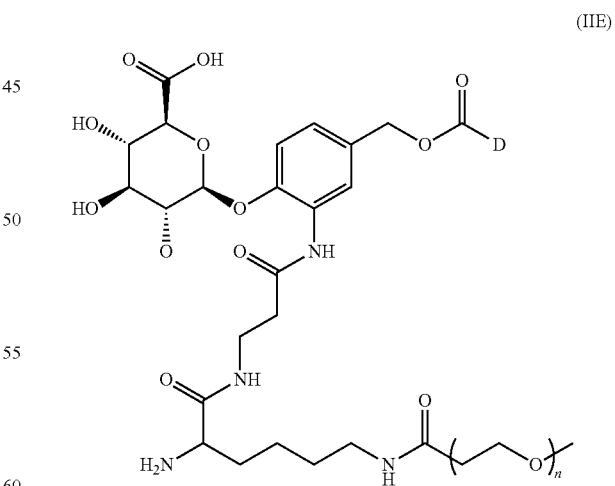

(IIE)

or a salt thereof, wherein the variable groups are as previously defined; and contacting the Formula IIE Drug Linker intermediate compound in a suitable solvent with a compound of Formula v:

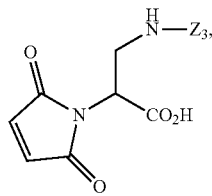

(v)

or a salt thereof, in the presence of a first activating agent, wherein said Formula v contacting provides the Formula IIF Drug Linker intermediate compound or its salt.

In other embodiments, provided herein are methods for preparing Drug Linker intermediate compounds of Formula IIF:

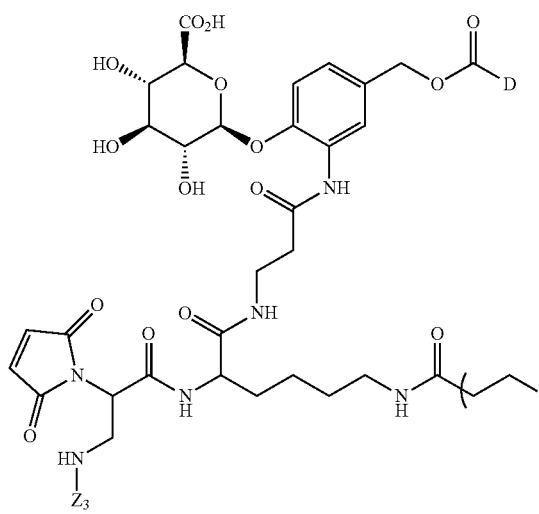

(IIF)

or a salt thereof, wherein

D is an auristatin Drug Unit;

$Z^3$ is a third suitable amino protecting group that is acid-labile; and subscript n ranges from 2 to 24 or is an integer ranging from 2 to 24, the method comprising the steps of:

(b) contacting a Drug Linker intermediate compound of Formula IIB in a suitable solvent with a compound of Formula iv:

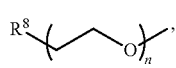

(iv)

wherein $R^8$ is an activated ester; and n ranges from 2 to 24 or is an integer ranging from 2 to 24, or (b') contacting a Drug Linker intermediate compound of Formula IB with a compound of Formula iv in which $R^8$ is —COOH and n ranges from 2 to 24 or is an integer ranging from 2 to 24 in the presence of first activating agent;

wherein the Formula IIB Drug Linker intermediate compound has the structure of:

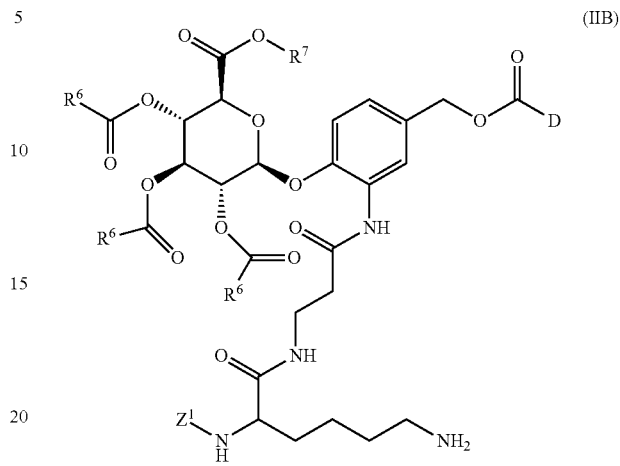

(IIB)

wherein $Z^1$ is a first suitable amino protecting group;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable group is as previously defined, wherein said contacting of step (b) or (b') provides a Drug Linker intermediate compound of Formula IIC:

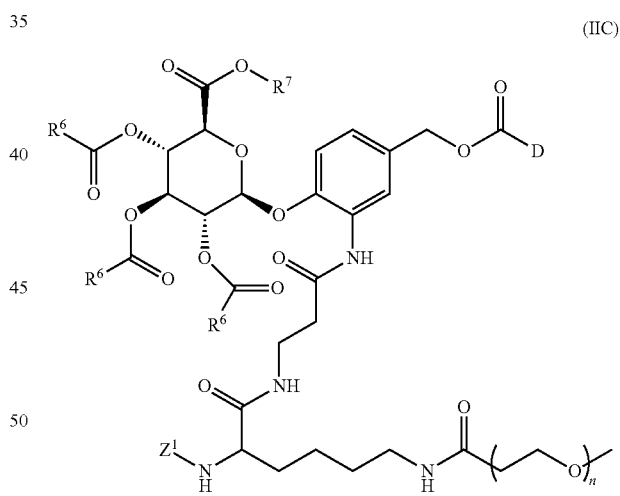

(IIC)

or a salt thereof, wherein the variable groups are as previously defined;

(c) contacting the Formula IIC Drug Linker intermediate compound with either a Grignard reagent or an alkoxy magnesium halide in a suitable alcohol-containing solvent; and (d) contacting the product of step (c) with a first deprotecting agent, wherein the first deprotecting agent is an aqueous-containing solution of a suitable base, wherein said contacting of steps (c) and (d) provide a Drug Linker intermediate compound of Formula IIE:

wherein the Formula IIE Drug Linker intermediate compound has the structure of:

(IIE)

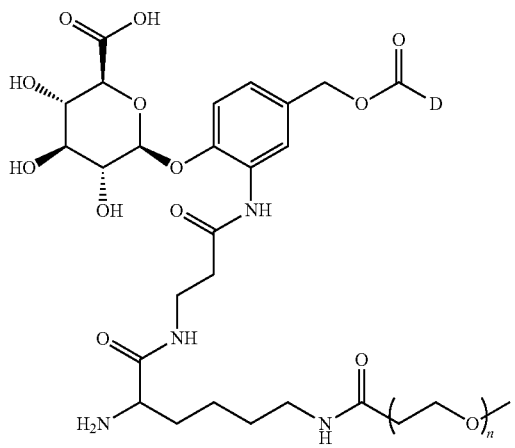

or a salt thereof, wherein the variable groups are as previously defined; and (e) contacting the Formula IIE Drug Linker intermediate compound with a compound of Formula v:

(v)

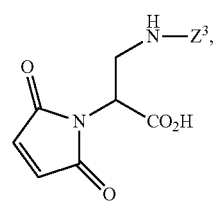

or a salt thereof, in the presence of a second activating agent, wherein said Formula v contacting provides the Formula IIF Drug Linker intermediate compound or its salt.

In other embodiments, provided herein are methods for preparing Drug Linker intermediate compounds of Formula IIF:

(IIF)

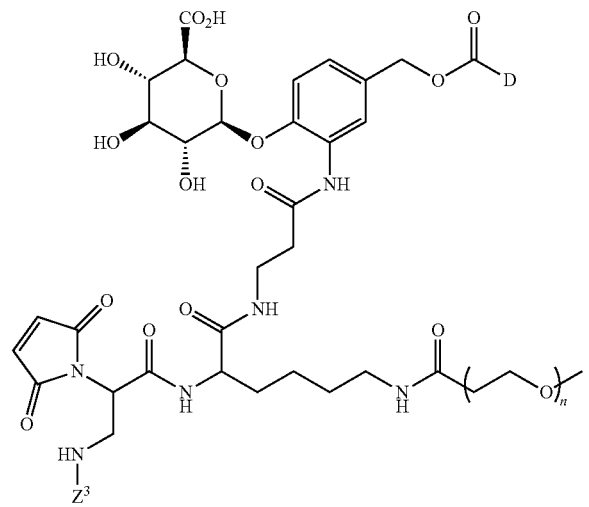

or a salt thereof, wherein

D is an auristatin drug moiety;

$Z^3$ is a third suitable amino protecting group that is acid-labile; and subscript n ranges from 2 to 24 or is an integer ranging from 2 to 24, the method comprising the steps of:

(a) contacting a Drug Linker intermediate compound of Formula IIA with a second deprotecting agent, wherein the Formula IIA Drug Linker intermediate compound has the structure of:

(IIA)

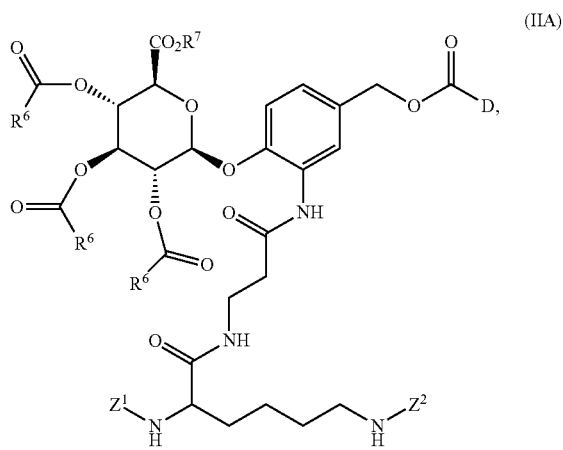

or a salt thereof, wherein $Z^1$ is a first suitable amino protecting group;

$Z^2$ is a second suitable amino protecting group;

each of $R^6$ and $R^7$ is independently $C_1$-$C_8$ alkyl or optionally substituted phenyl so that $R^6C(=O)—$ provides for an ester functional group that is a suitable hydroxyl protecting group, and $—OR^7$ provides for an ester functional group that is a suitable carboxylic acid protecting group;

wherein the second deprotecting agent contacting selectively removes the $Z^2$ amino protecting group to provide a compound of Formula IIB:

(IIB)

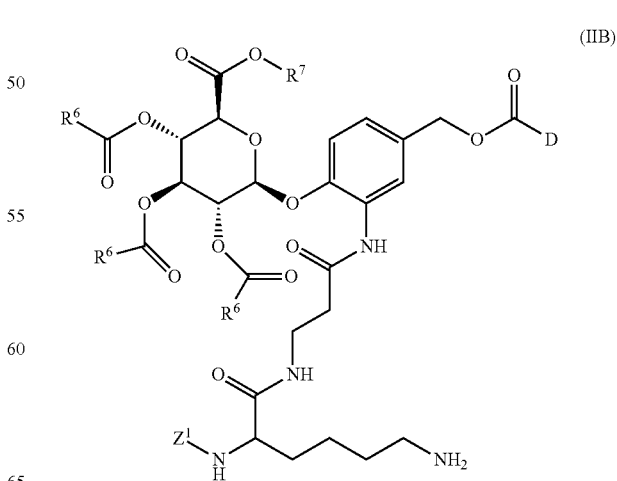

or a salt thereof, wherein the variable groups are as previously defined;

(b) contacting the Formula IIB Drug Linker intermediate compound in a suitable solvent with a compound of Formula iv:

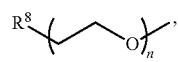
(iv)

wherein $R^8$ is an activated ester; and n ranges from 2 to 24 or is an integer ranging from 2 to 24, or (b') contacting the Formula IIB Drug Linker intermediate compound with a compound of Formula iv in which $R^8$ is —COOH and n ranges from 2 to 24 or is an integer ranging from 2 to 24 in the presence of a first activating agent;

wherein said contacting of step (b) or (b') provides a Drug Linker intermediate compound of Formula IIC:

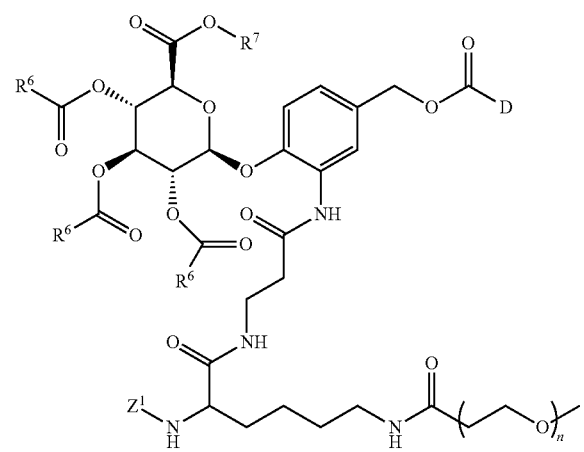
(IIC)

or a salt thereof, wherein the variable groups are as previously defined;

(c) contacting the Formula IIC Drug Linker intermediate compound with either a Grignard reagent or an alkoxy magnesium halide in a suitable alcohol-containing solvent; and (d) contacting the product of step (c) with a first deprotecting agent that is an aqueous-containing solution of a suitable base, wherein said contacting of steps (c) and (d) provide the Formula IIE Drug Linker intermediate compound of:

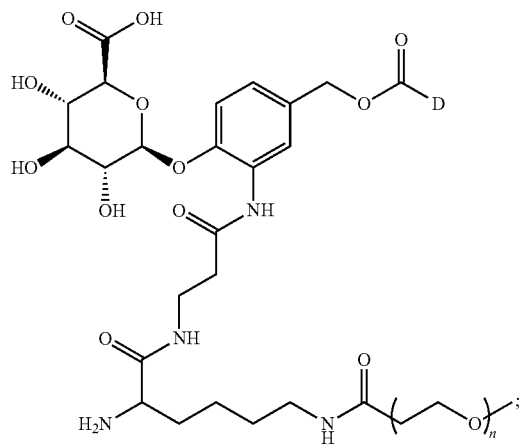
(IIE)

(e) contacting the Formula IIE Drug Linker intermediate with a compound of Formula v:

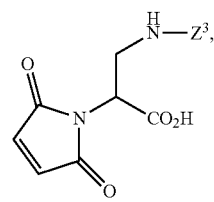
(v)

wherein $Z^3$ is as previously defined, in the presence of a second activating agent to form the Formula IIF Drug Linker intermediate compound or its salt.

In other embodiments, provided herein are methods for preparing Drug Linker compounds of Formula II:

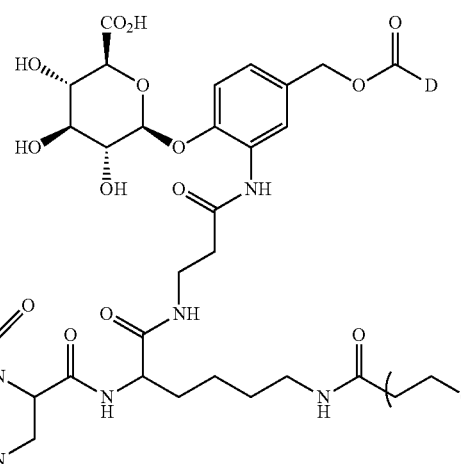
(II)

or a salt thereof, wherein

D is an auristatin drug moiety; and subscript n ranges from 2 to 24 or is an integer ranging from 2 to 24, the method comprising the step of:

contacting a Drug Linker intermediate compound of Formula IIF, with a third deprotecting agent that is an acidic aqueous-containing solvent, wherein the Formula IIF compound has the structure of:

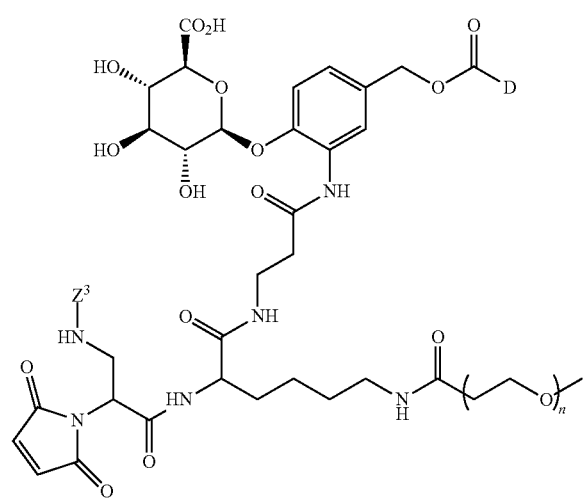

(IIF)

or a salt thereof, wherein $Z^3$ is a third amino protecting group that is an acid-labile and the remaining variable groups are as previously defined; and wherein the Formula IIF Drug Linker intermediate compound is prepared according to any one of the preceding methods providing that compound.

In selected embodiments of any one of the preceding methods, the auristatin Drug Unit (D) in compounds of Formula I, Formula IA, Formula IB, Formula IC, Formula ID, Formula IE, Formula II, Formula IIA, Formula IIB, Formula IIC, Formula IID, Formula IIE, and/or Formula IIF has structure of:

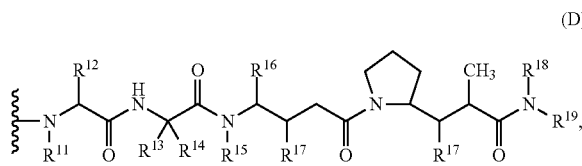

(D)

wherein the wavy line indicates covalent bonding of D to the remainder of the Drug Linker intermediate of Drug Linker compound structure, wherein $R^{11}$ is selected from the group consisting of H and $C_1$-$C_8$ alkyl;

$R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{14}$ is selected from the group consisting of H and methyl, or $R^{13}$ and $R^{14}$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

each $R^{17}$ is independently selected from the group consisting of H, OH, $C_1$-$C_8$ alkyl, $C_3$-$C_8$ carbocycle, and O—($C_1$-$C_5$ alkyl);

$R^{18}$ is selected from the group consisting of H and $C_1$-$C_8$ alkyl;

$R^{19}$ is selected from the group consisting of —$C(R^{17})_2$—$C(R^{17})_2$-aryl, —$C(R^{17})_2$—$C(R^{17})_2$—($C_3$-$C_8$ heterocycle), —$C(R^{17})_2$—$C(O)$—$ZR^{20}$, and —$C(R^{17})_2$—$C(R^{17})_2$—($C_3$-$C_8$ carbocycle);

Z is —O—, or —NH—; and $R^{20}$ is selected from the group consisting of H, $C_1$-$C_8$ alkyl, aryl, and $C_3$-$C_8$ heterocyclyl.

In some of those embodiments, the auristatin Drug Unit is represented by the structure of Formula $D_{E-1}$, $D_{E-2}$, or $D_{F-1}$:

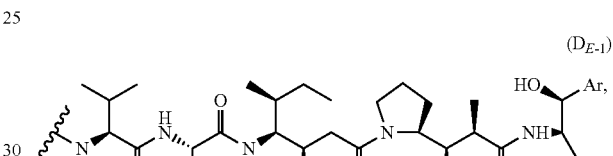

($D_{E-1}$)

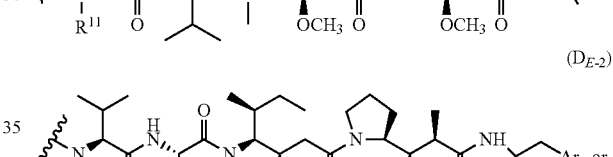

($D_{E-2}$)

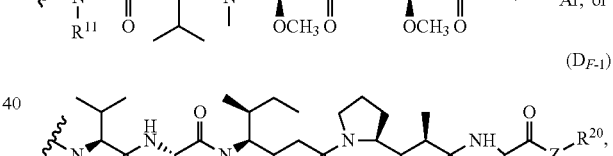

($D_{F-1}$)

wherein Ar is optionally substituted phenyl or $C_3$-$C_8$ heterocyclyl.

In some embodiments, the auristatin Drug Unit of compounds of Formula I, Formula IA, Formula IB, Formula IC, Formula ID, Formula IE, Formula II, Formula IIA, Formula IIB, Formula IIC, Formula IID, Formula IIE, and/or Formula IIF in any one of the preceding methods are of Formula $D_{E-1}$, $D_{E-2}$, or $D_{F-1}$, in which $R^{11}$ is preferably methyl.

In other embodiments, the auristatin Drug Unit of compounds of Formula I, Formula IA, Formula IB, Formula IC, Formula ID, Formula IE, Formula II, Formula IIA, Formula IIB, Formula IIC, Formula IID, Formula IIE, and/or Formula IIF in any one of the preceding methods has the structure of Formula $D_{E-1}$ or $D_{E-2}$, in which Ar is preferably optionally substituted phenyl or optionally substituted 2-pyridyl.

In other embodiments, the auristatin Drug Unit of compounds of Formula I, Formula IA, Formula IB, Formula IC, Formula ID, Formula IE, Formula II, Formula IIA, Formula IIB, Formula IIC, Formula IID, Formula IIE, and/or Formula IIF in any one of the preceding methods is represented by the Formula $D_{F-1}$, preferably —Z— is —O— and $R^{20}$ is lower alkyl. Alternatively, preferably Z is —NH— and $R^{20}$ is optionally substituted phenyl or optionally substituted heteroaryl.

In more preferred embodiments, the auristatin Drug Unit of compounds of Formula I, Formula IA, Formula IB, Formula IC, Formula ID, Formula IE, Formula II, Formula IIA, Formula IIB, Formula IIC, Formula IID, Formula IIE, and/or Formula IIF in any one of the preceding methods has the structure of $D_{F/E-3}$:

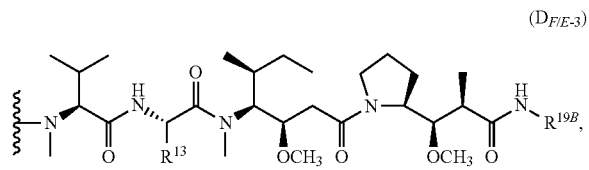

wherein $R^{13}$ is isopropyl or —$CH_2$—$CH(CH_3)_2$ and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph; and the wavy line indicates the site of attachment to the remainder of the compound structure.

In particularly preferred embodiments, the auristatin Drug Unit of compounds of Formula I, Formula IA, Formula IB, Formula IC, Formula ID, Formula IE, Formula II, Formula IIA, Formula IIB, Formula IIC, Formula IID, Formula IIE, and/or Formula IIF in any one of the preceding methods has the structure of:

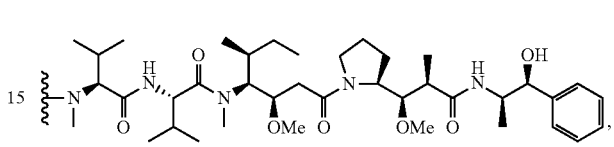

wherein the wavy line indicates the site of attachment to the remainder of the compound structure.

In another group of embodiments, provided herein are methods for preparing a Drug Linker compound of Formula 10:

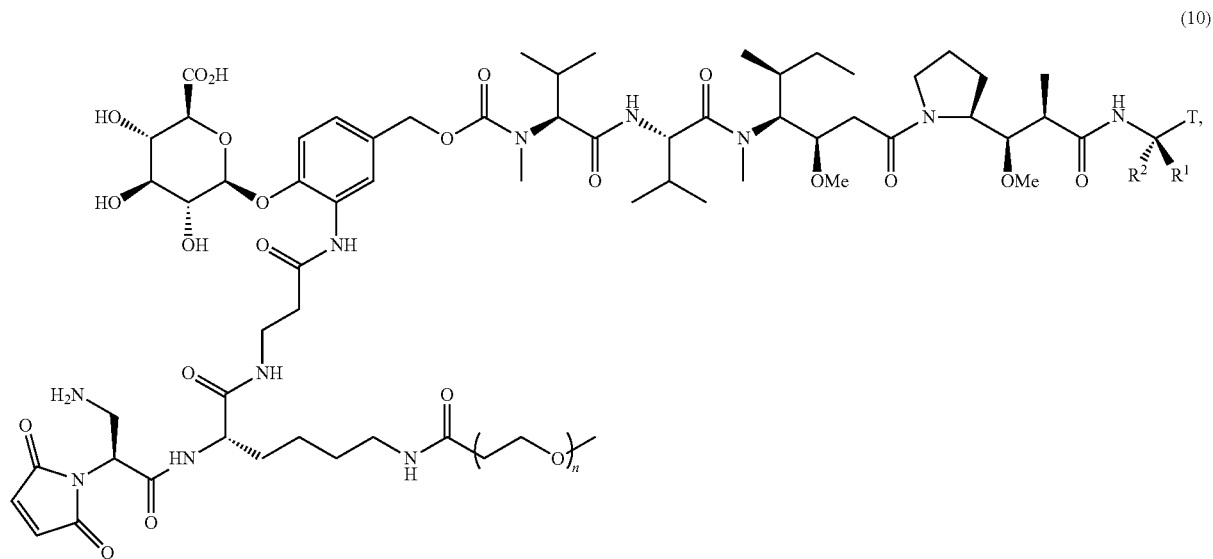

or a salt thereof, wherein
n ranges from 2 to 24 or is an integer ranging from 2 to 24;
R$^1$ is H or C$_1$-C$_4$ alkyl;
R$^2$ is H, C$_1$-C$_4$ alkyl, or —CH$_2$—R$^3$;
R$^3$ is C$_6$-C$_{10}$ aryl, C$_5$-C$_{10}$ heteroaryl, or C$_3$-C$_8$ heterocyclyl; and T is selected from the group consisting of —CH(OR$^4$)—R$^5$ or —C(=O)—OR$^4$, wherein R$^4$ is H, C$_1$-C$_4$ alkyl and R$^5$ is C$_6$-C$_{10}$ aryl, or C$_3$-C$_6$ heteroaryl;
wherein the method comprises the steps of:
(a) contacting a Drug Linker intermediate compound of Formula 4:

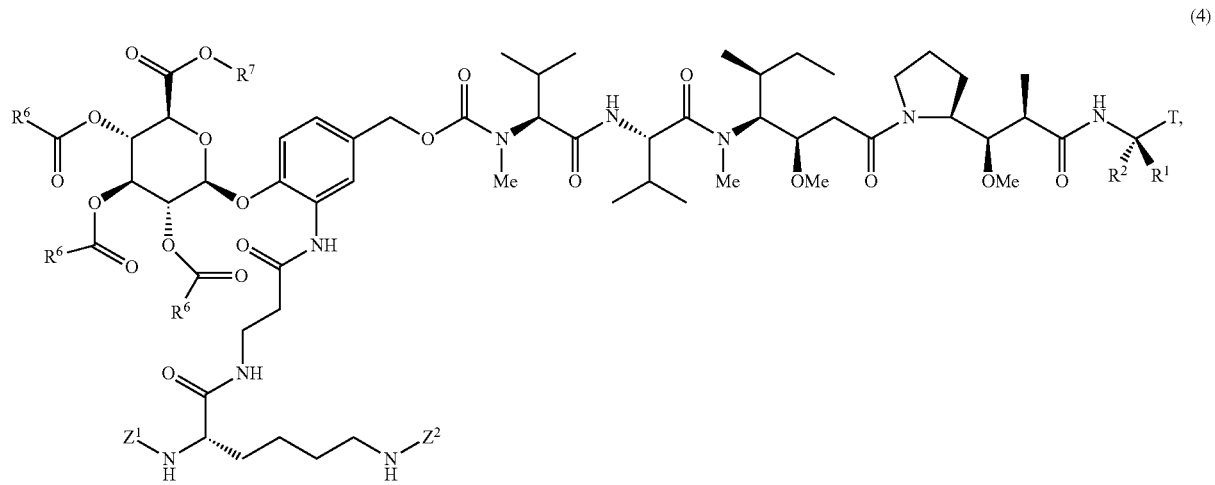

(4)

wherein
each of R$^6$ and R$^7$ is independently C$_1$-C$_8$ alkyl or optionally substituted phenyl, so that R$^6$C(=O)— provides for an acyl functional group that is a suitable hydroxyl protecting group, and —OR$^7$ provides for a ester functional group that is a suitable carboxylic acid protecting group, and
each of Z$^1$ and Z$^2$ is independently a first and second suitable amine protecting group, respectively,
with a second deprotecting agent wherein said second deprotecting agent contacting selectively removes the Z$^2$ amino protecting group to provide a Drug Linker intermediate compound of Formula 5:

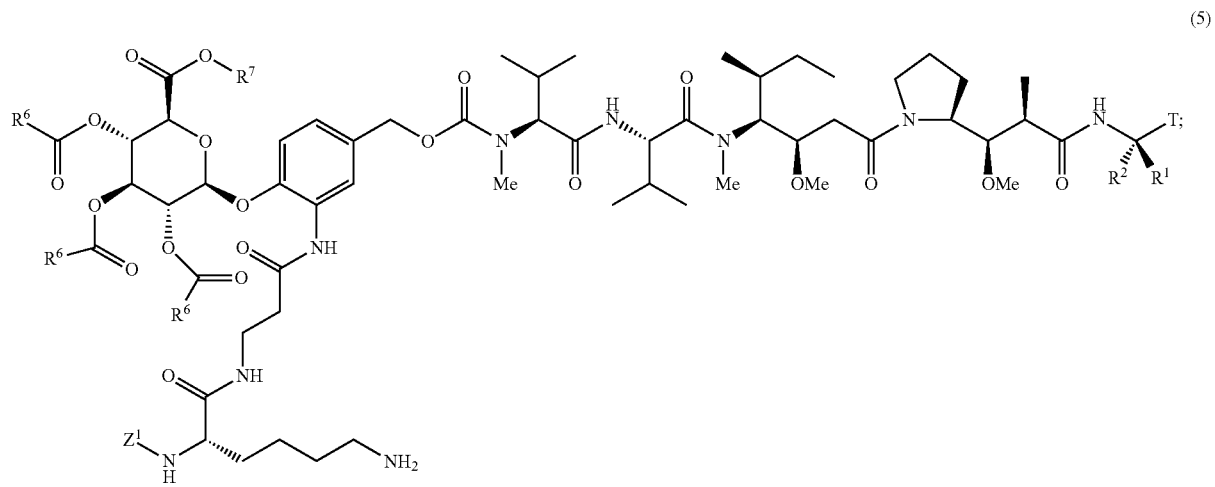

(5)

(b) contacting the Formula 5 Drug Linker intermediate in a suitable solvent with a compound of Formula iv:

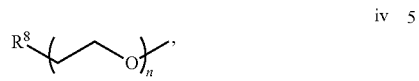

wherein $R^8$ is an activated ester; and n ranges from 2 to 24 or is an integer ranging from 2 to 24, or (b') contacting the Formula 5 Drug Linker intermediate compound with a compound of Formula iv in which $R^8$ is —COOH and n ranges from 2 to 24 or is an integer ranging from 2 to 24 in the presence of a first activating agent;

wherein said contacting of step (b) or (b') provides a Drug Linker intermediate compound of Formula 6:

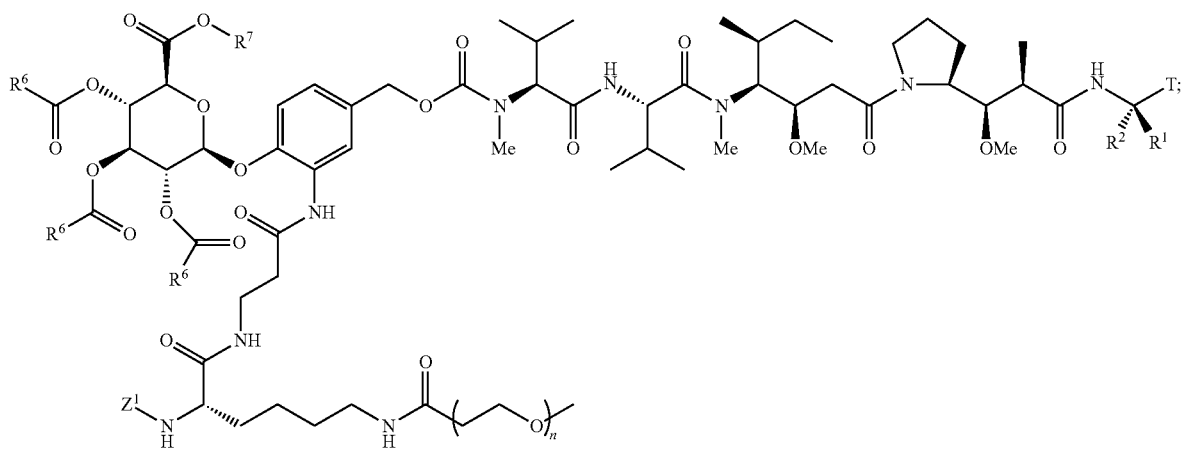

(c) contacting the Formula 6 Drug Linker intermediate compound with either a Grignard reagent or an alkoxy magnesium halide in a suitable alcohol-containing solvent, wherein said Grignard reagent or an alkoxy magnesium halide contacting selectively removes the hydroxyl protective groups to provide a Drug Linker intermediate compound of Formula 7:

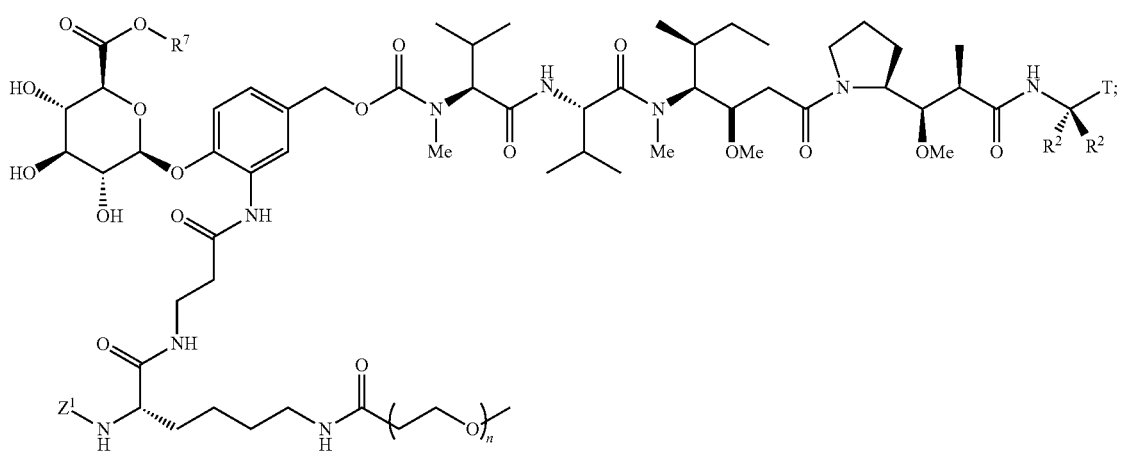

(d) contacting the compound of Formula 7 with an aqueous solution of a suitable base wherein said contacting removes the $Z^1$ amino and the carboxylic acid protective groups to provide a Drug Linker intermediate compound of Formula 8:

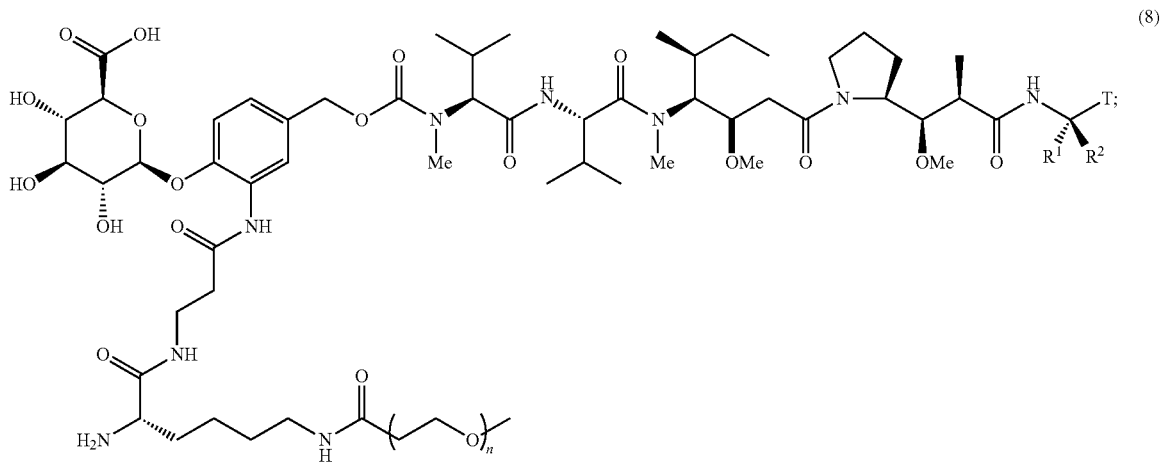

(e) contacting the Formula 8 Drug Linker intermediate compound in a suitable solvent with a compound of Formula v:

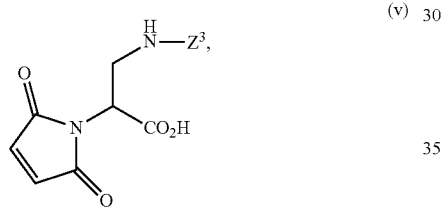

wherein $Z^3$ is a third suitable amino protecting group, in the presence of a second activating, wherein said Formula v contacting provides a Drug Linker intermediate compound of Formula 9:

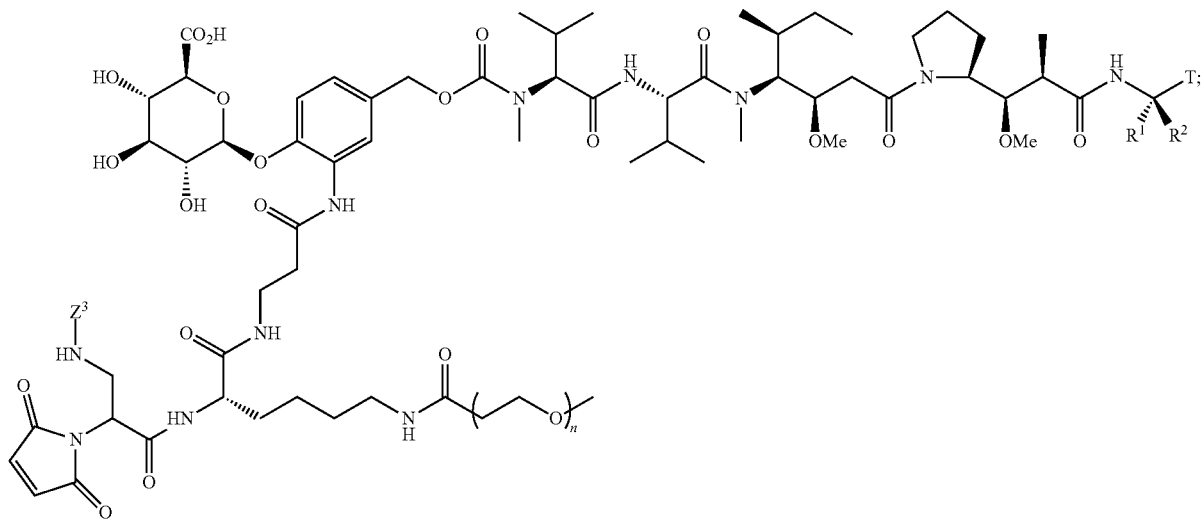

and (f) contacting the Formula 9 Drug Linker intermediate compound with a third deprotecting agent wherein said contacting removes the $Z^3$ amino protecting group to provide the Formula 10 Drug Linker compound.

In some preferred embodiments, the variable groups of a Formula 10 Drug Linker compound are as follows: $R_1$ is hydrogen or methyl, $R_2$ is hydrogen, and T is —CH(OR$_4$)—$R_5$, wherein $R_4$ is hydrogen or methyl and $R_5$ is $C_6$-$C_{10}$ aryl, e.g., an optionally substituted phenyl. More preferably, $R_1$ is methyl, $R_2$ is hydrogen, and T is CH(OH)Ph.

In some embodiments of the methods for preparing Formula 10 Drug Linker compounds, the Formula v compound has the following chemical structure:

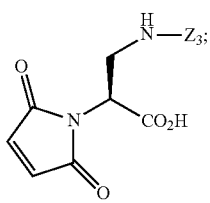

and the Formula 9 Drug Linker intermediate compound has the following chemical structure:

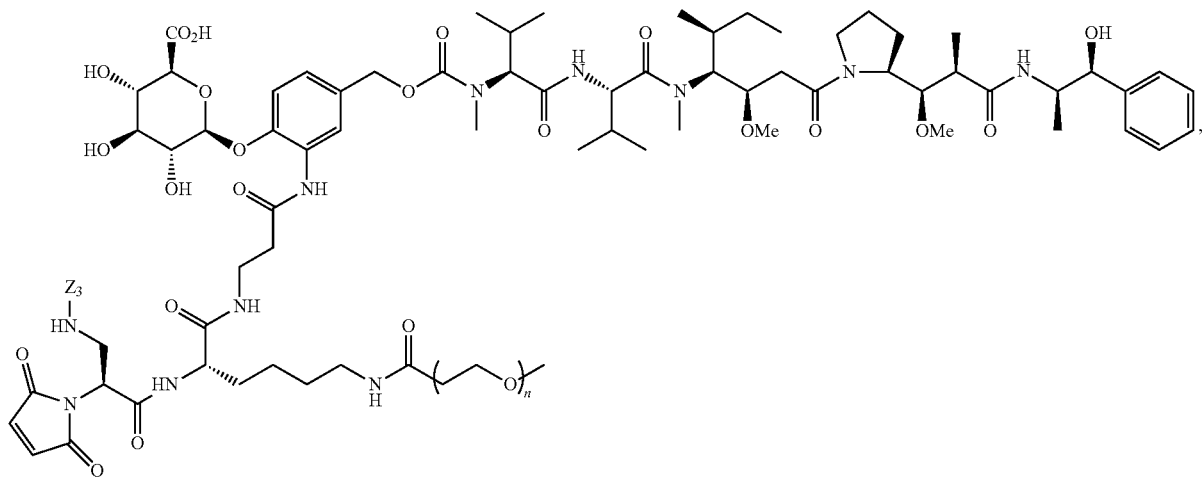

wherein the remaining variable groups are as previously defined.

In some embodiments of the methods for preparing Formula 10 Drug Linker compounds, the Formula v compound has the following chemical structure:

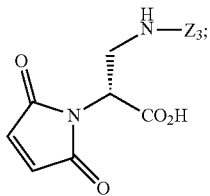

and the Formula 9 Drug Linker intermediate has the following chemical structure:
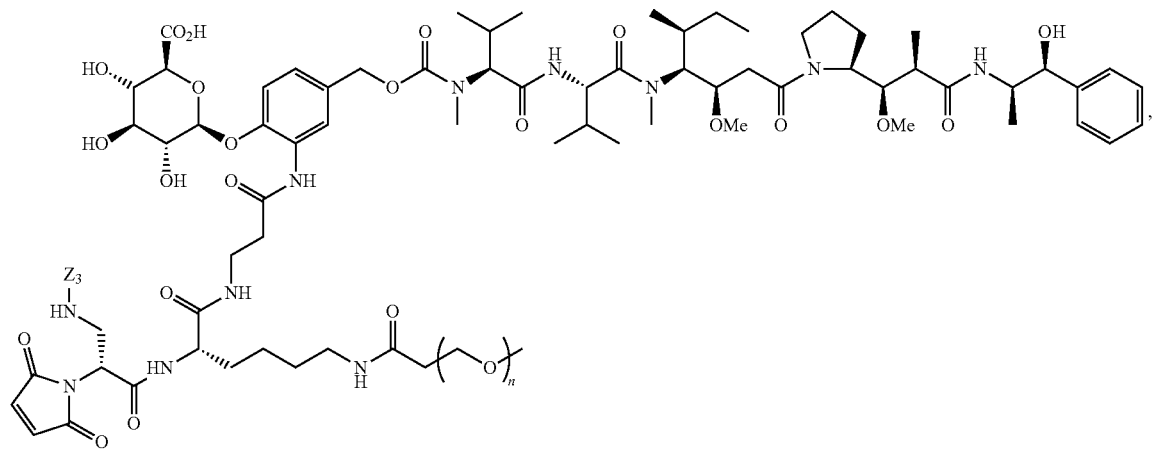
wherein the remaining variable groups are as previously defined.
In certain embodiments of the methods of the present invention, Formula 10 Drug Linker compound has the structure of Formula 10-(S) or Formula 10-(R):
10-(S)
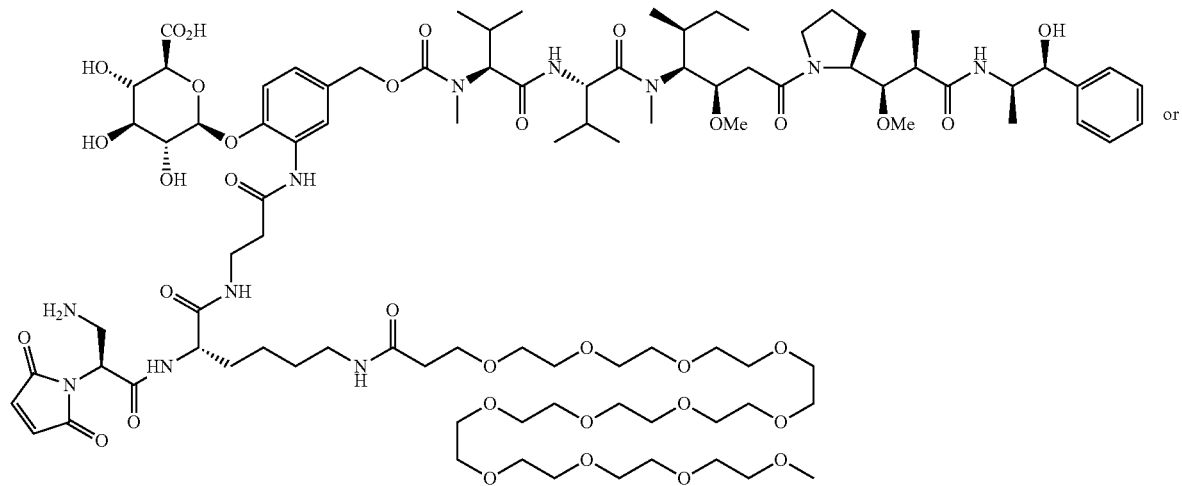
or -continued 10-(R)

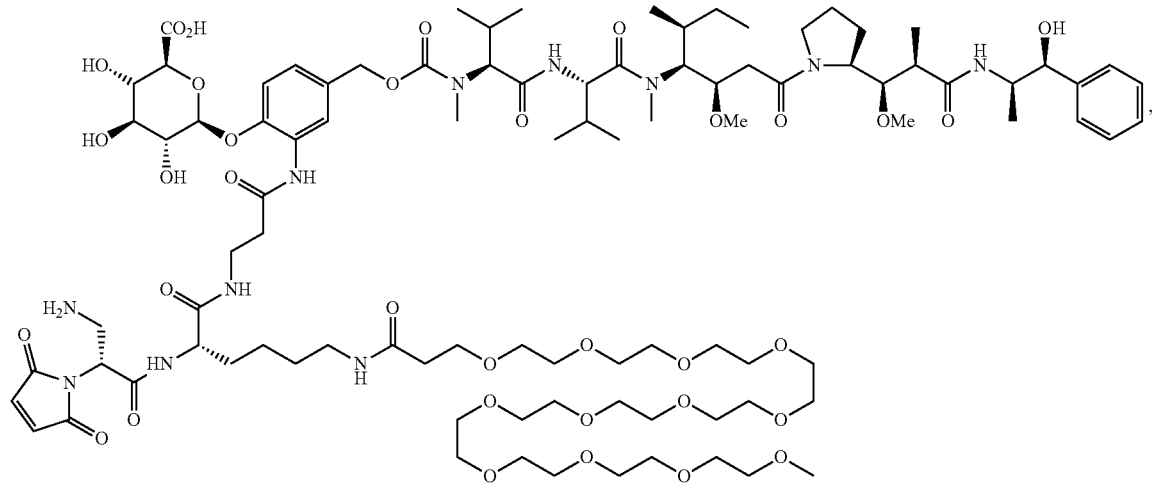

or their salts.

In certain embodiments of any one of the preceding methods, each $R^6$ of Drug Linker intermediate compounds of Formula IA, Formula IB, Formula IC, Formula IIA, Formula IIB, Formula IIC, Formula 4, Formula 5, and/or Formula 6 is $C_1$-$C_4$ alkyl. More preferably, each $R^6$ is methyl.

In certain embodiments of any one of the preceding methods, $R^7$ of Drug Linker intermediate compounds of Formula IA, Formula IB, Formula IC, Formula ID, Formula IIA, Formula IIB, Formula IIC, Formula IID, Formula 4, Formula 5, Formula 6, and/or Formula 7 is $C_1$-$C_4$ alkyl. More preferably, $R^7$ is methyl.

In particular preferred embodiments each of $R^6$ and $R^7$ of Drug Linker intermediate compounds of Formula IA, Formula IB, Formula IC, Formula IIA, Formula IIB, Formula IIC, Formula 4, Formula 5, and/or Formula 6 is $C_1$-$C_4$ alkyl. In those embodiments each of $R^6$ and $R^7$ is methyl is especially preferred In selected embodiments of the methods of the present invention, $L^1$ of compounds of Formula IA, Formula IB, Formula IC, Formula ID, Formula IE, and/or Formula I, is an optionally substituted $C_1$-$C_6$ alkylene or optionally substituted $C_4$-$C_{10}$ heteroalkylene, preferably, $L^1$ is a $C_1$-$C_6$ alkylene, and more preferably, $L^1$ is an unsubstituted $C_2$ alkylene.

In other selected embodiments of the methods of the present invention, $L^2$ of compounds of Formula I and/or Formula v is an optionally substituted $C_1$-$C_6$ alkylene or optionally substituted $C_4$-$C_{10}$ heteroalkylene. Preferably, $L^2$ is a substituted $C_1$-$C_6$ alkylene, and more preferably, $L^2$ is a methylene substituted with —$CH_2NH_2$ or $CH_2NHZ^3$, wherein $Z^3$ is an amino protecting group. In some preferred embodiments, $L^2$ is —$CH(CH_2NHBoc)$-.

In certain embodiments of the methods of the present invention, $L^3$ in compounds of Formula IA, Formula IB, Formula IC, Formula ID, Formula IE, and/or Formula I, is an optionally substituted $C_1$-$C_6$ alkylene or optionally substituted $C_4$-$C_{10}$ heteroalkylene. Preferably, $L^3$ is a $C_1$-$C_6$ alkylene, and more preferably, $L^3$ is unsubstituted $C_4$ alkylene, and even more preferably, $L^3$ is n-butylene.

In some embodiments of the methods of the present invention, the first amino protecting group $Z^1$ of Drug Linker intermediate compounds of Formula IA, Formula IB, Formula IC, Formula ID, Formula IIA, Formula IIB, Formula IIC, Formula IID, Formula 4, Formula 6 and/or Formula 7 is an amino protecting group that can be selectively removed by contacting the compound with a base. In some preferred embodiments, $Z^1$ is FMOC. A variety of bases can be used for removal of $Z^1$. Preferred bases include NaOH, KOH, $NaHCO_3$, and LiOH. Most preferably, the base is LiOH.

In selected embodiments of the methods of the present invention, the second amino protecting group $Z^2$ in compounds of Formula IIA and Formula 4 is an acid-labile amine protecting group. In certain preferred embodiments of these methods, $Z^2$ has the formula:

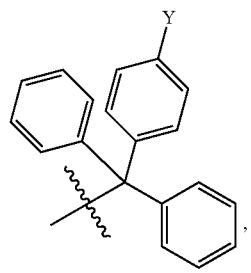

wherein Y is a H or —OMe; and the wavy line indicates the site of attachment to the remainder of the compound structure. Most preferably, $Z^2$ is MMTr (Y=—OMe).

Removal of the protecting group $Z^2$ can be carried out in any suitable manner. In some embodiments of the presently claimed methods, removal of $Z^2$ is achieved by contacting with an acid. Any suitable acid can be used, preferably having a pKa of between about 0 and about 3. More preferably, the acid is trichloroacetic acid or trifluoroacetic acid.

In selected embodiments of the methods of the present invention, $R^8$ of compound of Formula iv is an activated ester group.

An activated ester group, as used herein, is an ester group that can spontaneously react with an amino group to form an amide. In some embodiments, the activated ester group is selected from p-nitrophenyl, pentafluorophenyl, tetrafluorophenyl, and succinimido. In more preferred embodiments, the compound of Formula iv has the structure:

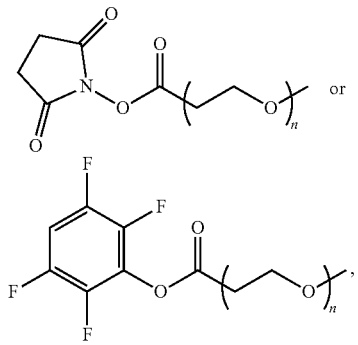

wherein n ranges from 2-24 or is an integer ranging from 2-24, preferably ranging from 8-16. Most preferably, n is 12.

In some embodiments of the presently claimed methods, when $R^8$ of the Formula iv compound is —COOH, said Formula iv contacting with a Drug Linker intermediate compound of Formula IB or Formula IIB is done in the presence of a suitable first activating agent. Preferably, said first activating agent is selected from a solution of N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy) dimethylamino-morpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N', N'-tetramethyluronium hexafluorophosphate, 2-Chloro-1-methylpyridinium iodide, or Propylphosphonic anhydride.

Any suitable solvent or a mixture of solvents can be used for contacting a Formula iv compound of with a Formula IB or Formula IIB Drug Linker intermediate compound. In some embodiments, the solvent is an aprotic solvent, which includes those selected from the group consisting of acetonitrile, THF, 2-methyl-THF, dichloromethane, dioxane, DMF, NMP and mixtures thereof. Preferably, the solvent comprises dichloromethane.

In selected embodiments of any of the preceding methods, the Grignard reagent has the formula of $R^gMgX$, wherein $R^g$ is $C_1$-$C_5$ alkyl or phenyl and X is I, Br, or Cl. In preferred embodiments, the Grignard reagent is MeMgI.

In certain embodiments of any of the preceding methods, the alkoxy magnesium halide has the formula of $R^gOMgX$, wherein $R^g$ is $C_1$-$C_5$ alkyl or phenyl and X is I, Br, or Cl. In preferred embodiments, the alkoxy magnesium halide is MeOMgCl.

In certain embodiments of the preceding methods, said Grignard reagent or alkoxy magnesium halide contacting with a Drug Linker intermediate compound of Formula IC, Formula IIC, or Formula 6 is done in a suitable alcohol-containing solvent. Preferably, the alcohol-containing solvent is comprised of a $C_1$-$C_4$ alcohol, more preferably, methanol or ethanol, and most preferably, methanol. In some embodiments, the suitable alcohol-containing solvent is a mixture of a $C_1$-$C_4$ alcohol with one or more other solvents other than an alcohol. Preferably, the other solvent is THF or 2-methyl-THF.

In some embodiments, said Grignard reagent or alkoxy magnesium halide contacting with a Drug Linker intermediate compound of Formula IC, Formula IIC, or Formula 6 is done in a 1:1 (V/V) mixture of methanol and 2-methyl-THF. In some embodiments, the Formula IC, Formula IIC, or Formula 6 Drug Linker intermediate compound is dissolved in a 1:1 (v/v) mixture of methanol and 2-methyl-THF or 1:1 (v/v) mixture of methanol and THF, and the Formula IC, Formula IIC, or Formula 6 Drug Linker intermediate compound solution is contacted by a Grignard reagent or alkoxy magnesium halide. In preferred embodiments, the alcohol-containing alkoxy magnesium halide solution is formed in situ by contacting a Grignard reagent in an alcohol-containing solvent, which is the contacted with the Formula IC, Formula IIC, or Formula 6 Drug Linker intermediate compound solution.

In method embodiments reciting step (c), contacting of a Drug Linker intermediate compound of Formula IC, Formula IIC, or Formula 6 with an alcohol-containing solution of a Grignard reagent or alkoxy magnesium halide produces a deprotected Drug Linker intermediate product of Formula ID, Formula IID, or Formula 7 in which the $R^6C(\!=\!O)$— hydroxyl protecting groups are removed by transesterification that contains less than about 10%, less than about 7 wt. %, less than about 6 wt. %, less than about 5 wt. %, less than about 4 wt. %, or less than about 3 wt. %, of an impurity as determined by HPLC comprising a beta-eliminated glucuronic acid moiety having the structure of:

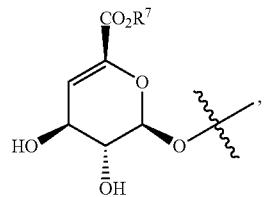

wherein the wavy line indicates the site of attachment to the phenyl moeity of a PAB (p-aminobenzyl) self-immolative Spacer Unit of a Drug Linker Intermediate compound of Formula ID, Formula IID, or Formula 7. In certain embodiments of the preceding methods, the product of contacting a Drug Linker intermediate compound of Formula IC, Formula IIC, or Formula 6 with a either Grignard reagent or alkoxy magnesium halide in a suitable alcohol-containing solvent is greater than about 90% pure, greater than about 93% pure, greater than about 94% pure, greater than about 95% pure, greater than about 96% pure, or greater than about 97% pure as determined by HPLC.

In some embodiments of the preceding methods, the product of contacting a Drug Linker intermediate compound of Formula IC, Formula IIC, or Formula 6 with an alcohol-containing Grignard reagent or alkoxy magnesium halide solution is contacted with a second deprotecting agent wherein said second deprotecting agent removes the $Z^1$ amino and the carboxylic acid protecting groups, wherein $Z^1$ and $R^7$ are as previously defined to provide a Drug Linker intermediate compound of Formula IE, Formula IIE, or Formula 8. Preferably, said second deprotecting agent contacting is done without isolation of the Drug Linker intermediate product of Formula ID, Formula IID, or Formula 7 of said Grignard reagent or alkoxy magnesium halide contacting. In some preferred embodiments, said Grignard reagent or alkoxy magnesium halide contacting and said second deprotecting agent contacting are done sequentially in one pot. In some preferred embodiments, the second deprotecting agent is an aqueous-containing solution of a base. Preferably, the base is LiOH.

In selected embodiments of the preceding methods, said Formula v contacting with a Drug intermediate compound of Formula IE, Formula IIE, and/or Formula 8 to provide a Drug Linker intermediate compound of Formula IIF or Formula 9, or a Drug Linker compound of Formula II, is done in the presence of a second activating agent. Preferably, the second activating agent is a solution of N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylamino-morpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, or Propylphosphonic anhydride. Preferably, the second activating agent is selected from a solution of EDC.HCl, EEDQ, and COMU. Most preferably, the activating agent is a solution of COMU.

In some embodiments of the preceding methods, the contacting of compound of Formula IE, Formula IIE, or Formula 8 with compound of Formula v is also done in the presence of a base. Any suitable base can be used to carry out this step. Preferably, the base is of the formula $(CH_3)_2C_5H_3N$, more preferably, the base is 2,6-lutidine.

In certain embodiments of the preceding methods, the compound of Formula 4 is prepared by the process comprising contacting the Formula 3:

(3)

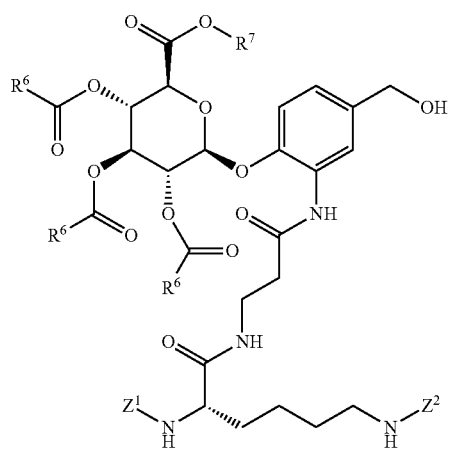

wherein all variable groups are as previously defined, in a suitable solvent with a compound of Formula iii:

(iii)

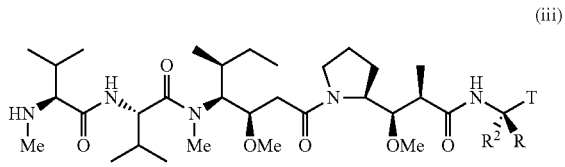

wherein all variable groups of the Formula iii compound are as previously defined by any one of the embodiments reciting that formula, with a carbamate coupling agent, wherein said contacting produces the Formula 4 Drug Linker intermediate compound.

In certain embodiments, the carbamate coupling agent is a solution of phosgene, trichloromethyl chloroformate (Diphosgene), bis(trichloromethyl) carbonate (Triphosgene), 1,1'-Carbonyldiimidazole (CDI), or 1,1'-Carbonyl-di-(1,2,4-triazole) (CDT). Preferably, the carbamate coupling agent is 1,1'-Carbonyl-di-(1,2,4-triazole) (CDT) solution.

In certain embodiments of the preceding methods, the Formula 3 Drug Linker intermediate compound is prepared by a process comprising contacting the compound of Formula 1:

(1)

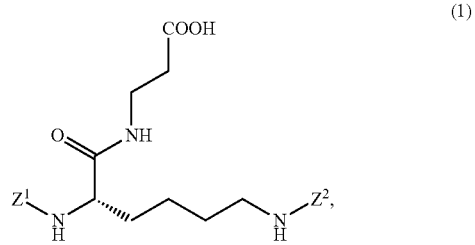

wherein all variable groups in the Formula 1 compound are as previously defined by any one of the embodiments reciting that compound, with a compound of Formula 2:

(2)

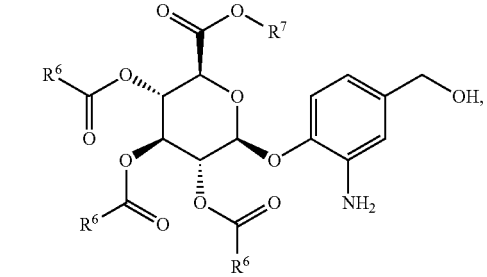

wherein all variable groups in Formula 2 are as previously defined by any one of the embodiments reciting that formula, with a third activating agent, wherein said third activating agent contacting provides a Drug Linker intermediate compound of Formula 3. Preferably, the third activating agent is a solution of: N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylaminomorpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethyl-imidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, or Propylphosphonic anhydride. More preferably, the activating agent is a solution of: EDC.HCl, EEDQ, or COMU, and most preferably, the activating agent is a solution of COMU.

Those and other aspects of the present invention may be more fully understood by reference to the following non-limiting numbered embodiments. Particular materials used, protocols and conditions are intended to be further illustrative of the inventions and should not be construed to limit the reasonable scope thereof.

NUMBERED EMBODIMENTS

The following numbered embodiments exemplify various aspects of the invention and are not intended to limit the invention in any manner.

1. A method for preparing a Drug Linker intermediate of Formula ID:

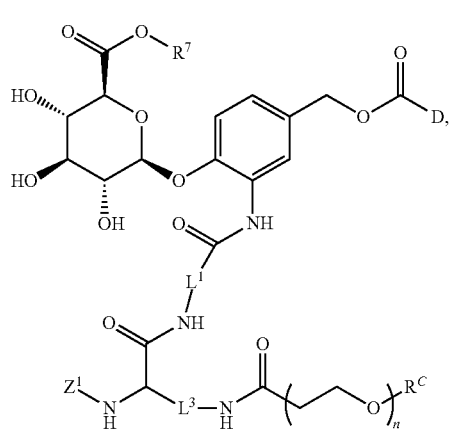

(ID)

or a salt thereof, wherein D is an auristatin Drug Unit; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $Z^1$ is a first suitable amino protecting group; $R^C$ is hydrogen or a PEG Capping Unit; and subscript n ranges from 2 to 24, the method comprising the step of: (c) contacting a compound of Formula IC with either a Grignard reagent or an alkoxy magnesium halide in a suitable alcohol-containing solvent, wherein the Formula IC compound has the structure of

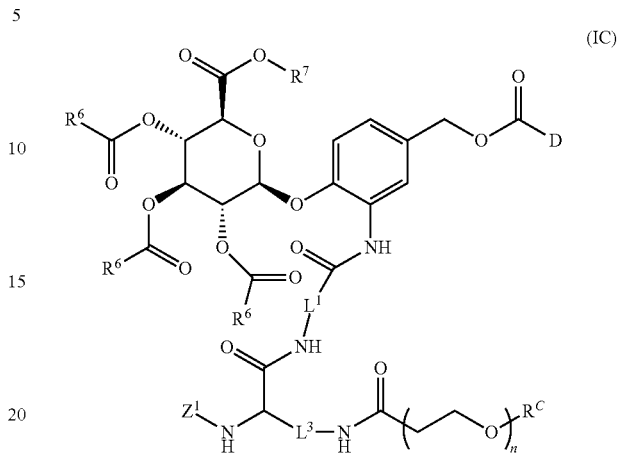

(IC)

wherein each of $R^6$ is independently optionally substituted $C_1$-$C_8$ alkyl, optionally substituted $C_6$-$C_{10}$ arylene or optionally substituted $C_5$-$C_{10}$ heteroarylene so that $R^6C$(=O)— provides for an ester functional group that is a suitable hydroxyl protecting group; and the remaining variable groups are as previously described; and wherein said Grignard reagent or an alkoxy magnesium halide contacting selectively removes the hydroxyl protecting groups to provide the Formula IC compound.

2. A method for preparing a Drug Linker intermediate of Formula IE:

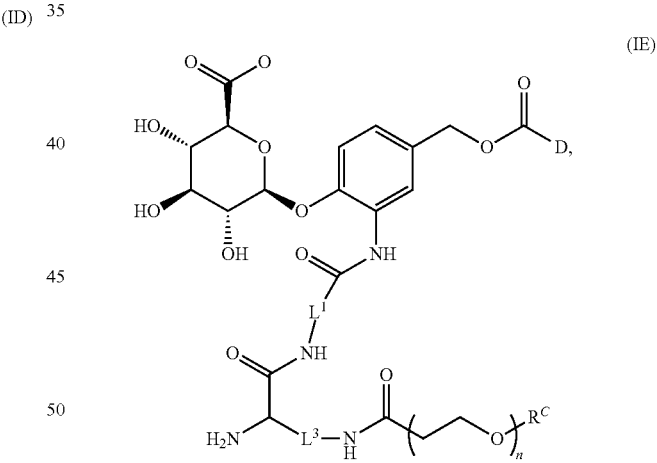

(IE)

or a salt thereof, wherein D is an auristatin Drug Unit; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $R^C$ is a hydrogen or a PEG Capping Unit; and subscript n ranges from 2 to 24, the method comprising the steps of: (c) contacting a Drug Linker intermediate compound of Formula IC with either a Grignard reagent or an alkoxy magnesium halide in a suitable alcohol-containing solvent, wherein the Formula IC Drug Linker intermediate compound has the structure of:

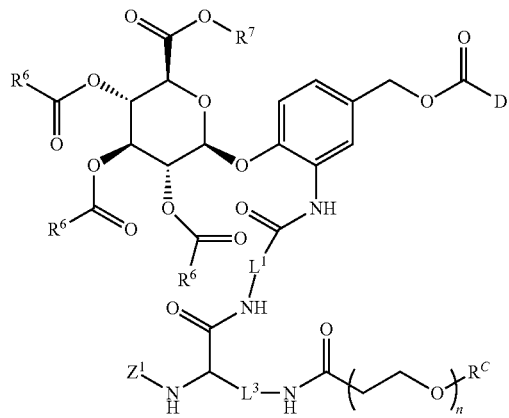

(IC)

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)—$ provides for an ester functional group that is a suitable hydroxyl protecting group and $—OR^7$ provides an ester functional group that is a suitable carboxylic acid protecting group; $Z^1$ is a first suitable amino protecting group; and the remaining variable groups are as previously defined, wherein said Grignard reagent or alkoxy magnesium halide contacting selectively removes the hydroxyl protecting groups; and (d) contacting the product of step (c) with a first deprotecting agent, wherein said first deprotecting agent contacting removes the $Z^1$ amino and carboxylic acid protecting groups to provide the Formula IE Drug Linker intermediate compound.

3. The method of embodiment 1 or 2, wherein each of $L^1$ and $L^3$ is independently $C_1$-$C_4$ alkylene.

4. The method of embodiment 1, wherein the Formula IC and Formula ID Drug Linker intermediate compounds have the structures of:

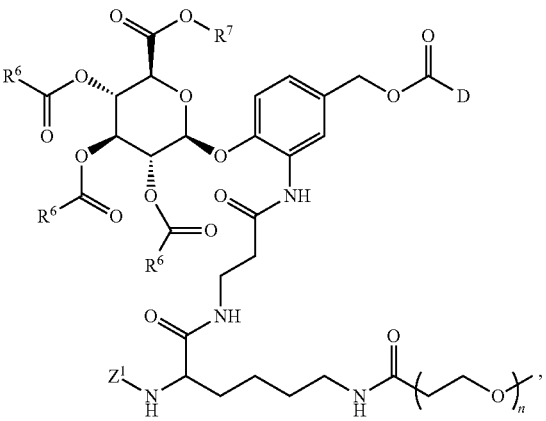

or salts thereof.

5. The method of embodiment 2, wherein the Formula IC and Formula IE Drug Linker intermediate compounds have the structures of:

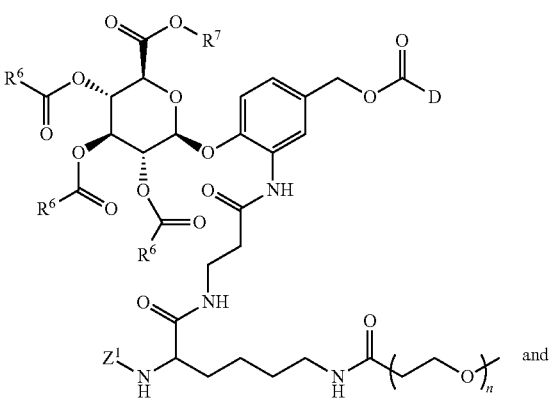

and

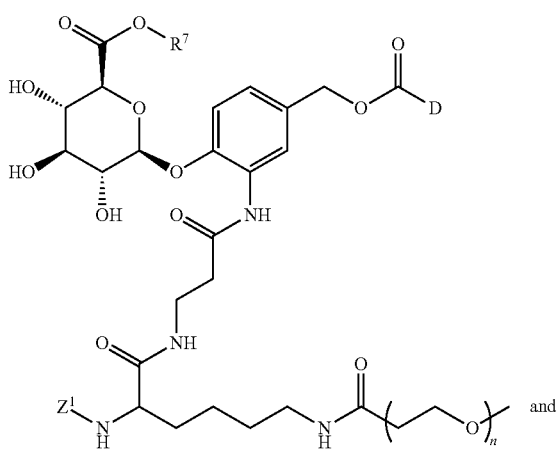

and

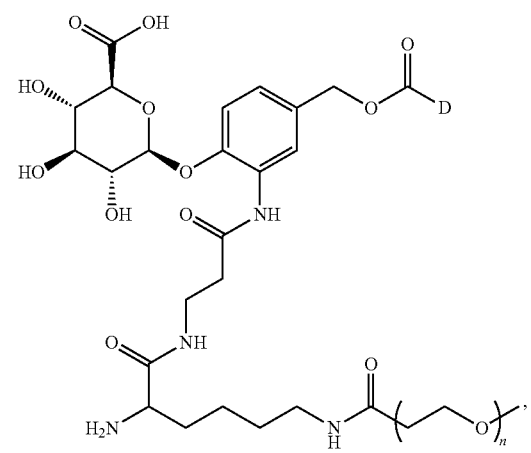

or salts thereof.

6. A method for preparing a Drug Linker compound of Formula I:

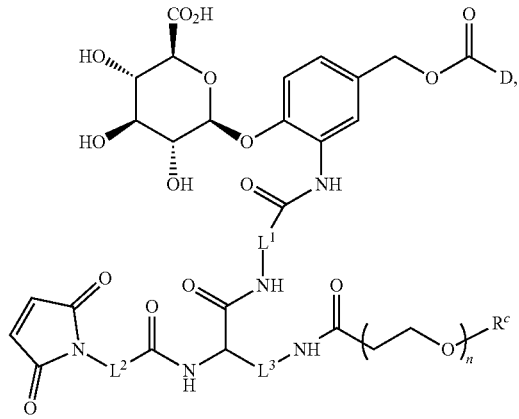

(I)

or a salt thereof, wherein D is an auristatin Drug Unit; each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is a hydrogen or a PEG Capping Unit; and subscript n ranges from 2 to 24, the method comprising the steps of: (a) contacting a Drug Linker intermediate of Formula IA with a second deprotecting agent, wherein the Formula IA Drug Linker intermediate compound has the structure of:

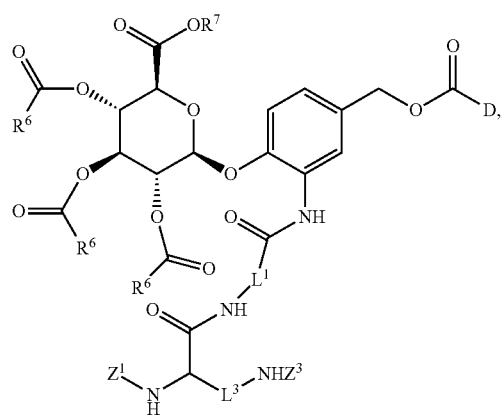

(IA)

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(\!=\!O)\!-\!$ provides for an ester functional group that is a suitable hydroxyl protecting group and $-\!OR^7$ provides an ester functional group that is a suitable carboxylic acid protecting group; each of $Z^1$ and $Z^2$ is independently a first and second suitable amino protecting group, respectively; and the remaining variable groups as previously defined, wherein said second deprotecting agent contacting selectively removes the $Z^2$ amino protecting group to provide a Drug Linker intermediate compound of Formula IB:

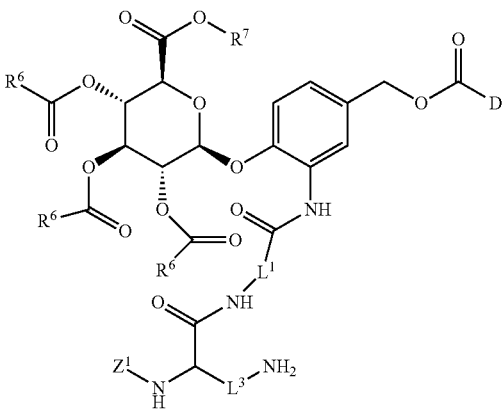

(IB)

or a salt thereof, wherein the variable groups are as previously defined; (b) contacting the Formula IB compound in a suitable solvent with a compound of Formula iv:

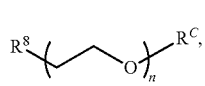

(iv)

wherein $R^8$ is an activated ester group; and the remaining variable groups are as previously defined, or (b') contacting the Formula IB Drug Linker intermediate compound in a suitable solvent with a Formula iv compound in which $R^8$ is —COOH and the remaining variable groups are as previously defined in the presence of a first activating agent, wherein said contacting step (b) or (b') provides a Drug Linker intermediate compound of Formula IC:

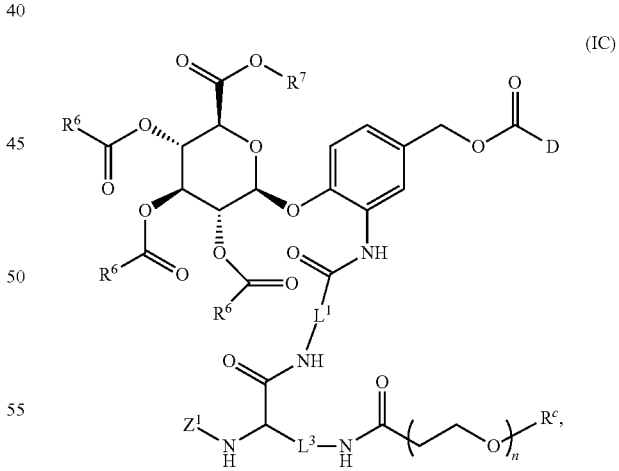

(IC)

or a salt thereof, wherein the variable groups are as previously defined; (c) contacting the Formula IC Drug Linker intermediate compound with either a Grignard reagent or an alkoxy magnesium halide in a suitable alcohol-containing solvent, wherein said Grignard reagent or an alkoxy magnesium halide contacting selectively removes the hydroxyl protecting groups to provide a Drug Linker intermediate compound of Formula ID:

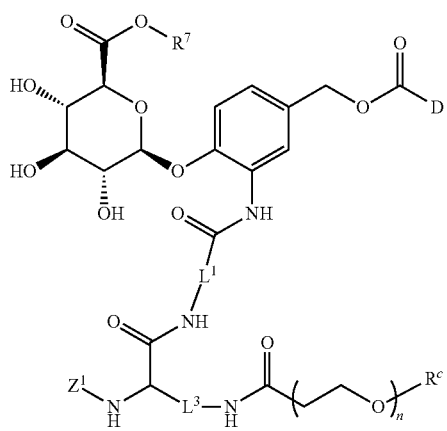

(ID)

or a salt thereof, wherein the variable groups are as previously defined; (d) contacting the Formula ID Drug Linker intermediate compound with a first deprotecting agent, wherein said first deprotecting agent contacting removes the $Z^1$ amino and carboxylic acid protecting groups to provide a Drug Linker intermediate compound of Formula IE:

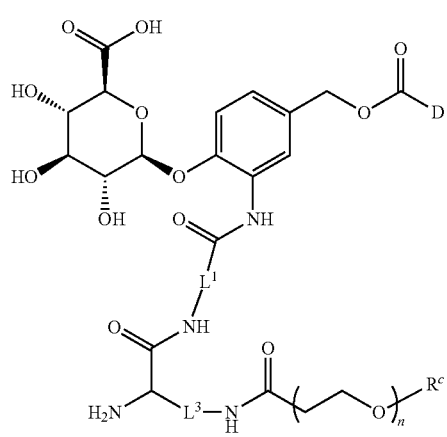

(IE)

or a salt thereof, wherein the variable groups are as previously defined; and (e) contacting the Formula IE Drug Linker intermediate compound in a suitable solvent with a compound of Formula v:

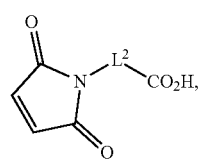

(v)

or a salt thereof, wherein $L^2$ is as previously defined, in the presence of a second activating agent; and wherein said Formula v contacting provides the Formula I Drug Linker compound or salt thereof.

7. The method of embodiment 6 wherein each of $L^1$ and $L^3$ is independently $C_1$-$C_4$ alkylene and $L^2$ is independently optionally substituted $C_1$-$C_4$ alkylene.

8. A method for preparing a Drug Linker compound of Formula II:

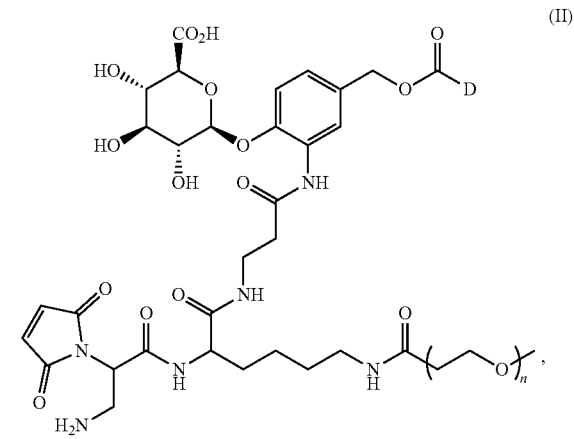

(II)

or a salt thereof, wherein D is an auristatin Drug Unit; and subscript n ranges from 2 to 24, the method comprising the steps of: (a) contacting a Drug Linker intermediate compound of Formula IIA with a second deprotecting agent wherein the Formula IIA Drug Linker intermediate compound has the structure of:

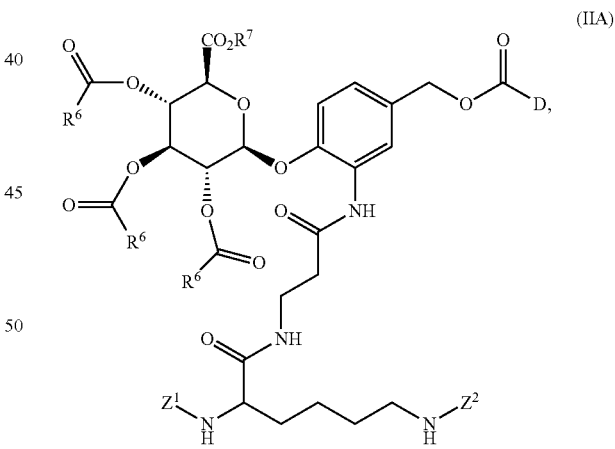

(IIA)

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; each of $Z^1$ and $Z^2$ is independently a first and second suitable amino protecting group, respectively, wherein said first deprotecting agent contacting provides a Drug Linker intermediate compound of Formula IIB:

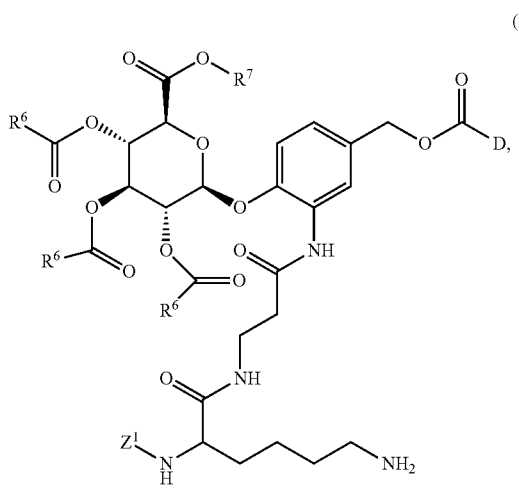

(IIB)

or a salt thereof, wherein the variable groups are as previously defined; (b) contacting the Formula IIB Drug Linker intermediate compound in a suitable solvent with a compound of Formula iv:

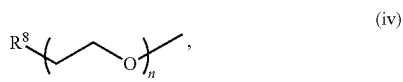

(iv)

wherein $R^8$ is an activated ester; and subscript n is as previously defined, or (b') contacting the Formula IIB Drug Linker intermediate compound in a suitable solvent with a Formula iv compound in which $R^8$ is —COOH and subscript n is a previously defined in the presence of a first activating agent; wherein said contacting of step (b) or (b') provides a Drug Linker intermediate compound of Formula IIC:

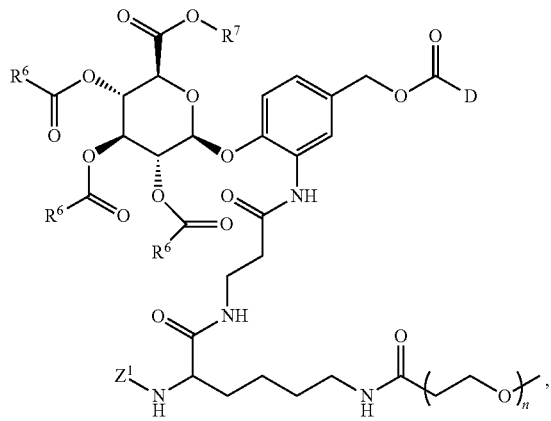

(IIC)

or a salt thereof, wherein the variable groups are as previously defined; (c) contacting the Formula IIC Drug Linker intermediate compound with either a Grignard reagent or an alkoxy magnesium halide in a suitable alcohol-containing solvent, wherein said Grignard reagent or an alkoxy magnesium halide contacting selectively removes the hydroxyl protecting groups to provide a Drug Linker intermediate compound of Formula IID:

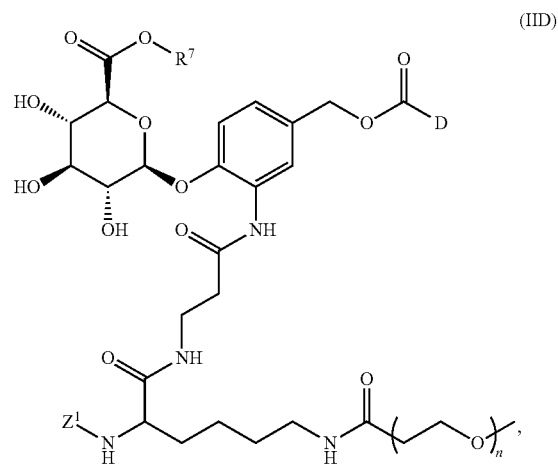

(IID)

or a salt thereof, wherein the variable groups are as previously defined; (d) contacting the Formula IID Drug Linker intermediate compound with a second deprotecting agent, wherein said second deprotecting agent contacting removes the amine and carboxylic acid protecting groups to provide a Drug Linker intermediate compound of Formula IIE:

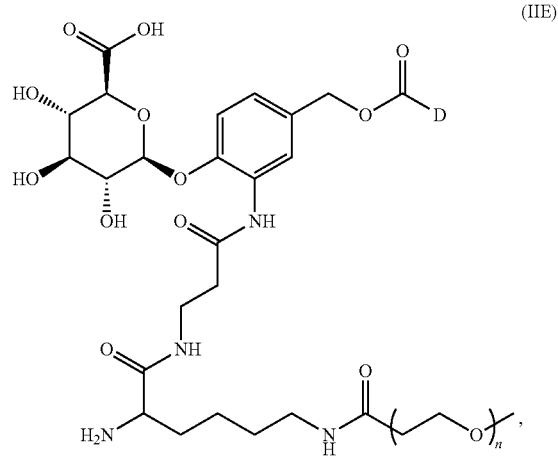

(IIE)

or a salt thereof, wherein the variable groups are as previously defined; (e) contacting the Formula IIE Drug Linker intermediate compound with a compound of Formula v:

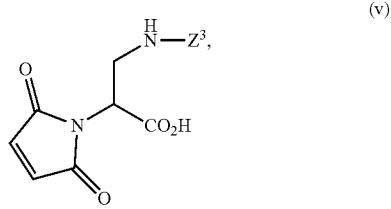

(v)

wherein $Z^3$ is a third suitable amino protecting group, in the presence of a second activating agent to form a Drug Linker intermediate compound of Formula IIF:

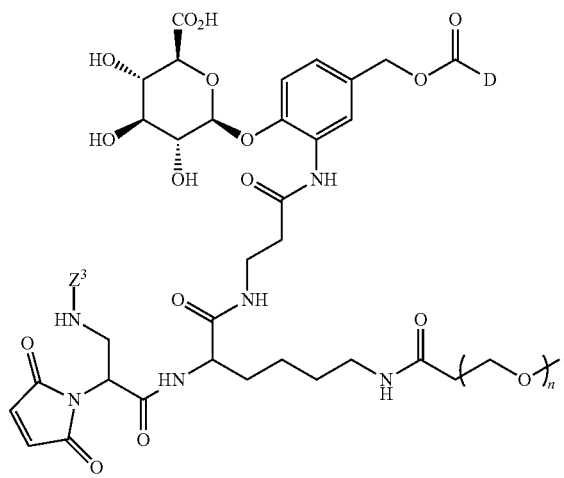

(IIF)

or a salt thereof, wherein the variable groups are as previously defined; and (d) contacting the Formula IIF Drug Linker intermediate compound of with a third deprotecting agent, wherein said third deprotecting reagent contacting removes the $Z^3$ amino protecting group whereby the Formula II Drug Linker compound or salt thereof is provided.

9. The method of embodiment 8 wherein $Z^3$ is an third amino protecting group that is acid-labile, in particular —C(=O)O-t-Bu.

10. The method of any one of embodiments 1-9, wherein the auristatin Drug Unit (D) has the structure of:

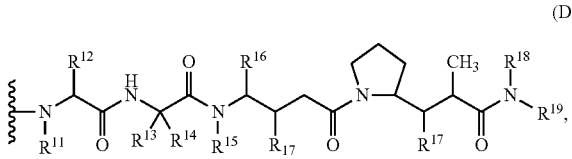

(D)

wherein the wavy line indicates covalent bonding of D to the remainder of the Formula II Drug Linker compound; $R^{11}$ is selected from the group consisting of H and $C_1$-$C_8$ alkyl; $R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); $R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); $R^{14}$ is selected from the group consisting of H and methyl, or $R^{13}$ and $R^{14}$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle, and n is selected from the group consisting of 2, 3, 4, 5 and 6; $R^{15}$ is selected from the group consisting of H and $C_1$-$C_8$ alkyl; $R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); each $R^{17}$ is independently selected from the group consisting of H, OH, $C_1$-$C_8$ alkyl, $C_3$-$C_8$ carbocycle, and O—($C_1$-$C_8$ alkyl); $R^{18}$ is selected from the group consisting of H and $C_1$-$C_8$ alkyl; $R^{19}$ is selected from the group consisting of —$C(R^{17})_2$—$C(R^{17})_2$-aryl, —$C(R^{17})_2$—$C(R^{17})_2$—($C_3$-$C_8$ heterocycle), —$C(R^{17})_2$—$C(O)$—$ZR^{20}$, and —$C(R^{17})_2$—$C(R^{17})_2$—($C_3$-$C_8$ carbocycle); Z is —O—, or —NH—; and $R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl.

11. The method of embodiment 10, wherein the auristatin Drug Unit (D) has the structure of Formula $D_{E-1}$, $D_{E-2}$, or $D_{F-1}$:

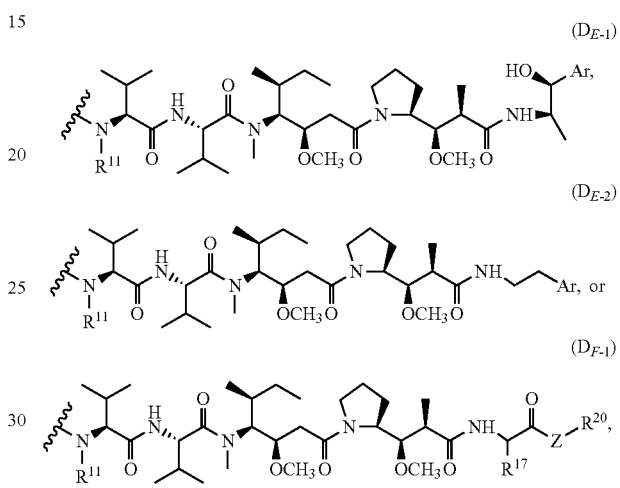

wherein Ar is optionally substituted $C_6$-$C_{10}$ aryl or optionally substituted $C_3$-$C_8$ heterocyclyl.

12. The method of embodiment 11, wherein D has the structure of Formula $D_{E-1}$.

13. The method of embodiment 11, wherein D has the structure of Formula $D_{E-2}$.

14. The method of embodiment 11, wherein D has the structure of Formula $D_{F-1}$.

15. The method of embodiment 12 or 13, wherein Ar is optionally substituted phenyl or optionally substituted 2-pyridyl.

16. The method of embodiment 14, wherein —Z— is —O— and $R^{20}$ is $C_1$-$C_4$ alkyl.

17. The method of embodiment 14, wherein Z is —NH— and $R^{20}$ is optionally substituted phenyl or optionally substituted $C_5$-$C_6$ heteroaryl.

18. The method of any one of embodiments 10-17, wherein $R^{11}$ is methyl.

19. The method of embodiment 10, wherein D has the structure of Formula $D_{F/E-3}$:

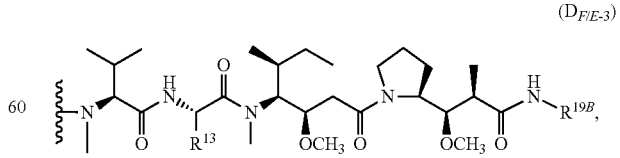

($D_{F/E-3}$)

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-

CH$_2$CH$_2$SCH$_3$, CH(CH$_2$CH$_2$SCH$_3$)C(=O)NH-3-quinolyl, or —CH(CH$_2$Ph)C(=O)NH-p-Cl-Ph.

20. The method of embodiment 10, wherein D has the structure of:

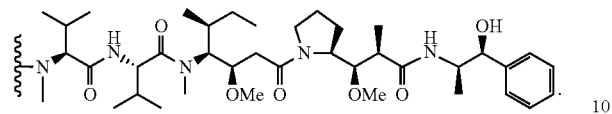

21. A method for preparing a Drug Linker intermediate of Formula 8 having the structure of:

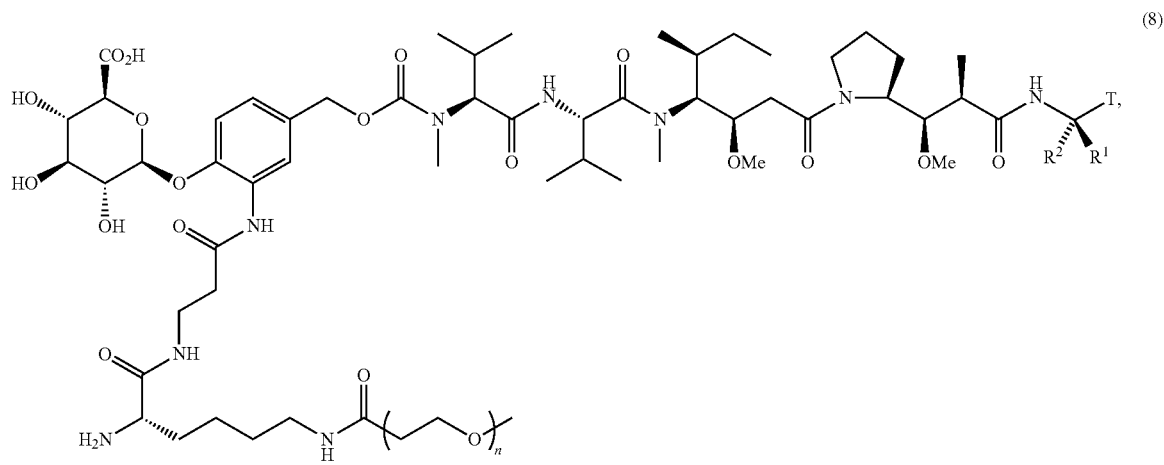

(8)

or a salt thereof, wherein subscript n ranges from 2 to 24; $R^1$ is H or $C_1$-$C_4$ alkyl; $R^2$ is H, $C_1$-$C_4$ alkyl or —CH$_2$—$R^3$; $R^3$ is $C_6$-$C_{10}$ aryl or $C_3$-$C_8$ heterocyclyl; and T is selected from the group consisting of —CH(OR$^4$)—R$^5$ and —C(=O)—OR$^4$, wherein $R^4$ is H or $C_1$-$C_4$ alkyl; and $R^5$ is $C_6$-$C_{10}$ aryl or $C_3$-$C_6$ heteroaryl, the method comprising the steps of: (c) contacting a Drug Linker intermediate compound of Formula 6 in a suitable solvent with either a Grignard reagent or an alkoxy magnesium halide in a suitable alcohol-containing solvent, wherein the Formula 6 Drug Linker intermediate compound has the structure of:

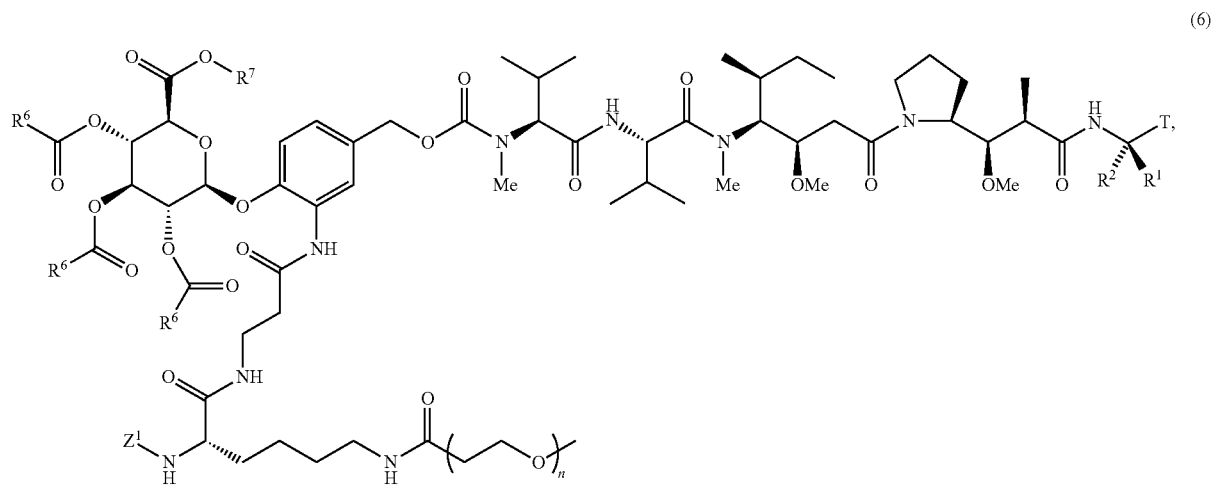

(6)

wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(\!=\!O)$— provides for an ester functional group that is a suitable hydroxyl protecting group and —$OR^7$ provides an ester functional group that is a suitable carboxylic acid protecting group; $Z^1$ is a first suitable amino protecting group; and the remaining variable groups are as previously defined; and (d) contacting the product of step (c) with first deprotecting agent wherein the first deprotecting agent is an aqueous solution of a base, wherein steps (c) and (d) provide the Formula 8 Drug Linker intermediate compound.

22. A method for preparing a Drug Linker compound of Formula 10 having the structure of:

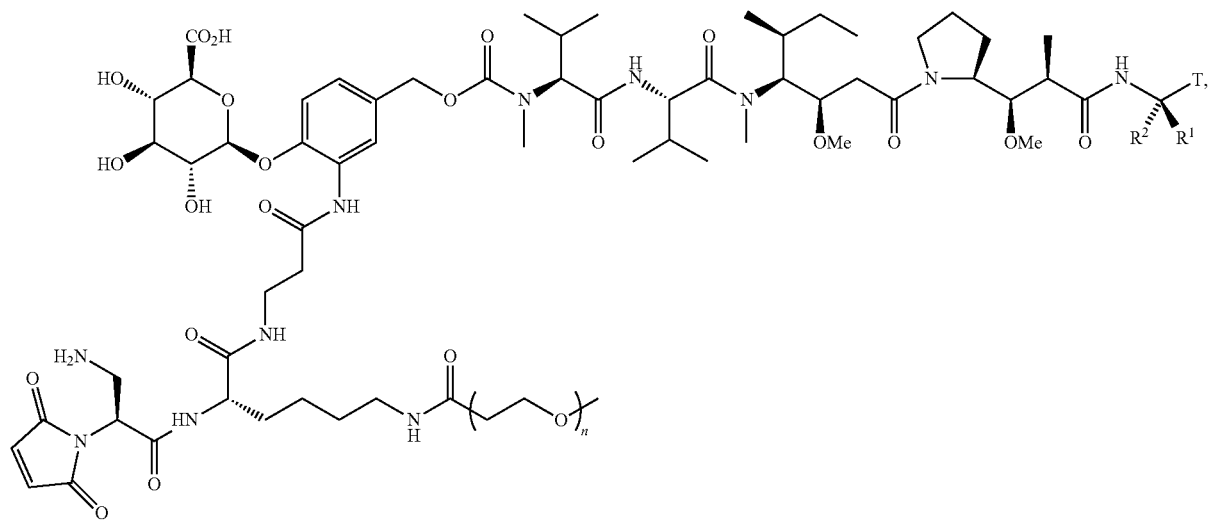

(10)

or a salt thereof, wherein subscript n ranges from 2 to 24; $R^1$ is H or $C_1$-$C_4$ alkyl; $R^2$ is H, $C_1$-$C_4$ alkyl or —$CH_2$—$R^3$; $R^3$ is $C_6$-$C_{10}$ aryl or $C_3$-$C_8$ heterocyclyl; and T is selected from the group consisting of —$CH(OR^4)$—$R^5$ and —$C(\!=\!O)$—$OR^4$, wherein $R^4$ is H or $C_1$-$C_4$ alkyl; and $R^5$ is $C_6$-$C_{10}$ aryl or $C_3$-$C_6$ heteroaryl, the method comprising the steps of: (a) contacting a Drug Linker intermediate compound of Formula 4 with a second deprotecting agent, wherein the Formula 4 Drug Linker intermediate compound has the structure of

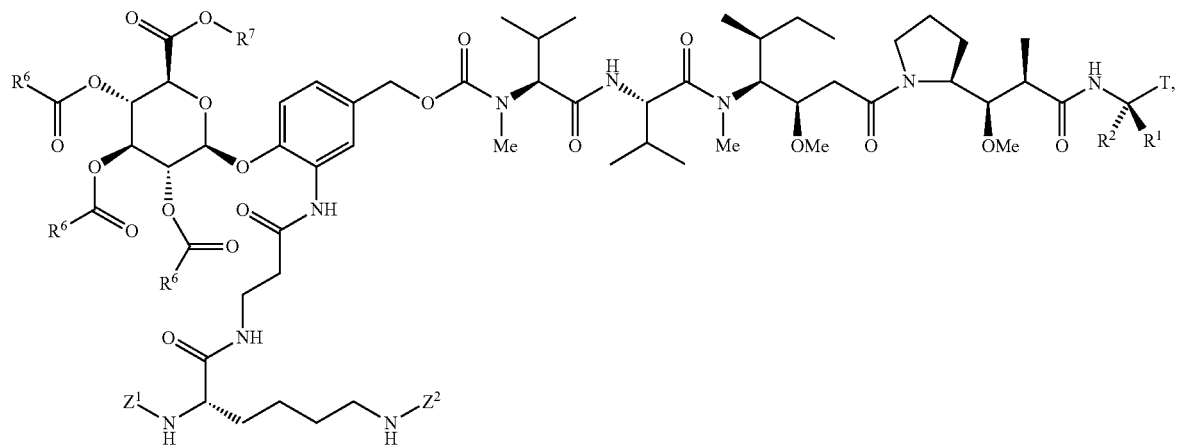

(4)

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; each of $Z^1$ and $Z^2$ is independently a first and second suitable amino protecting group, respectively; and the remaining variable groups are as previously defined, wherein said second deprotecting agent contacting selectively removes the $Z^2$ amino protecting group to provide a Drug Linker intermediate compound of Formula 5:

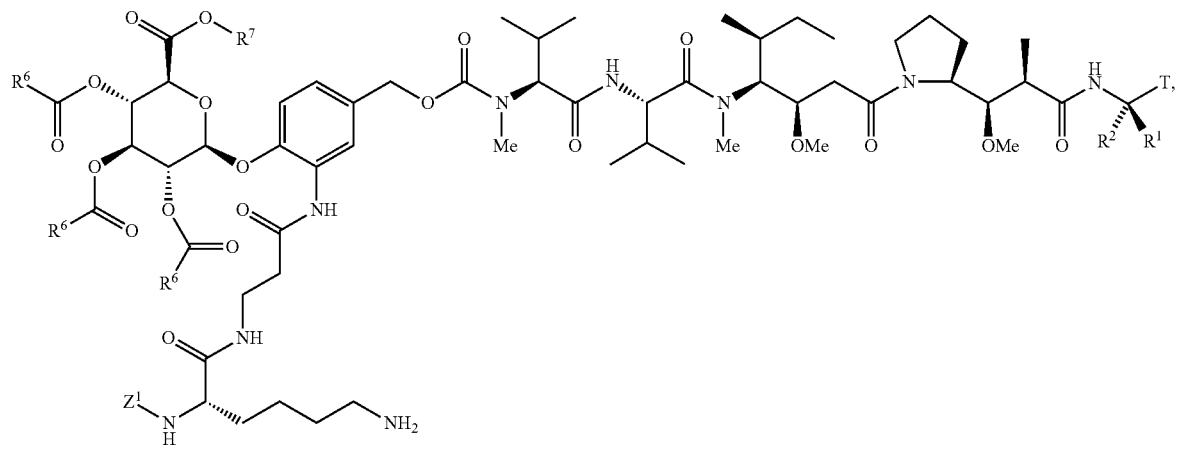

(5)

or a salt thereof, wherein the variable groups are as previously defined; (b) contacting the Formula 5 Drug Linker intermediate compound in a suitable solvent with a compound of Formula iv:

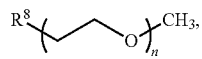

(iv)

wherein $R^8$ is an activated ester; and subscript n is as previously defined, or (b') contacting a Formula IB Drug Linker intermediate compound in a suitable solvent with a Formula iv compound in which $R^8$ is —COOH and subscript n is as previously defined in the presence of a first activating agent, wherein said contacting of step (b) or (b') provides a Drug Linker intermediate compound of Formula 6:

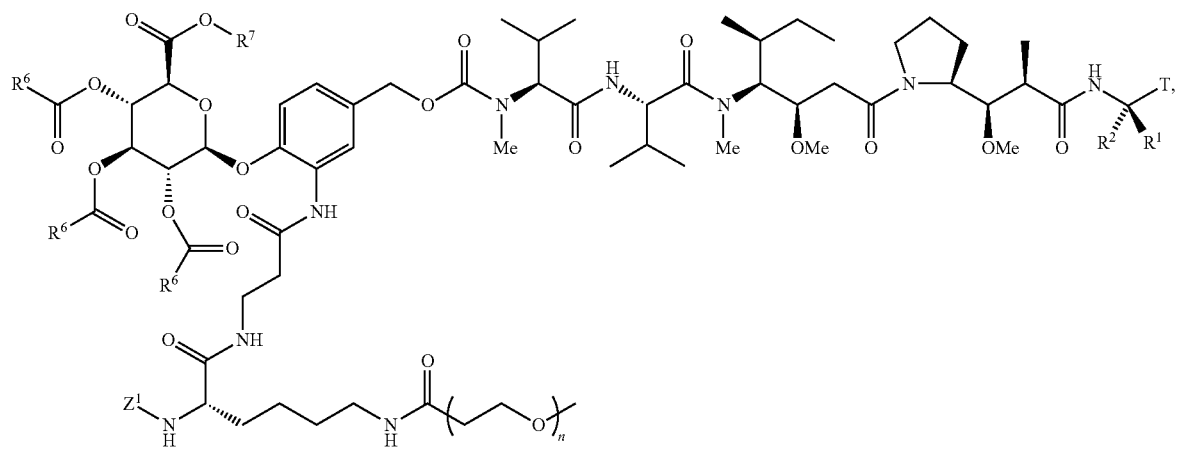

(6)

or a salt thereof, wherein the variable groups are as previously defined; (c) contacting the Formula 6 Drug Linker intermediate compound in a suitable solvent with either a Grignard reagent or an alkoxy magnesium halide in a suitable alcohol-containing solvent; (d) contacting the product of step (c) with a first deprotecting agent wherein the first deprotecting agent is an aqueous solution of a base, wherein steps (b) and (c) provide a Drug Linker intermediate compound of Formula 8, wherein the Formula 8 Drug Linker intermediate compound has the structure of:

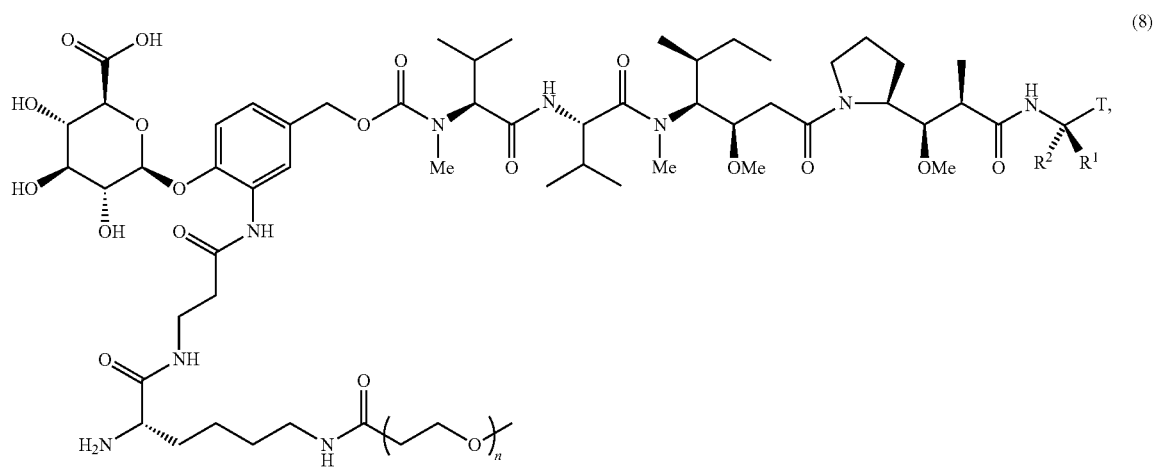

or a salt thereof, wherein the variable groups are as previously defined; (e) contacting the Formula 8 Drug Linker intermediate compound in a suitable solvent with a compound of Formula v:

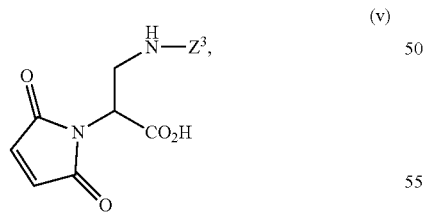

or salt thereof, wherein $Z^3$ is a third suitable amino protecting group, in the presence of a second activating agent, wherein said Formula v contacting provides a Drug Linker intermediate compound of Formula 9:

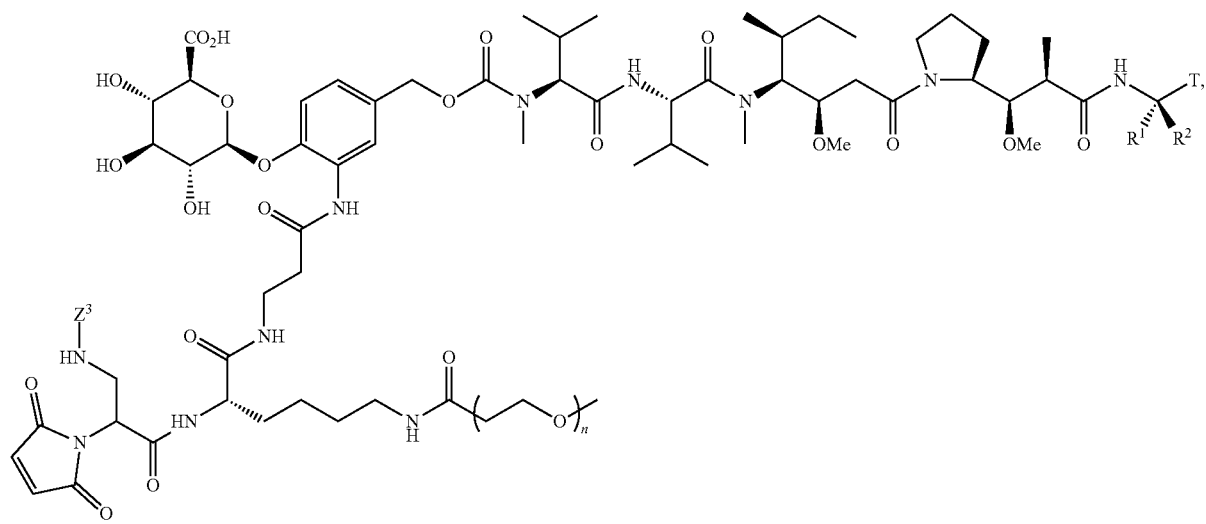

or a salt thereof, wherein the variable groups are as previously defined; and (f) contacting the Formula 9 Drug Linker intermediate compound with a third deprotecting agent wherein said third deprotecting agent contacting removes the $Z^3$ amino protecting group whereby the Formula 10 Drug Linker compound or salt thereof is provided.

23. The method of embodiment 21 or 22, wherein $R^1$ is H or methyl, $R^2$ is H, and T is —CH(OR$^4$)—R$^5$, wherein $R^4$ is H or methyl and $R^5$ is $C_6$-$C_{10}$ aryl.

24. The method of embodiment 21 or 22, wherein $R^1$ is methyl, $R^2$ is H, and T is —CH(OH)Ph.

25. The method of any one of embodiments 1-24, wherein $Z^1$ has the formula:

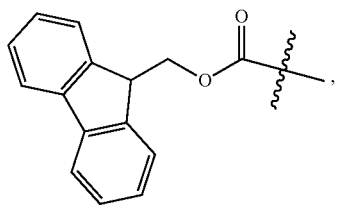 [SMILES: *C(=O)OCC1c2ccccc2-c2ccccc21]

wherein the wavy line indicates the site of attachment to the remainder of the compound structure.

26. The method of any one of embodiments 6-25, wherein $Z^2$ has the formula

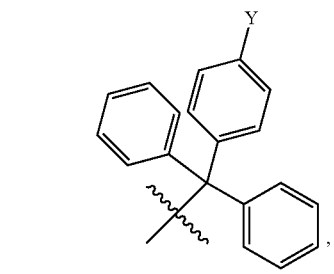

wherein Y is a H or OMe; and the wavy line indicates the site of attachment to the remainder of the compound structure.

27. The method of embodiment 26, wherein Y is —OMe.

28. The method of embodiment 22, wherein the Formula v compound has the structure of:

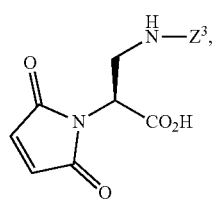

(v)

or a salt thereof: the Formula 9 Drug linker intermediate has the structure of:

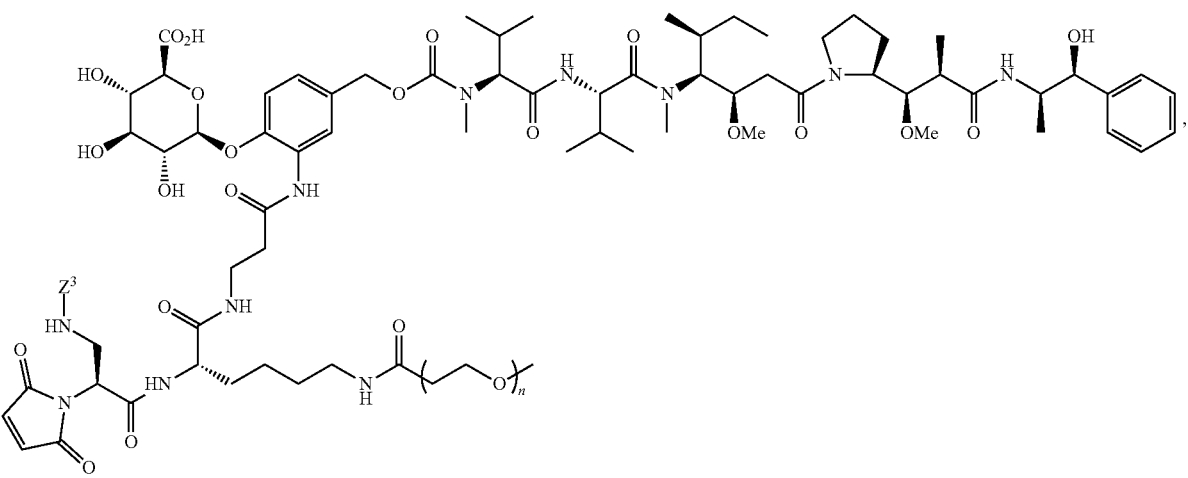
or a salt thereof; and the Formula 10 Drug Linker compound has the structure of:
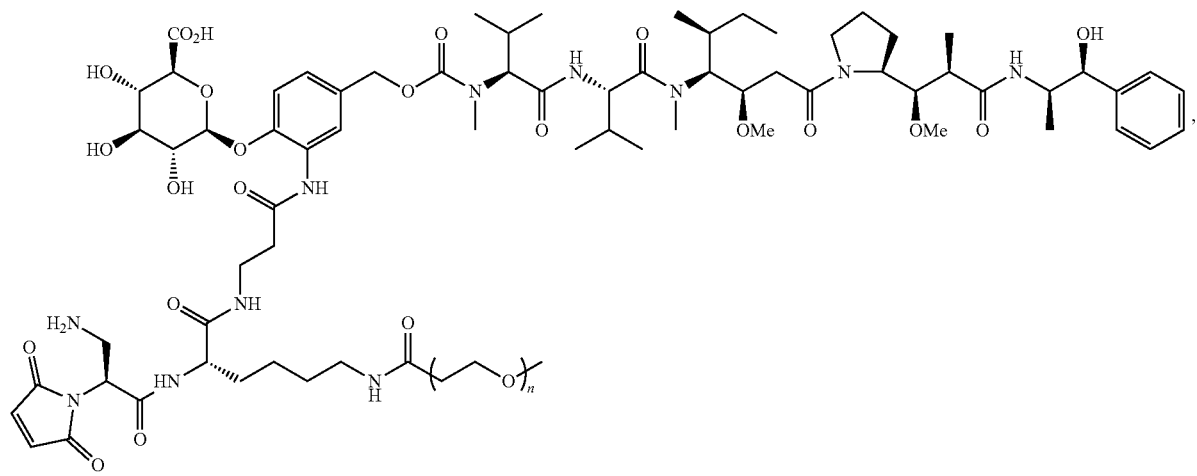
or a salt thereof.
29. The method of embodiment 22, wherein the Formula v compound has the structure of:
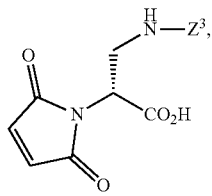
or a salt thereof; the Formula 9 Drug Linker intermediate compound has the structure of:

105

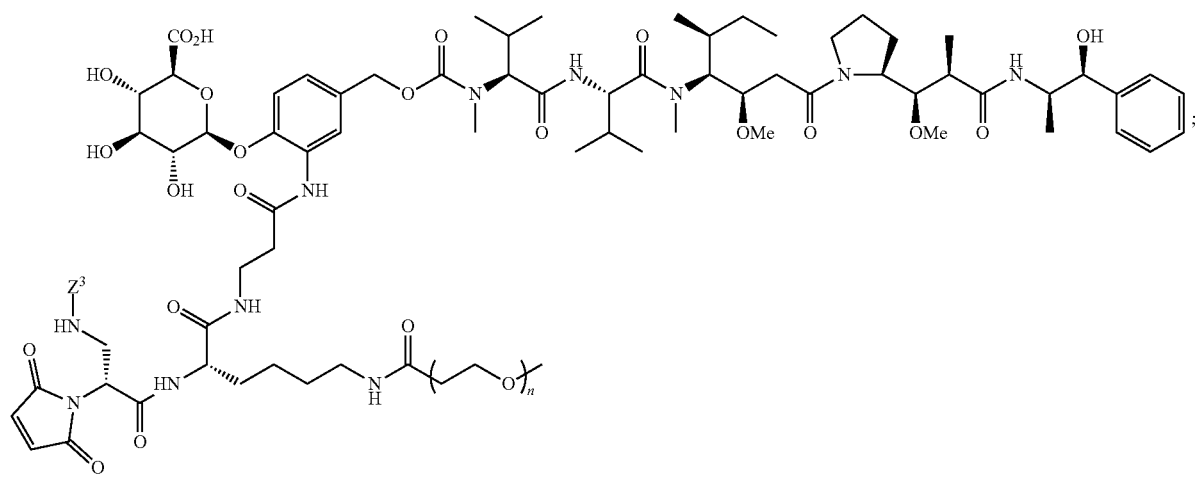

and the Drug Linker compound of Formula 10 has the structure of:

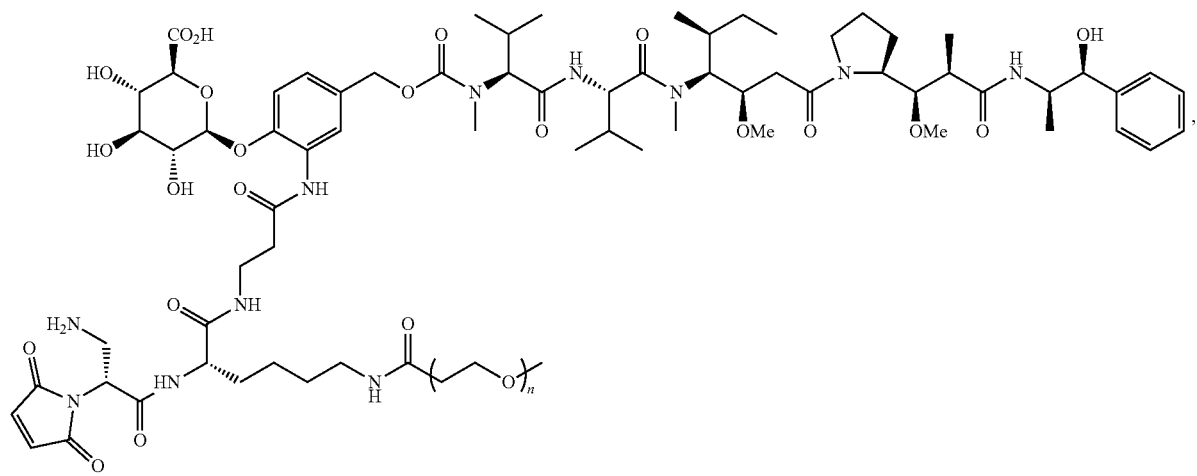

or a salt thereof.

30. The method of any one of embodiments 22-29 wherein $Z^3$ is —C(=O)O-t-Bu.

31. The method of any one of embodiments 1-30, wherein each of $R^6$ and $R^7$ is independently $C_1$-$C_4$ alkyl.

32. The method of embodiment 31, wherein each of $R^6$ and $R^7$ is methyl or ethyl, in particular both are methyl.

33. The method of any one of embodiments 6-32, wherein the Formula iv compound has the structure of:

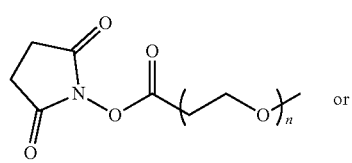

106

-continued

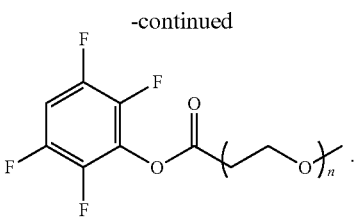

34. The method of any one of embodiments 1-33, wherein subscript n ranges from 8 to 16.

35. The method of embodiment 34, wherein subscript n is 12.

36. The method of embodiment 26, wherein the Formula 10 compound the structure of:

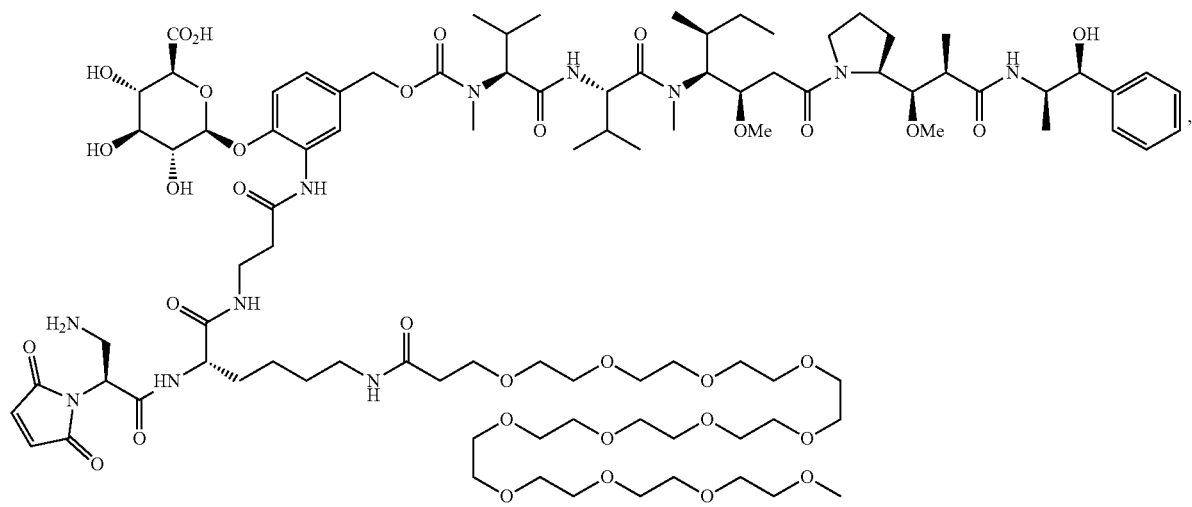 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c(NC(=O)CCNC(=O)[C@H](CCCCNC(=O)CCOCCOCCOCCOCCOCCOCCOCCOCCOCCOCCOCCOC)NC(=O)[C@H](CN)N2C(=O)C=CC2=O)c1)C(C)C]

or a salt thereof.

37. The method of embodiment 27, wherein the Formula 10 compound has the structure of:

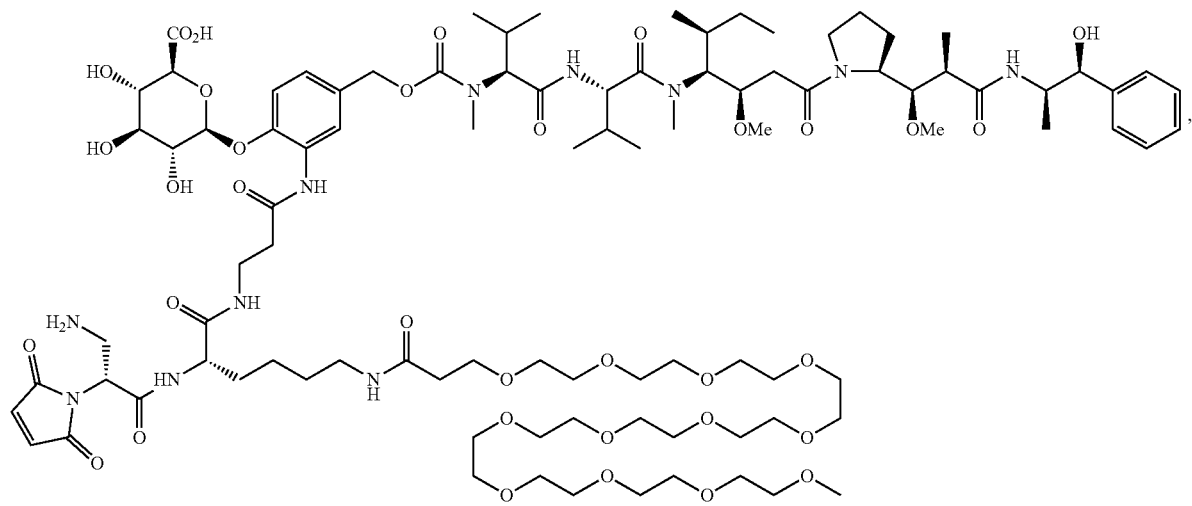 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c(NC(=O)CCNC(=O)[C@H](CCCCNC(=O)CCOCCOCCOCCOCCOCCOCCOCCOCCOCCOCCOCCOC)NC(=O)[C@@H](CN)N2C(=O)C=CC2=O)c1)C(C)C]

or a salt thereof.

38. The method of any one of embodiments 6-35, wherein $Z^3$ of the Formula v compound is BOC (—C(=O)—O-t-Bu).

39. The method of any one of embodiments 6-38, wherein the second or third deprotecting agent for removal of $Z^2$ or $Z^3$ is an aqueous-containing acid solution having a pKa ranging from 0-3.

40. The method of embodiment 39, wherein the acid of the aqueous-containing acid solution is trifluoroacetic acid or trichloroacetic acid.

41. The method of any one of embodiments 1-40, wherein the Grignard reagent has the formula of $R^gMgX$ and the alkoxy magnesium halide has the formula of $R^gOMgX$, wherein $R^g$ is $C_1$-$C_5$ alkyl or phenyl and X is I, Br, or Cl.

42. The method of embodiment 41, wherein the Grignard reagent is MeMgI or MeMgCl.

43. The method of embodiment 41, wherein the alkoxy magnesium halide is MeOMgI or MeOMgCl.

44. The method of any one of embodiments 1-43, wherein the alcohol-containing solvent comprises a $C_1$-$C_4$ alcohol.

45. The method of embodiment 44, wherein the alcohol-containing solvent further comprises THF.

46. The method of embodiment 45, wherein the solvent is a 1:1 (v/v) mixture of methanol and THF.

47. The method any one of embodiments 1-39, wherein the first deprotecting agent for removal of $Z^1$ is an aqueous-containing solution of LiOH.

48. The method of any one of embodiments 6-47, wherein said Grignard reagent or alkoxy magnesium halide contacting and said first deprotecting agent contacting to remove $Z^1$ are done in one pot.

49. The method of any one of embodiments 6-44, wherein the activating agent for said Formula iv contacting is a solution of: N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylamino-morpholinocarbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, or Propylphosphonic anhydride.

50. The method of embodiment 49, wherein the activating agent for said Formula iv contacting is a solution of EDC.HCl, EEDQ or COMU.

51. The method of embodiment 50, wherein the activating agent for said Formula iv contacting is a solution of COMU.

52. The method of embodiment 22, wherein the Drug Linker intermediate compound of Formula 4 or salt thereof is prepared by the method comprising the step of:
contacting a compound of Formula 3 having the structure of:

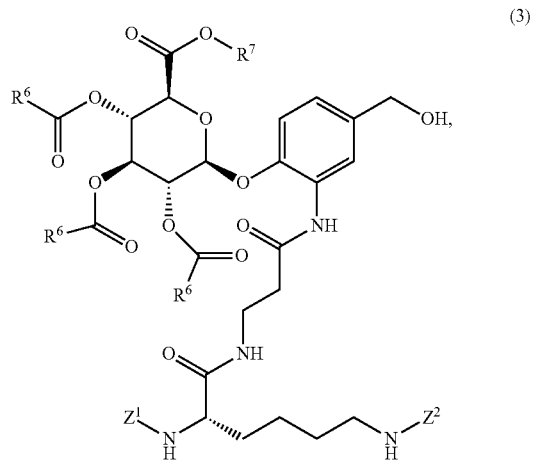

(3)

or a salt thereof, in a suitable solvent with a auristatin compound of Formula iii having the structure of:

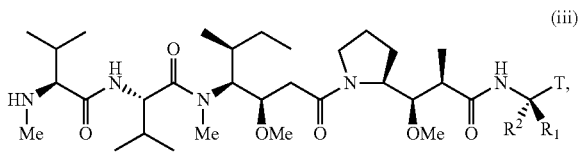

(iii)

in the presence of a carbamate coupling agent, wherein said Formula 3 contacting provides the Formula 4 Drug Linker intermediate compound or salt thereof.

54. The method of embodiment 53, wherein the carbamate coupling agent is a solution of: phosgene, trichloromethyl chloroformate (Diphosgene) and bis(trichloromethyl) carbonate (Triphosgene), 1,1'-Carbonyldiimidazole (CDI), or 1,1'-Carbonyl-di-(1,2,4-triazole) (CDT).

55. The method of embodiment 54, wherein the carbamate coupling agent is a solution of 1,1'-Carbonyl-di-(1,2,4-triazole) (CDT).

56. The method of any one of embodiments 52-55, wherein the Formula 3 compound is prepared by a method comprising the step of: contacting a Parallel Connector Unit precursor ($L_P'$) of Formula 1 or salt thereof and a compound of Formula 2 in a suitable solvent in the presence of a third coupling reagent, wherein the Formula 1 $L_P'$ compound has the structure of:

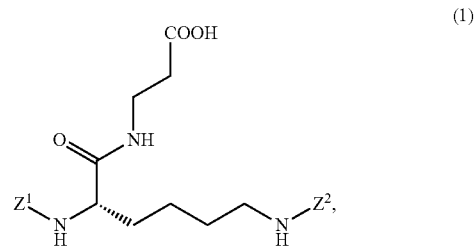

(1)

or a salt hereof, wherein each of $Z^1$ and $Z^2$ is independently a first and second suitable amino protecting group, respectively; and the Formula 2 compound has the structure of:

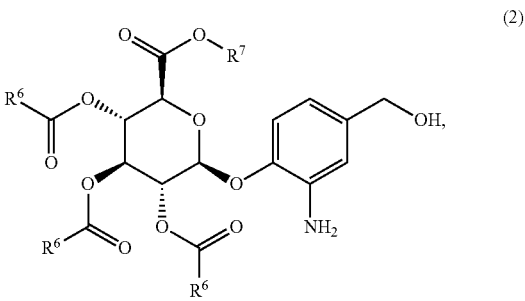

(2)

wherein said contacting provides the Formula 3 compound or salt thereof.

57. The method of embodiment 51, wherein the peptide coupling agent is a solution of: N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylamino-morpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, or Propylphosphonic anhydride.

58. The method of embodiment 56, wherein the peptide coupling reagent is a solution of EDC HCl, EEDQ or COMU.

59. The method of embodiment 58, wherein the peptide coupling reagent is a solution of COMU.

60. A compound of Formula 3 having the structure of:

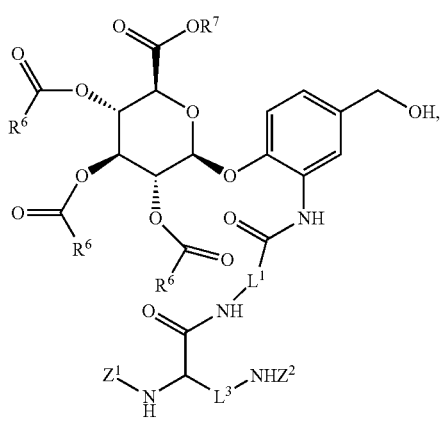

(3)

or a salt thereof, wherein L and L³ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; and each of $Z^1$ and $Z^2$ is independently a first and second suitable amino protecting group, respectively.

61. The compound of embodiment 60, wherein $L^1$ and $L^3$ independently are $C_1$-$C_4$ alkylene.

62. The compound of embodiment 60 or 61, wherein each $R^6$ is $C_1$-$C_4$ alkyl or optionally substituted phenyl.

63. The compound of embodiment 60, 61 or 62, wherein $R^7$ is methyl or ethyl.

64. The compound of embodiment 60, wherein the Formula 3 compound has the structure of:

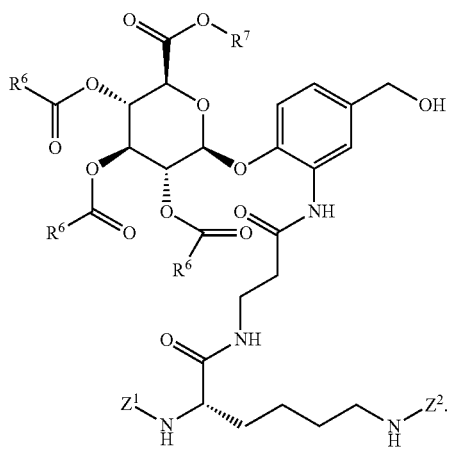

65. The compound of any one of embodiments 60-64, wherein each of $R^6$ and $R^7$ is methyl.

66. The compound of any one of embodiments 60-65 wherein $Z^1$ has the structure of:

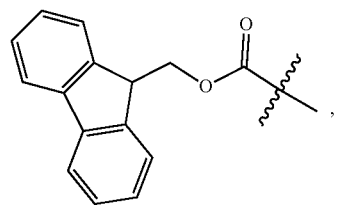 [SMILES: *C(=O)OCC1c2ccccc2-c2ccccc21]

wherein the wavy line indicates the site of attachment to the remainder of the compound structure.

67. The compound of any one of embodiments 60-66, wherein $Z^2$ has the structure of:

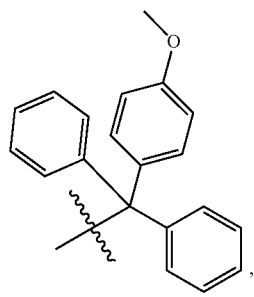 [SMILES: *C(c1ccccc1)(c1ccccc1)c1ccc(OC)cc1]

wherein the wavy line indicates the site of attachment to the remainder of the compound structure.

68. The compound of embodiment 60, wherein the Formula 3 compound has the structure of:

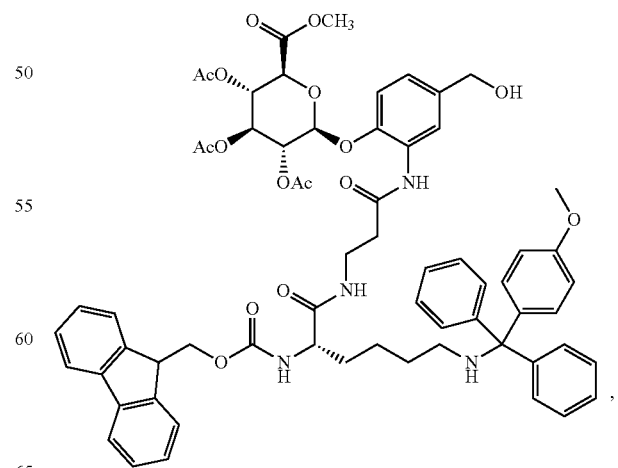

or a salt thereof.

69. A Drug Linker intermediate compound having the structure of Formula 4 of:

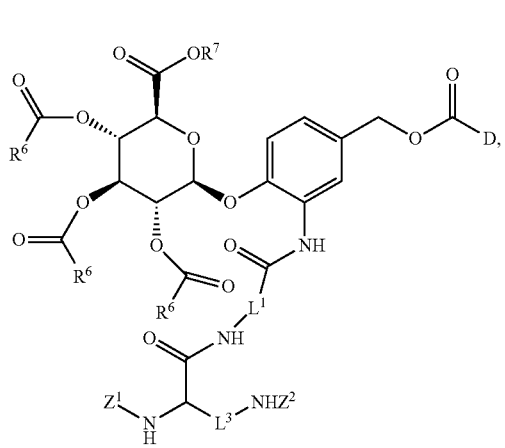

(4)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; and each of $Z^1$ and $Z^2$ is independently a first and second suitable amino protecting group, respectively.

70. The Drug Linker intermediate compound of embodiment 69, wherein the Formula 4 compound has the structure of:

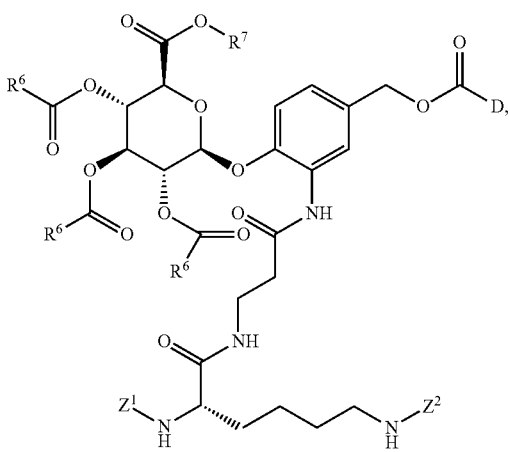

or a salt thereof.

71. A Drug Linker intermediate compound of embodiment 69 or 70, wherein $Z^2$ has the structure of:

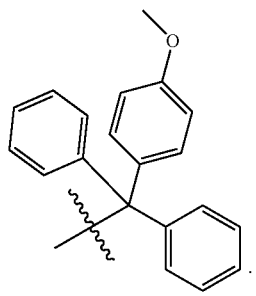 [SMILES: *C(c1ccccc1)(c1ccccc1)c1ccc(OC)cc1]

72. A Drug Linker intermediate compound, wherein the Drug Linker intermediate compound has the structure of Formula 5 of:

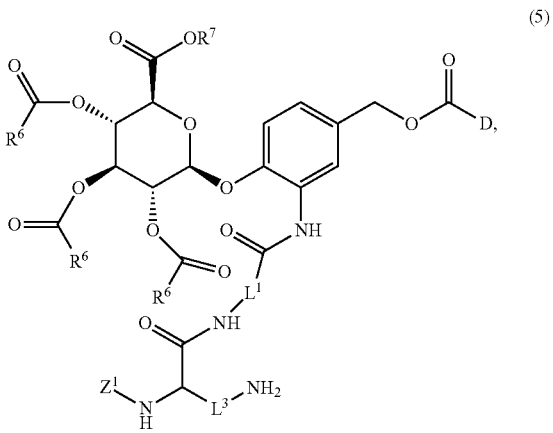

(5)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; and $Z^1$ is a first suitable amino protecting group.

73. The Drug Linker intermediate compound of embodiment 68, wherein the Formula 5 compound has the structure of:

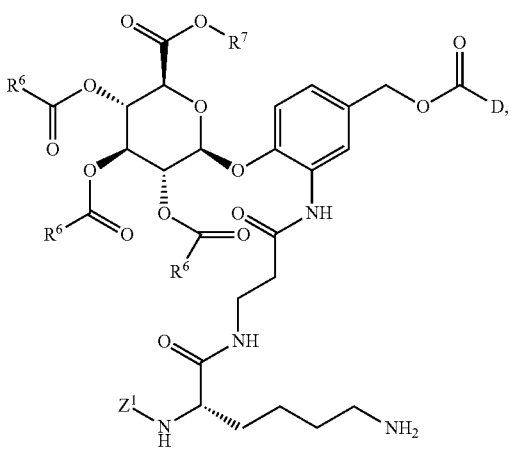

or a salt thereof.

74. A Drug Linker intermediate compound, wherein the Drug Linker intermediate compound has the structure of Formula 6 of:

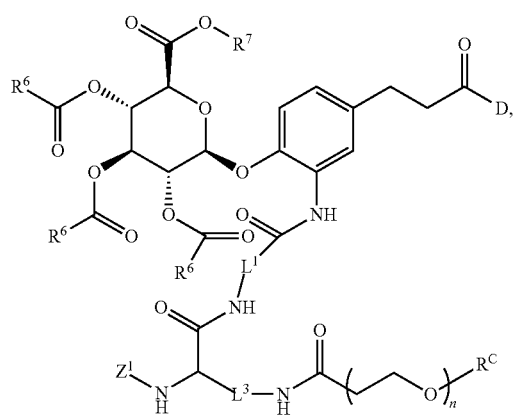

(6)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; $Z^1$ is a first suitable amino protecting group; $R^C$ is hydrogen or a PEG Capping Unit; and subscript n ranges from 1 to 24.

75. The Drug Linker intermediate compound of embodiment 74, wherein the Formula 6 compound has the structure of:

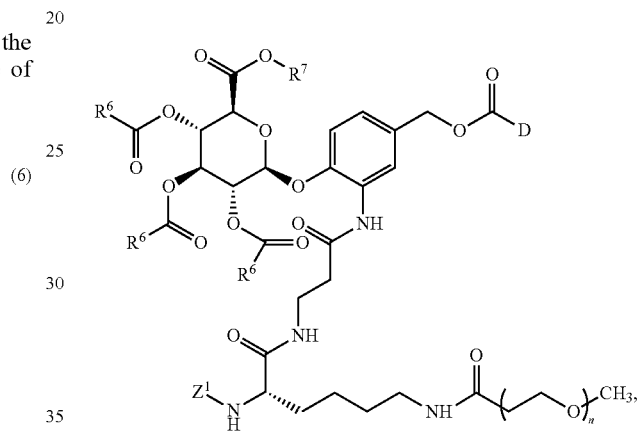

or a salt thereof.

76. The compound of embodiment 74 or 75, wherein subscript n is 8 or 12.

77. The compound of any one of embodiments 69-76, wherein the auristatin Drug Unit (D) has the structure of Formula $D_{E-1}$, $D_{E-2}$, or $D_{F-1}$:

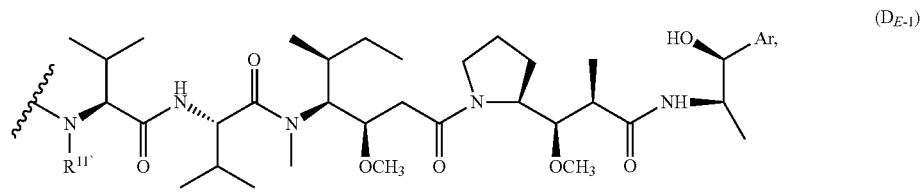

(D$_{E-1}$)

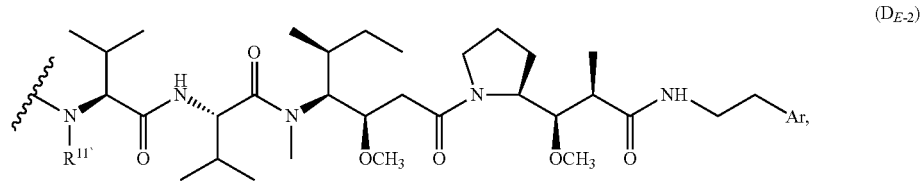

(D$_{E-2}$)

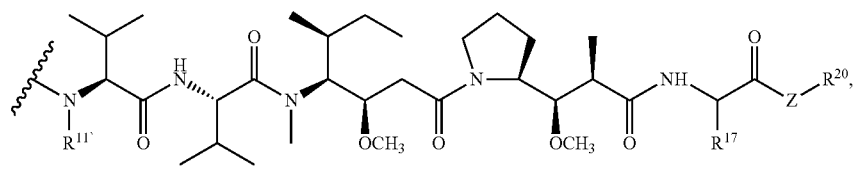

(D_{F-1})

wherein Ar is optionally substituted $C_6$-$C_{10}$ aryl or optionally substituted $C_3$-$C_8$ heterocyclyl.

78. The compound of embodiment 77, wherein D has the structure of Formula $D_{E-1}$.
79. The compound of embodiment 77, wherein D has the structure of Formula $D_{E-2}$.
80. The compound of embodiment 77, wherein D has the structure of Formula $D_{F-1}$.
81. The compound of embodiment 78 or 79, wherein Ar is optionally substituted phenyl or optionally substituted 2-pyridyl.
82. The compound of embodiment 80, wherein —Z— is —O— and $R^{20}$ is $C_1$-$C_4$ alkyl.
83. The compound of embodiment 80, wherein Z is —NH— and $R^{20}$ is optionally substituted phenyl or optionally substituted $C_5$-$C_6$ heteroaryl.
84. The compound of any one of embodiments 77-83, wherein $R^{11}$ is methyl.
85. The compound of any one of embodiments 69-77, wherein D has the structure of Formula $D_{F/E-3}$:

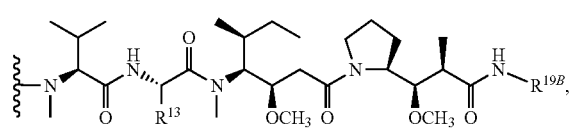

(D_{F/E-3})

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —CH($CH_2Ph$)-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph.

86. The compound of any one of embodiments 69-77, wherein D has the structure of:

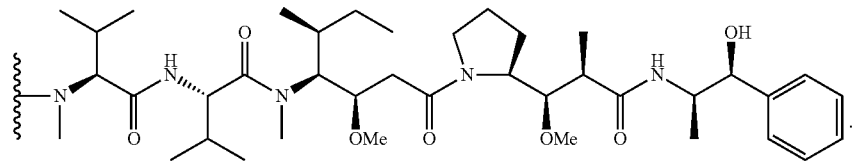 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

87. The compound of embodiment 69, wherein the Formula 4 Drug Linker intermediate compound has the structure of:

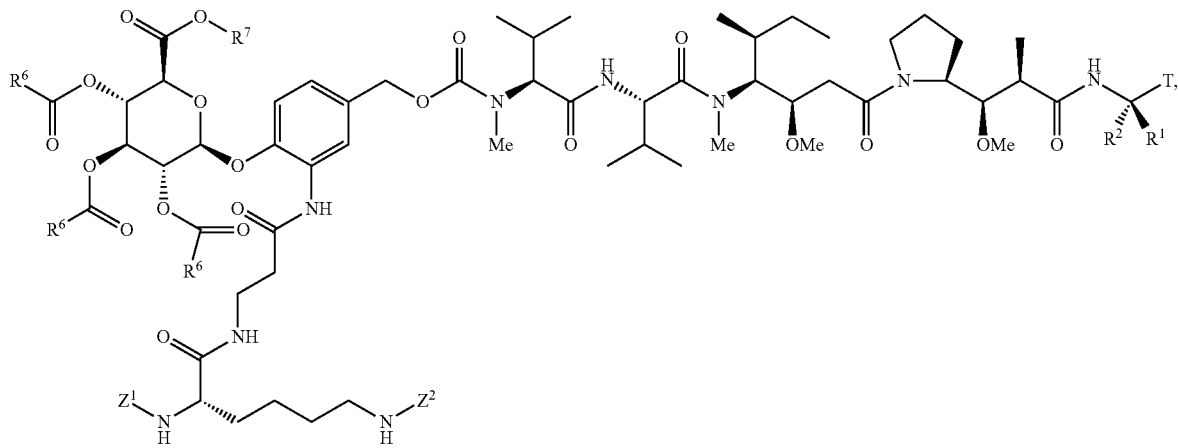

or a salt thereof, wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

88. The Drug Linker intermediate compound of embodiment 87 wherein $Z^2$ has the structure of:

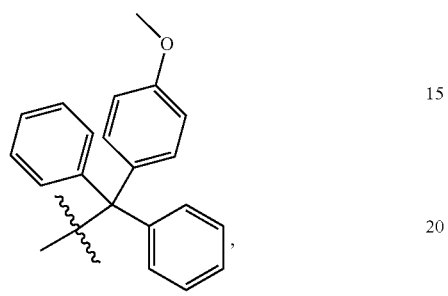

wherein the wavy line indicates the site of attachment to the remainder of the compound structure.

89. The Drug Linker intermediate compound of embodiment 72, wherein the Formula 5 compound has the structure of

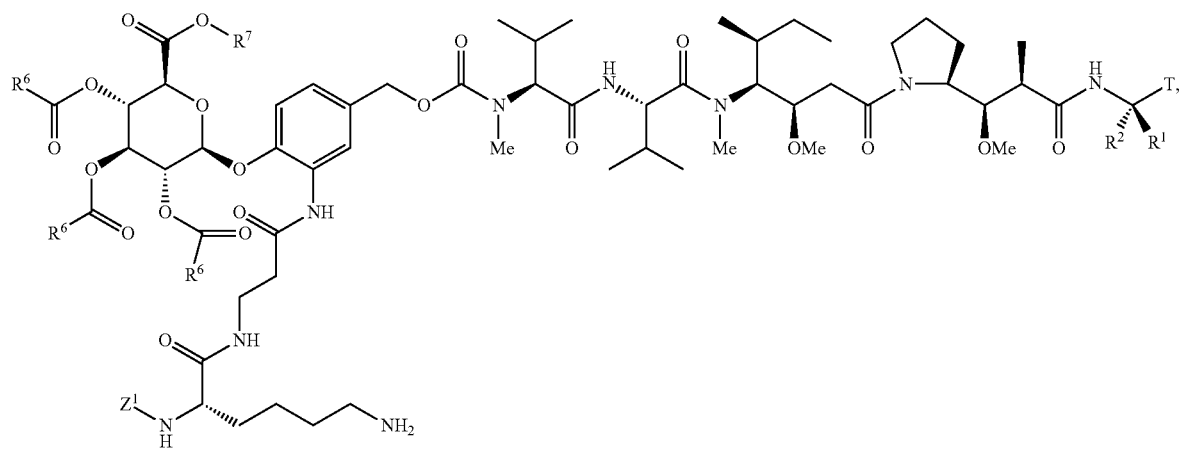

or a salt thereof, wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

90. The Drug Linker intermediate compound of embodiment 74, wherein the Formula 6 compound has the structure of:

121

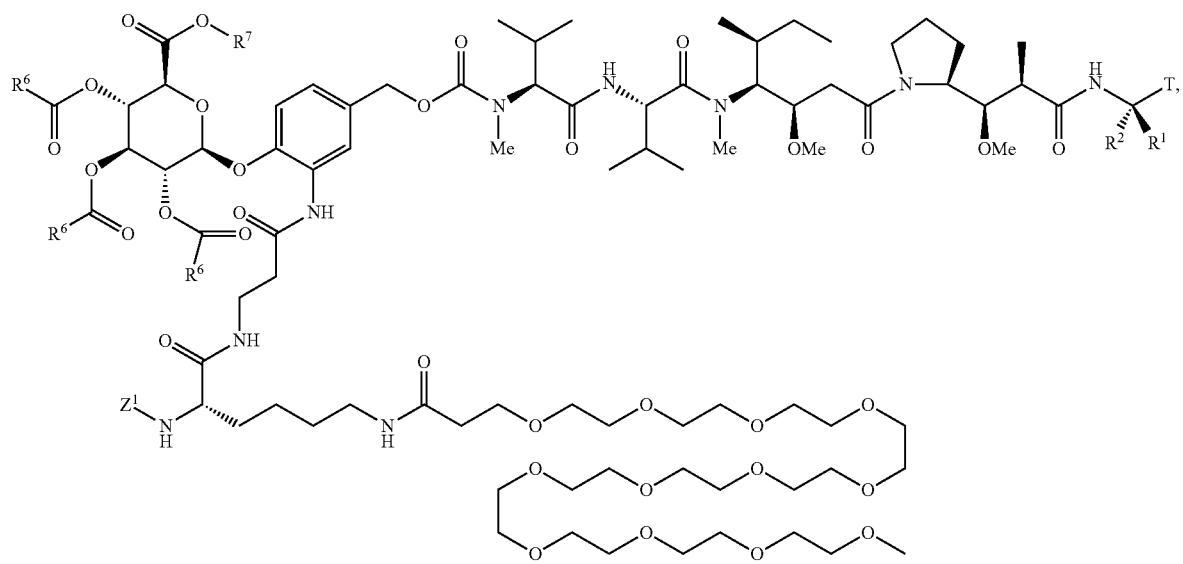

or a salt thereof, wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

91. The Drug Linker intermediate compound of any one of embodiments 69-90 wherein each of $R^6$ and $R^7$ is independently $C_1$-$C_4$ alkyl.

92. The Drug Linker intermediate compound of embodiment 91, wherein each of $R^6$ and $R^7$ is methyl or each of $R^6$ and $R^7$ is ethyl.

93. The Drug Linker intermediate compound of any one of embodiments 89-92, wherein $R^1$ is hydrogen or methyl; $R^2$ is hydrogen; and T is —CH($OR^4$)—$R^5$; wherein $R^4$ is hydrogen or methyl and $R^5$ is $C_6$-$C_{10}$ aryl.

94. The Drug Linker intermediate compound of embodiment 93, wherein $R^1$ is methyl, $R^2$ is H, and T is —CH(OH)-Ph.

122

95. The Drug Linker intermediate compound of any one of embodiments 69-94, wherein $Z^1$ has the structure of:

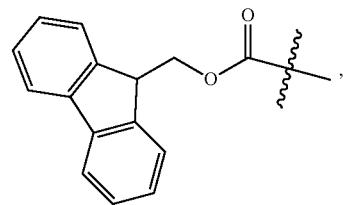 [SMILES: *C(=O)OCC1c2ccccc2-c2ccccc21]

wherein the wavy line indicates the site of attachment to the remainder of the compound structure.

96. The Drug Linker intermediate compound of embodiment 69, wherein the Formula 4 compound has the structure of:

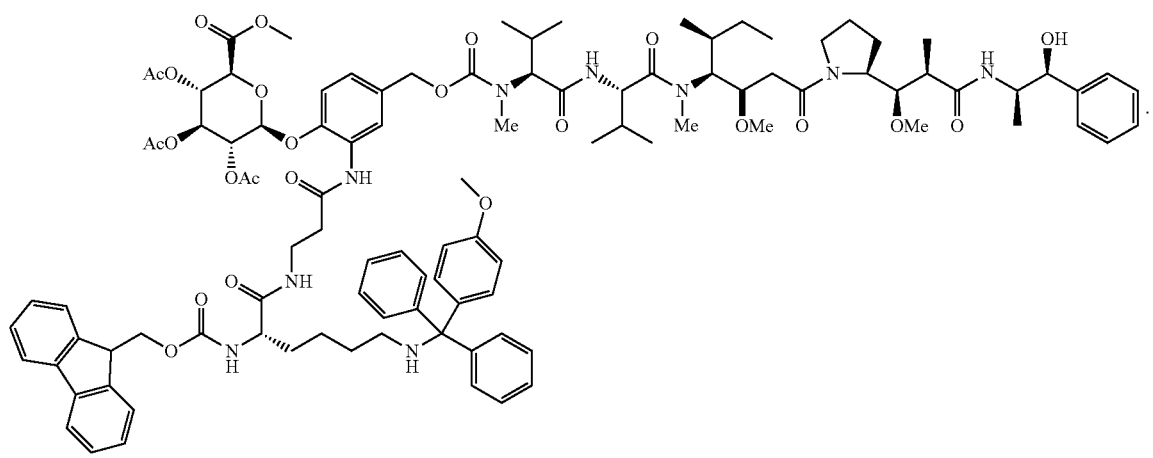 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCNC(c2ccccc2)(c2ccccc2)c2ccc(OC)cc2)NC(=O)OCC2c3ccccc3-c3ccccc32)c1)C(C)C]

97. The Drug Linker intermediate compound of embodiment 72, wherein the Formula 5 compound has the structure of:
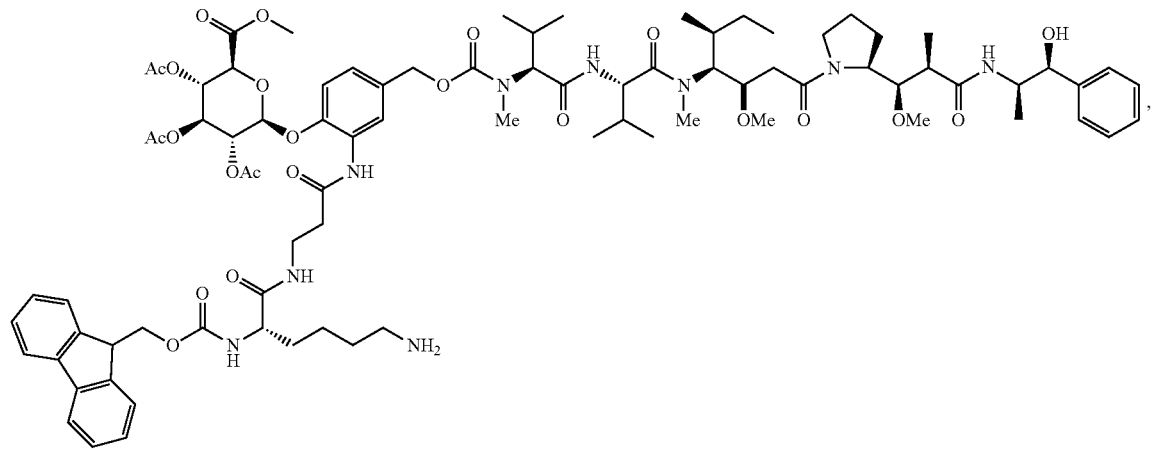 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCN)NC(=O)OCC2c3ccccc3-c3ccccc32)c1)C(C)C]
or a salt thereof.
98. The Drug Linker intermediate compound of embodiment 74, wherein the Formula 6 compound has the structure of:
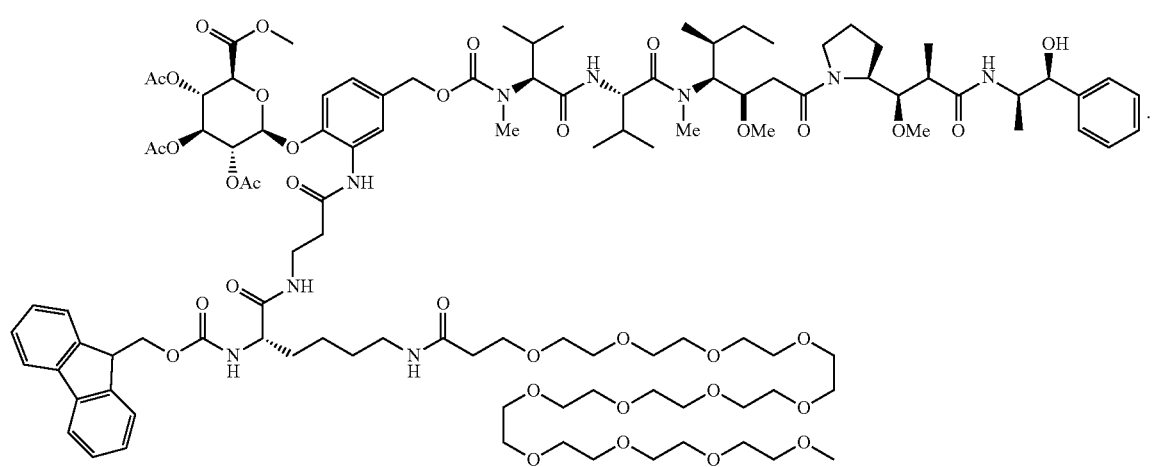 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCNC(=O)CCOCCOCCOCCOCCOCCOCCOCCOCCOCCOCCOCCOC)NC(=O)OCC2c3ccccc3-c3ccccc32)c1)C(C)C]

99. A composition comprising a Drug Linker intermediate of Formula 7 having the structure of:

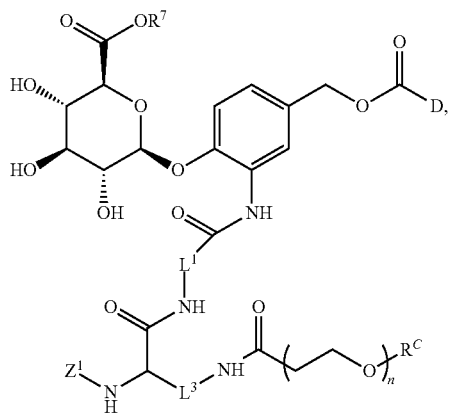

(7)

or a salt thereof, wherein D is an auristatin Drug Unit; each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $Z^1$ is a suitable amino protecting group; $R^C$ is hydrogen or a PEG Capping Unit; and subscript n ranges from 2 to 24, the composition further comprising no more than about 10 wt. %, in particular no more than about 5 wt. %, of a compound of Formula 7A having the structure of:

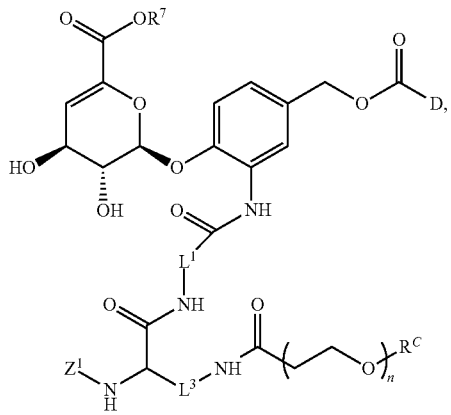

(7A)

or a salt thereof, wherein the variable groups are as previously defined.

100. The composition of embodiment 99, wherein the Formula 7 and Formula 7A compounds have the structures of:

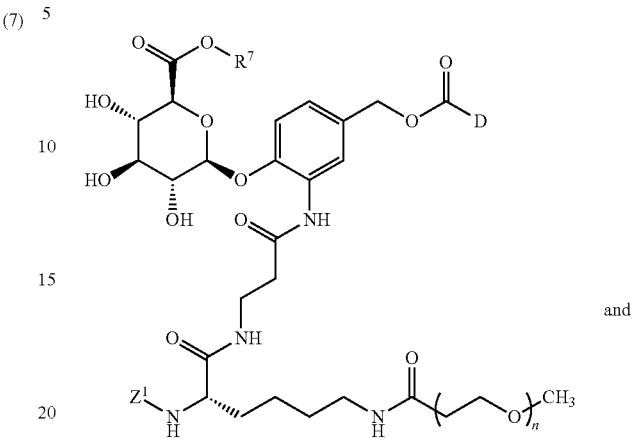

and

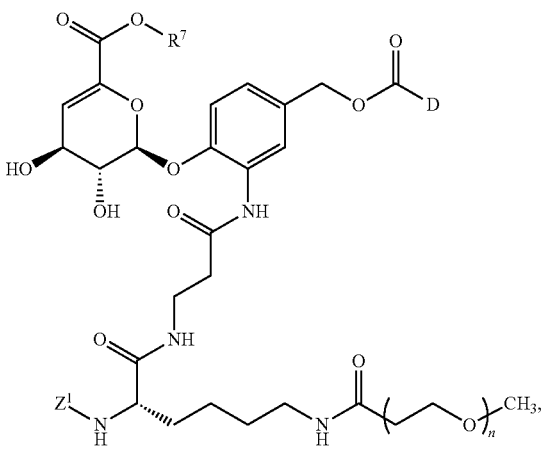

or salts thereof.

101. The composition of embodiment 99 or 100, wherein $Z^1$ has the structure of:

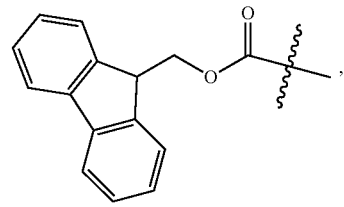 [SMILES: *C(=O)OCC1c2ccccc2-c2ccccc21]

wherein the wavy line indicates the site of attachment to the remainder of the compound structure.

102. The composition of embodiment 99, 100 or 101, wherein $R^7$ is methyl.

103. A composition comprising a Drug Linker intermediate of Formula 8 having the structure of:

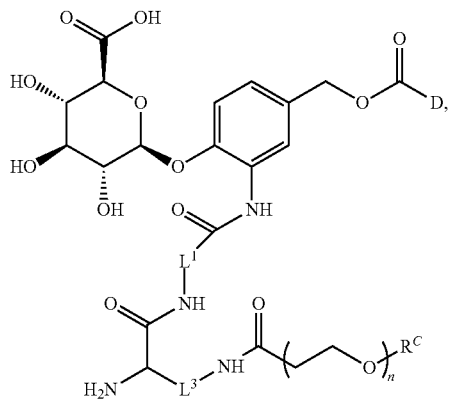
(8)

or a salt thereof, wherein D is an auristatin Drug Unit; each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is a PEG Capping Unit; and subscript n ranges from 2 to 24, the composition further comprising no more than about 10 wt. %, in particular no more than about 5 wt. %, of a compound of Formula 8A having the structure of:

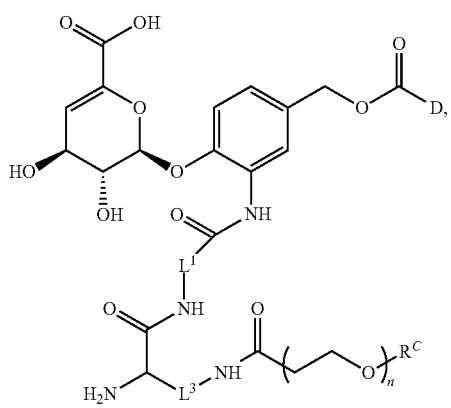
(8A)

or a salt thereof, wherein the variable groups are as previously defined.

104. The composition of embodiment 103, wherein the Formula 8 and Formula 8A compounds have the structures of:

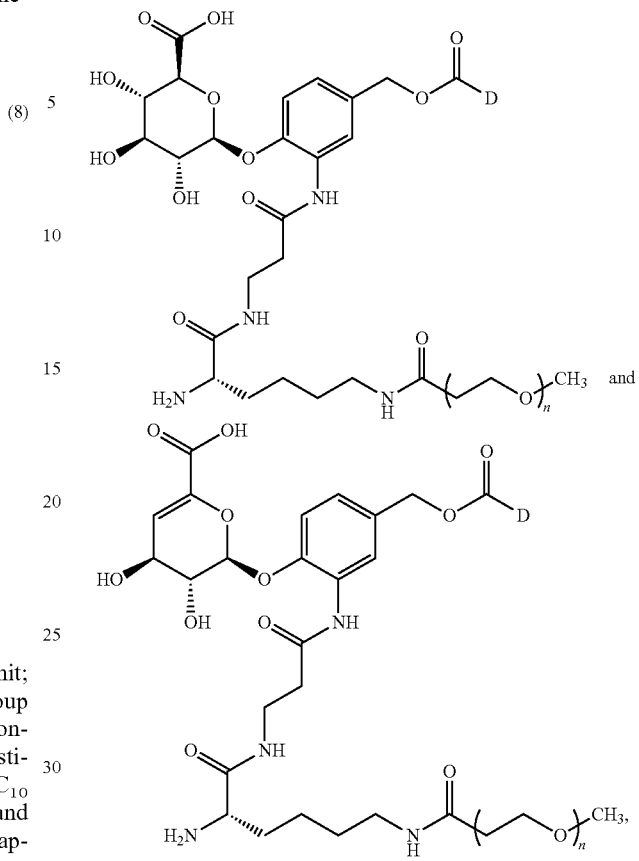

or salts thereof.

105. A composition comprising a Drug Linker intermediate of Formula 9 having the structure of:

(9)

or a salt thereof, wherein D is an auristatin Drug Unit; each of $L^1$, $L^2$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; and subscript n ranges from 2 to 24, the composition further comprising no more than about 10 wt. %, in particular no more than 5 wt. % of a compound of Formula 9A having the structure of:

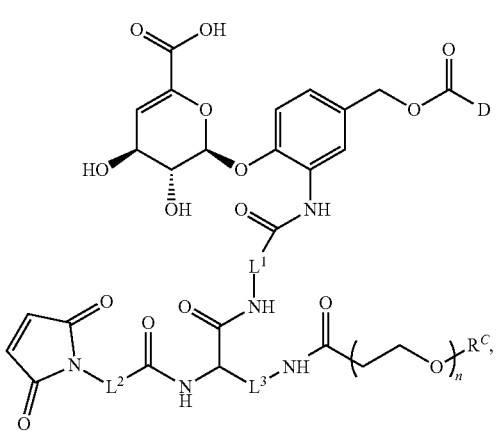

(9A)

or a salt thereof, wherein the variable groups are as previously defined.

106. The composition of embodiment 105, wherein the Formula 9 and Formula 9A compounds have the structures of:

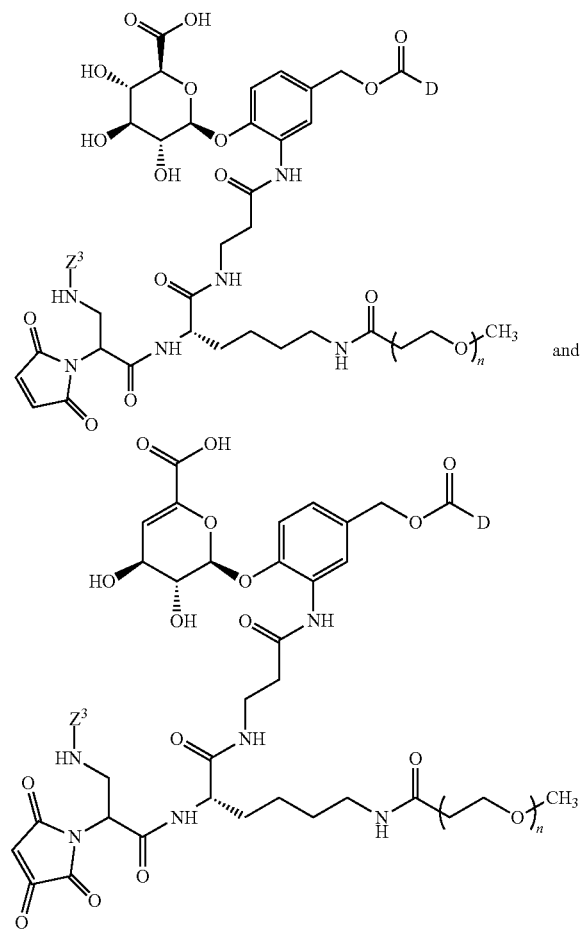

or salts thereof, wherein $Z^3$ is a third suitable amino protecting group that is acid-labile, particularly a carbamate of formula —C(=O)O—$R^8$, wherein $R^8$ is $C_1$-$C_4$ alkyl or optionally substituted phenyl.

107. A composition comprising Drug Linker compound of Formula 10 having the structure of:

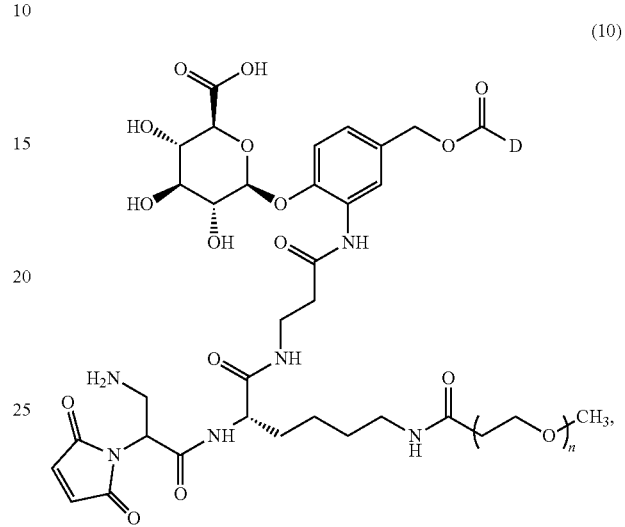

(10)

or a salt thereof, wherein D is an auristatin Drug Unit; and subscript n ranges from 2 to 24, the composition further comprising no more than about 10 wt. %, in particular no more than about 5 wt. %, of a compound of Formula 10A having the structure of:

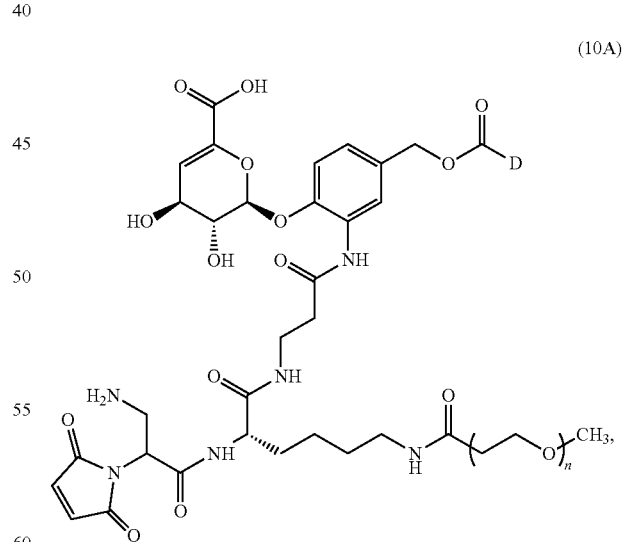

(10A)

or a salt thereof, wherein the variable groups are as previously defined.

108. The composition of any one of embodiments 99-107, wherein the auristatin Drug Unit (D) has the structure of Formula $D_{E-1}$, $D_{E-2}$, or $D_{F-1}$:

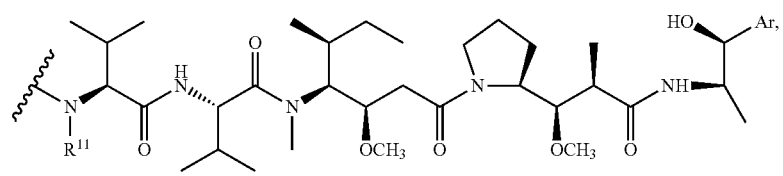

(D$_{E\text{-}1}$)

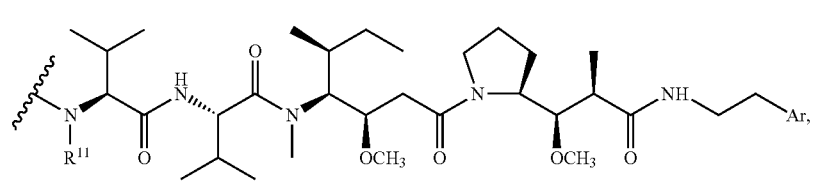

(D$_{E\text{-}2}$)

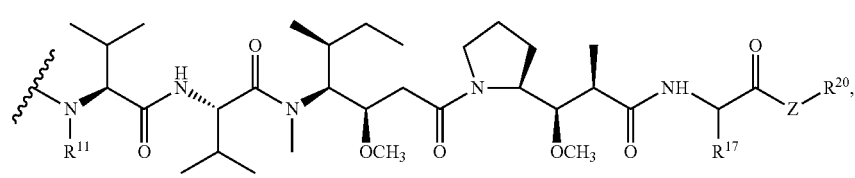

(D$_{F\text{-}1}$)

wherein Ar is optionally substituted $C_6$-$C_{10}$ aryl or optionally substituted $C_3$-$C_8$ heterocyclyl wherein the wavy line indicates the site of attachment to the remainder of the compound structure.

110. The composition of embodiment 109, wherein D has the structure of Formula D$_{E\text{-}1}$.

111. The composition of embodiment 109, wherein D has the structure of Formula D$_{E\text{-}2}$.

112. The composition of embodiment 109, wherein D has the structure of Formula D$_{F\text{-}1}$.

113. The composition of embodiment 110 or 111, wherein Ar is optionally substituted phenyl or optionally substituted 2-pyridyl.

114. The composition of embodiment 112, wherein —Z— is —O— and $R^{20}$ is $C_1$-$C_4$ alkyl.

115. The composition of embodiment 112, wherein Z is —NH— and $R^{20}$ is optionally substituted phenyl or optionally substituted $C_5$-$C_6$ heteroaryl.

116. The composition of any one of embodiments 108-116, wherein $R^{11}$ is methyl.

117. The composition of any one of embodiments 99-107, wherein D has the structure of Formula D$_{F/E\text{-}3}$:

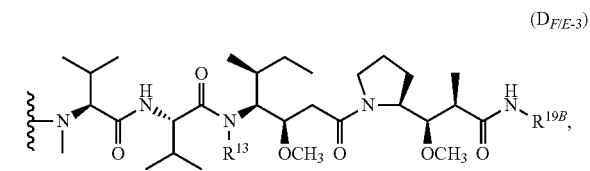

(D$_{F/E\text{-}3}$)

wherein $R^{13}$ is isopropyl or —CH$_2$—CH(CH$_3$)$_2$; and $R^{19B}$ is —CH(CH$_3$) CH(OH)Ph, —CH(CO$_2$H)CH$_2$Ph, —CH(CH$_2$Ph)-2-thiazole, —CH(CH$_2$Ph)-2-pyridyl, —CH(CH$_2$-p-Cl-Ph), —CH(CO$_2$Me)-CH$_2$Ph, —CH(CO$_2$Me)-CH$_2$CH$_2$SCH$_3$, CH(CH$_2$CH$_2$SCH$_3$)C(═O)NH-3-quinolyl, or —CH(CH$_2$Ph)C(═O)NH-p-Cl-Ph; and wherein the wavy line indicates the site of attachment to the remainder of the compound structure.

118. The composition of any one of embodiments 99-107, wherein D has the structure of:

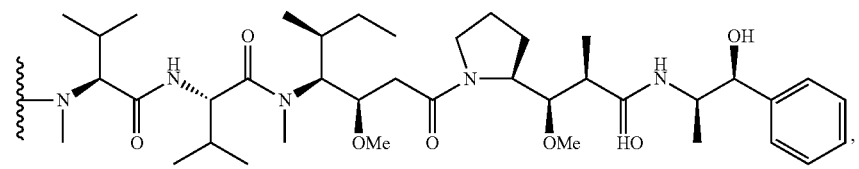 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

wherein the wavy line indicates the site of attachment to the remainder of the compound structure.

119. The composition of embodiment 99, wherein the Formula 7 and Formula 7A compounds have the structures of:

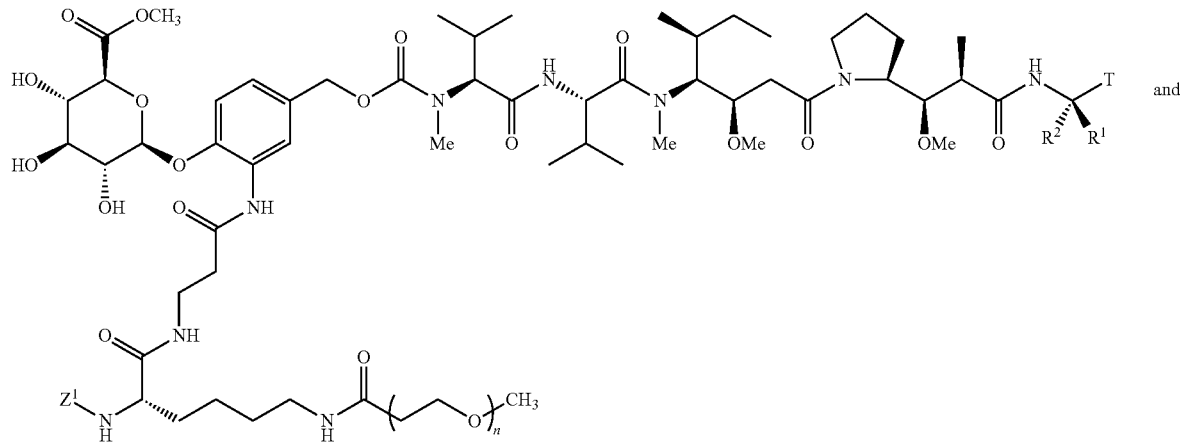

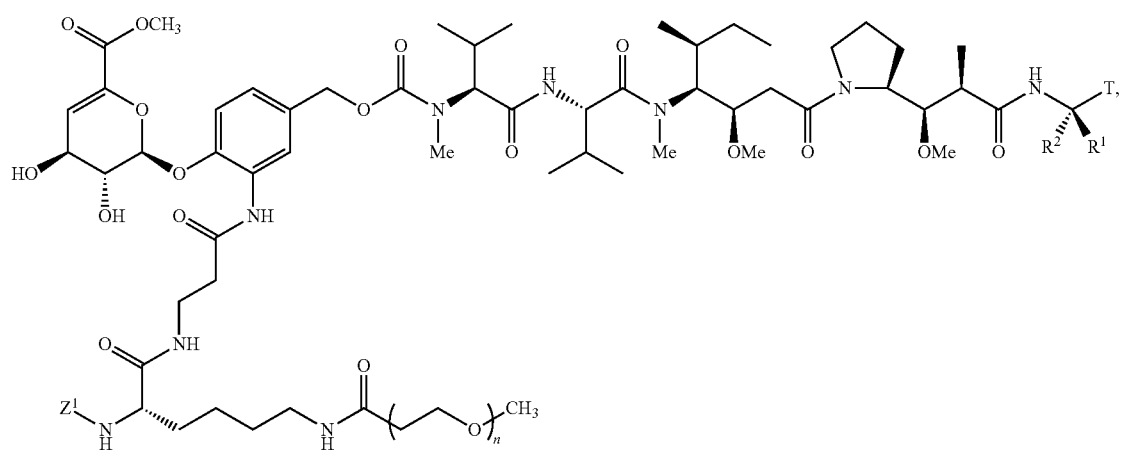

or salts thereof, wherein $R^1$ is H or $C_1$-$C_4$ alkyl; $R^2$ is H, $C_1$-$C_4$ alkyl, or —CH$_2$—$R^3$; $R^3$ is $C_6$-$C_{10}$ aryl or $C_3$-$C_8$ heterocyclyl; and T is selected from the group consisting of —CH(OR$^4$)—R$^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl; and $Z^1$ has the structure of:

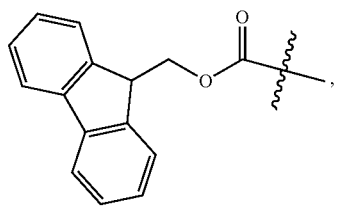 [SMILES: *C(=O)OCC1c2ccccc2-c2ccccc21]

wherein the wavy line indicates the site of attachment to the remainder of the compound structure.

120. The composition of embodiment 103, wherein the Formula 8 and Formula 8A compounds have the structures of:

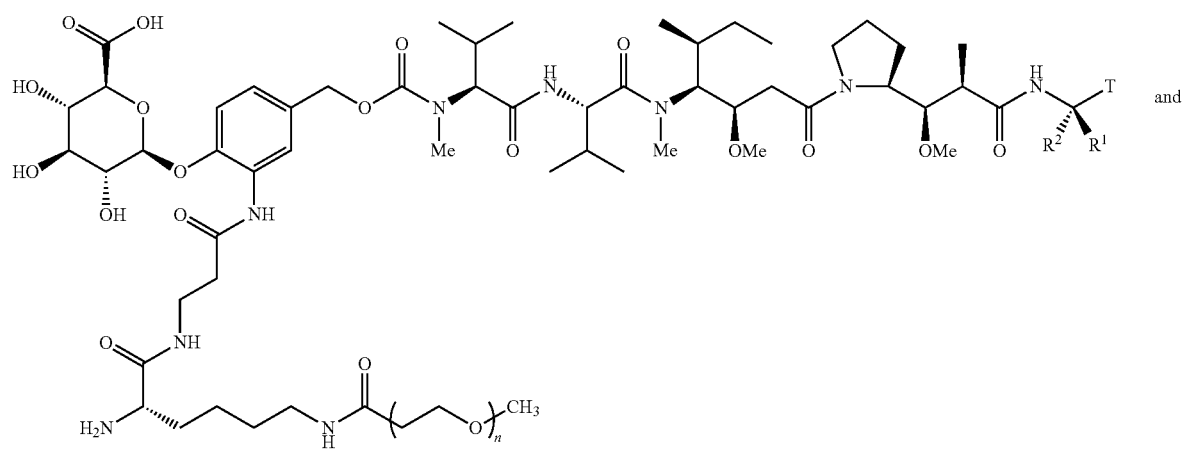

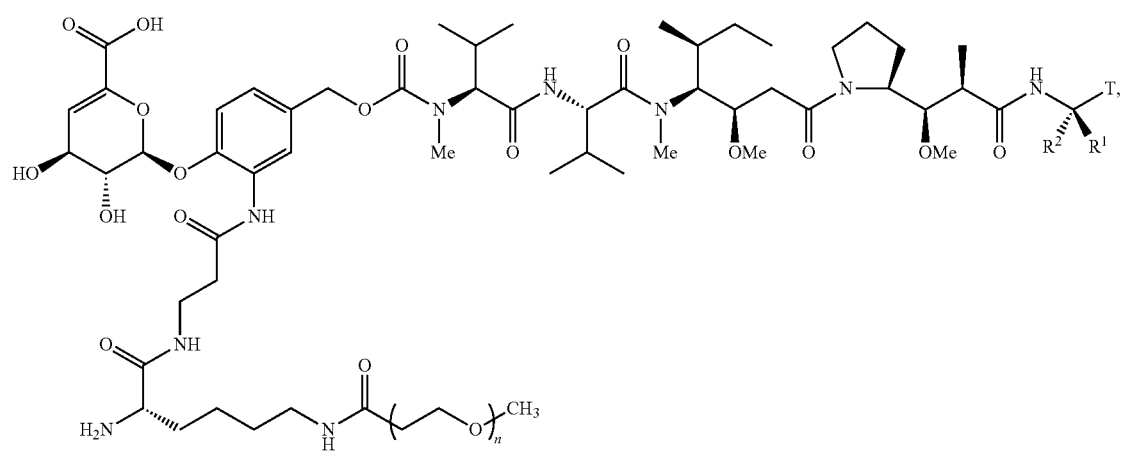

or salts thereof, wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

121. The composition of embodiment 105, wherein the Formula 9 and Formula 9A compounds have the structures of:

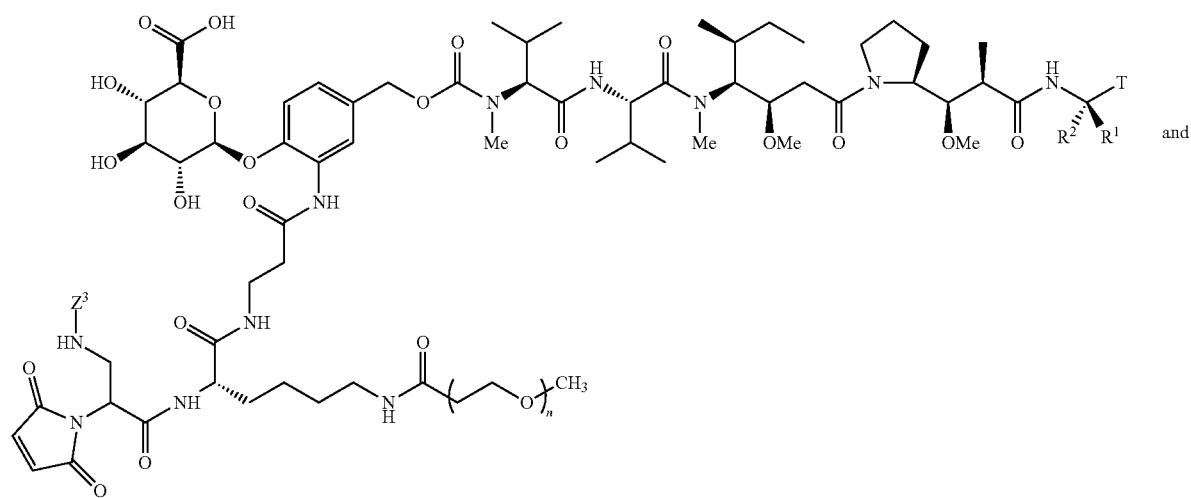

-continued

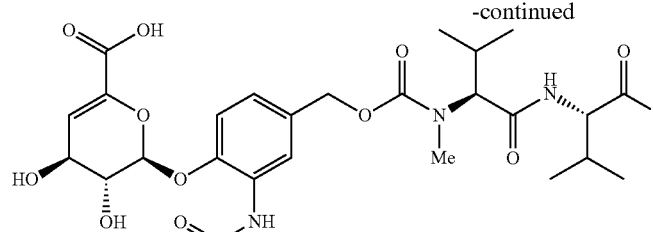

or salts thereof, wherein $Z^3$ is —C(=O)O-t-Bu; $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; T is selected from the group consisting of —CH(O$R^4$)—$R^5$ and —C(=O)—O$R^4$, wherein $R^4$ is H, $C_1$-$C_4$ alkyl and $R^5$ is $C_6$-$C_{10}$ aryl or $C_3$-$C_6$ heteroaryl.

122. The composition of embodiment 107, wherein the Formula 10 and Formula 10A compounds have the structures of:

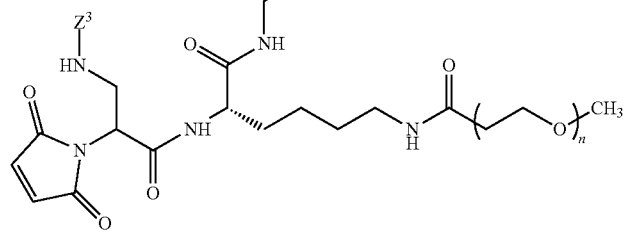

and

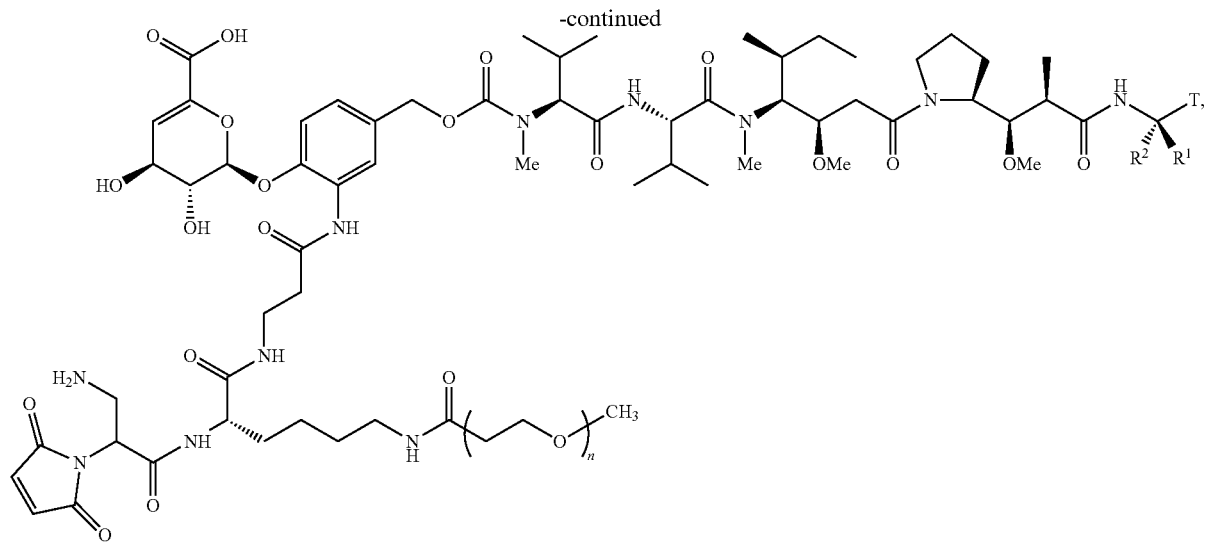

or salts thereof, wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

123. The composition of embodiment 120, 121 or 122, wherein $R^1$ is hydrogen or methyl; $R^2$ is hydrogen; and T is —CH($OR^4$)—$R^5$; wherein $R^4$ is hydrogen or methyl and $R^5$ is $C_6$-$C_{10}$ aryl.

124. The composition of embodiment 123, wherein $R^1$ is methyl, $R^2$ is H, and T is —CH(OH)-Ph.

125. The composition of any one of embodiments 99-124, wherein subscript n is 8 or 12.

126. The composition of embodiment 99, wherein the Formula 7 and Formula 7A compounds have the structures of:

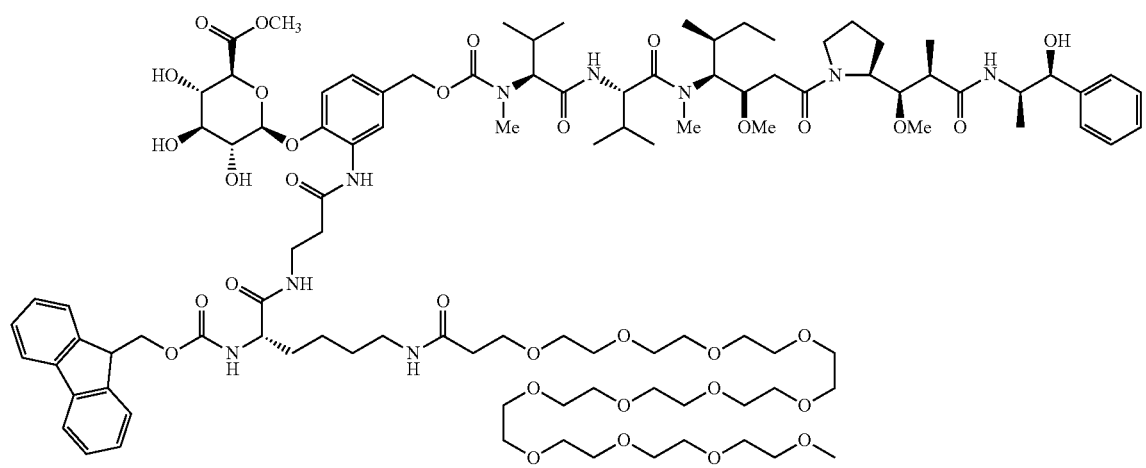

and

-continued
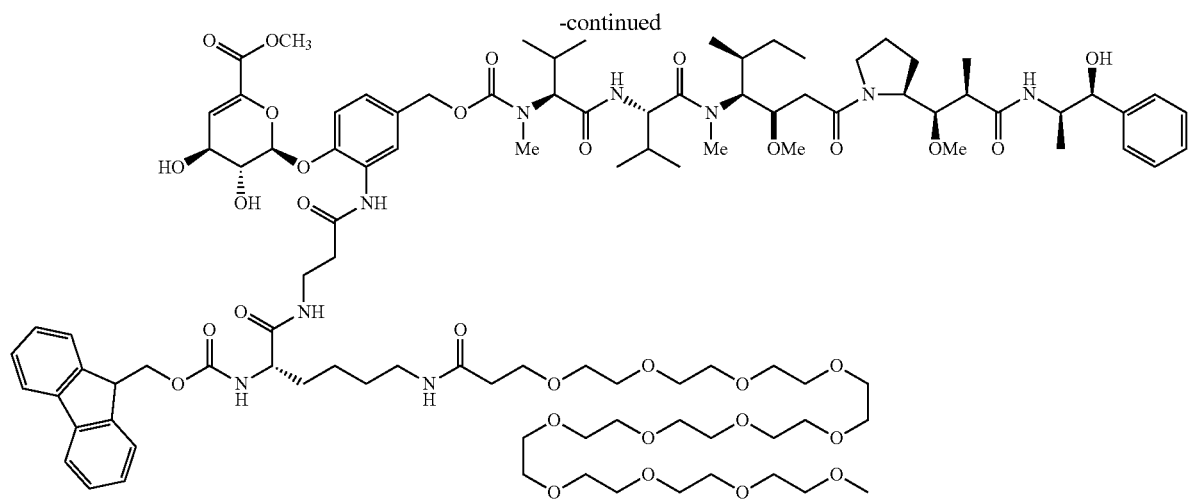
127. The composition of embodiment 103, wherein the Formula 8 and Formula 8A compounds have the structures of:
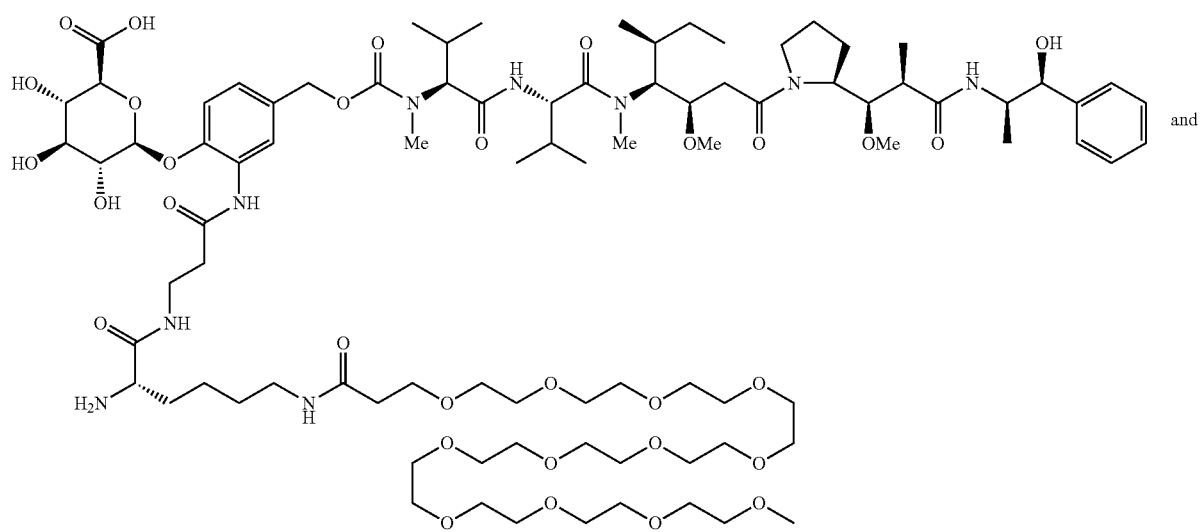

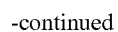

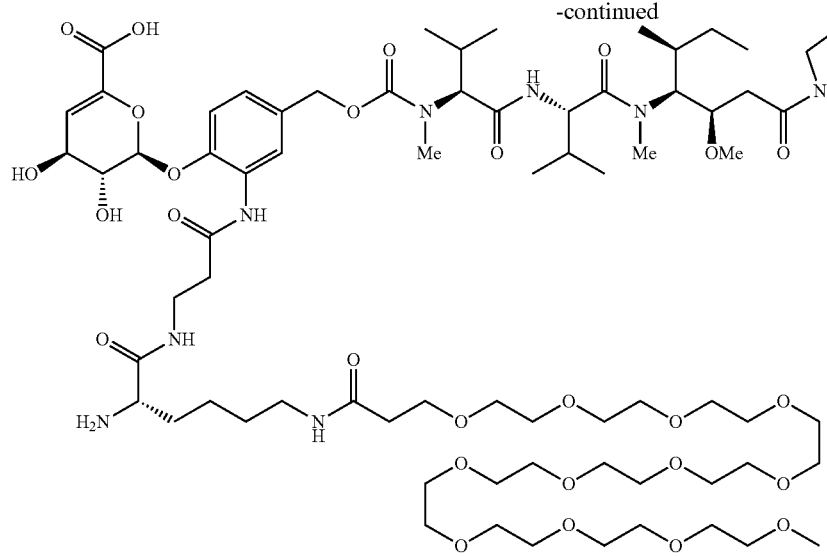

or salts thereof.

128. The composition of embodiment 119, wherein the composition is comprised of no more than about 5 wt. % of the Formula 8A compound.

129. The composition of embodiment 119, wherein the composition is comprised of between about 3 wt. % to about 4 wt. % of the Formula 8A compound.

130. The composition of embodiment 105, wherein the Formula 9 and Formula 9A compounds have the structures of:

-continued
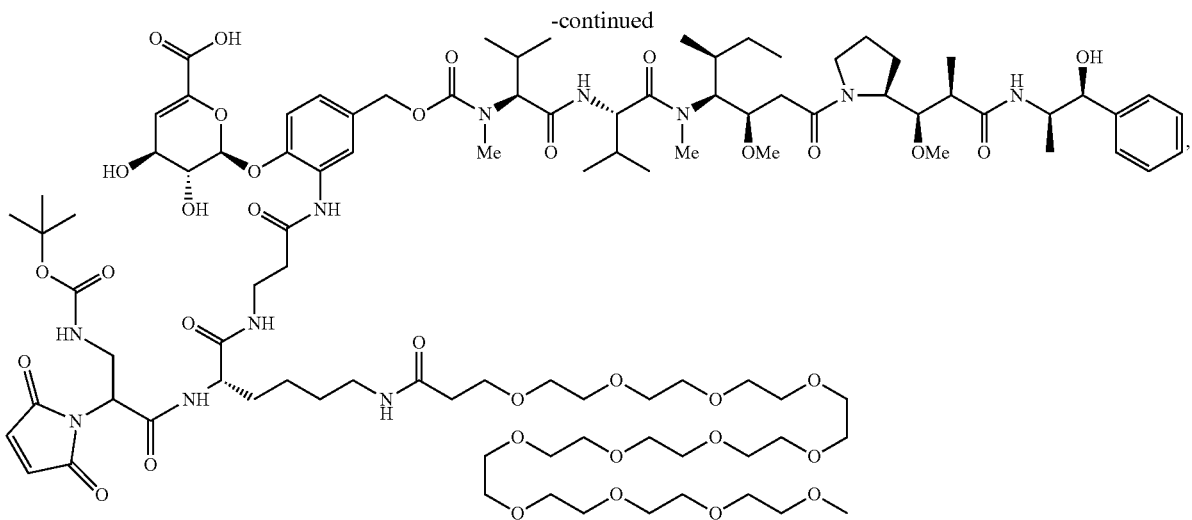
or salts thereof.
131. The composition of embodiment 107, wherein the Formula 10 and Formula 10A compounds have the structures of
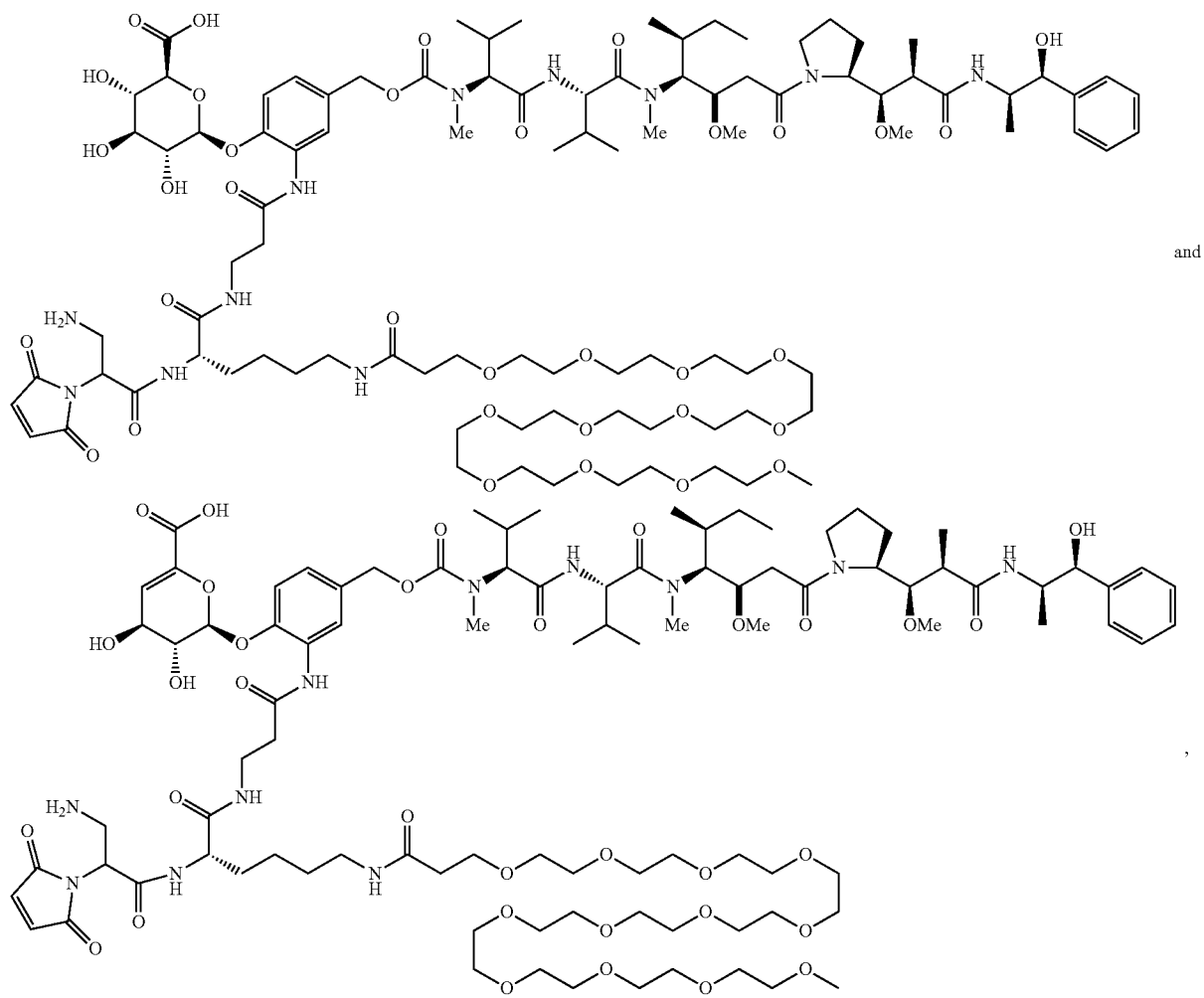
and or salts thereof.

132. A compound, wherein the compound has the structure of:

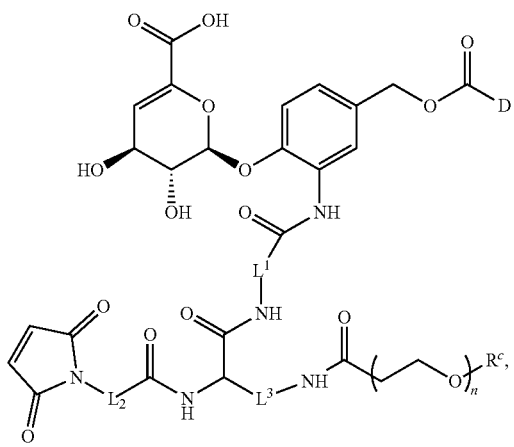

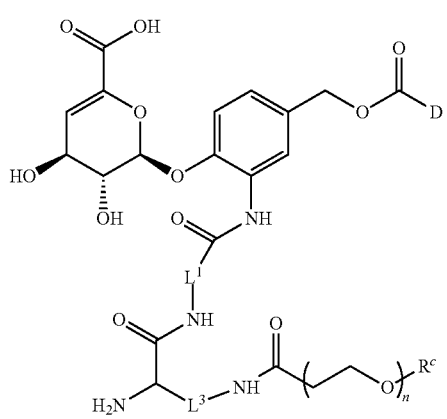

or

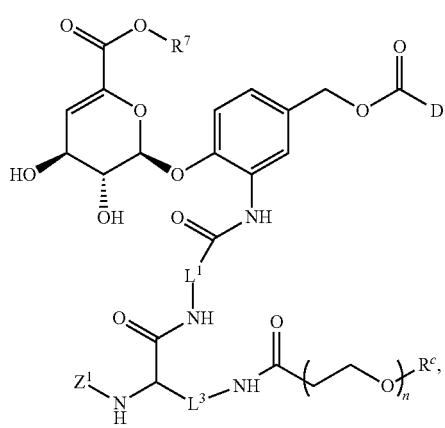

or a salt thereof, wherein D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $Z^1$ is a first suitable amino protecting group; $R^7$ is optionally substituted $C_1$-$C_8$ alkyl, optionally substituted $C_6$-$C_{10}$ arylene or optionally substituted $C_5$-$C_{10}$ heteroarylene; $R^C$ is a PEG Capping Unit; and subscript n ranges from 2 to 24.

133. The compound of embodiment 132, wherein $L^1$ and $L^3$ are independently $C_1$-$C_4$ alkyl and $L^2$ is independently optionally substituted $C_1$-$C_4$ alkyl.

134. The compound of embodiment 133, wherein the compound has the structure selected from the group consisting of:

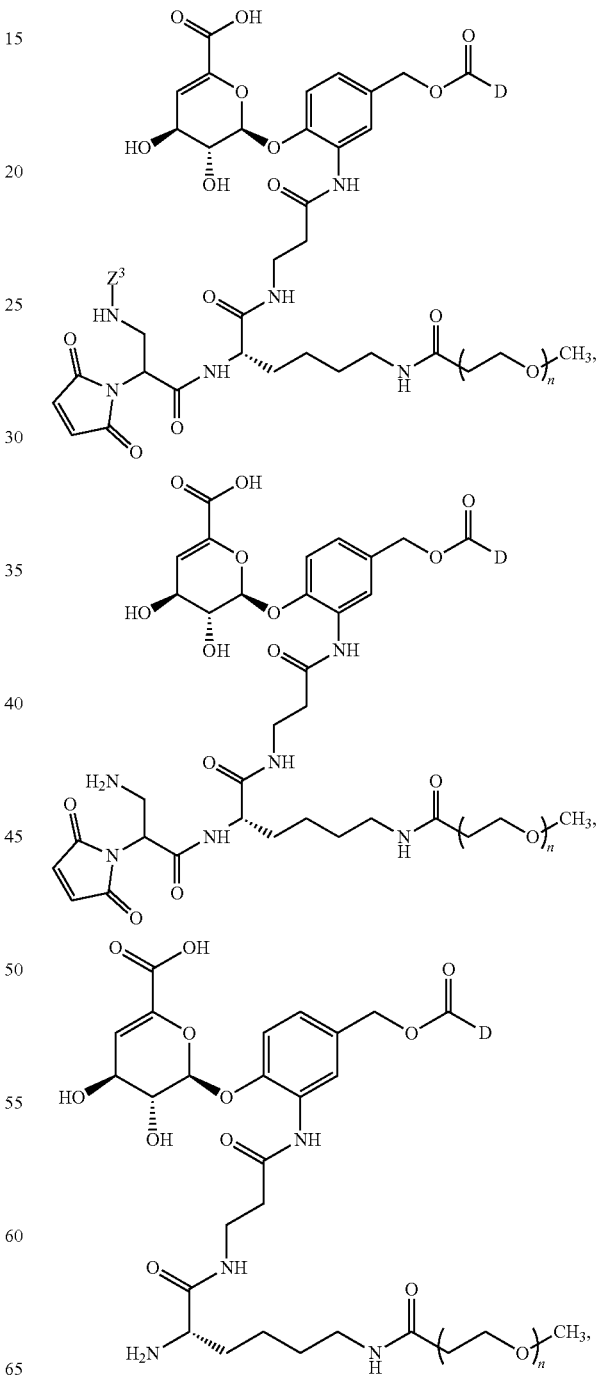

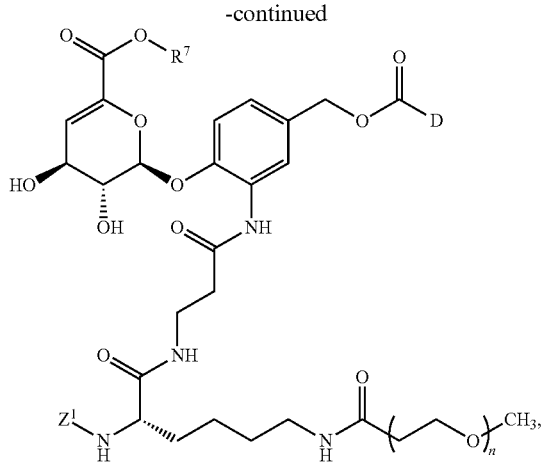

and salts thereof, wherein $Z^3$ is a third suitable amino protecting group that is acid-labile, particularly a carbamate having the structure of —C(=O)O—$R^8$, wherein $R^8$ is $C_1$-$C_4$ alkyl or optionally substituted phenyl; and $R_7$ is a $C_1$-$C_4$ alkyl, particularly methyl or ethyl.

135. A composition comprising Antibody Drug Conjugates represented by Formula 11 and Formula 11A having the structures of:

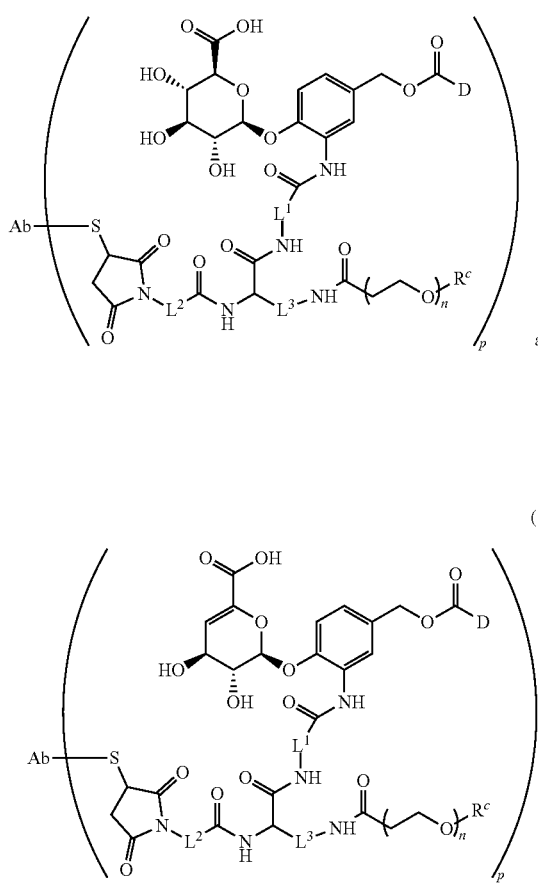

or pharmaceutically acceptable salts thereof, wherein Ab is an antibody; S is a sulfur atom from the antibody; D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. %, in particular no more than 5 wt. %, of Formula 11A Antibody Drug Conjugate.

136. A composition comprising Antibody Drug Conjugates represented by Formula 12 and Formula 12A having the structures of:

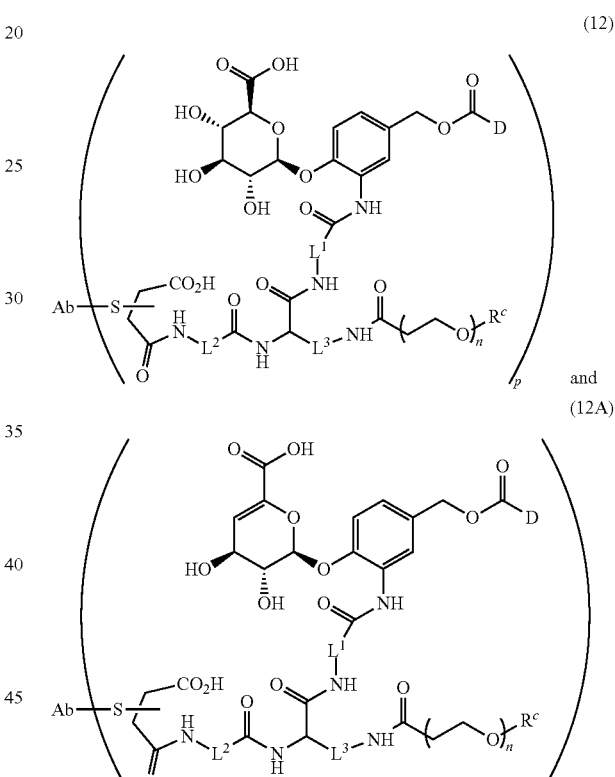

or pharmaceutically acceptable salts thereof, wherein Ab is an antibody; S is a sulfur atom from the antibody; the Ab-S— moeity is attached to the carbon atom α or β to the carboxylic acid functional group; D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. % Formula 12A Antibody Drug Conjugate.

137. The composition of embodiment 136, wherein the Formula 12 and Formula 12A Antibody drug Conjugates have the structures of:

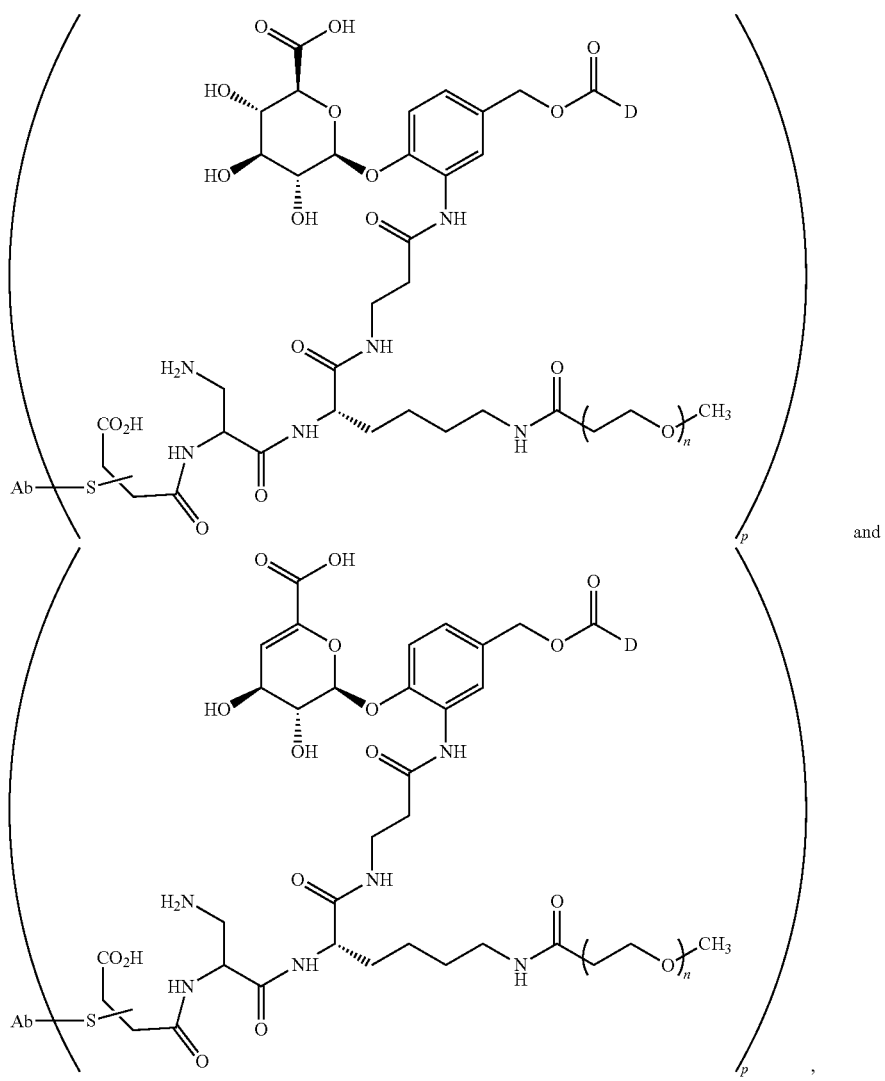
or pharmaceutically acceptable salts thereof.
138. The composition or compound of any one of embodiments 132-137, wherein the auristatin Drug Unit has the has the structure of Formula $D_{E-1}$, $D_{E-2}$, or $D_{F-1}$:
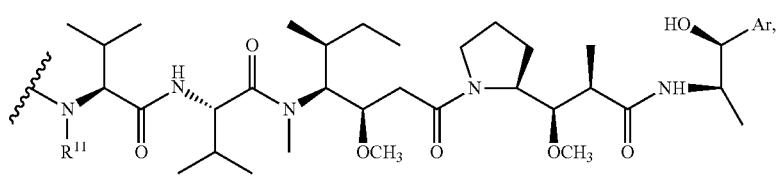
($D_{E-1}$)
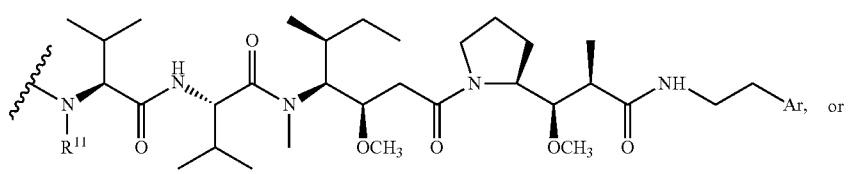
($D_{E-2}$)
or -continued (D$_{F-1}$)

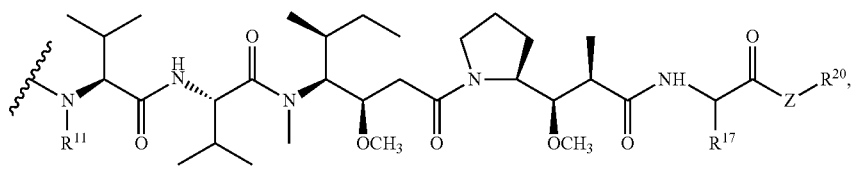

wherein Ar is optionally substituted $C_6$-$C_{10}$ aryl or optionally substituted $C_3$-$C_5$ heterocyclyl and the wavy line indicates the site of attachment to the remainder of Conjugate structure; and the wavy line indicates the site of attachment to the remainder of the Conjugate structure.

139. The composition or compound of embodiment 138, wherein D has the structure of Formula $D_{E-1}$.

140. The composition or compound of embodiment 138, wherein D has the structure of Formula $D_{E-2}$.

141. The composition or compound of embodiment 138, wherein D has the structure of Formula $D_{F-1}$.

142. The composition or compound of embodiment 139 or 140, wherein Ar is optionally substituted phenyl or optionally substituted 2-pyridyl.

143. The composition or compound of embodiment 141, wherein —Z— is —O— and $R^{20}$ is $C_1$-$C_4$ alkyl.

144. The composition or compound of embodiment 141, wherein Z is —NH— and $R^{20}$ is optionally substituted phenyl or optionally substituted $C_5$-$C_6$ heteroaryl.

145. The composition or compound of any one of embodiments 138-144, wherein $R^{11}$ is methyl.

146. The composition or compound of any one of embodiments 132-137, wherein D has the structure of Formula $D_{F/E-3}$:

(D)$_{F/E-3}$

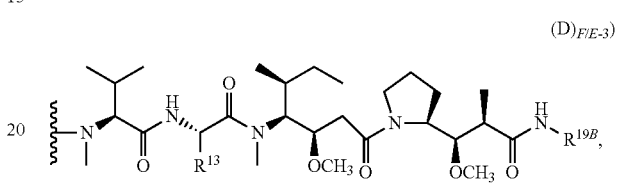

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —CH($CH_2Ph$)-2-thiazole, —CH($CH_2Ph$)-2-pyridyl, —CH($CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph; and the wavy line indicates the site of attachment to the remainder of the Conjugate structure.

147. The composition or compound of any one of embodiments 132-137, wherein D has the structure of:

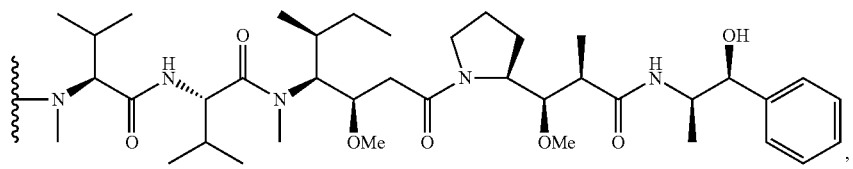 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

wherein the wavy line indicates the site of attachment to the remainder of the Conjugate structure.

148. The composition of embodiment 136, wherein Formula 12 and Formula 12A have the structures of:

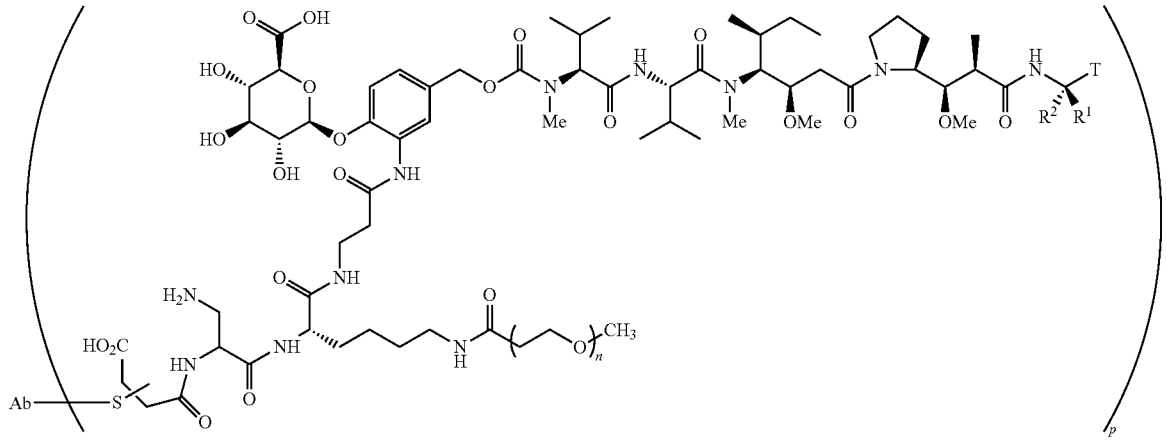

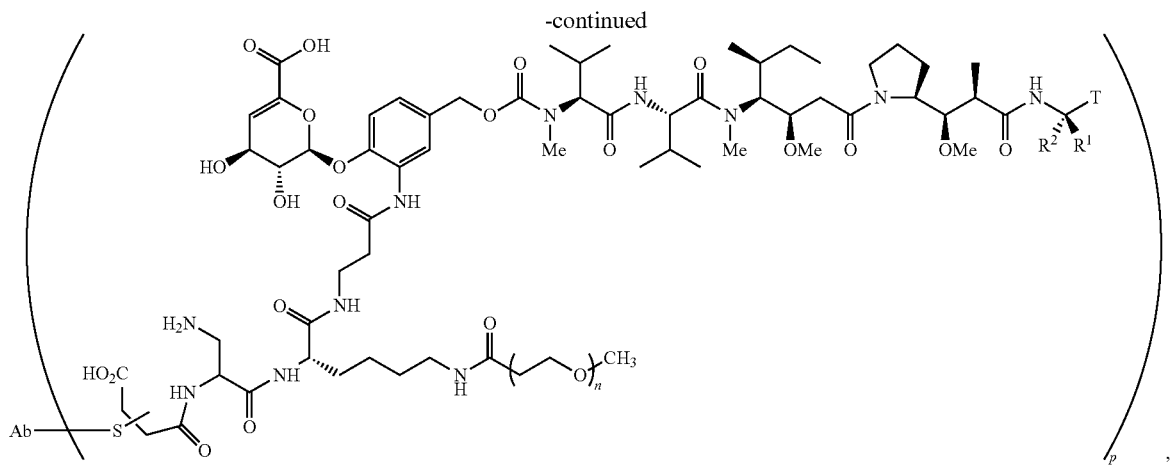
or pharmaceutically acceptable salts thereof.
149. The compound of embodiment 132, wherein the compound has the structure selected from the group consisting of:
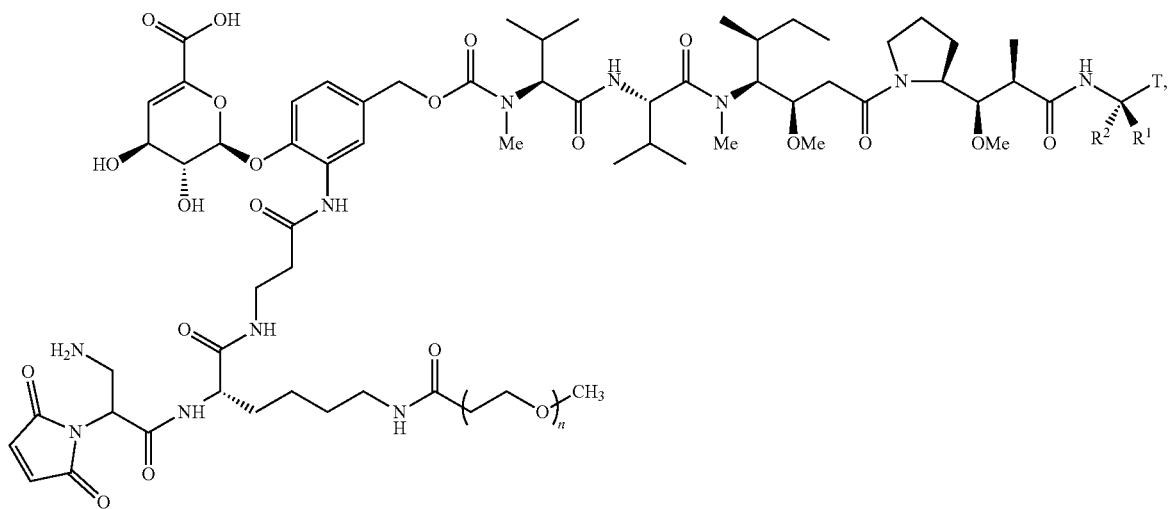
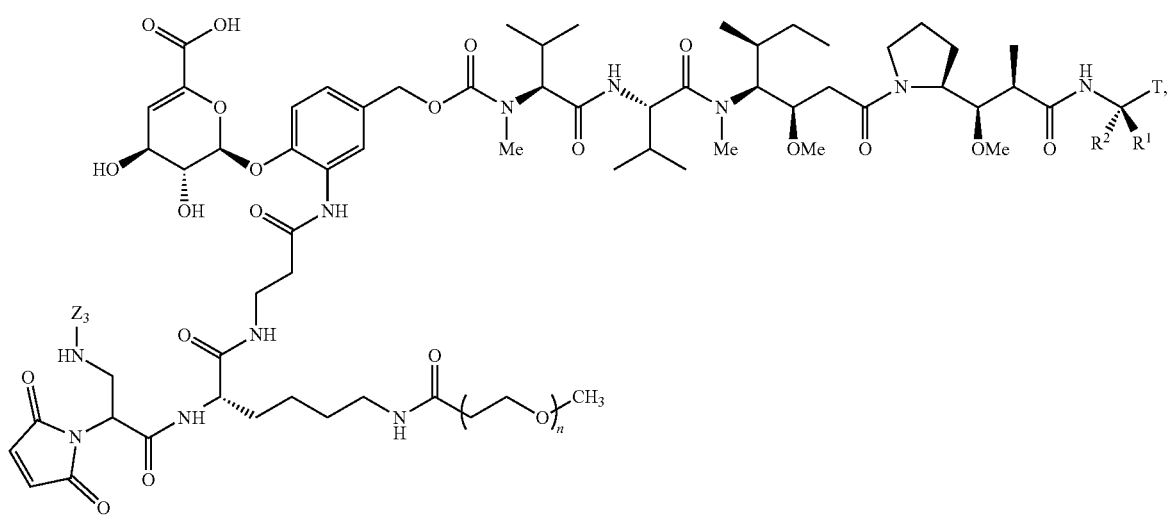

-continued

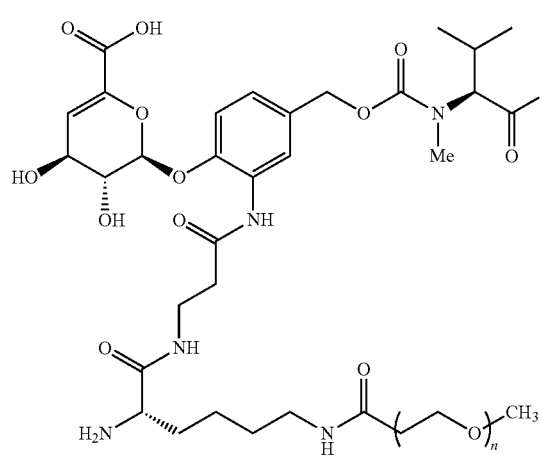
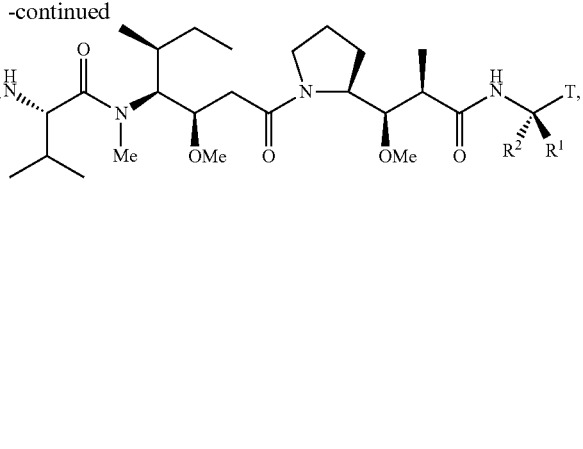

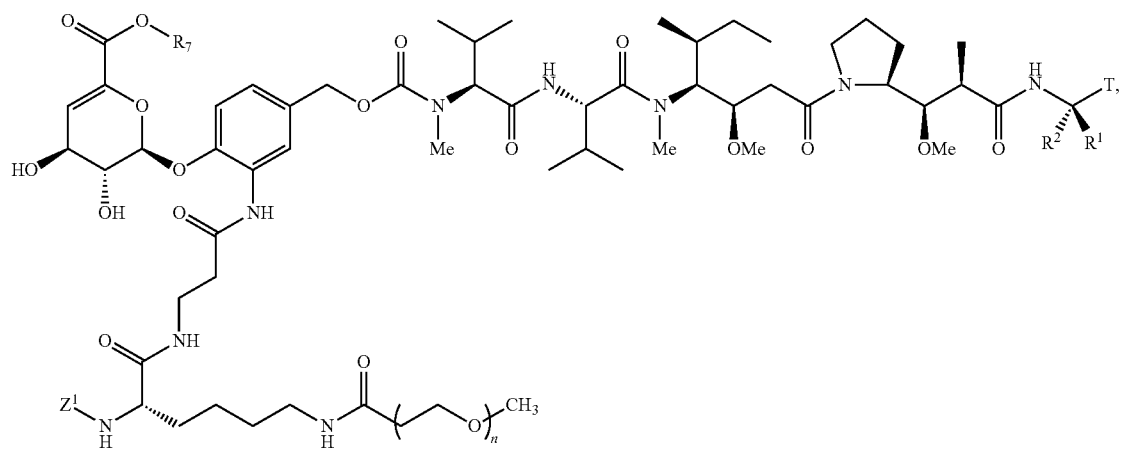

and salts thereof, wherein $R^7$ is methyl; $Z^1$ has the structure of:

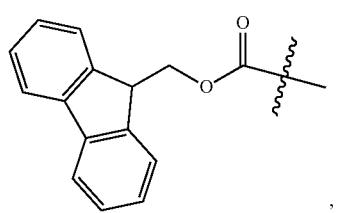 [SMILES: *C(=O)OCC1c2ccccc2-c2ccccc21]

wherein the wavy line indicates the site of attachment to the remainder of the compound structure; $Z^3$ is —C(=O)—O-t-Bu; $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH(OR$^4$)—R$^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl.

150. The compound or composition of embodiment 148 or 149, wherein $R^1$ is hydrogen or methyl; $R^2$ is hydrogen; and T is —CH(OR$^4$)—R$^5$; wherein $R^4$ is hydrogen or methyl and $R^5$ is $C_6$-$C_{10}$ aryl.

151. The compound or composition of embodiment 150, wherein $R^1$ is methyl, $R^2$ is H, and T is —CH(OH)-Ph.

152. The compound or composition of any one of embodiments 132-151, wherein subscript n is 8 or 12.

153. The compound of embodiment 132, wherein the compound has the structure selected from the group consisting of:

159
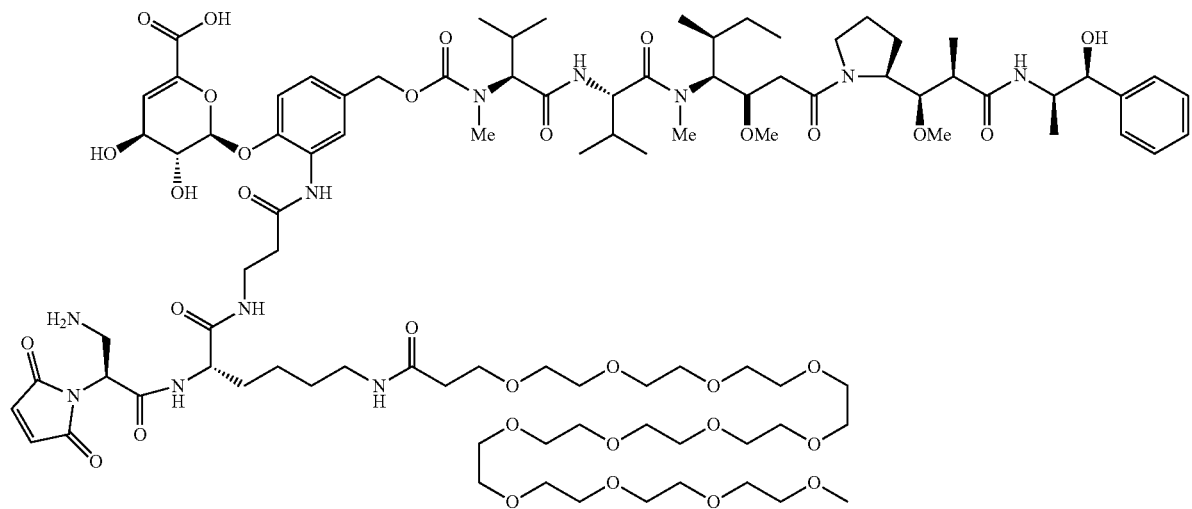
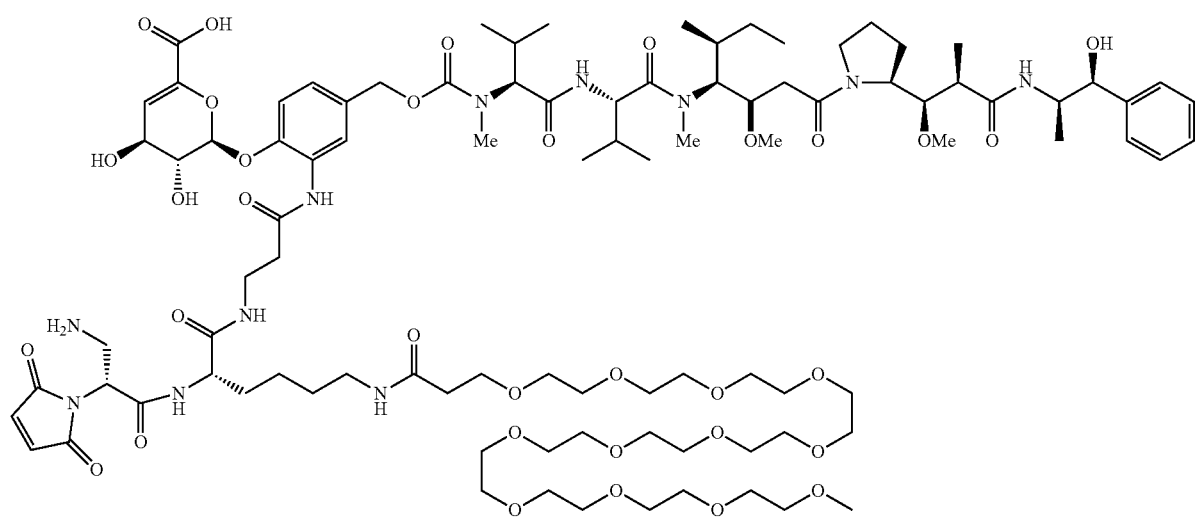
160
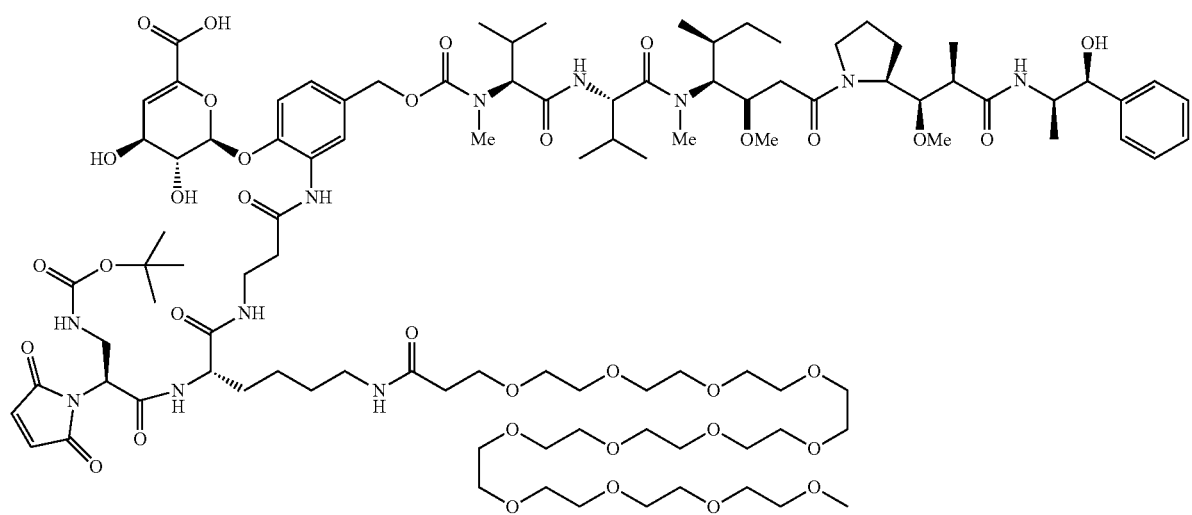

-continued
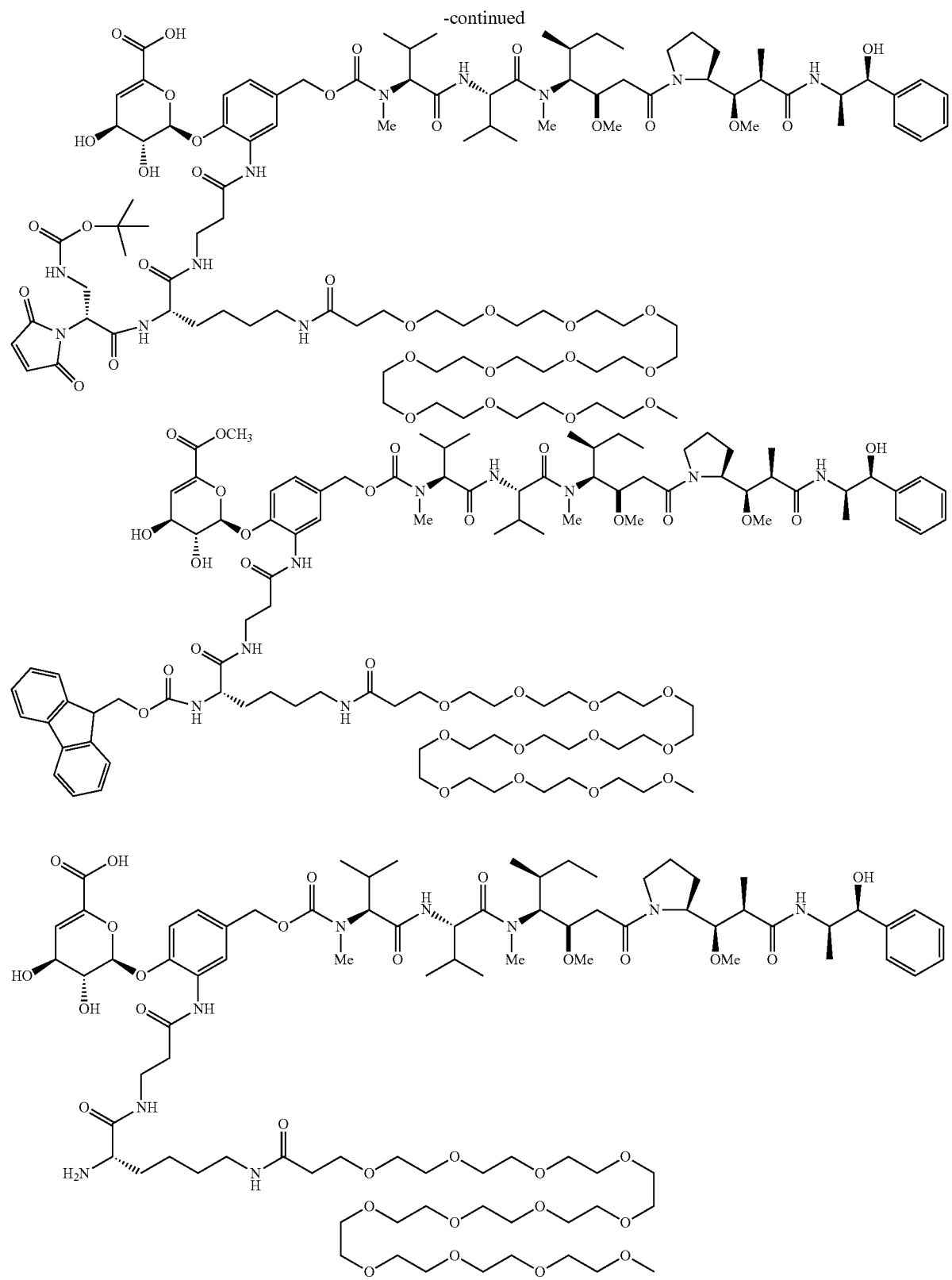
and salts thereof.
154. The composition of embodiment 137, wherein the Formula 12 and Formula 12A Antibody Drug Conjugates have the structures of:

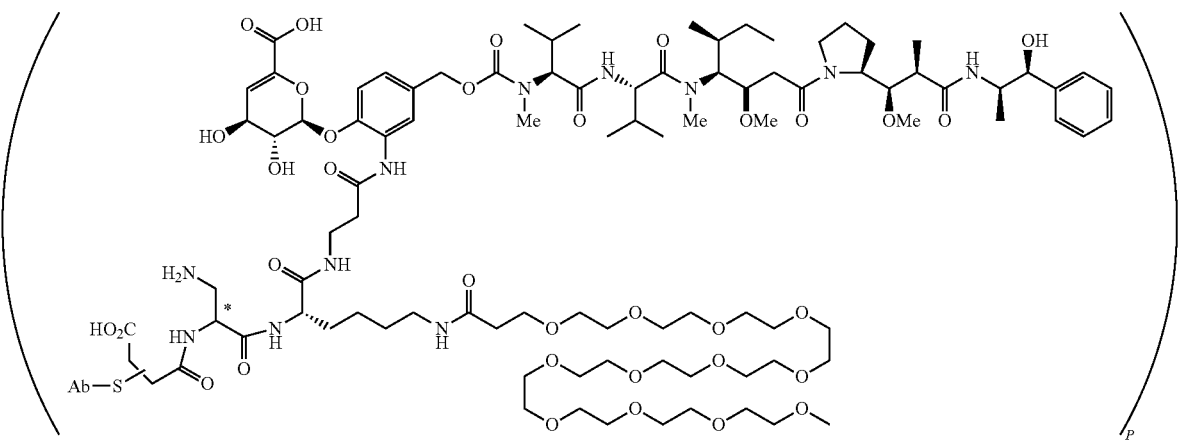

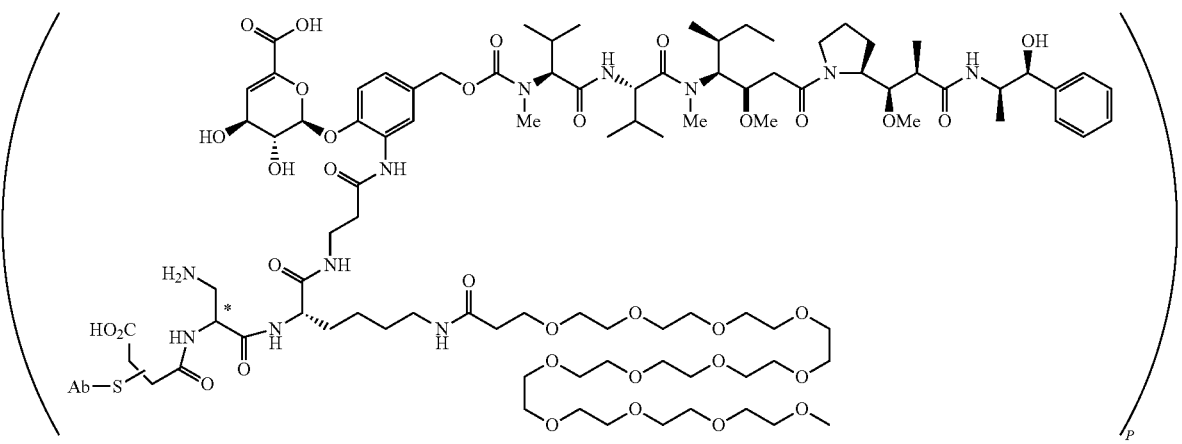

or pharmaceutically acceptable salts thereof.

155. The composition of embodiment 154 wherein the indicated carbon atom (*) is predominately in the S-configuration.

156. The composition of any one of embodiments 135-148 and 150-155, wherein the antibody is capable of selectively binding to a tumor associated antigen.

157. The composition of embodiment 156, wherein the tumor associated antigen is comprised of an extracellular domain of a cell-surface protein or glycoprotein to which the antibody is capable of binding.

158. The composition of embodiment 157, wherein the cell-surface protein or glycoprotein is that of an abnormal cell.

159. The composition of embodiment 158, wherein the cell-surface protein or glycoprotein of the abnormal cell is capable of internalization upon binding by an Antibody Drug Conjugate compound of the composition.

160. The composition of any one of embodiments 135-148 and 150-159, wherein subscript p is about 8.

161. A method of treating a cancer or contacting cancer cells comprising the step of administering to a subject having the cancer or contacting the cancer cells with an Antibody Drug Conjugate composition of any one of embodiments 135-148 and 154-160.

162. A composition for treating a cancer in a subject, wherein the composition is of any one of embodiments 135-148 and 154-160.

163. Use of a composition for preparation of a medicant for treating a cancer in a subject, wherein the composition is of any one of embodiments 135-148 and 154-160.

164. The method, composition or use of embodiment 161, 162 or 163, wherein the subject is a mammal.

165. The method, composition or use of embodiment 164, wherein the mammal is a human or a non-human primate.

166. The method, composition or use of any one of embodiments 161-165, wherein the cancer or cancer cells thereof is that of a leukemia or lymphoma.

167. The method, composition or use of embodiment of embodiment 161-165, wherein the cancer or cancer cell thereof is a B cell malignancy.

1A. A method for preparing a Drug Linker intermediate compound of Formula ID:

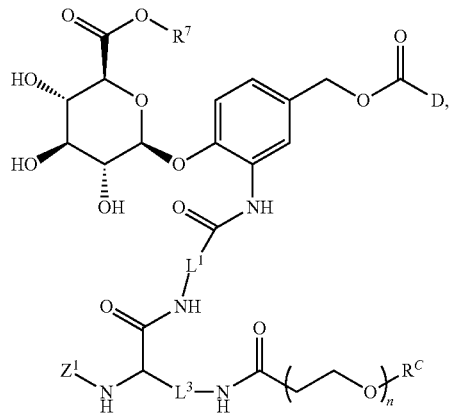

or a salt thereof, wherein D is an auristatin Drug Unit; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $Z^1$ is a first suitable amino protecting group; $R^C$ is hydrogen or a PEG Capping Unit; and subscript n ranges from 2 to 24, the method comprising the step of: (c) contacting a Drug Linker intermediate compound of Formula IC with either a Grignard reagent or an alkoxy magnesium halide in a suitable alcohol-containing solvent, wherein the Formula IC Drug Linker intermediate compound has the structure of:

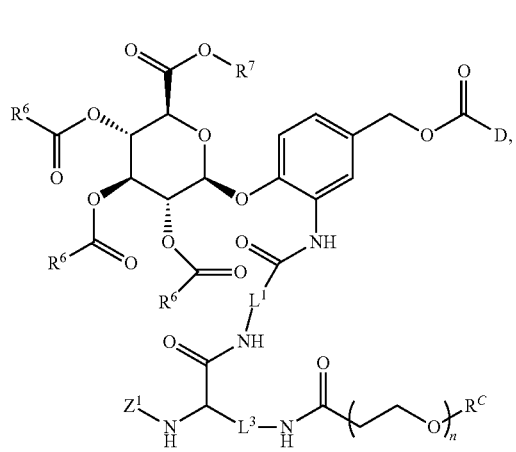

wherein each of $R^6$ is independently optionally substituted $C_1$-$C_8$ alkyl, optionally substituted $C_6$-$C_{10}$ arylene or optionally substituted $C_5$-$C_{10}$ heteroarylene so that $R^6C$ (=O)— provides for an ester functional group that is a suitable hydroxyl protecting group; and the remaining variable groups are as previously described; and wherein said Grignard reagent or an alkoxy magnesium halide contacting selectively removes the hydroxyl protecting groups to provide the Formula IC compound.

2A. A method for preparing a Drug Linker intermediate of Formula IE:

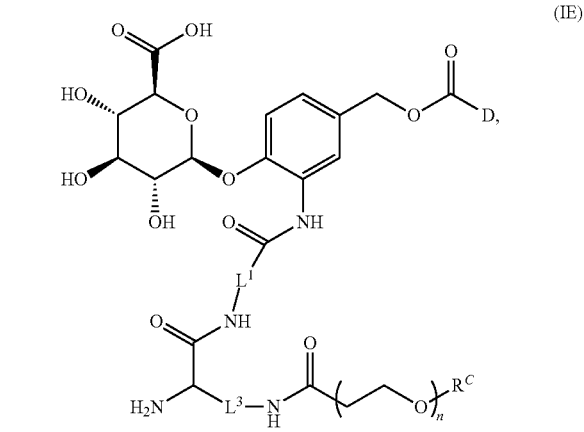

or a salt thereof, wherein D is an auristatin Drug Unit; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group; $R^C$ is hydrogen or a PEG Capping Unit; and subscript n ranges from 2 to 24, the method comprising step (c) of embodiment 1A, further comprising the subsequent step of: (d) contacting the product of step (c) with a first deprotecting agent, wherein said first deprotecting agent contacting removes the $Z^1$ amino and carboxylic acid protecting groups to provide the Formula IE Drug Linker intermediate compound.

3A. The method of embodiment 1A, wherein the Formula IC and Formula ID Drug Linker intermediate compounds have the structures of Formula IIC and Formula IID:

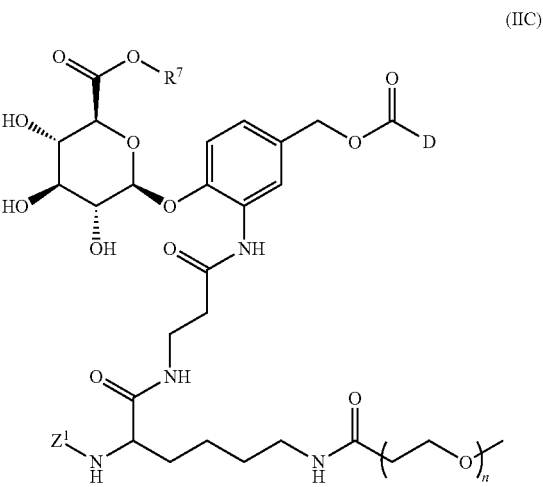

(IID)

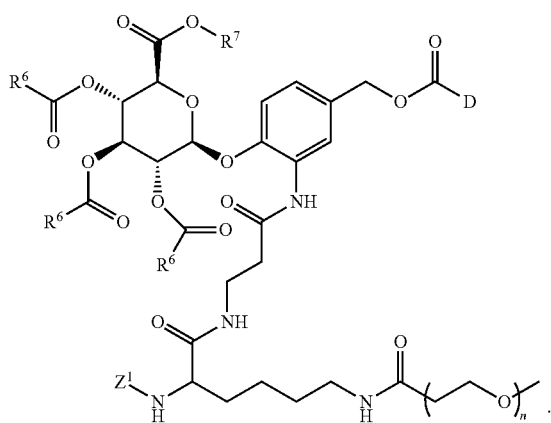

4A. The method of embodiment 2A, wherein the Formula IC and Formula IE Drug Linker intermediate compounds, or salts thereof, have the structures of Formula IIC and Formula IIIE:

(IIC)

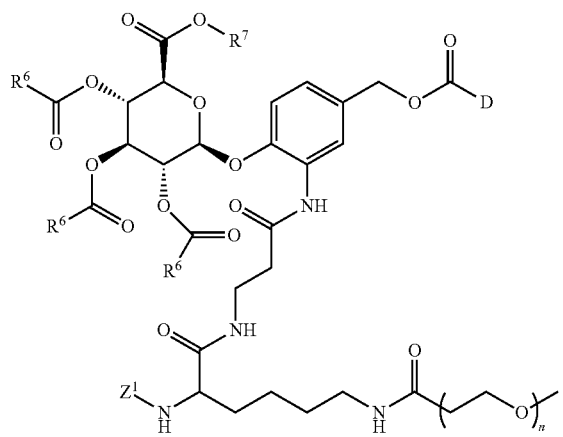

(IIIE)

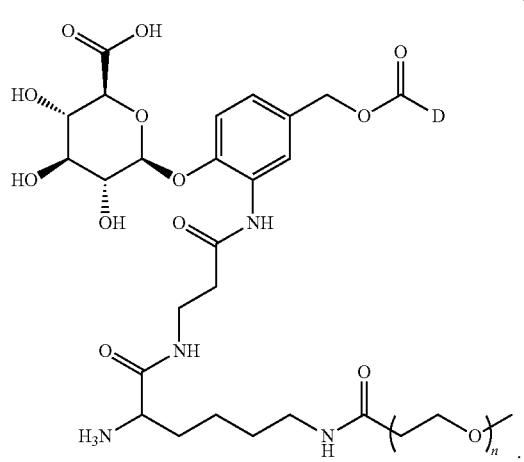

5A. A method for preparing a Drug Linker intermediate compound of Formula IE:

(IE)

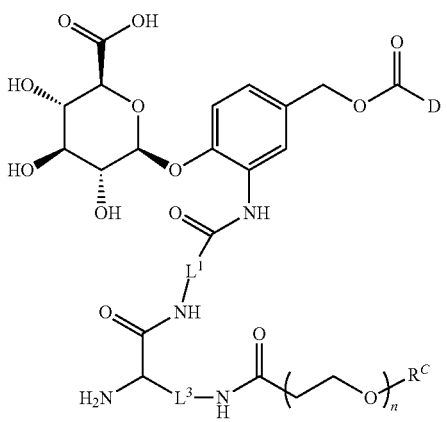

or a salt thereof, wherein D is an auristatin Drug Unit; each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; and subscript n ranges from 2 to 24, the method comprising the steps of embodiment 2A, further comprising prior to steps (c) and (d) the steps of: (a) contacting a Drug Linker intermediate of Formula IA with a second deprotecting agent, wherein the Formula IA Drug Linker intermediate compound has the structure of:

(IA)

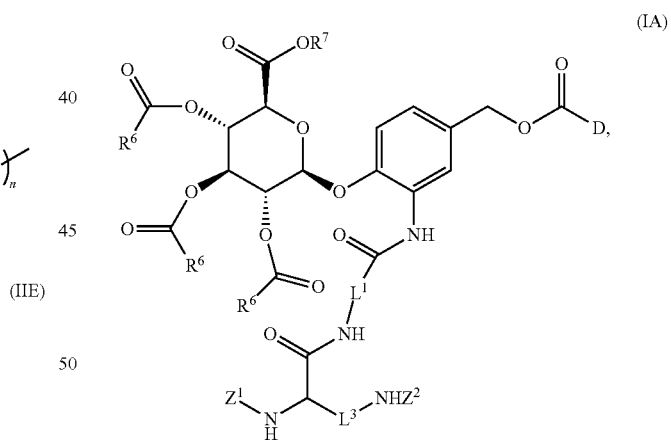

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(\!=\!O)$— provides for an ester functional group that is a suitable hydroxyl protecting group and —$OR^7$ provides an ester functional group that is a suitable carboxylic acid protecting group; each of $Z^1$ and $Z^2$ is independently a first and second suitable amino protecting group, respectively; and the remaining variable groups as previously defined, wherein said second deprotecting agent contacting selectively removes the $Z^2$ amino protecting group to provide a Drug Linker intermediate compound of Formula IB:

(IB)

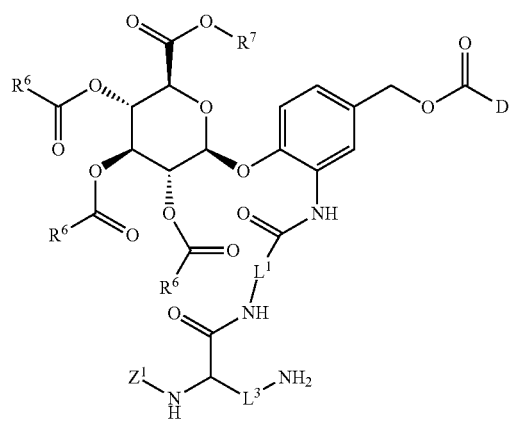

or a salt thereof, wherein the variable groups are as previously defined;

(b) contacting the Formula IB compound in a suitable solvent with a compound of Formula iv:

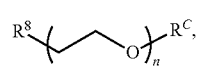

(iv)

wherein $R^8$ is an activated ester group; and the remaining variable groups are as previously defined, or (b') contacting the Formula IB Drug Linker intermediate compound in a suitable solvent with a Formula iv compound in which $R^8$ is —COOH and the remaining variable groups are as previously defined in the presence of a first activating agent, wherein said contacting step (b) or (b') provides the Formula IC Drug Linker intermediate compound of:

(IC)

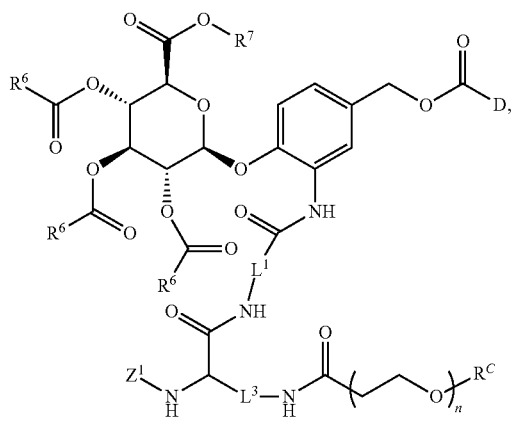

or a salt thereof, wherein the variable groups are as previously defined.

6A. A method for preparing a Drug Linker compound or intermediate thereof of Formula I:

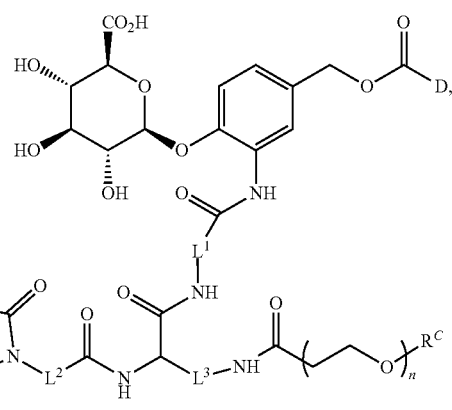

or a salt thereof, wherein D is an auristatin Drug Unit; each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is a PEG Capping Unit; and subscript n ranges from 2 to 24, the method comprising steps (a)-(d) of embodiment 6, followed by the step of: (e) contacting the Formula IE Drug Linker intermediate compound in a suitable solvent with a compound of Formula v:

(v)

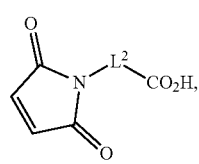

or a salt thereof, wherein $L^2$ is as previously defined, in the presence of a second activating agent; and wherein said Formula v contacting provides the Formula I Drug Linker or Drug Linker intermediate compound or salt thereof.

7A. The method of any one of embodiments 1A-7A wherein each of $L^1$ and $L^3$ is independently $C_1$-$C_4$ alkylene and $L^2$ is independently optionally substituted $C_1$-$C_4$ alkylene.

8A. A method for preparing a Drug Linker compound of Formula II:

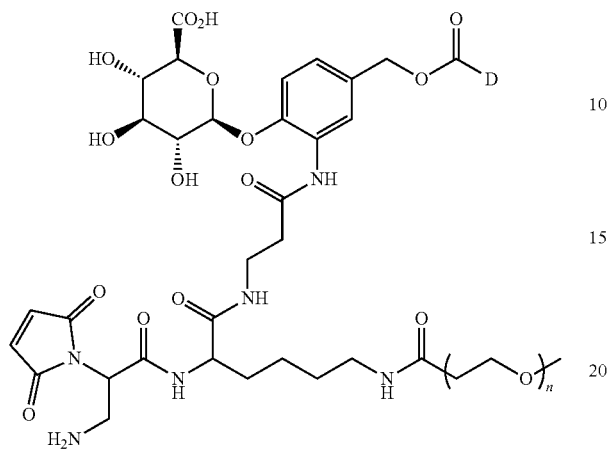

(II)

or a salt thereof, wherein D is an auristatin Drug Unit; and subscript n ranges from 2 to 24, the method comprising steps (a)-(e) of embodiment 7A, wherein the Formula v compound has the structure of:

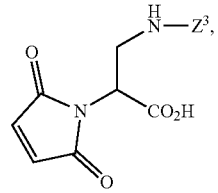

(v)

and wherein the Formula IA, Formula IB, Formula IC, Formula ID and Formula IE Drug Linker intermediate compounds, optionally in salt form, have the structures of Formula IIA, Formula IIB, Formula IIC, Formula IID, Formula IIE, Formula IIF:

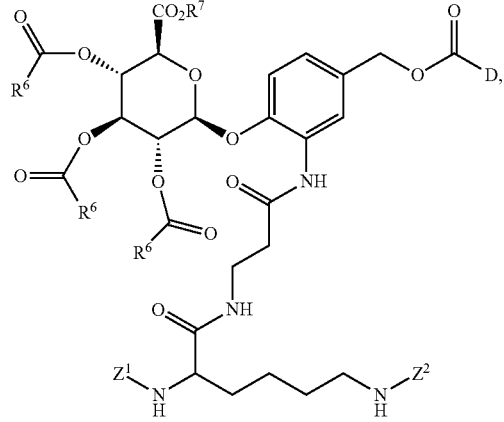

(IIA)

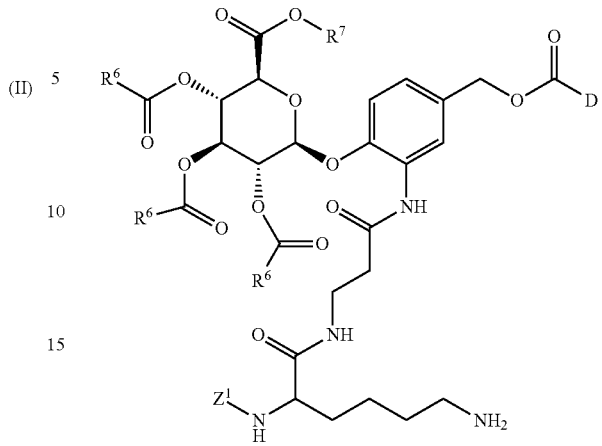

(IIB)

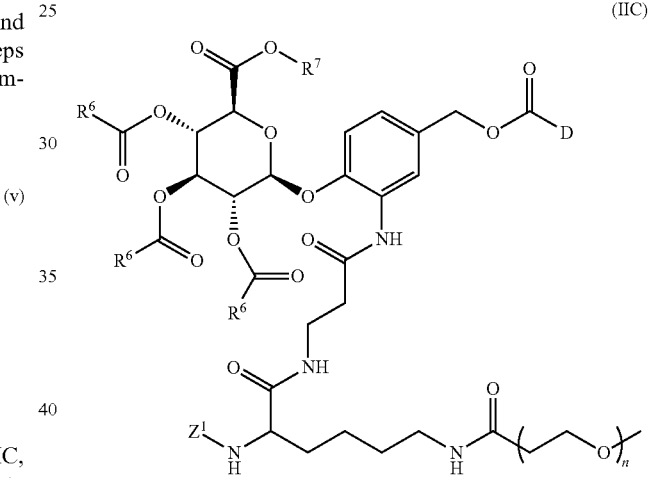

(IIC)

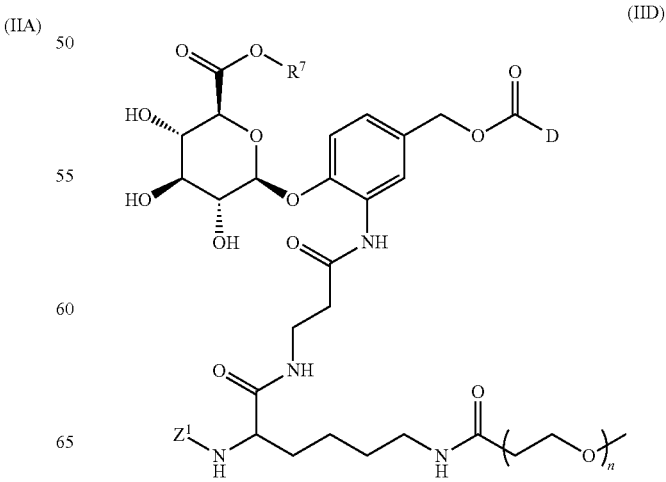

(IID)

-continued

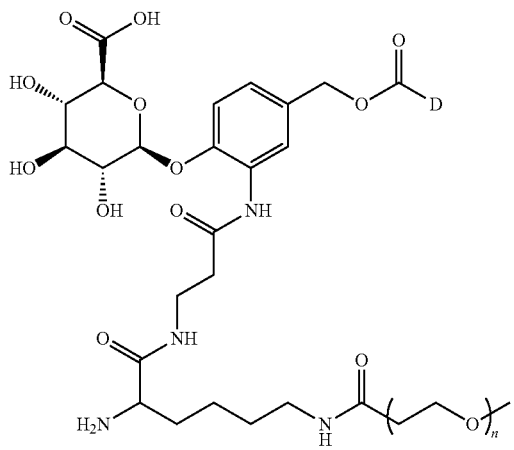

(IIE)

(IIF)

wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; each of $Z^1$, $Z^2$ and $Z^3$ is independently a first, second and third suitable amino protecting group, respectively, in particular $Z^3$ is an acid-labile amino protecting group, more particularly —C(=O)O-t-Bu, the method further comprising the step of: (f) contacting the Formula IF Drug Linker intermediate compound of with a third deprotecting agent, wherein said third deprotecting reagent contacting removes the $Z^3$ amino protecting group whereby the Formula II Drug Linker compound or salt thereof is provided.

9A. The method of any one of embodiments 1-8, wherein the auristatin Drug Unit (D) has the structure of:

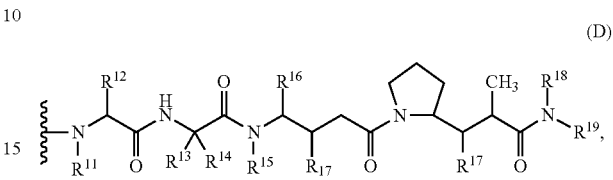

(D)

wherein the wavy line indicates covalent bonding of D to the remainder of the Drug Linker or Drug Linker intermediate compound; $R^{11}$ is selected from the group consisting of H and $C_1$-$C_8$ alkyl, in particular methyl; $R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); $R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); $R^{14}$ is selected from the group consisting of H and methyl, or $R^{13}$ and $R^{14}$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle, and n is selected from the group consisting of 2, 3, 4, 5 and 6; $R^{15}$ is selected from the group consisting of H and $C_1$-$C_8$ alkyl; $R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_5$ carbocycle), $C_3$-$C_8$ heterocycle, and $C_1$-$C_8$ alkyl-($C_3$-$C_5$ heterocycle); each $R^{17}$ is independently selected from the group consisting of H, OH, $C_1$-$C_8$ alkyl, $C_3$-$C_8$ carbocycle, and O—($C_1$-$C_8$ alkyl); $R^{18}$ is selected from the group consisting of H and $C_1$-$C_8$ alkyl; $R^{19}$ is selected from the group consisting of —$C(R^{17})_2$—$C(R^{17})_2$-aryl, —$C(R^{17})_2$—$C(R^{17})_2$—($C_3$-$C_8$ heterocycle), —$C(R^{17})_2$—$C(O)$—$ZR^{20}$, and —$C(R^{17})_2$—$C(R^7)_2$—($C_3$-$C_5$ carbocycle); $R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; Z is —O—, or —NH—, or Z— is —O— and $R^{20}$ is $C_1$-$C_4$ alkyl or Z is —NH— and $R^{20}$ is optionally substituted phenyl or optionally substituted $C_5$-$C_6$ heteroaryl, in particular, the auristatin Drug Unit (D) has the structure of Formula $D_{E-1}$, $D_{E-2}$, $D_{F-1}$ or $D_{F/E-3}$:

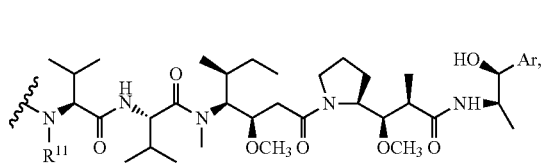

($D_{E-1}$)

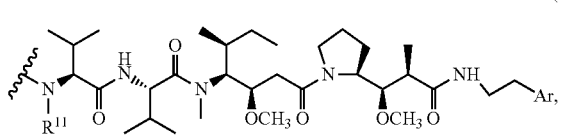

($D_{E-2}$)

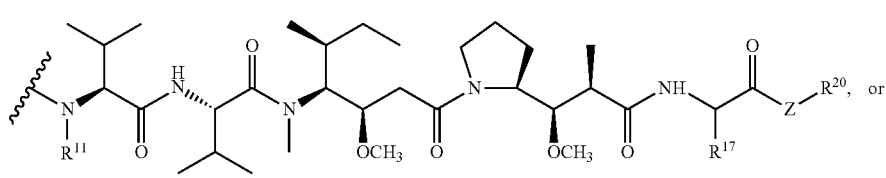

($D_{F-1}$)

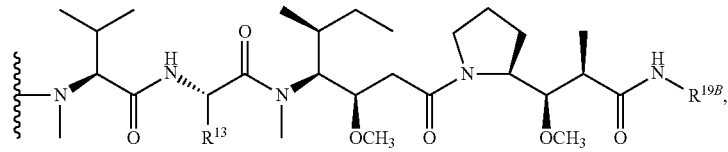

(D<sub>F/E-3</sub>)

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph; Ar is optionally substituted $C_6$-$C_{10}$ aryl or optionally substituted $C_3$-$C_8$ heterocyclyl, in particular, optionally substituted phenyl or optionally substituted 2-pyridyl;

more particularly, D has the structure of:

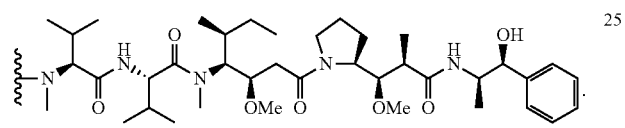

10A. The method of embodiment 5A, wherein the Formula IE Drug Linker intermediate has the structure of Formula 8:

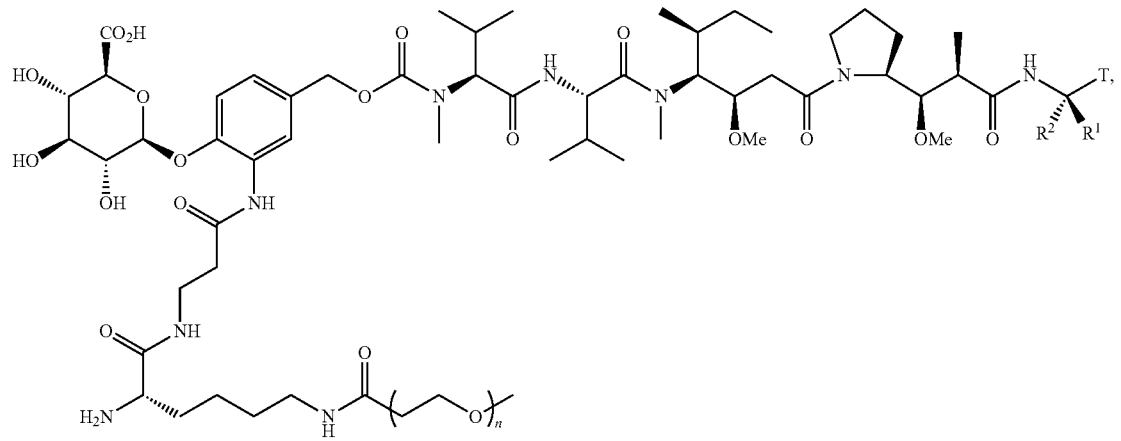

(8)

or a salt thereof, wherein subscript n ranges from 2 to 24; $R^1$ is H or $C_1$-$C_4$ alkyl; $R^2$ is H, $C_1$-$C_4$ alkyl or —$CH_2$—$R^3$; $R^3$ is $C_6$-$C_{10}$ aryl or $C_3$-$C_8$ heterocyclyl; and T is selected from the group consisting of —$CH(OR^4)$—$R^5$ and —$C(=O)$—$OR^4$, wherein $R^4$ is H or $C_1$-$C_4$ alkyl; and $R^5$ is $C_6$-$C_{10}$ aryl or $C_3$-$C_6$ heteroaryl, wherein the Formula IC and Formula ID Drug Linker intermediate compounds, optionally in salt form, have the structures of Formula 6 and Formula 7:

(6)

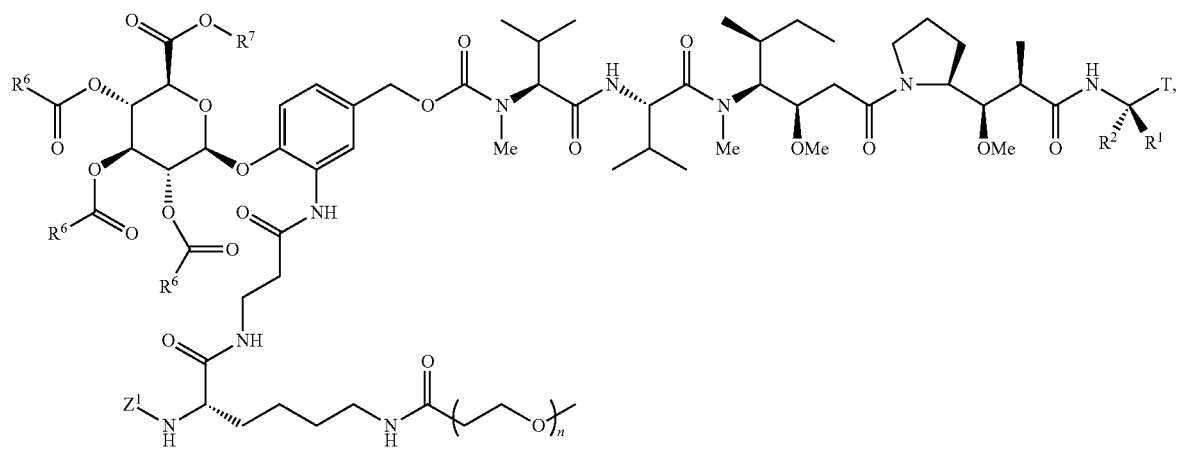

(7)

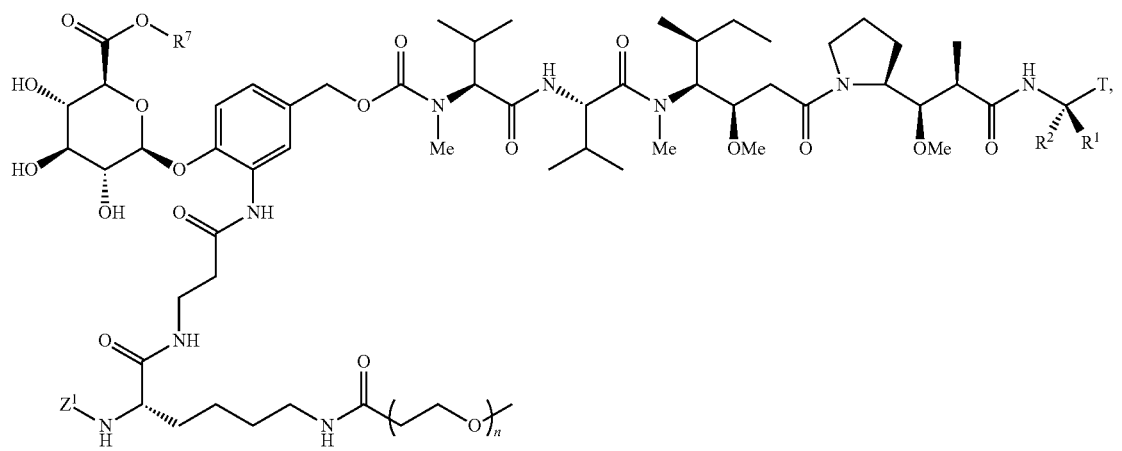

wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; $Z^1$ is a first suitable amino protecting group; and the remaining variable groups are as previously defined, in particular, $R^1$ is H or methyl, $R^2$ is H, and T is —CH($OR^4$)—$R^5$, wherein $R^4$ is H or methyl and $R^5$ is $C_6$-$C_{10}$ aryl, more particularly $R^1$ is methyl, $R^2$ is H, and T is —CH(OH)Ph.

11A. The method of embodiment 8A, wherein the Formula II Drug Linker compound has the structure of Formula 10:

(10)

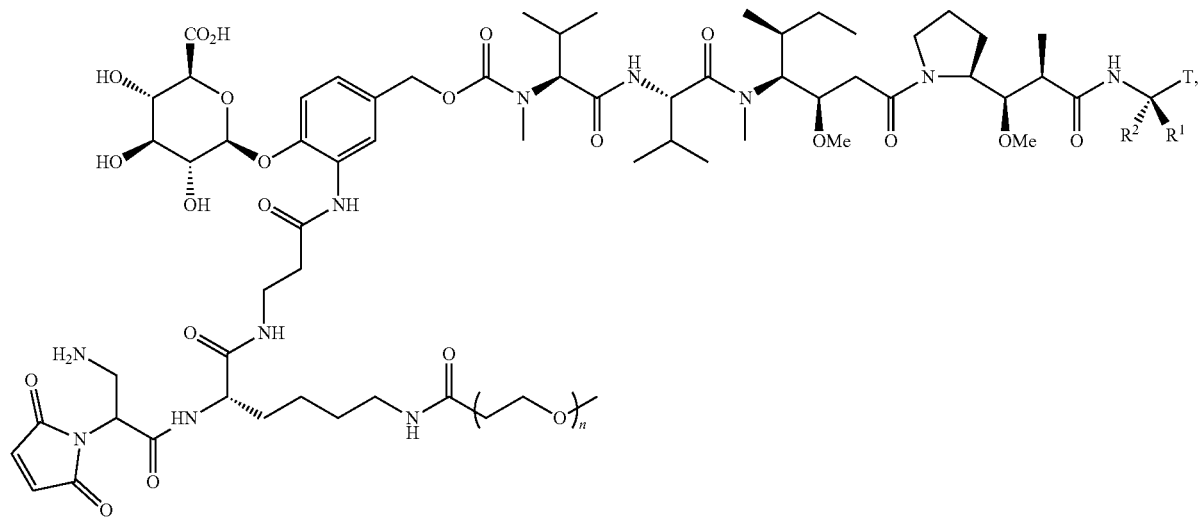

or a salt thereof, wherein subscript n ranges from 2 to 24; $R^1$ is H or $C_1$-$C_4$ alkyl; $R^2$ is H, $C_1$-$C_4$ alkyl or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H or $C_1$-$C_4$ alkyl; and $R^5$ is $C_6$-$C_{10}$ aryl or $C_3$-$C_6$ heteroaryl; and wherein the Drug Linker intermediate compounds, optionally in salt form, of Formula IA, Formula IB, Formula IC, Formula ID, Formula IE and Formula IF have the structure of Formula 4, Formula 5, Formula 6, Formula 7, Formula 8, and Formula 9, respectively:

(4)

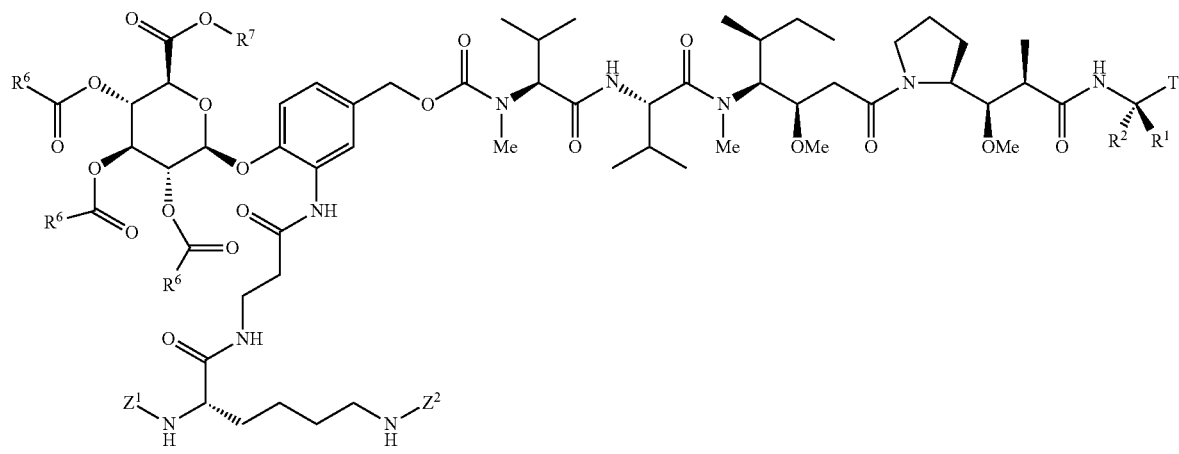

(5)

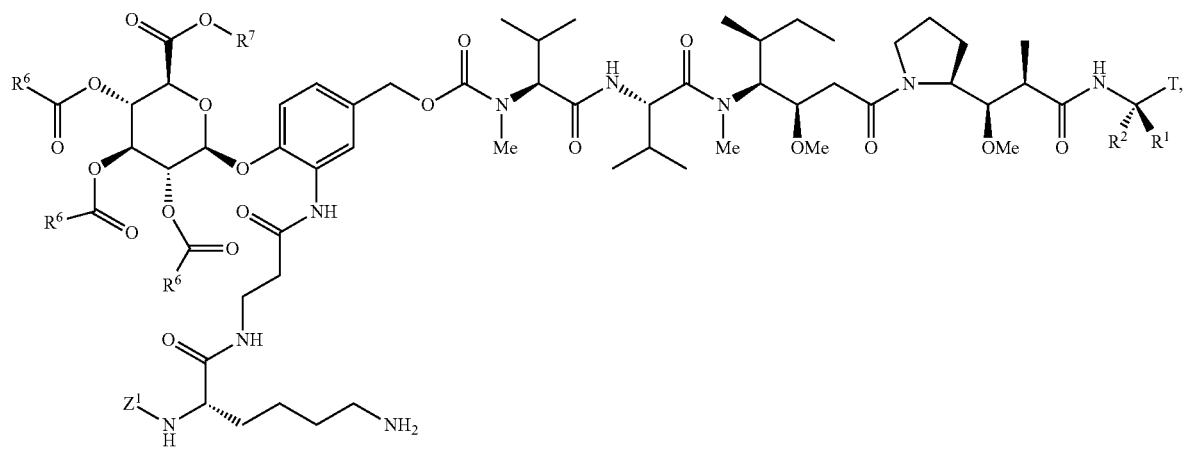

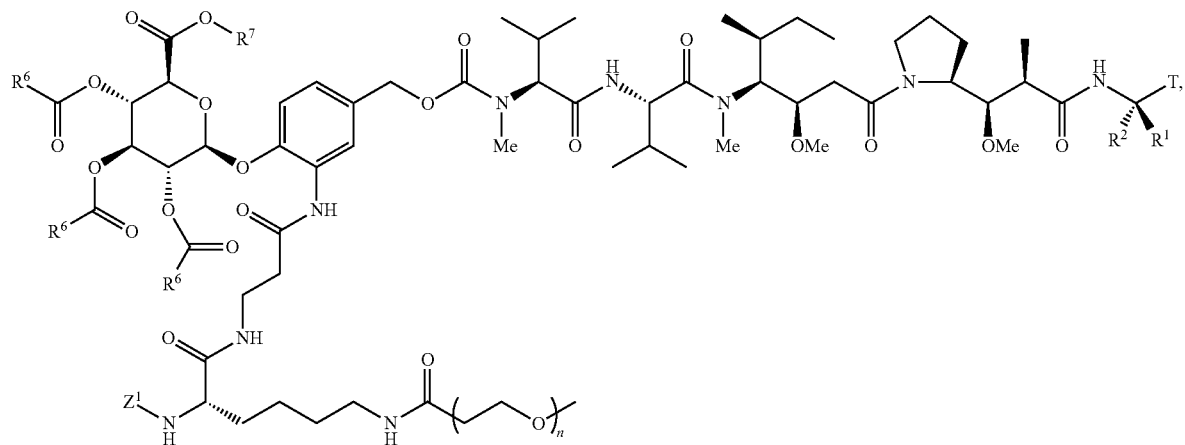
(6)
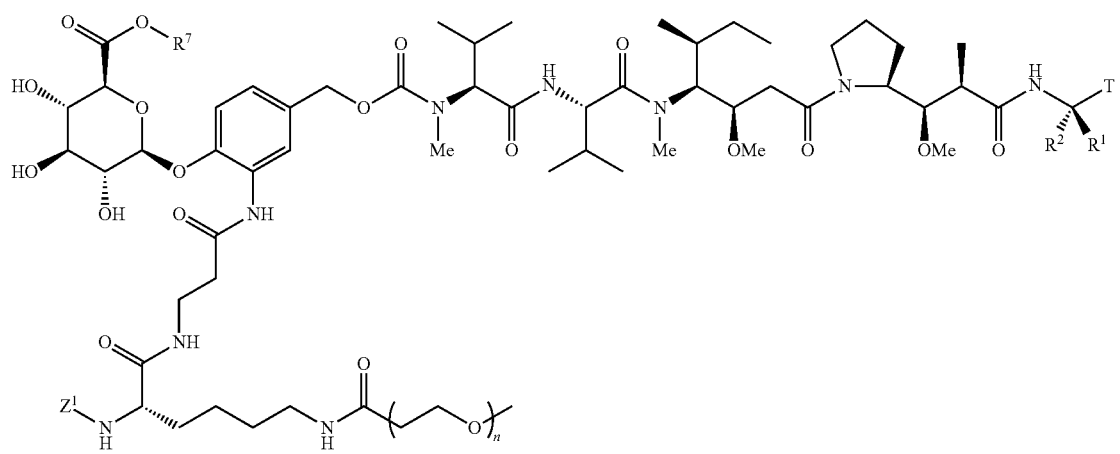
(7)
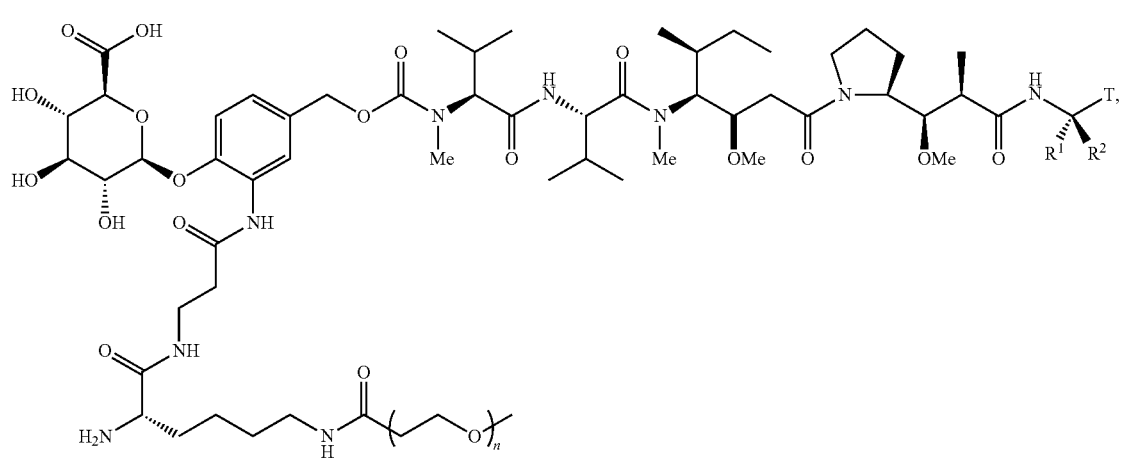
(8)

(9)

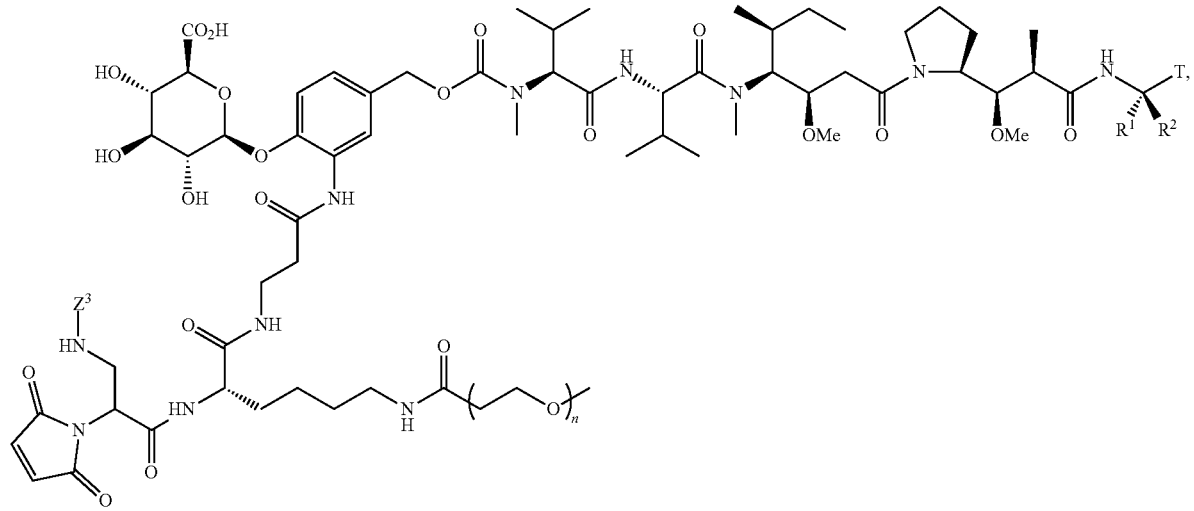

and the Formula v compound has the structure of:

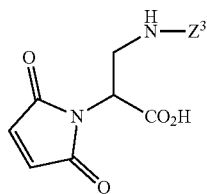

or salt thereof, wherein each of $R^6$ and $R^7$ is independently optionally substituted $C_1$-$C_5$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; and $Z^1$, $Z^2$ and $Z^3$ are independently a first, second, and third suitable amino protecting group, respectively, in particular, $R^1$ is H or methyl, $R^2$ is H, and T is —$CH(OR^4)$—$R^5$, wherein $R^4$ is H or methyl and $R^5$ is $C_6$-$C_{10}$ aryl, more particularly $R^1$ is methyl, $R^2$ is H, and T is —CH(OH)Ph.

12A. The method of any one of embodiments 1A-11A, wherein $Z^1$ is FMOC, or the method of any one of embodiments 6A-11A, wherein $Z^1$ is FMOC and/or $Z^2$ is optionally substituted trityl, in particular 4-methoxy-trityl (MMT).

13A. The method of embodiment 11A, wherein the Formula 10 Drug linker compound has the structure of:

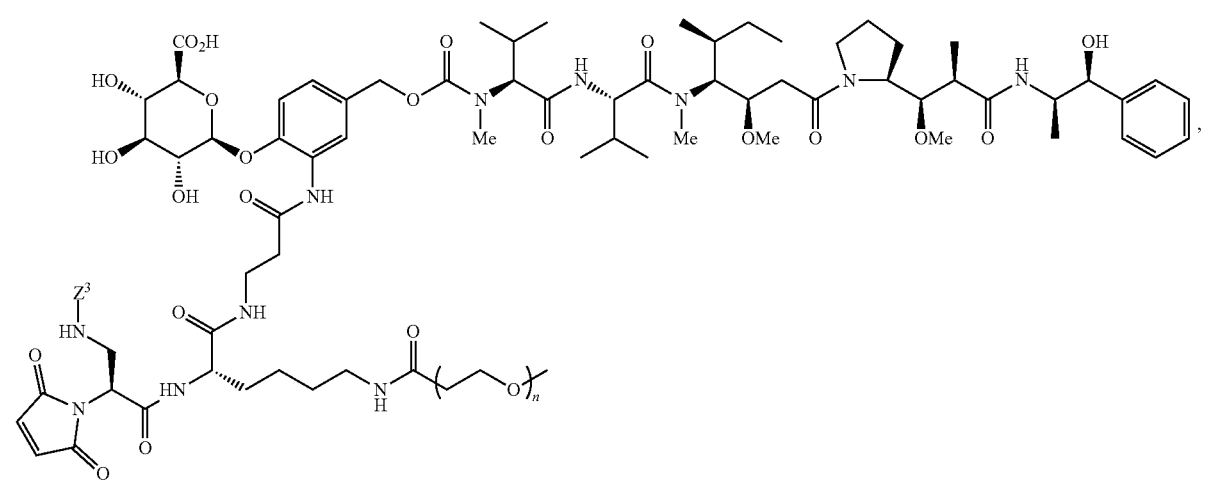

the Formula 9 Drug Linker intermediate and Formula v compounds, or salts thereof, have structures of:
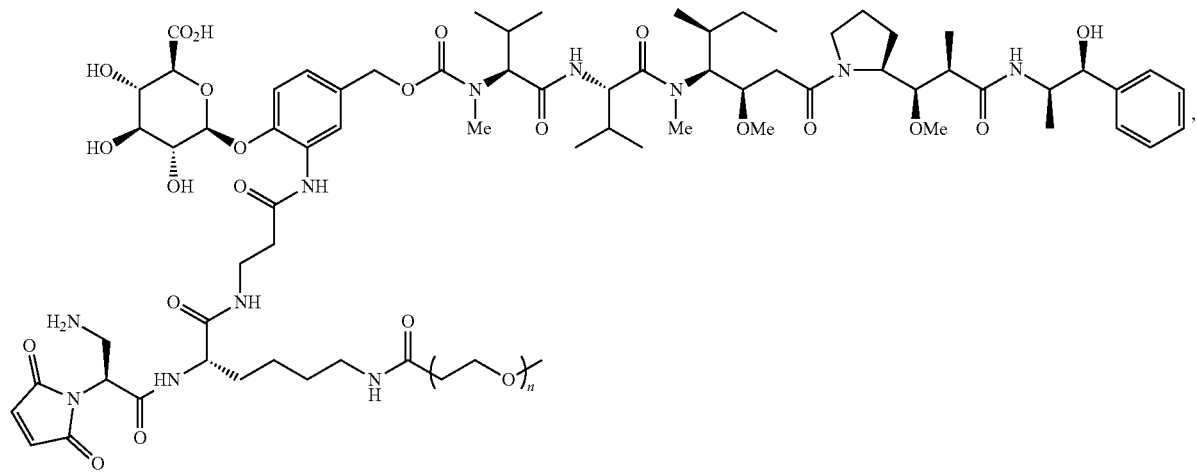
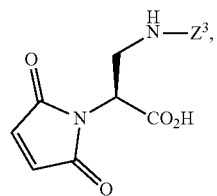
or the Formula 9 Drug Linker intermediate and Formula v compounds, optionally in salt form, have the structures of:
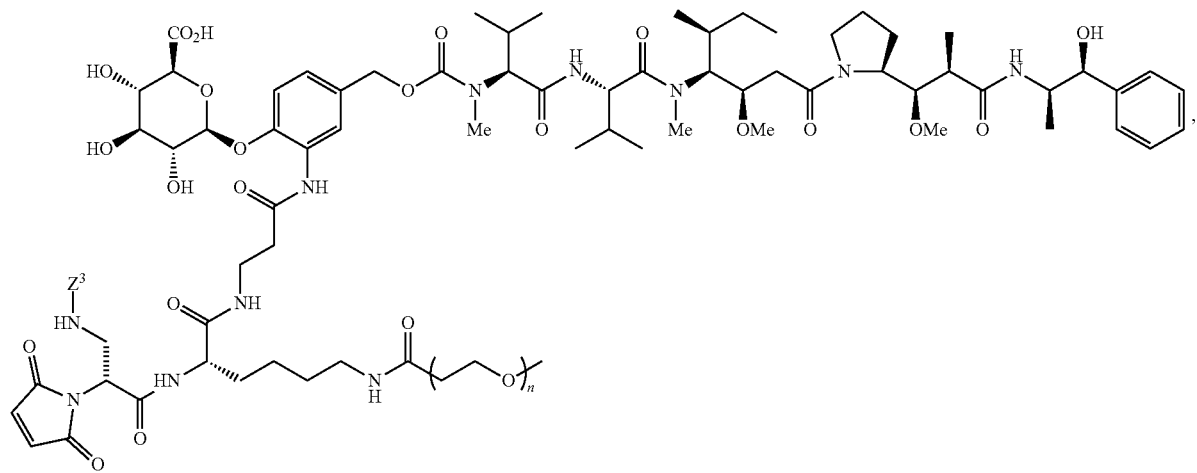

and the Formula 10 Drug Linker compound, optionally in salt form has the structure of:
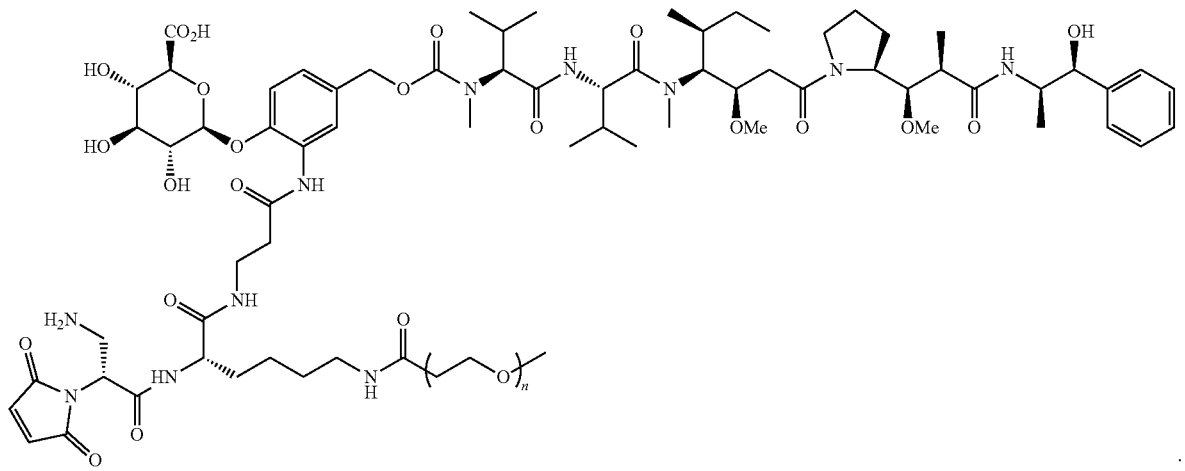
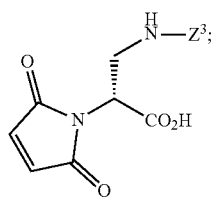
and wherein the other Drug Linker intermediate compounds of Formula 4, Formula 5, Formula 6, Formula 7 and Formula 8 are those of embodiment 22, and
in particular, the Formula 9 Drug Linker Intermediate compound has the structure of:
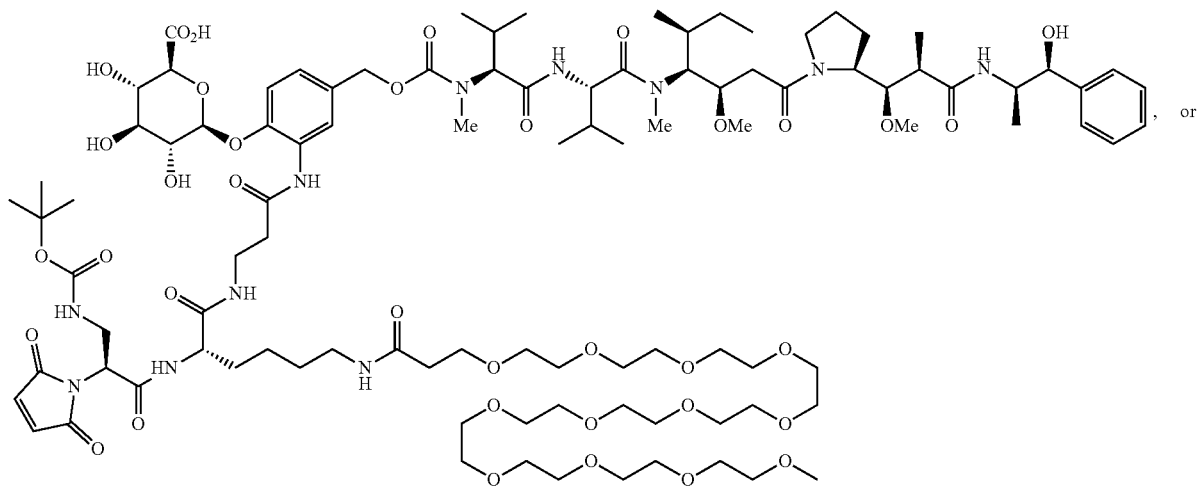

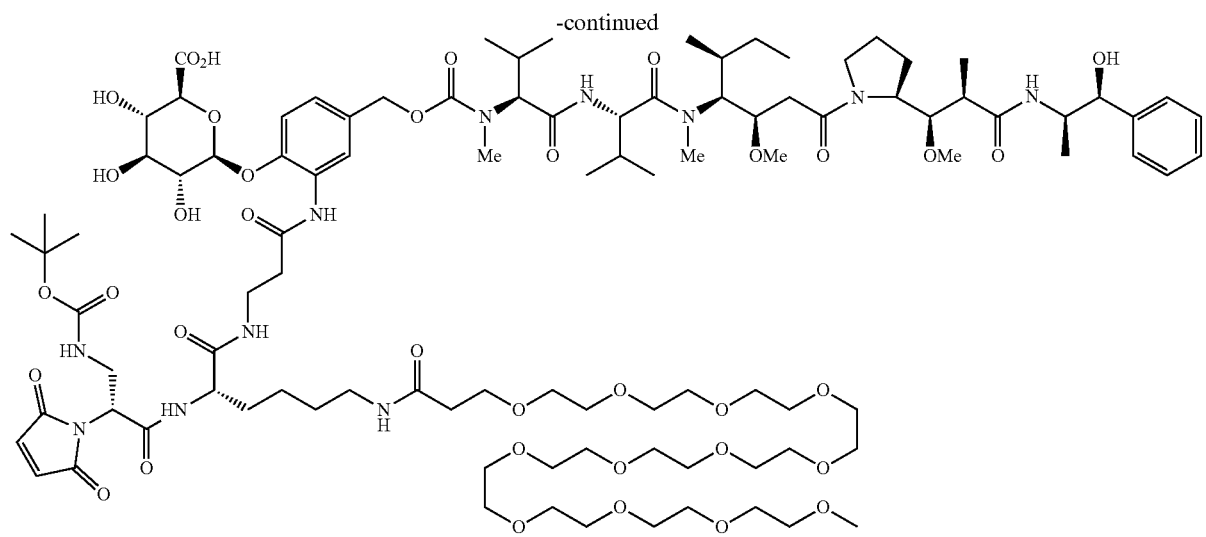
and Formula 10 Drug Linker compound has the structure of:
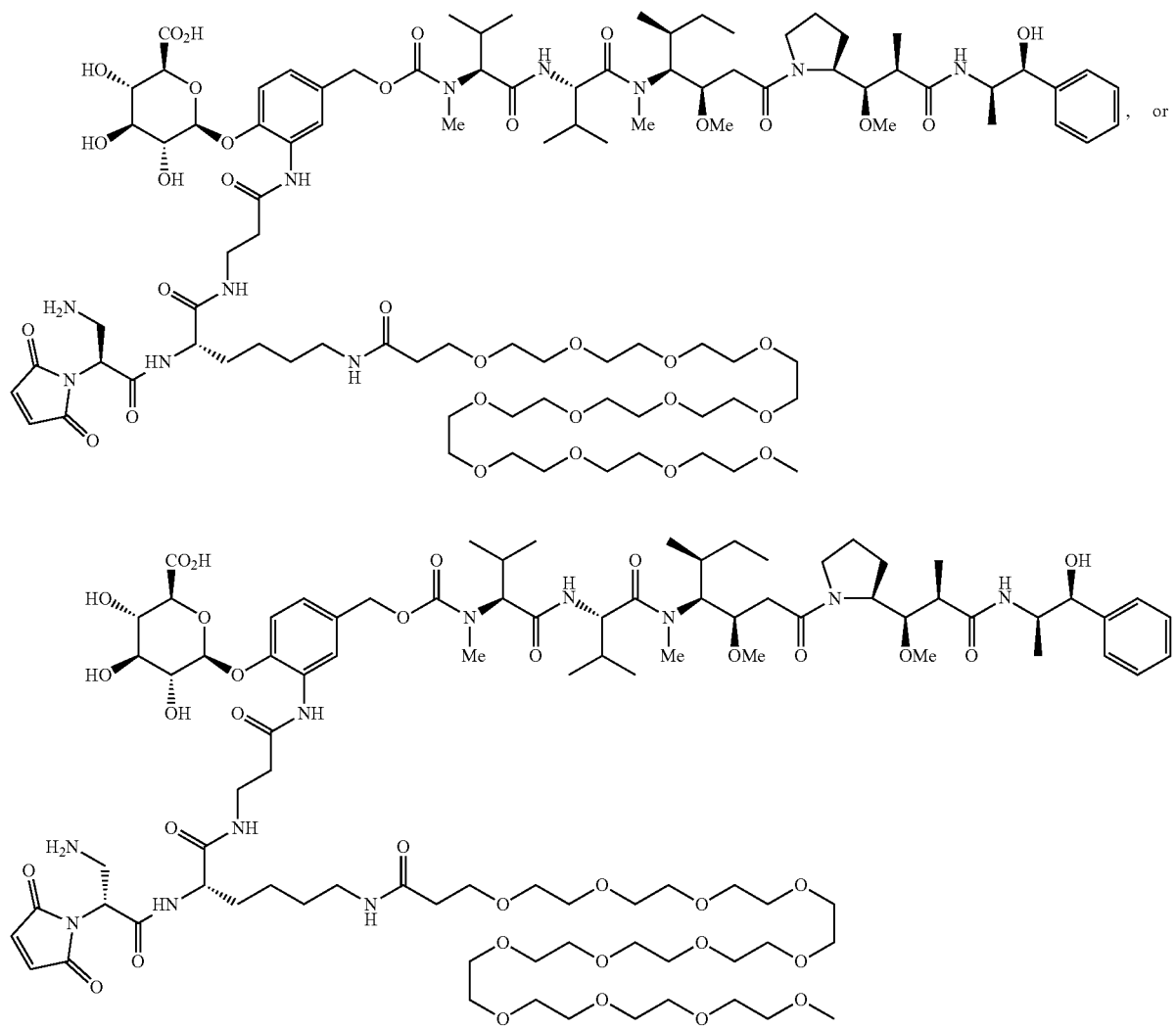

14A. The method of embodiment 13A, wherein $Z^3$ is —C(=O)O-t-Bu and/or each of $R^6$ and $R^7$ is independently $C_1$-$C_4$ alkyl, in particular, $R^6$ and $R^7$ is methyl or ethyl, more particularly both are methyl.

15A. The method of any one of embodiments 6A-14A, wherein the Formula iv compound has the structure of:

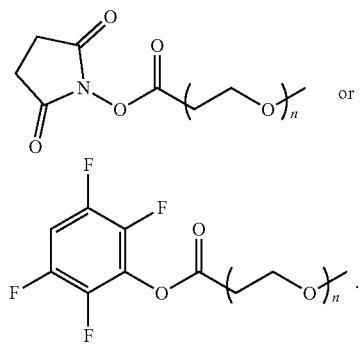

16A. The method of any one of embodiments 1A-14A, wherein subscript n ranges from 8 to 16, in particular, wherein subscript n is 12.

17A. The method of any one of embodiments 6A-16A, wherein the second or third deprotecting agent for removal of $Z^2$ or $Z^3$ is an aqueous-containing acid solution having a pKa ranging from 0-3, in particular, the aqueous-containing acid solution is that of trifluoroacetic acid or trichloroacetic acid.

18A. The method of any one of embodiments 1A-17A, wherein the Grignard reagent in a suitable alcohol-containing solvent has the formula of $R^gMgX$ and the alkoxy magnesium halide in a suitable alcohol-containing has the formula of $R^gOMgX$, wherein $R^g$ is $C_1$-$C_4$ alkyl or phenyl; and X is I, Br, or Cl, in particular, the Grignard reagent is MeMgI or MeMgCl, the alkoxy magnesium halide is MeOMgI or MeOMgCl and the alcohol-containing solvent comprises a $C_1$-$C_4$ alcohol, more particularly the alcohol-containing solvent is a 1:1 (v/v) mixture of methanol and THF.

19A. The method any one of embodiments 1A-18A, wherein the first deprotecting agent for removal of $Z^1$ is an aqueous-containing solution of LiOH.

20A. The method of any one of embodiments 6A-19A, wherein the first activating agent for said Formula iv contacting is a solution of: N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylamino-morpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethyl-imidazolidinium tetrafluoroborate, (Benzotriazol-1-yloxy) tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, or Propylphosphonic anhydride, in particular, a solution of EDC.HCl, EEDQ or COMU, more particularly a solution of COMU.

21A. The method of embodiment 11A, wherein the Drug Linker intermediate compound of Formula 4 or salt thereof is prepared by the method comprising the step of: contacting a compound of Formula 3 having the structure of:

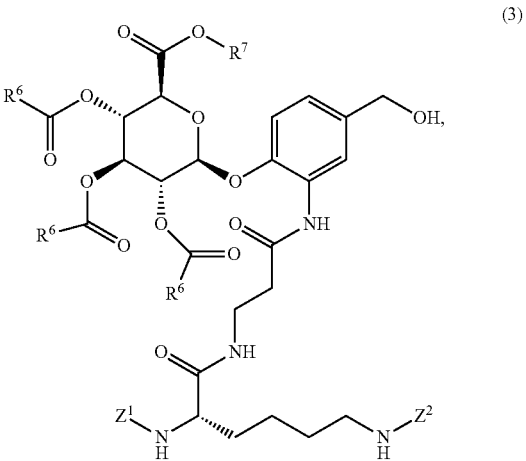

or a salt thereof, in a suitable solvent with a auristatin compound of Formula iii having the structure of:

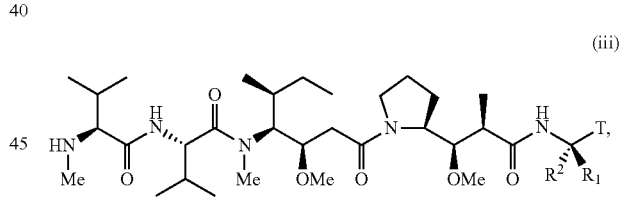

in the presence of a carbamate coupling agent, in particular, the carbamate coupling agent is a solution of phosgene, trichloromethyl chloroformate (Diphosgene) and bis(trichloromethyl) carbonate (Triphosgene), 1,1'-Carbonyldiimidazole (CDI), or 1,1'-Carbonyl-di-(1,2,4-triazole) (CDT), more particularly a solution of 1,1'-carbonyl-di-(1,2,4-triazole) (CDT), wherein said Formula 3 contacting provides the Formula 4 Drug Linker intermediate compound or salt thereof.

22A. The method of embodiment 21A, wherein the Formula 3 compound is prepared by a method comprising the step of: contacting a Parallel Connector Unit precursor ($L_P'$) of Formula 1, or salt thereof, and a compound of Formula 2 in a suitable solvent in the presence of a embodiment 32 activating agent, wherein the Formula 1 $L_P'$ compound has the structure of:

193

(1)

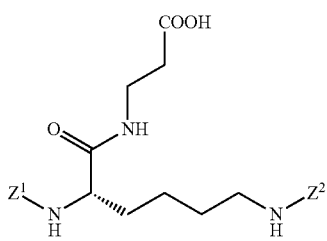

or a salt hereof, wherein each of $Z^1$ and $Z^2$ is independently a first and second suitable amino protecting group, respectively; and the Formula 2 compound has the structure of:

(2)

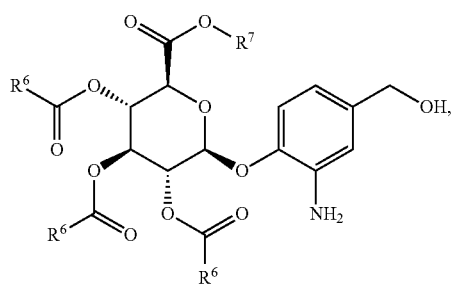

wherein said contacting provides the Formula 3 compound or salt thereof.

23A. A compound of Formula 3 having the structure of:

(3)

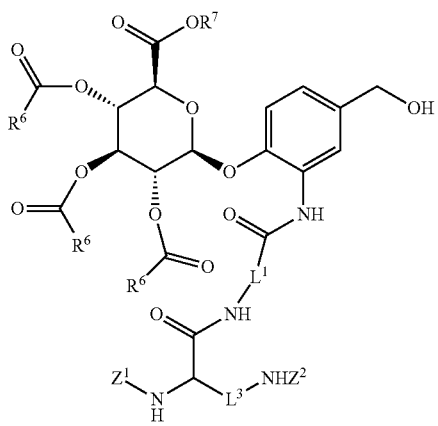

194 or a salt thereof, wherein $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo, in particular $L^1$ and $L^3$ independently are $C_1$-$C_4$ alkylene; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group, in particular, each $R^6$ is $C_1$-$C_4$ alkyl or optionally substituted phenyl and/or $R^7$ is methyl or ethyl, more particularly $R^6$ and $R^7$ are each methyl, or Formula 3 has the structure of:

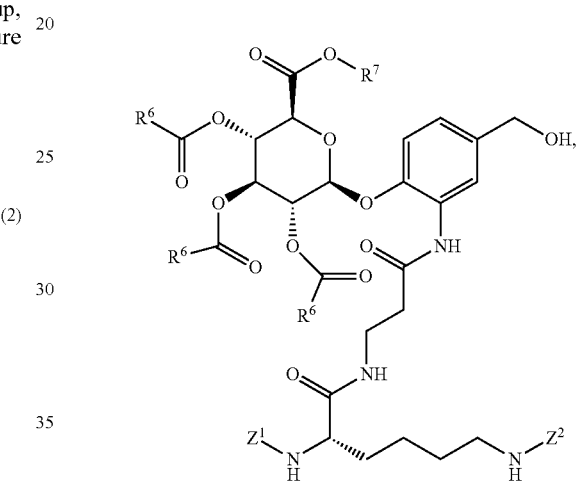

wherein $Z^1$ and $Z^2$ independently are a first and second suitable amino protecting group, respectively, in particular, $Z^1$ and/or $Z^2$ is fluorenylmethyloxy carbonyl (FMOC) and/or 4-methoxy trityl (MMTr), more particularly, the Formula 3 compound has the structure of:

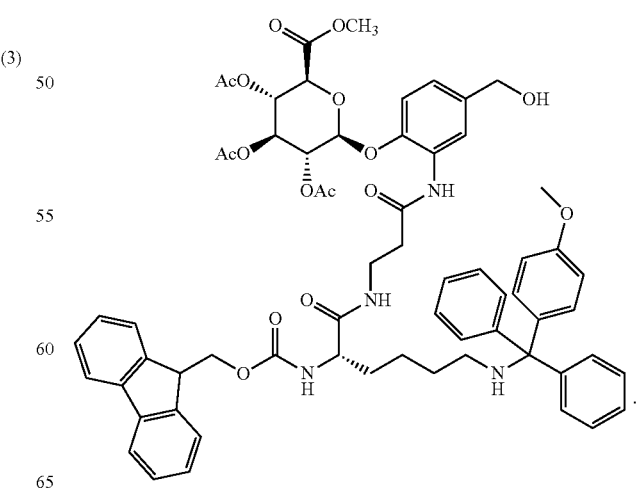

24A. A Drug Linker intermediate compound having the structure of Formula 4 of:

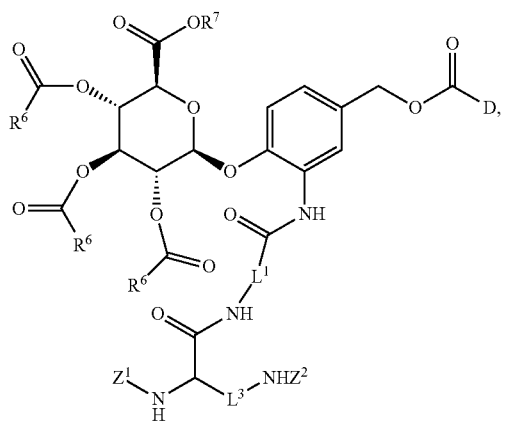
(4)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —$OR^7$ provides an ester functional group that is a suitable carboxylic acid protecting group; and $Z^1$ and $Z^2$ independently are a first and second suitable amino protecting group, respectively, in particular, $Z^2$ is MMTr and/or the Formula 4 compound, or salt thereof, has the structure of:

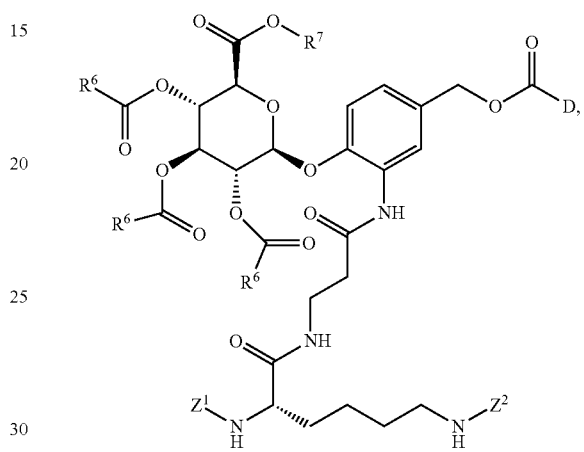

more particularly, the Formula 4 Drug Linker intermediate compound, optionally in salt form, has the structure of:

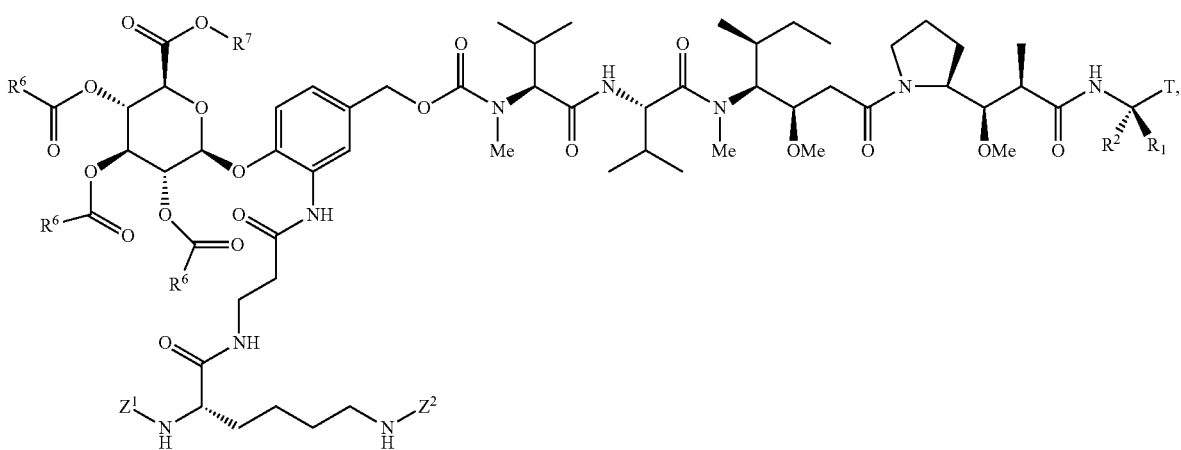

wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH(OR$^4$)—R$^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl.

25A. A Drug Linker intermediate compound, wherein the Drug Linker intermediate compound has the structure of Formula 5 of:

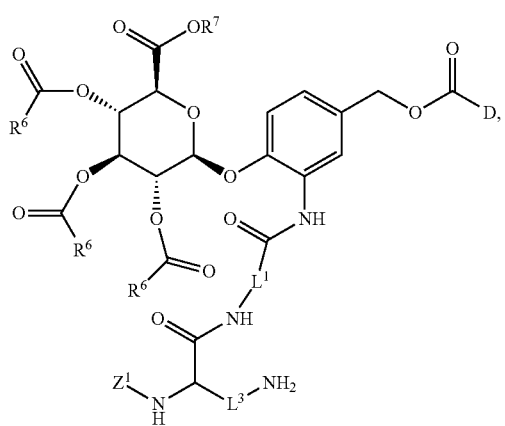

(5)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_5$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —OR$^7$ provides an ester functional group that is a suitable carboxylic acid protecting group; and $Z^1$ is a first suitable amino protecting group, in particular, the Formula 5 Drug Linker intermediate compound, optionally in salt form, has the structure of:

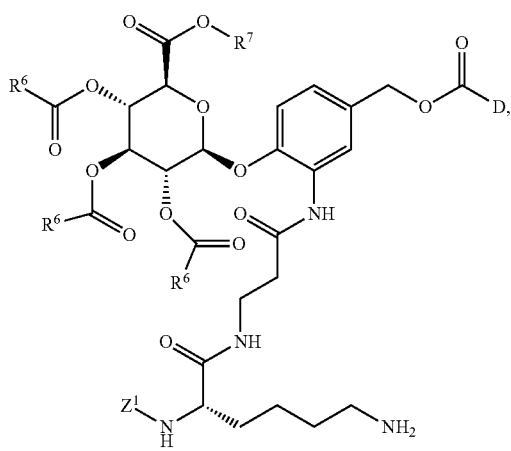

more particularly, the Formula 5 Drug Linker intermediate compound, optionally in salt form, has the structure of:

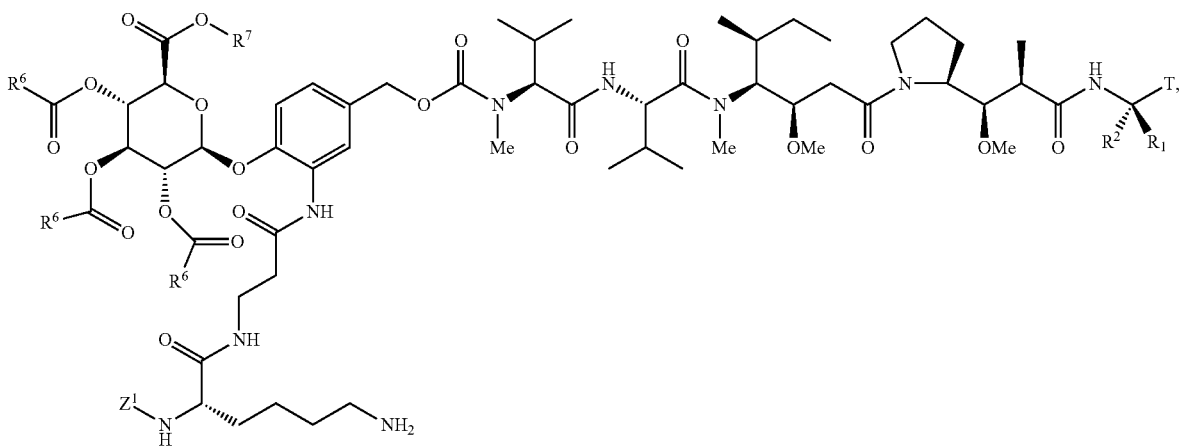

wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH(OR$^4$)—R$^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl.

26. A Drug Linker intermediate compound, wherein the Drug Linker intermediate compound has the structure of Formula 6 of:

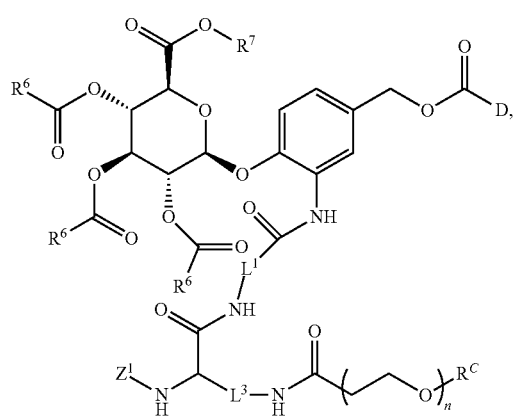

(6)

or a salt thereof, wherein D is an auristatin Drug Unit; $L^1$ and $L^3$ are independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$— provides for an ester functional group that is a suitable hydroxyl protecting group and —OR$^7$ provides an ester functional group that is a suitable carboxylic acid protecting group; $Z^1$ is a first suitable amino protecting group; $R^C$ is a PEG Capping Unit; and subscript n ranges from 1 to 24, in particular, subscript n is 8 or 12 and/or the Formula 6 Drug Linker intermediate compound, optionally in salt form, has the structure of:

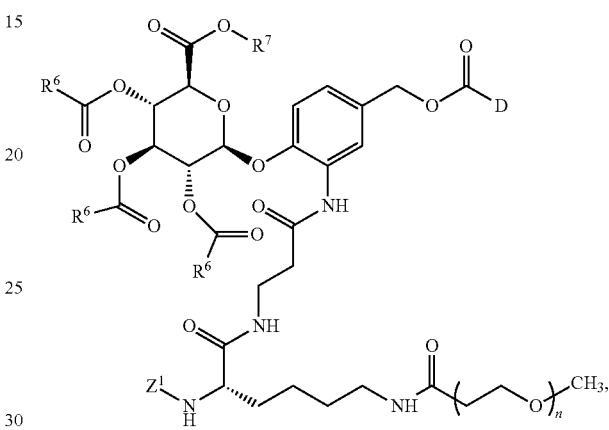

more particularly, the Formula 6 Drug Linker intermediate compound, optionally in salt form, has the structure of:

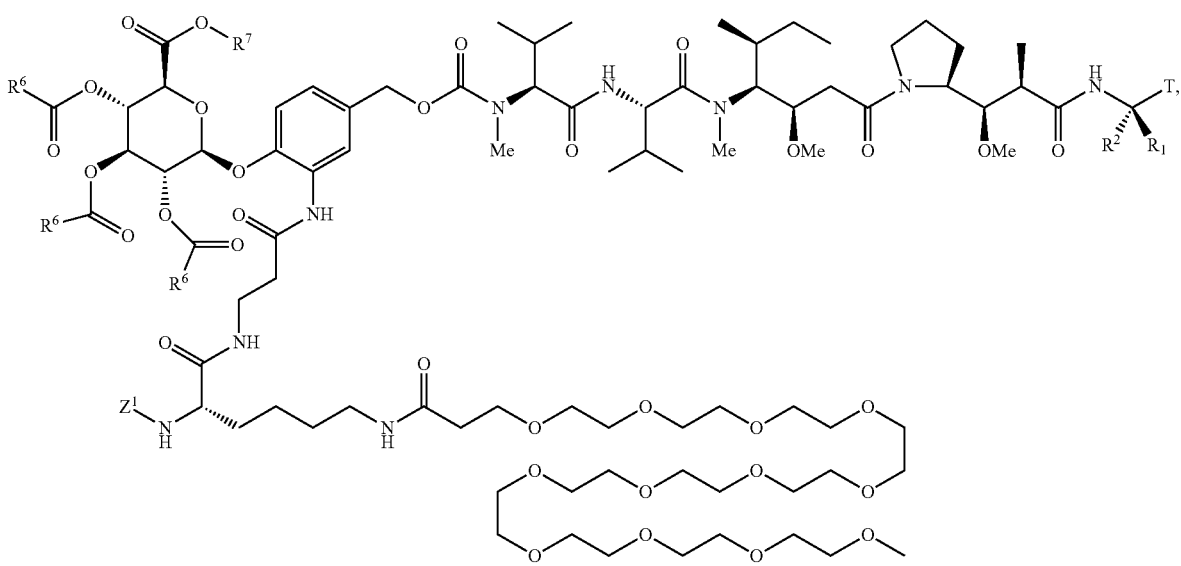

wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_5$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl.

27A. The compound of any one of embodiments 23A-26A, wherein the auristatin Drug Unit (D) has any one of the structures of embodiment 9A, in particular of Formula $D_{F/E-3}$:

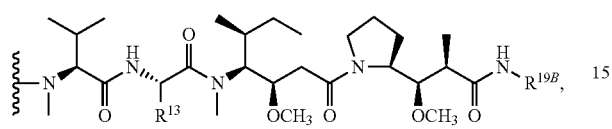

($D_{F/E-3}$)

wherein $R^{13}$ is isopropyl or —$CH_2$—CH($CH_3$)$_2$; and $R^{19B}$ is —CH($CH_3$)—CH(OH)Ph, —CH($CO_2$H)$CH_2$Ph, —CH($CH_2$Ph)-2-thiazole, —CH($CH_2$Ph)-2-pyridyl, —CH($CH_2$-p-Cl-Ph), —CH($CO_2$Me)-$CH_2$Ph, —CH($CO_2$Me)-$CH_2CH_2SCH_3$, CH($CH_2CH_2SCH_3$)C(=O)NH-3-quinolyl, or —CH($CH_2$Ph)C(=O)NH-p-Cl-Ph, more particularly,

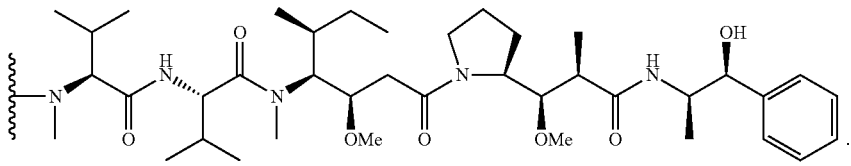 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

28A. The Drug Linker intermediate compound of any one of embodiments 24A-27A wherein each of $R^6$ and $R^7$ is independently $C_1$-$C_4$ alkyl, particularly, each of $R^6$ and $R^7$ is methyl or each of $R^6$ and $R^7$ is ethyl.

29A. The Drug Linker intermediate compound of embodiment 24A, 25A or 26A, wherein $R^1$ is hydrogen or methyl; $R^2$ is hydrogen; and T is —CH($OR^4$)—$R^5$; wherein $R^4$ is hydrogen or methyl and $R^5$ is $C_6$-$C_{10}$ aryl, in particular, $R^1$ is methyl, $R^2$ is H, and T is —CH(OH)-Ph, and/or $Z^1$ is FMOC.

30A. The Drug Linker intermediate compound of embodiment 24A, wherein the Formula 4 Drug Linker intermediate compound has the structure of:

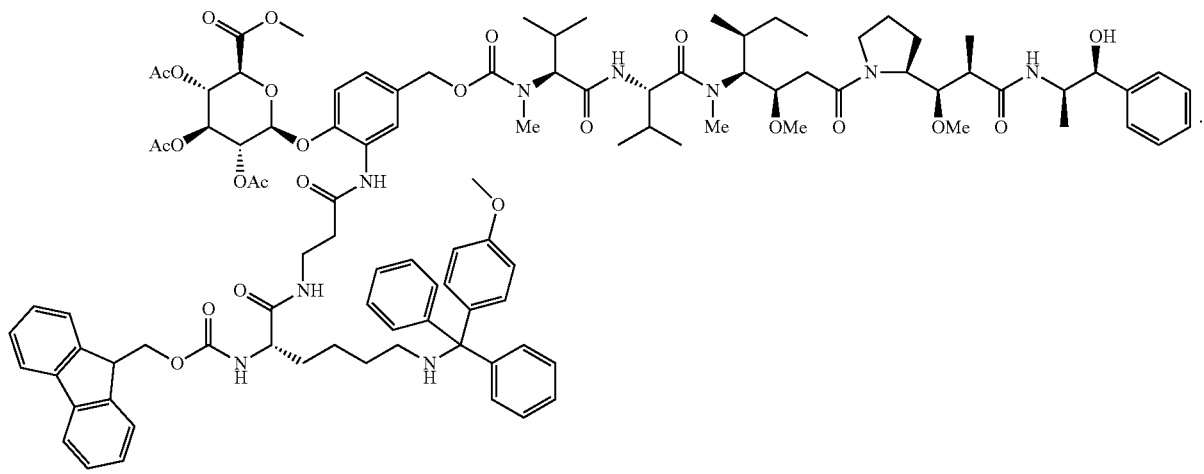 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCNC(c2ccccc2)(c2ccccc2)c2ccc(OC)cc2)NC(=O)OCC2c3ccccc3-c3ccccc32)c1)C(C)C]

31A. The Drug Linker intermediate compound of embodiment 25A, wherein the Formula 5 Drug Linker intermediate compound, optionally in salt form, has the structure of:
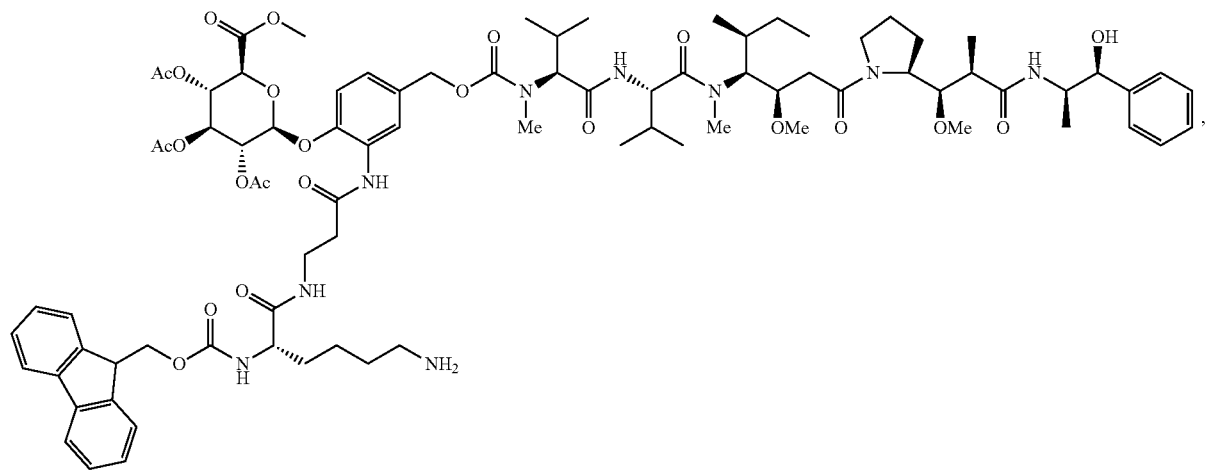 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCN)NC(=O)OCC2c3ccccc3-c3ccccc32)c1)C(C)C]
32A. The Drug Linker intermediate compound of embodiment 26A, wherein the Formula 6 compound has the structure of:
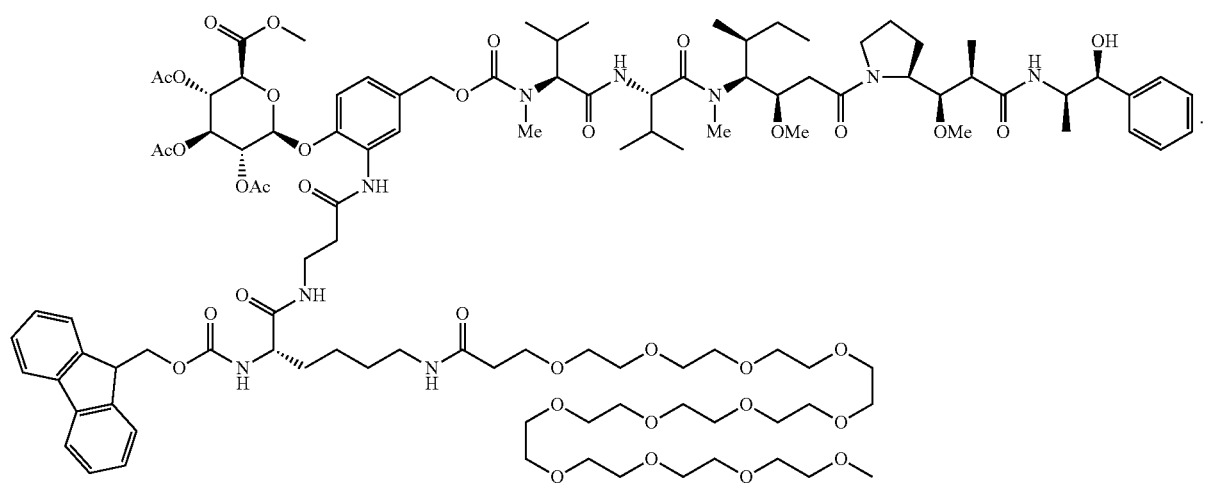 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCNC(=O)CCOCCOCCOCCOCCOCCOCCOCCOCCOCCOCCOCCOC)NC(=O)OCC2c3ccccc3-c3ccccc32)c1)C(C)C]

33A. A composition comprising a Drug Linker intermediate of Formula 7, optionally in salt form, having the structure of:

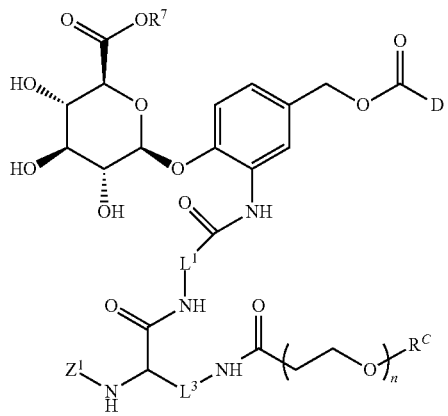
(7)

wherein D is an auristatin Drug Unit; each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene so-$OR^7$ provides an ester functional group that is a suitable carboxylic acid protecting group, in particular $R^7$ is methyl; $Z^1$ is a first suitable amino protecting group; $R^C$ is hydrogen or a PEG Capping Unit; and subscript n ranges from 2 to 24, the composition further comprising no more than about 10 wt. %, in particular no more than about 5 wt. %, of a Drug Linker intermediate compound of Formula 7A having the structure of:

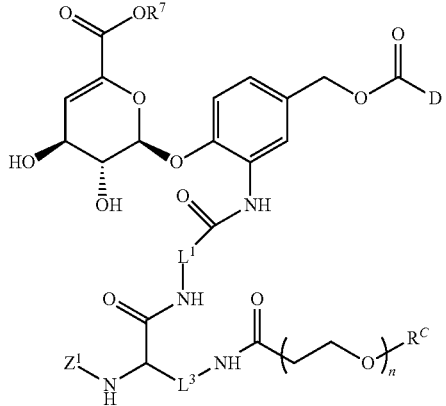
(7A)

or a salt thereof, wherein the variable groups are as previously defined, in particular, $Z^1$ is FMOC and/or the Formula 7 and Formula 7A Drug linker intermediate compounds, optionally in salt form, have the structures of:

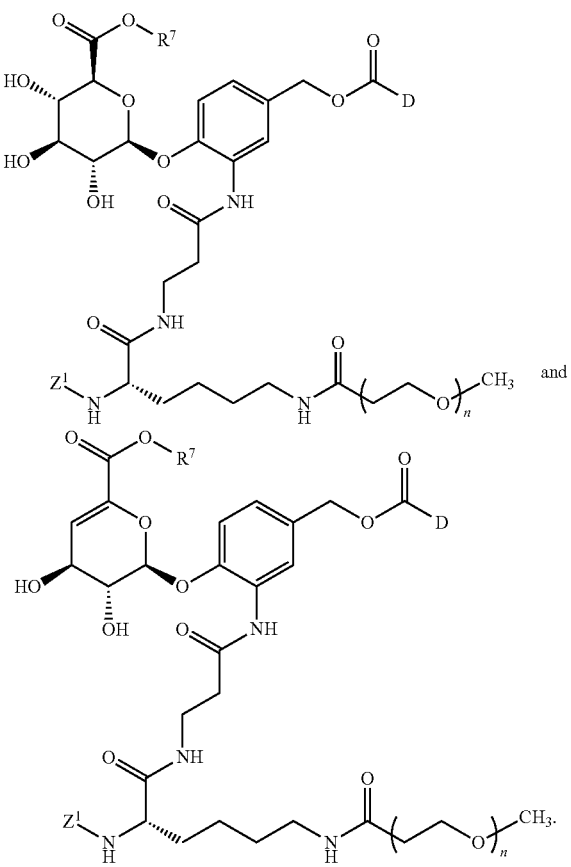

34A. A composition comprising a Drug Linker intermediate of Formula 8 having the structure of:

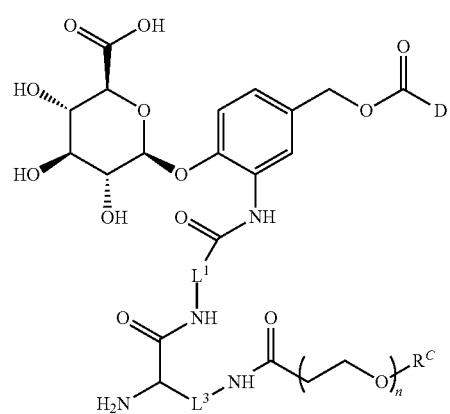
(8)

or a salt thereof, wherein D is an auristatin Drug Unit; each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; and subscript n ranges from 2 to 24, the composition further comprising no more than about 10 wt. %, in particular no more than about 5 wt. %, more particularly, no more than between about 3 wt. % and 4 wt. %, of a Drug Linker intermediate compound of Formula 8A having the structure of:

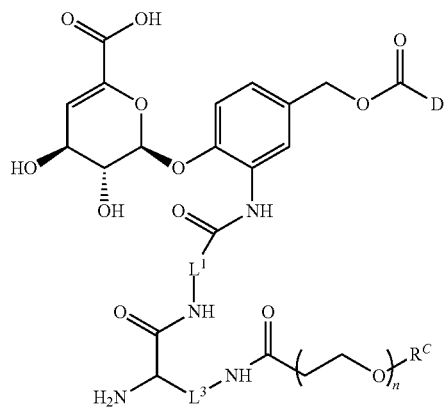

(8A)

or a salt thereof, wherein the variable groups are as previously defined, in particular, the Formula 8 and Formula 8A Drug Linker intermediate compounds, optionally in salt form have the structures of:

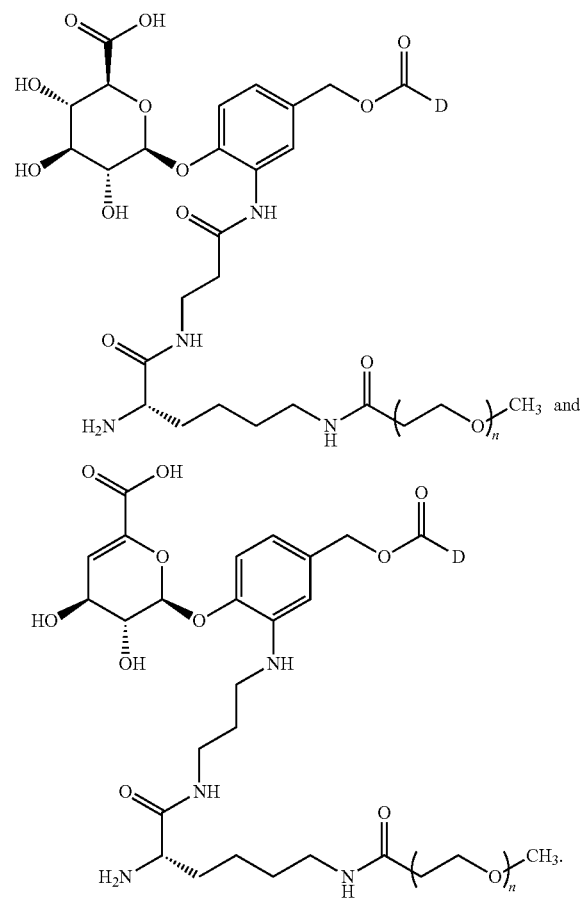

35A. A composition comprising a Drug Linker intermediate or Drug Linker compound of Formula 9 having the structure of:

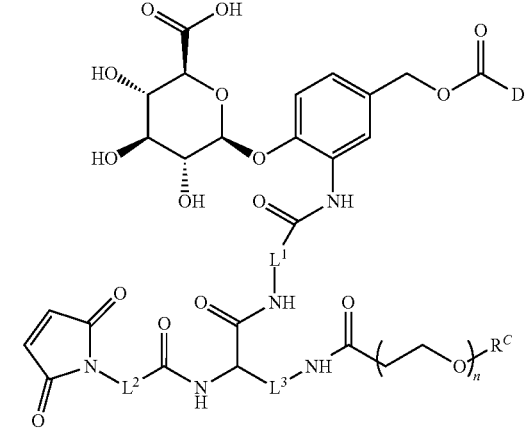

(9)

or a salt thereof, wherein D is an auristatin Drug Unit; each of $L^1$, $L^2$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen a PEG Capping Unit; and subscript n ranges from 2 to 24, the composition further comprising no more than about 10 wt. %, in particular no more than 5 wt. % of a Drug Linker intermediate or Drug Linker compound of Formula 9A having the structure of:

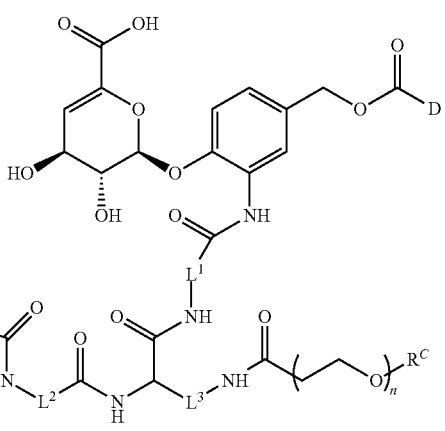

(9A)

or a salt thereof, wherein the variable groups are as previously defined, in particular, the Formula 9 and Formula 9A Drug Linker intermediate or Drug Linker compounds, optionally in salt form, have the structures of:

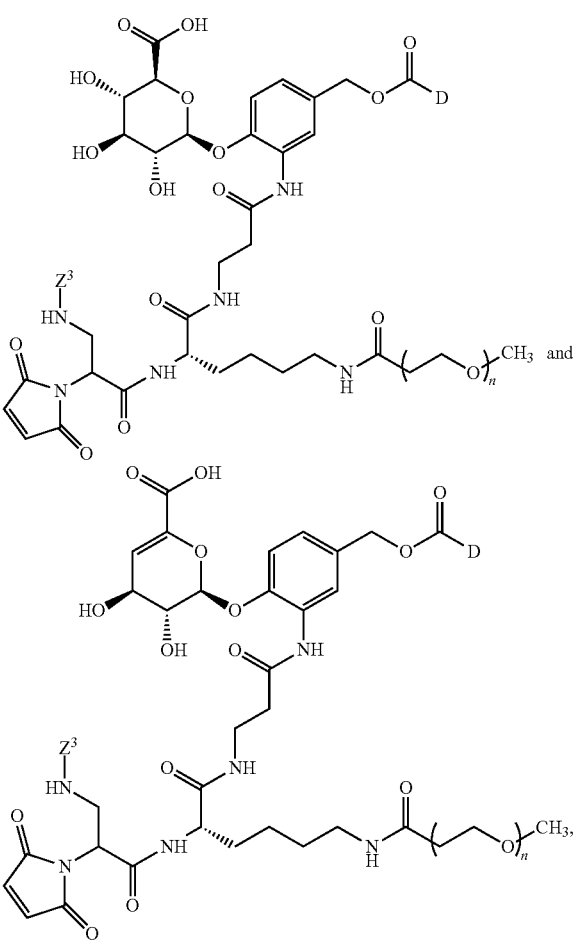

wherein Z³ is a third suitable amino protecting group that is acid-labile, particularly a carbamate of formula —C(=O)O—R⁸, wherein R⁸ is $C_1$-$C_4$ alkyl or optionally substituted phenyl.

36A. A composition comprising Drug Linker compound of Formula 10 having the structure of:

(10)

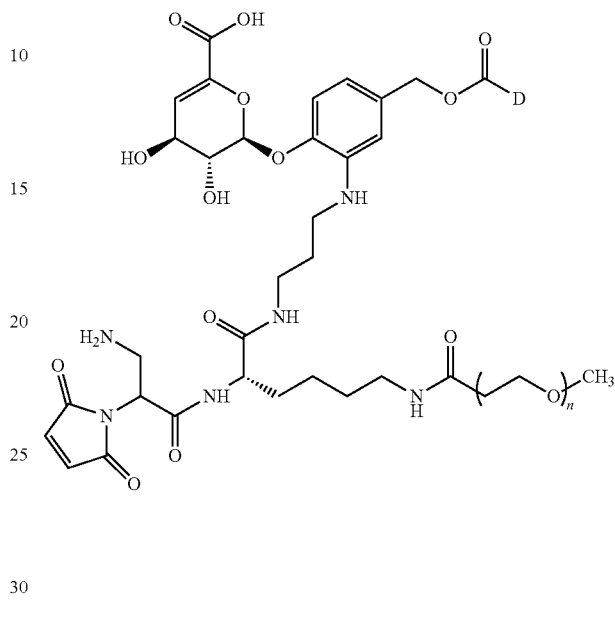

or a salt thereof, wherein D is an auristatin Drug Unit; and subscript n ranges from 2 to 24, the composition further comprising no more than about 10 wt. %, in particular no more than about 5 wt. %, of a Drug Linker compound of Formula 10A having the structure of:

or a salt thereof, wherein the variable groups are as previously defined, in particular, the Formula 10 and Formula 10A Drug Linker compounds, optionally in salt form, have the structures of:

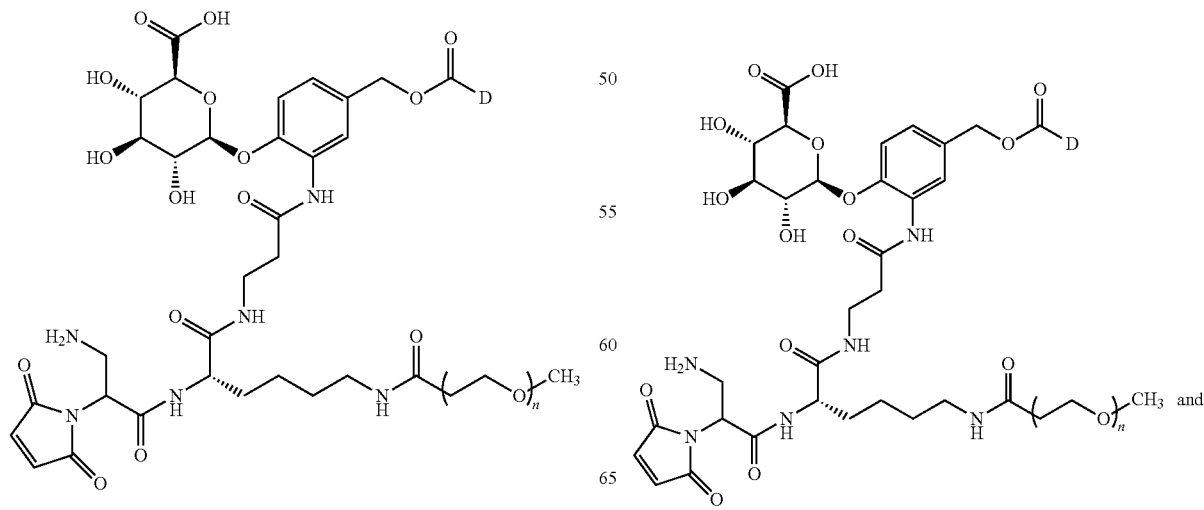

211

-continued

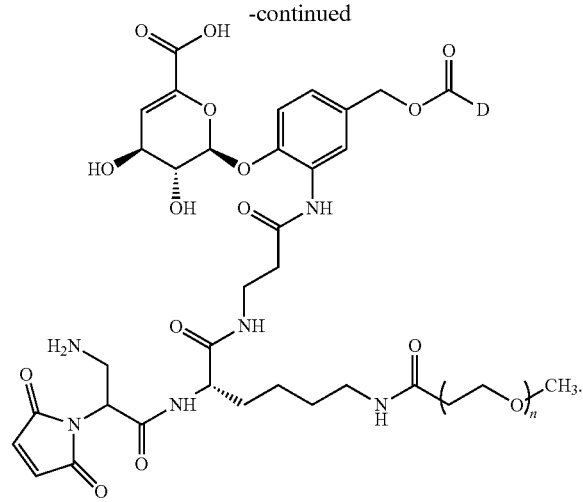

37A. The composition of any one of embodiments 33A-36A, wherein the auristatin Drug Unit (D) has any one of the structures of embodiment 9A, in particular, of Formula $D_{F/E-3}$:

212

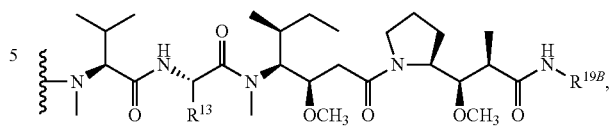

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph, more particularly,

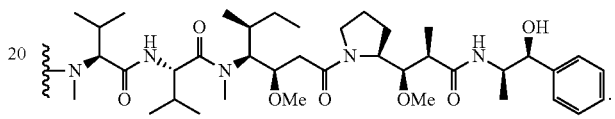

38A. The composition of embodiment 33A, wherein the Formula 7 and Formula 7A Drug Linker intermediate compounds, optionally in salt form, have the structures of:

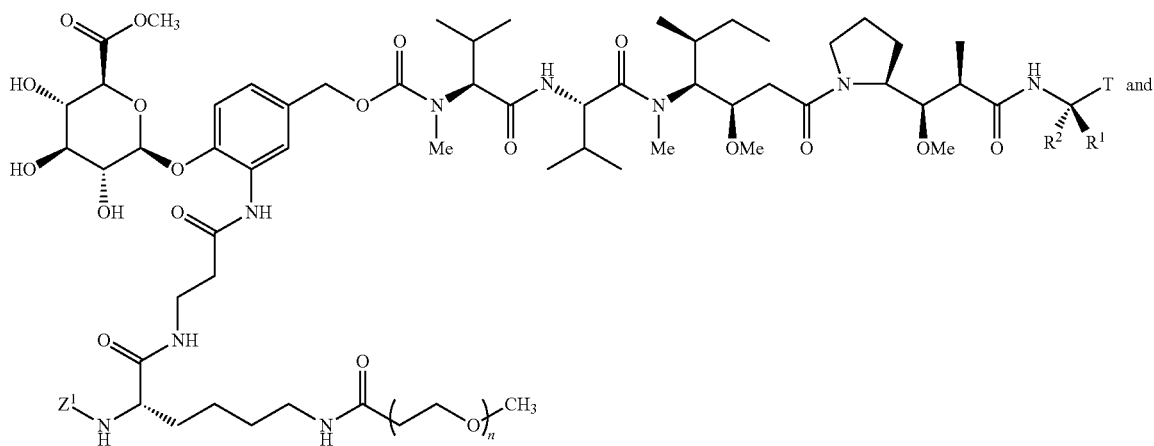

213

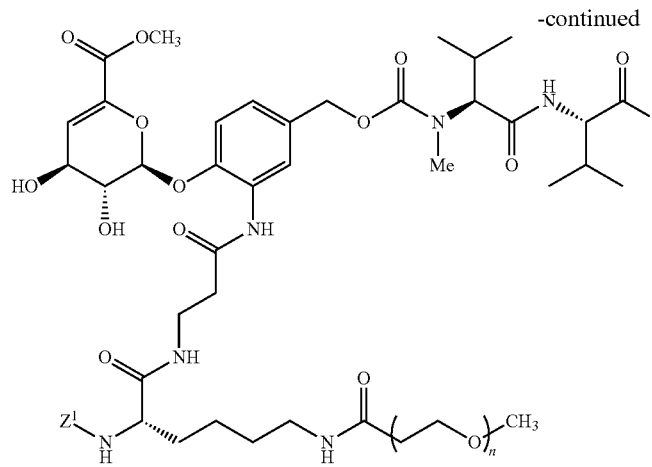

214

-continued

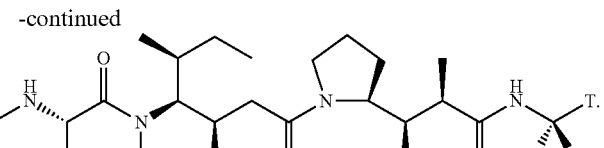

wherein $Z^1$ is FMOC; $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl, in particular, $R^2$ is hydrogen; and T is —CH($OR^4$)—$R^5$;

wherein $R^4$ is hydrogen or methyl and $R^5$ is $C_6$-$C_{10}$ aryl, more particularly $R^2$ is H, and T is —CH(OH)-Ph and/or subscript n is 8 or 12; and more particularly, the Formula 7 and Formula 7A Drug linker intermediate compounds, optionally in salt form, have the structures of:

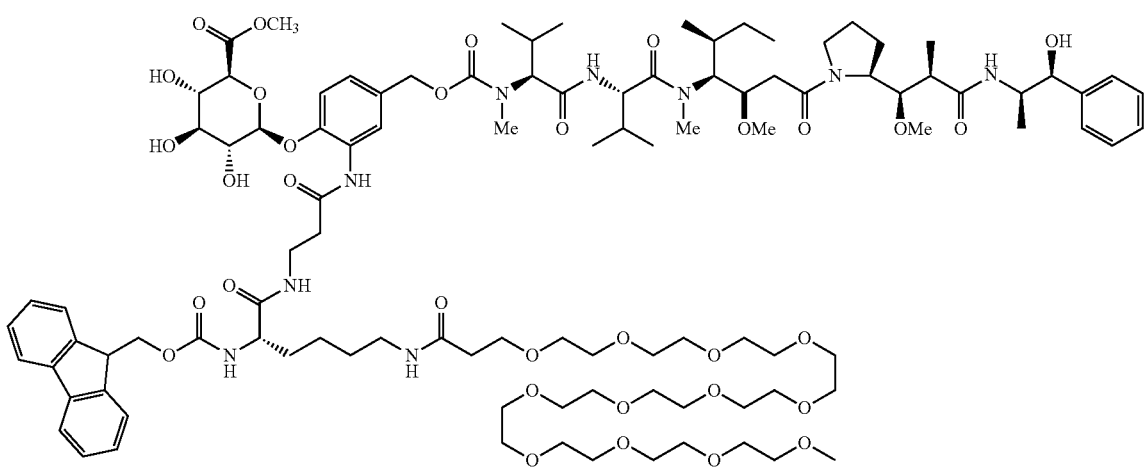

and

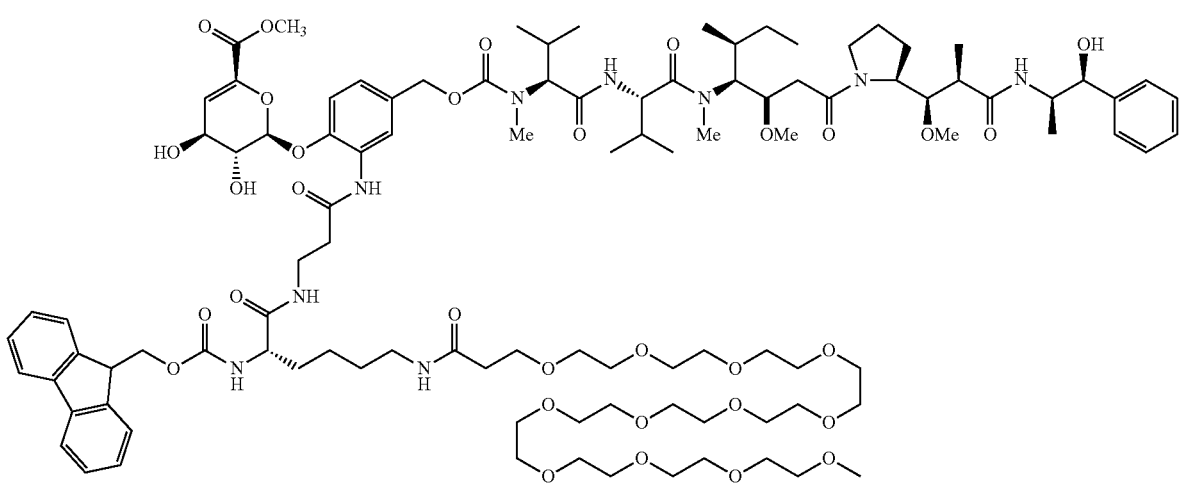

39A. The composition of embodiment 34A, wherein the Formula 8 and Formula 8A Drug Linker intermediate compounds, optionally in salt form have the structures of:

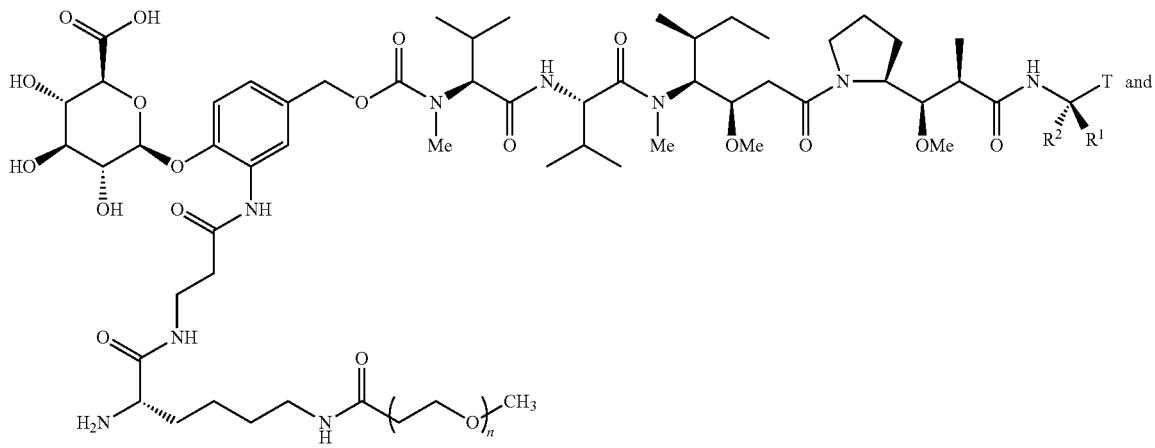

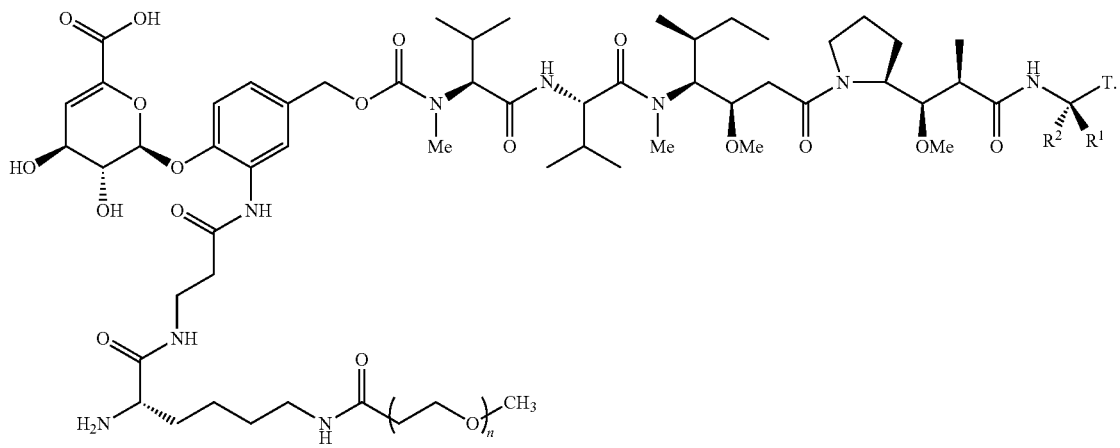

wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; T is selected from the group consisting of —CH($OR^4$)—$R^5$ and —C(=O)—$OR^4$, wherein $R^4$ is H, $C_1$-$C_4$ alkyl and $R^5$ is $C_6$-$C_{10}$ aryl or $C_3$-$C_6$ heteroaryl, in particular, $R^2$ is hydrogen; and T is —CH($OR^4$)—$R^5$; wherein $R^4$ is hydrogen or methyl and $R^5$ is $C_6$-$C_{10}$ aryl, more particularly $R^2$ is H, and T is —CH(OH)-Ph and/or subscript n is 8 or 12, more particularly, the Formula 8 and Formula 8A Drug Linker intermediate compounds, optionally in salt form, have the structures of:

217
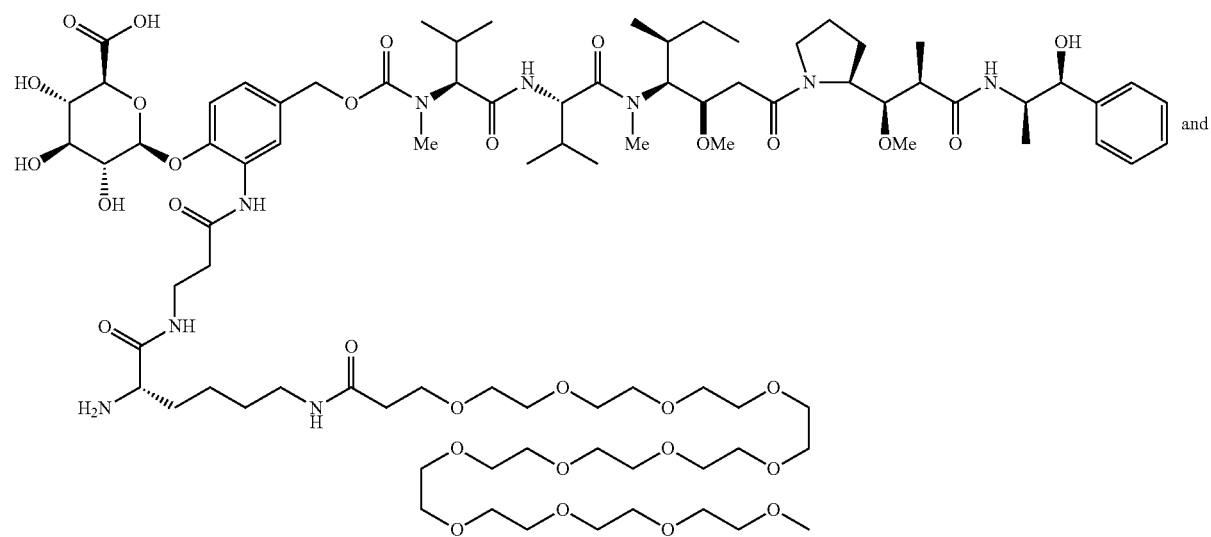
and
218
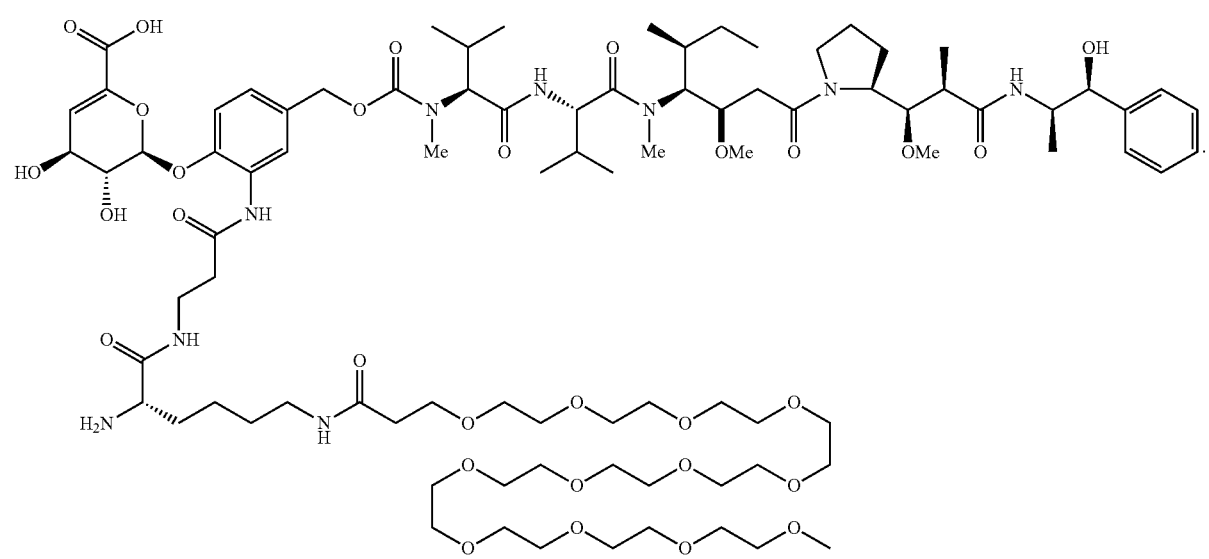
40A. The composition of embodiment 35A, wherein the Formula 9 and Formula 9A Drug Linker intermediate or Drug Linker compounds, optionally in salt form, have the structures of:

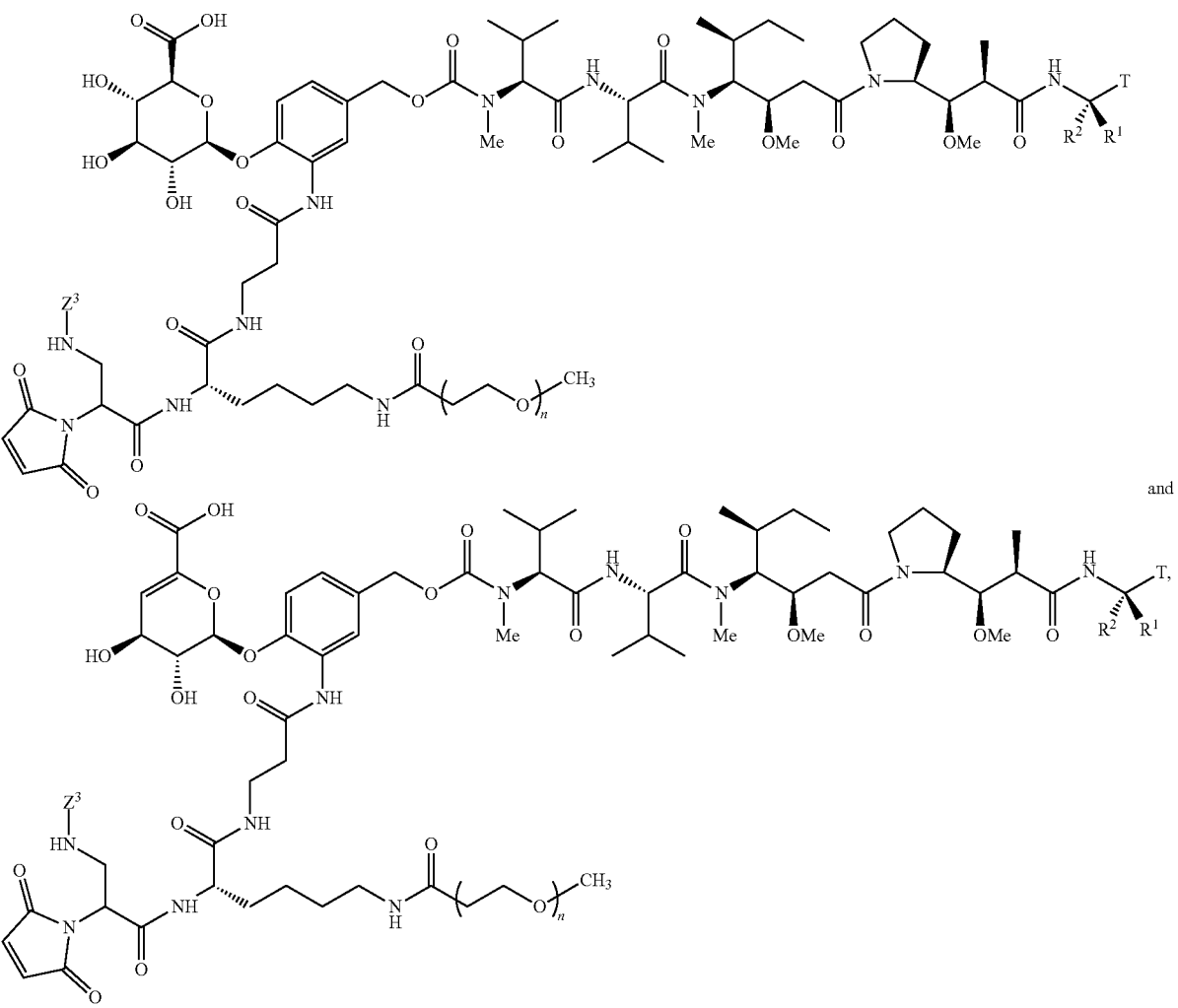

wherein $Z^3$ is —C(=O)O-t-Bu; $R^1$ is H or $C_1$-$C_4$ alkyl; $R^2$ is H, $C_1$-$C_4$ alkyl, or —CH$_2$—$R^3$; $R^3$ is $C_6$-$C_{10}$ aryl or $C_3$-$C_8$ heterocyclyl; and T is selected from the group consisting of —CH(OR$^4$)—$R^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl, in particular, $R^2$ is hydrogen; and T is —CH(OR$^4$)—$R^5$;

wherein $R^4$ is hydrogen or methyl and $R^5$ is $C_6$-$C_{10}$ aryl, more particularly $R^2$ is H, and T is —CH(OH)-Ph, and/or subscript n is 8 or 12, more particularly, the Formula 9 and Formula 9A Drug Linker intermediate or Drug Linker compounds, optionally in salt form, have the structures of:

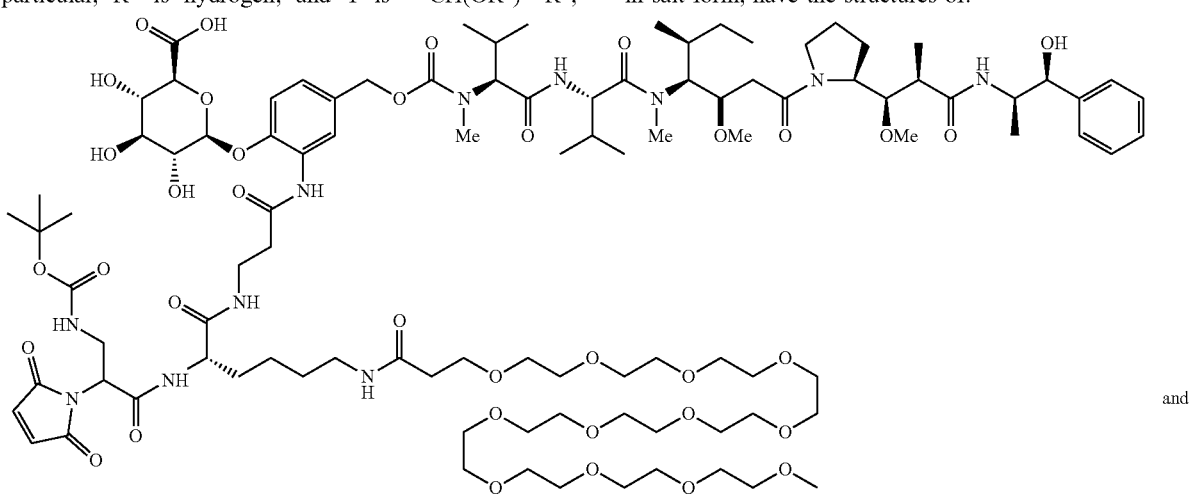

and

-continued
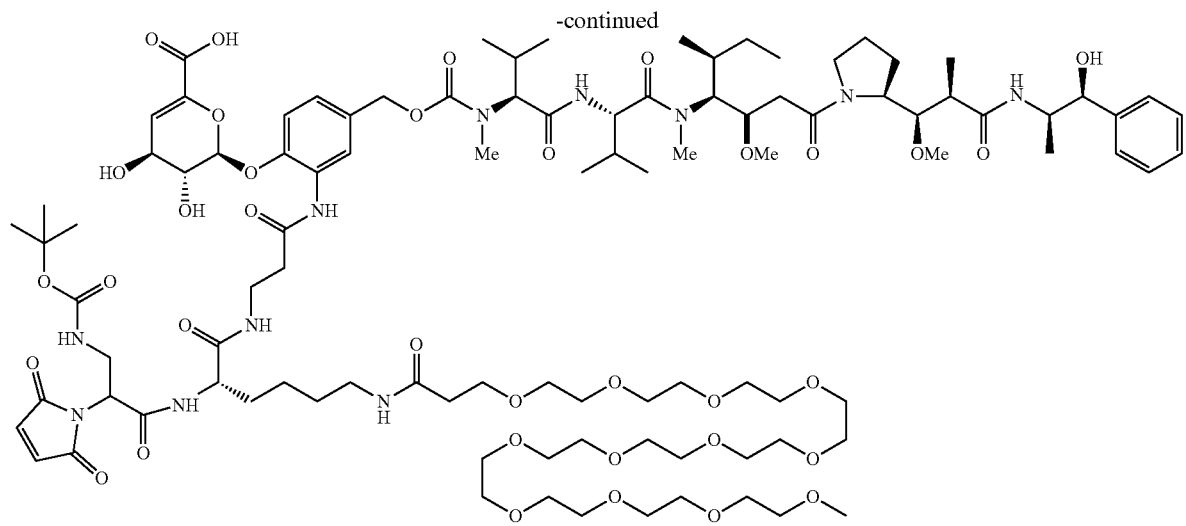
41A. The composition of embodiment 36A, wherein the Formula 10 and Formula 10A Drug Linker compounds, optionally in salt form, have the structures of:
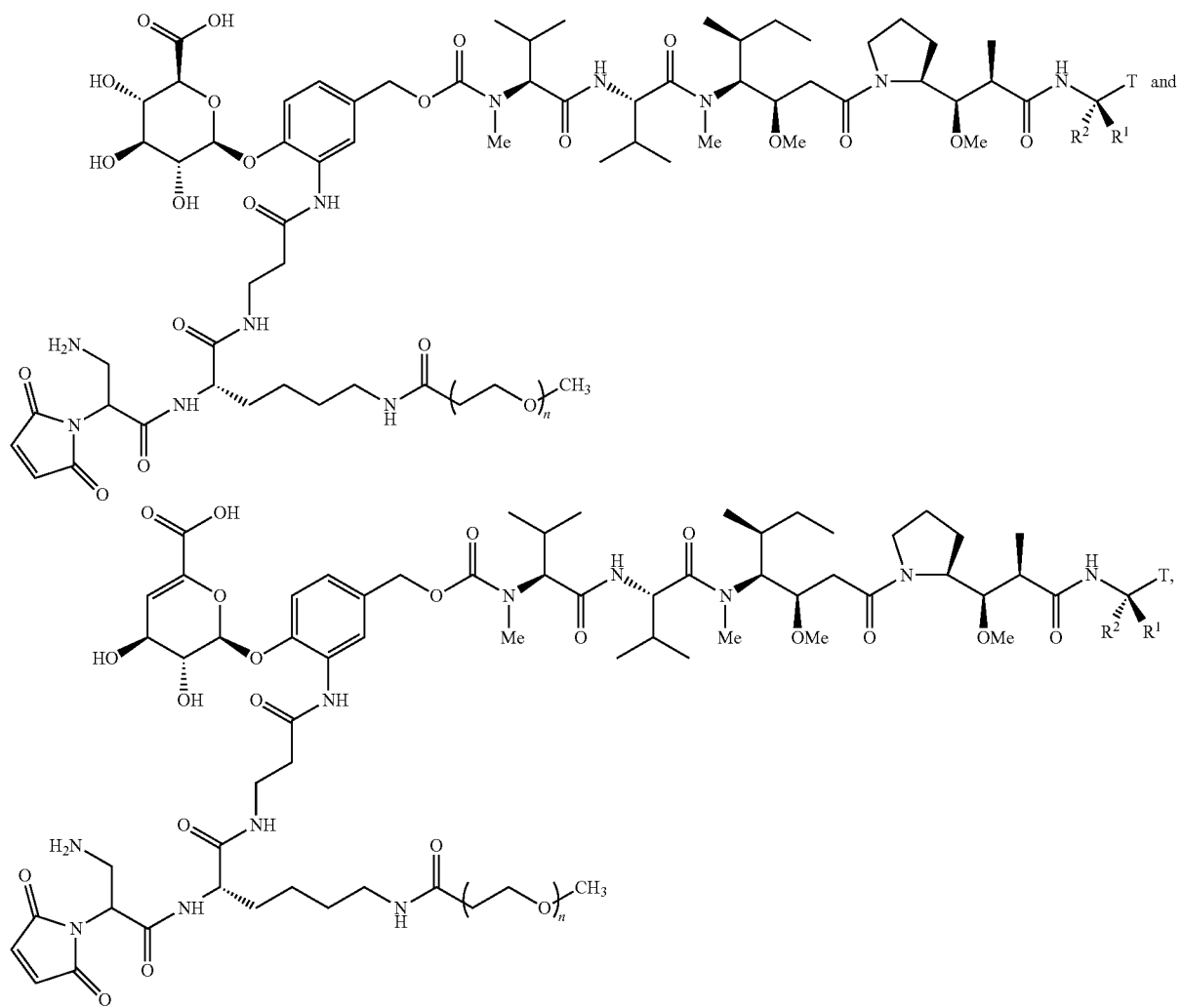

wherein $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH(O$R^4$)—$R^5$ and —C(=O)—O$R^4$, wherein $R^4$ is H, $C_1$-$C_4$ alkyl and $R^5$ is $C_6$-$C_{10}$ aryl or $C_3$-$C_6$ heteroaryl, in particular, $R^2$ is hydrogen; and T is —CH(O$R^4$)—$R^5$; wherein $R^4$ is hydrogen or methyl and $R^5$ is $C_6$-$C_{10}$ aryl, more particularly $R^2$ is H, and T is —CH(OH)-Ph and/or subscript n is 8 or 12, more particularly, the Formula 10 and Formula 10A Drug Linker compounds, optionally in salt form, have the structures of:

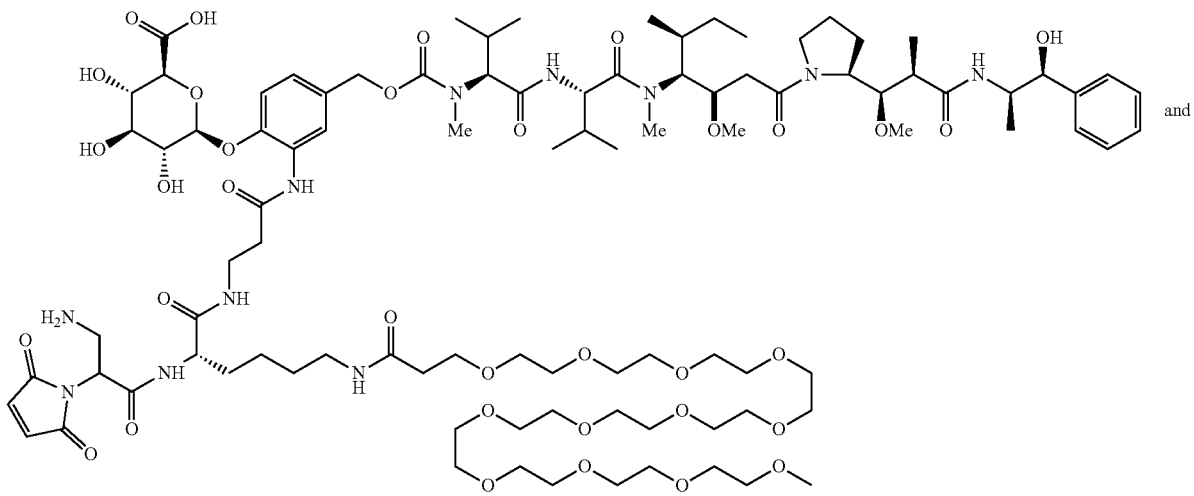

and

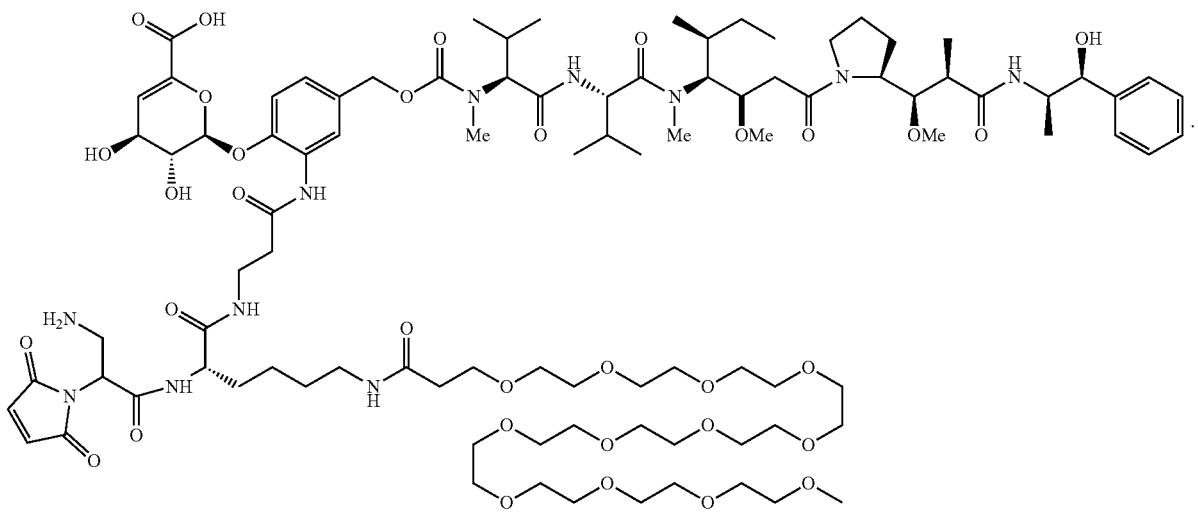

.

42A. A Drug Linker intermediate or Drug Linker compound, wherein the Drug Linker intermediate or Drug Linker compound, optionally in salt form, has the structure of:

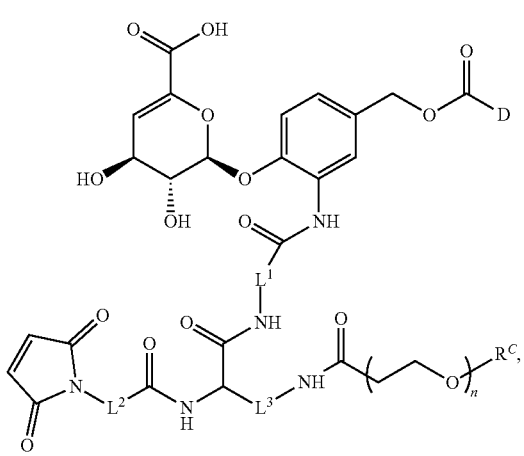

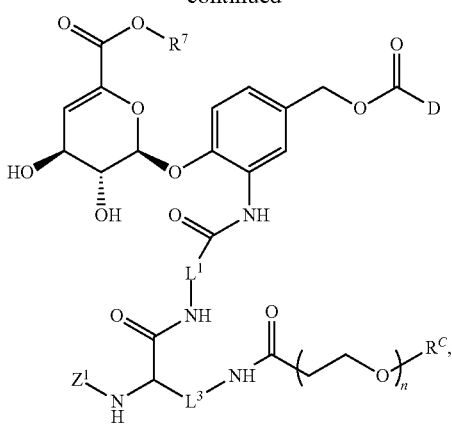

wherein D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo, in particular $L^1$, $L^2$ and $L^3$ are independently $C_1$-$C_4$ alkyl and $L^2$ is independently optionally substituted $C_1$-$C_4$ alkyl; $Z^1$ is a first suitable amino protecting group; $R^7$ is optionally substituted $C_1$-$C_8$ alkyl, optionally substituted $C_6$-$C_{10}$ arylene or optionally substituted $C_5$-$C_{10}$ heteroarylene; $R^C$ is hydrogen or a PEG Capping Unit; and subscript n ranges from 2 to 24, in particular, subscript n is 8 or 12 and/or the Drug Linker intermediate or Drug Linker compound has the structure selected from the group consisting of:

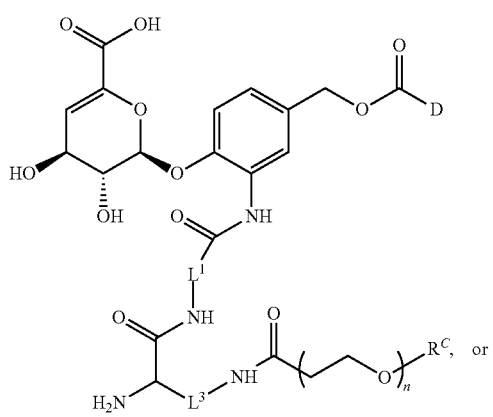

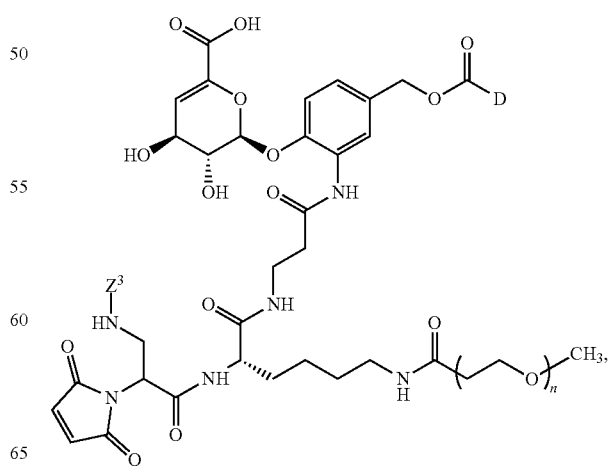

227
-continued

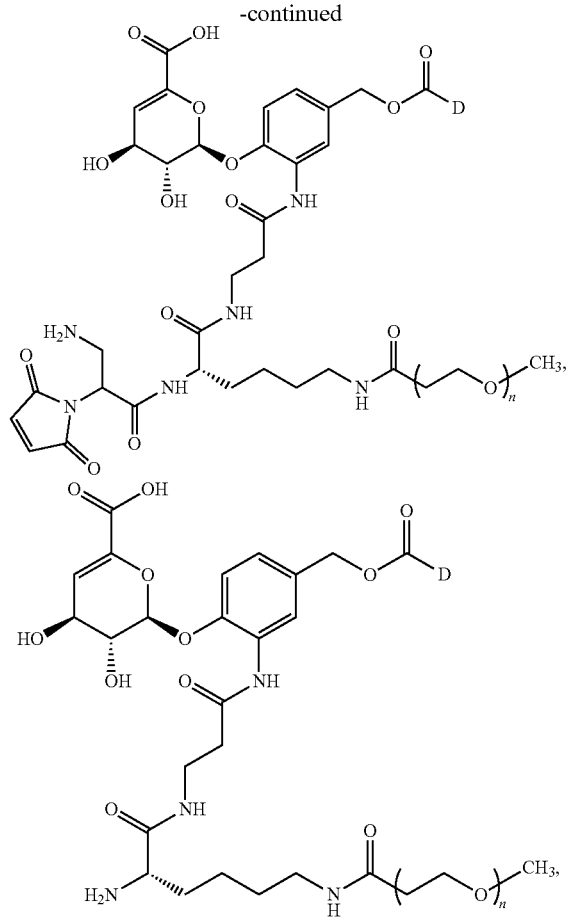

228
-continued

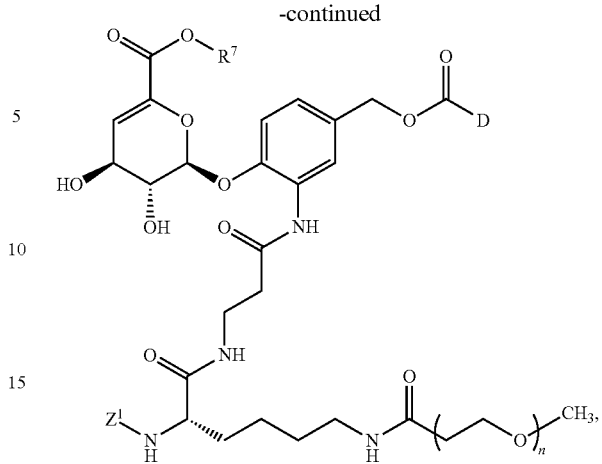

and salts thereof, wherein

Z³ is a third suitable amino protecting group that is acid-labile p, particularly a carbamate having the structure of —C(=O)O—R⁸, wherein $R^8$ is $C_1$-$C_4$ alkyl or optionally substituted phenyl; and $R_7$ is a $C_1$-$C_4$ alkyl, particularly methyl or ethyl.

43A. The compound of embodiment 42A, wherein the compound has the structure selected from the group consisting of:

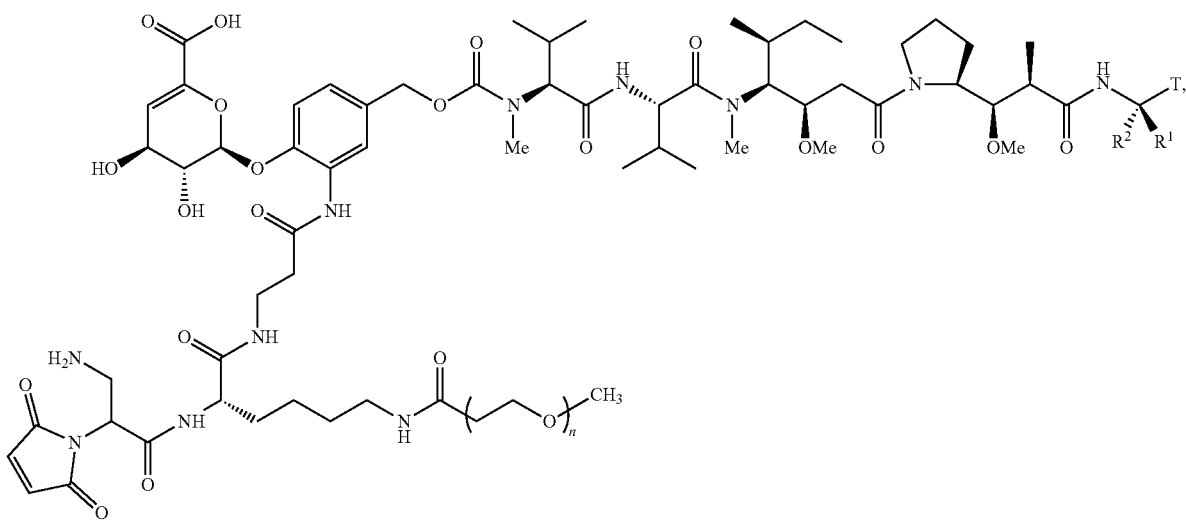

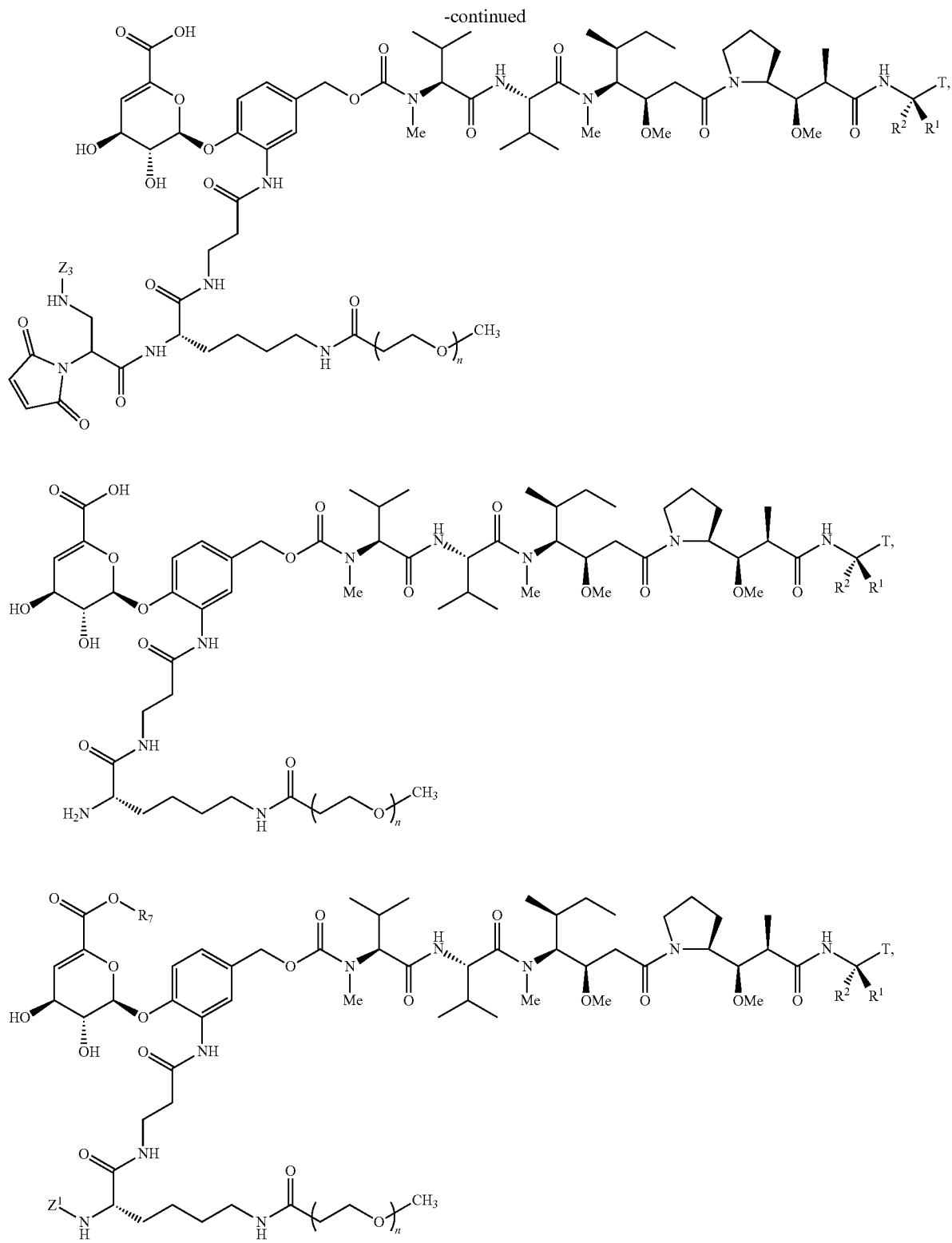

and salts thereof, wherein $R^7$ is methyl; $Z^1$ is FMOC $Z^3$ is —C(=O)O-t-Bu; $R^1$ is H or $C_1$-$C_4$ alkyl; $R^2$ is H, $C_1$-$C_4$ alkyl, or —$CH_2$—$R^3$; $R^3$ is $C_6$-$C_{10}$ aryl or $C_3$-$C_8$ heterocyclyl; and T is selected from the group consisting of —CH(OR$^4$)—$R^5$ and —C(=O)—OR$^4$, wherein $R^4$ is H, $C_1$-$C_4$ alkyl and $R^5$ is $C_6$-$C_{10}$ aryl or $C_3$-$C_6$ heteroaryl, in particular subscript n is 8 or 12 and/or $R^1$ is methyl, $R^2$ is H, and T is —CH(OH)-Ph, more particularly, the Drug Linker intermediate or Drug Linker compound, optionally in salt form, has the structure selected from the group consisting of:

231
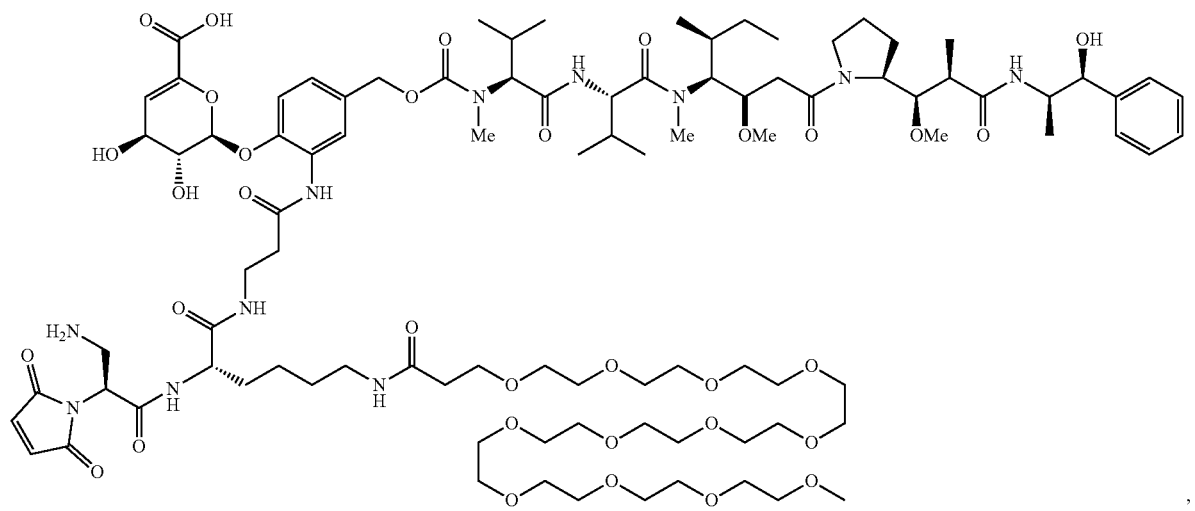
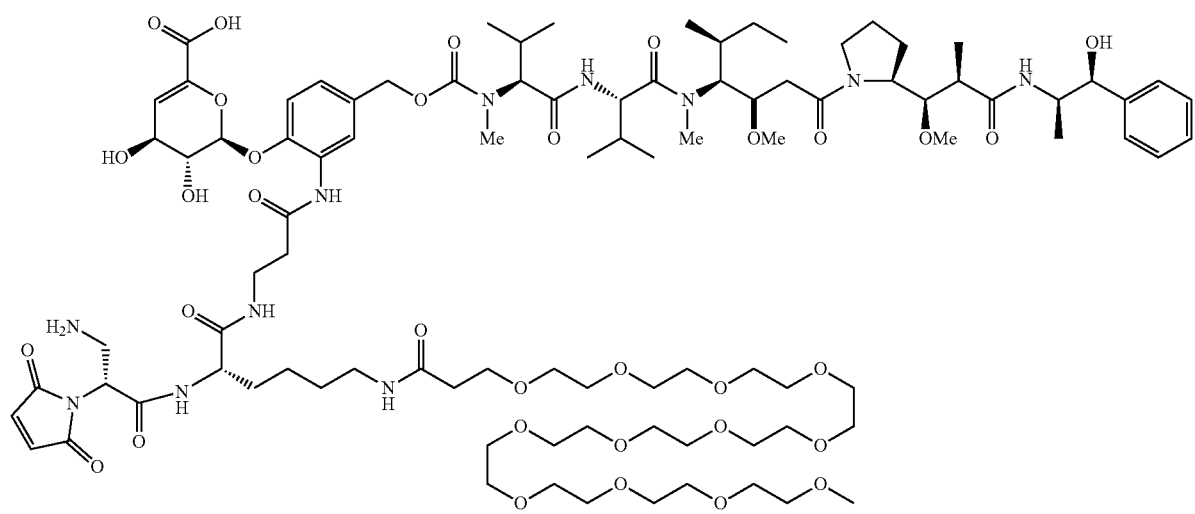
232
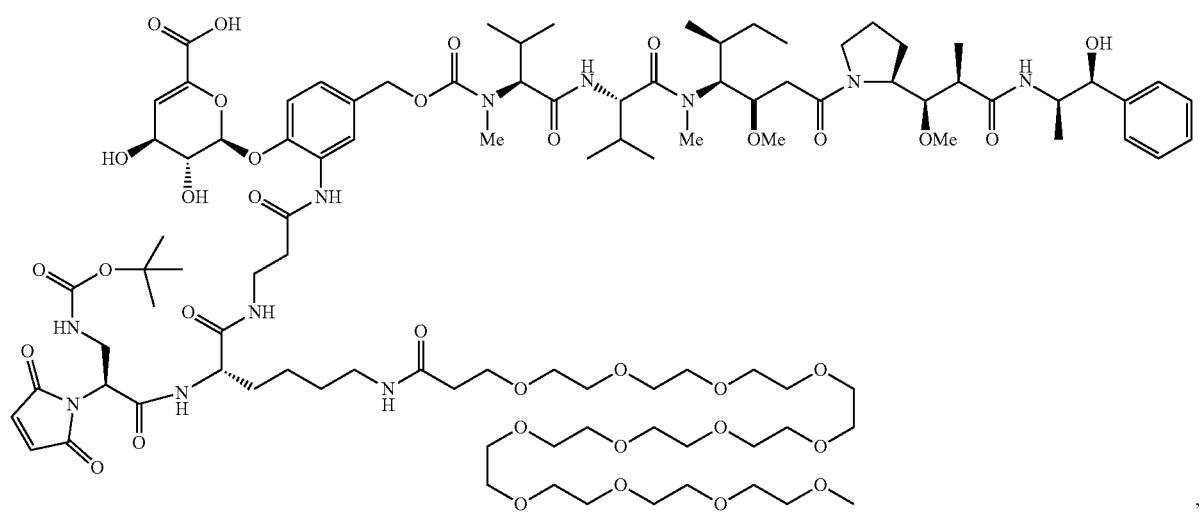

233
-continued
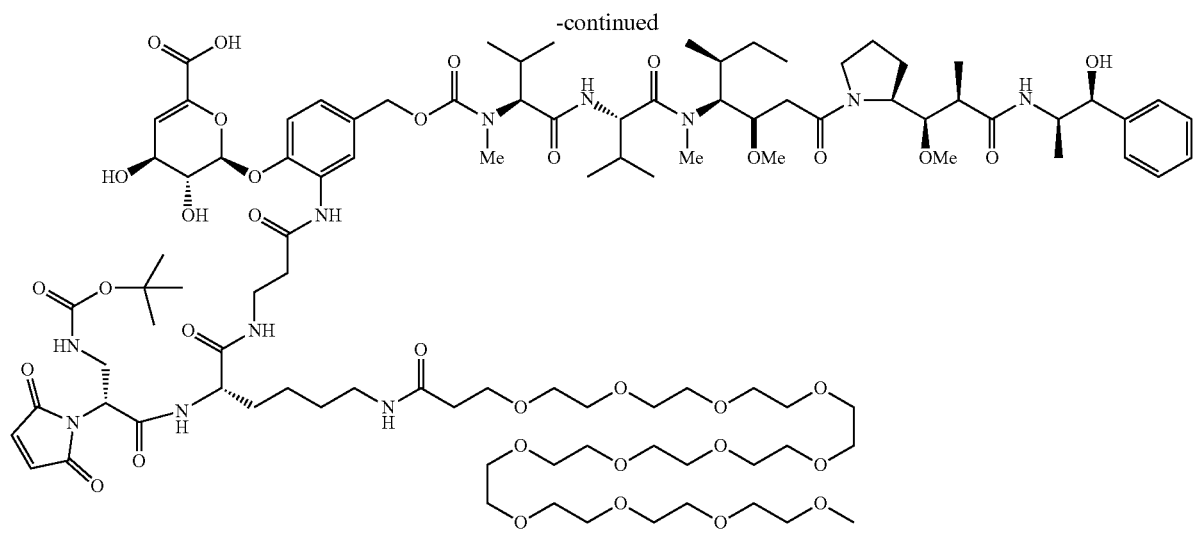
234
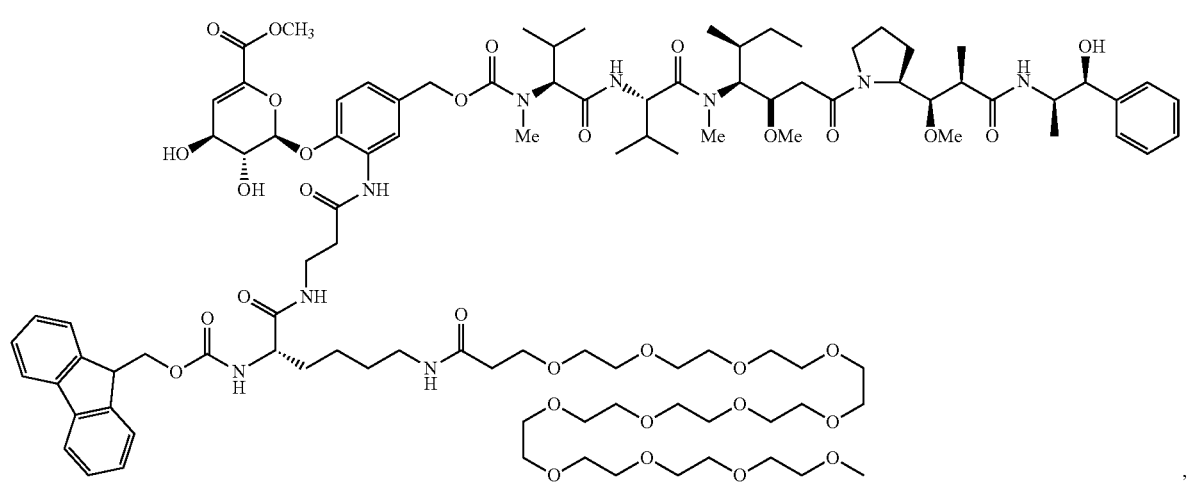
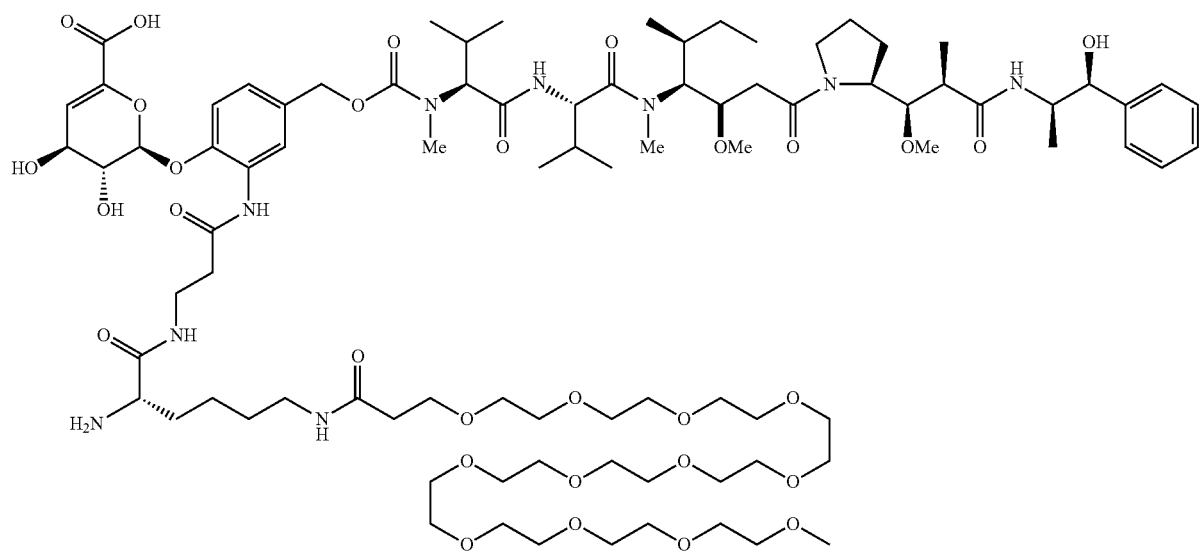

44A. A composition comprising Antibody Drug Conjugates represented by Formula 11 and Formula 11A having the structures of:

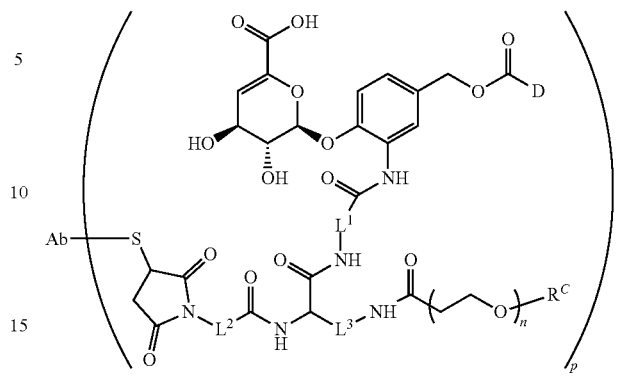

(11A)

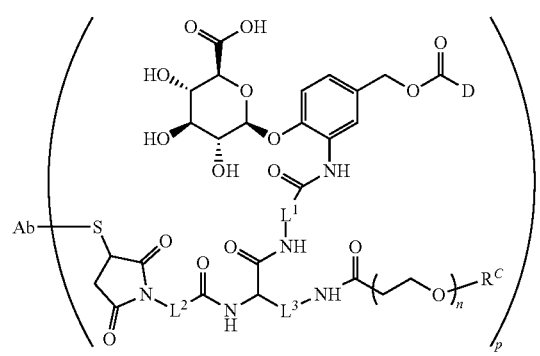

(11)

and or pharmaceutically acceptable salts thereof, wherein Ab is an antibody; S is a sulfur atom from the antibody; D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. %, in particular no more than 5 wt. %, of Formula 11A Antibody Drug Conjugate.

45A. A composition comprising Antibody Drug Conjugates represented by Formula 12 and Formula 12A, optionally in pharmaceutically acceptable salt form, having the structures of:

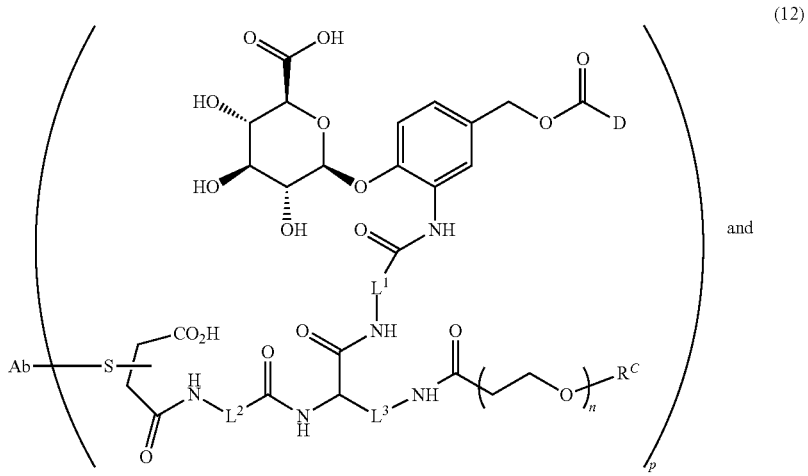

(12)

and

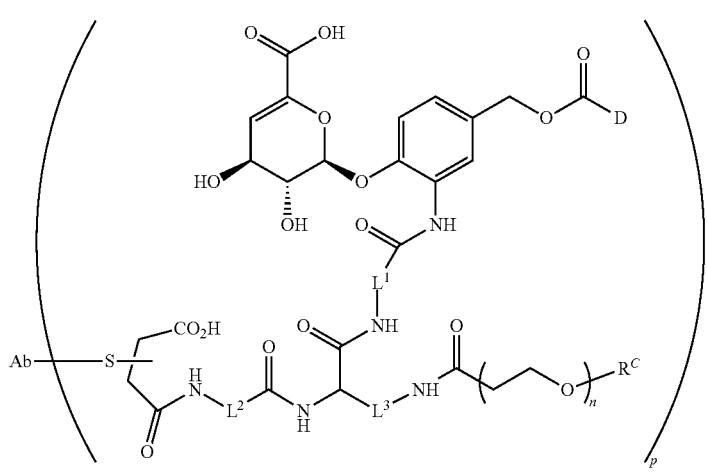

(12A)

wherein Ab is an antibody; S is a sulfur atom from the antibody; the Ab-S— moeity is attached to the carbon atom α or β to the carboxylic acid functional group; D is an auristatin Drug Unit; $L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. % Formula 12A Antibody Drug Conjugate, in particular, the Formula 12 and Formula 12A Antibody drug Conjugates, optionally in pharmaceutically acceptable salt form, have the structures of:

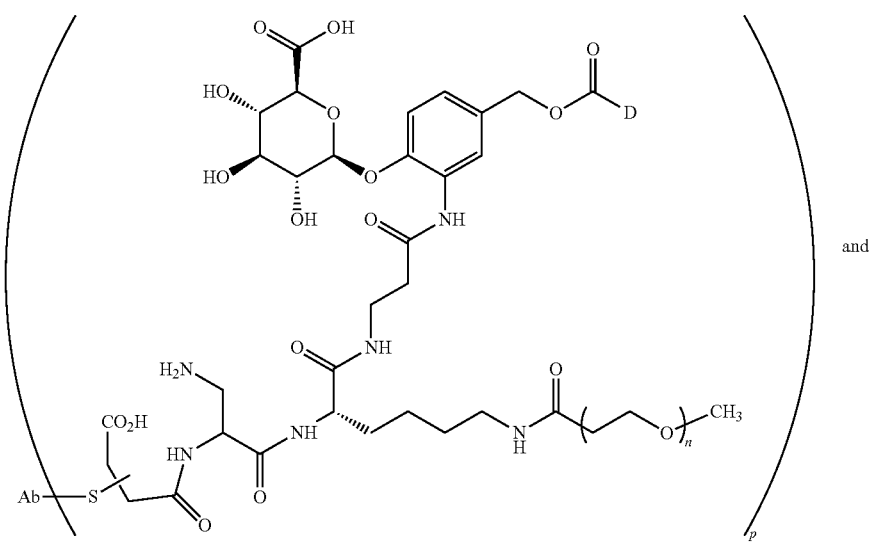

and

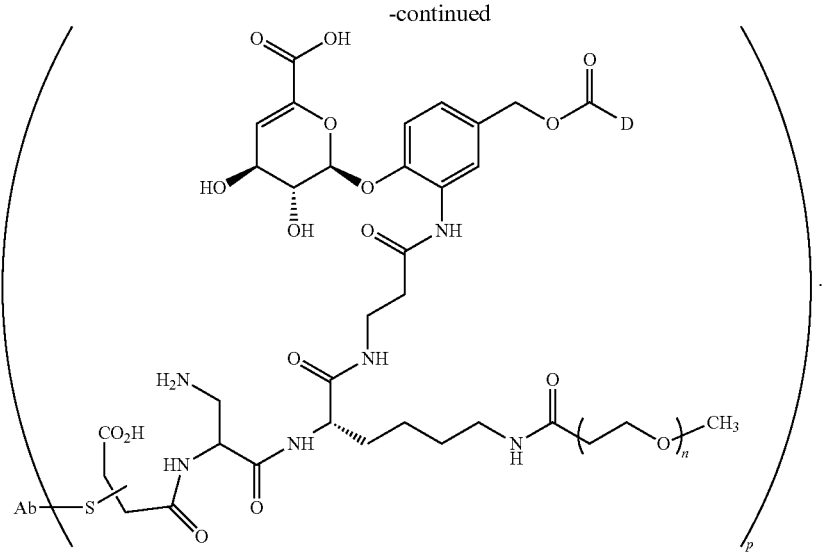

46A. The composition or compound of embodiment 44A or 45A, wherein the auristatin Drug Unit has the has any one of the structures of embodiment 9A, in particular, D has the structure of Formula $D_{F/E-3}$:

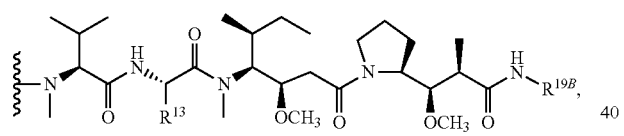

($D_{F/E-3}$)

wherein $R^{13}$ is isopropyl or —CH$_2$—CH(CH$_3$)$_2$; and $R^{19B}$ is —CH(CH$_3$)—CH(OH)Ph, —CH(CO$_2$H)CH$_2$Ph, —CH(CH$_2$Ph)-2-thiazole, —CH(CH$_2$Ph)-2-pyridyl, —CH(CH$_2$-p-Cl-Ph), —CH(CO$_2$Me)-CH$_2$Ph, —CH(CO$_2$Me)-CH$_2$CH$_2$SCH$_3$, CH(CH$_2$CH$_2$SCH$_3$)C(=O)NH-3-quinolyl, or —CH(CH$_2$Ph)C(=O)NH-p-Cl-Ph, more particularly, D has the structure of:

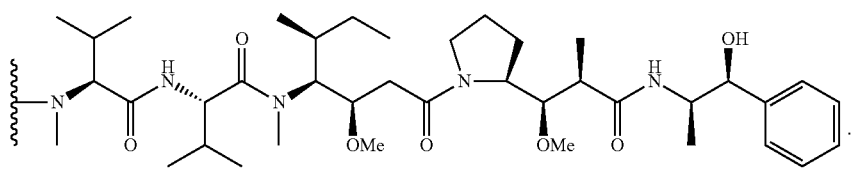 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

47A. The composition of embodiment 45A, wherein Formula 12 and Formula 12A Antibody Drug Conjugates, optionally in pharmaceutically acceptable salt form, have the structures of:

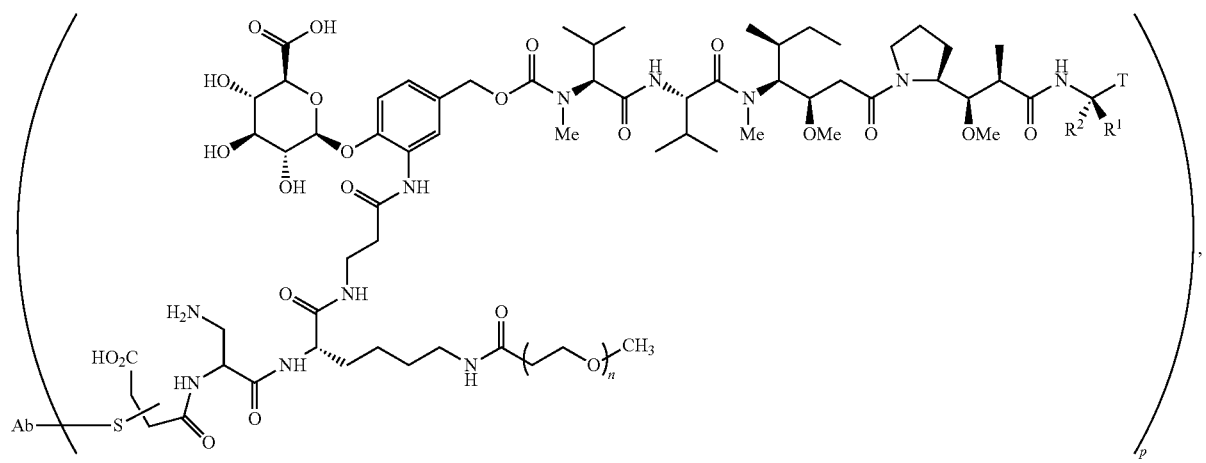
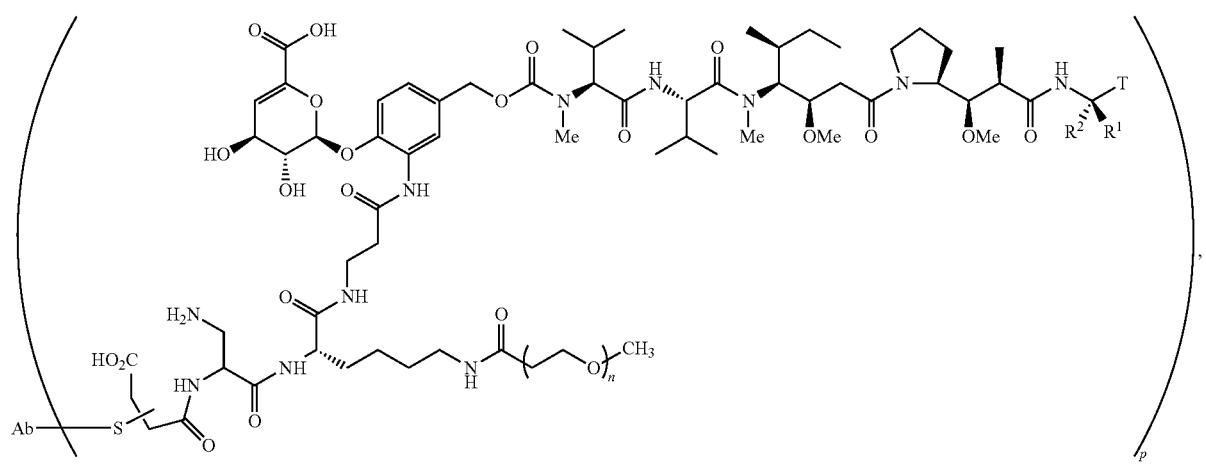
in particular, the Formula 12 and Formula 12A Antibody Drug Conjugates, optionally in pharmaceutically acceptable salt form, have the structures of:
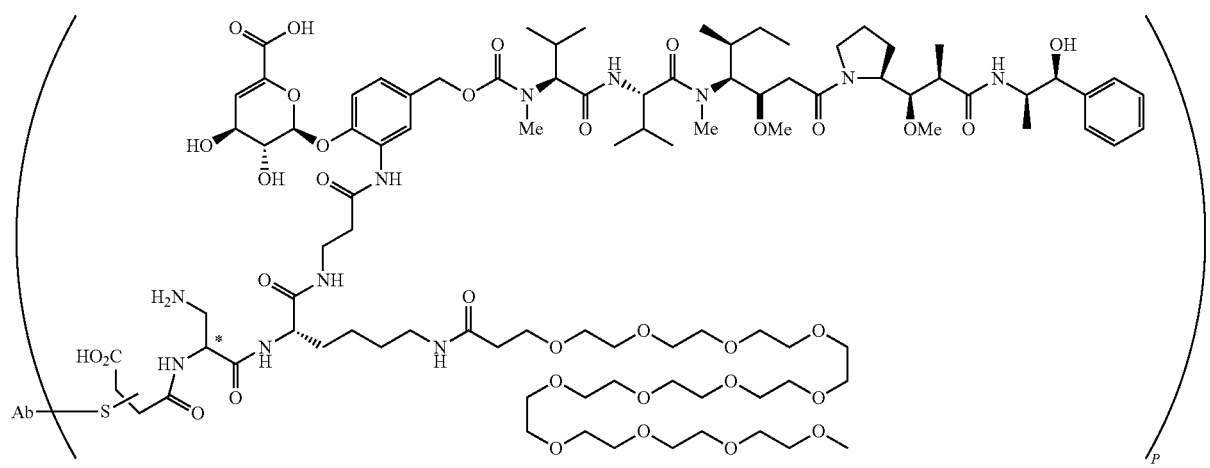

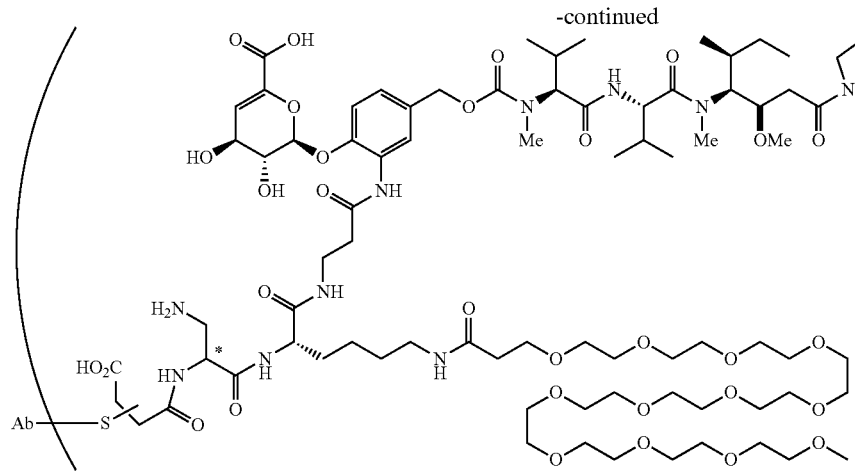
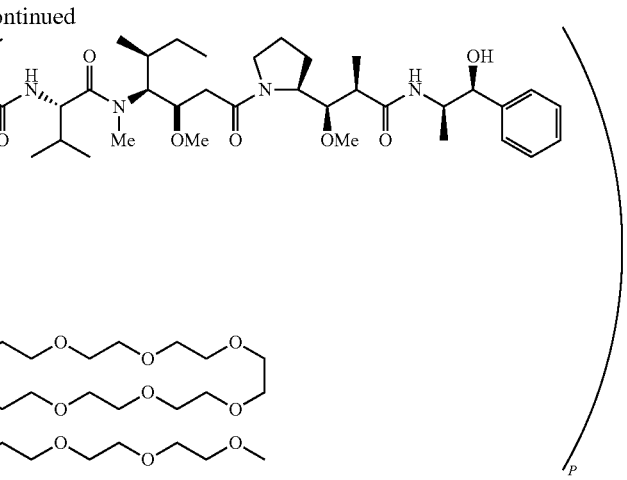

more particularly, having the indicated carbon atom (*) is predominately in the S configuration, and or in which subscript p is about 8.

48A. The composition of any one of embodiments 44A-47A, wherein the antibody is capable of selectively binding to a tumor associated antigen.

49A. The composition of embodiment 48A, wherein the tumor associated antigen is comprised of an extracellular domain of a cell-surface protein or glycoprotein to which the antibody is capable of binding, particular wherein the cell-surface protein or glycoprotein is that of an abnormal cell, more particularly one that is capable of internalization upon binding by an Antibody Drug Conjugate compound of the composition.

50A. A method of treating a subject having a haematological malignancy, comprising administering an effective amount of a composition of any one of embodiments 44A-49A, particularly a leukemia or lymphoma, more particularly a B-cell malignancy.

EXAMPLES

General Information.

All commercially available anhydrous solvents were used without further purification. Analytical thin layer chromatography was performed on silica gel MF254 (Agela Technologies). Column chromatography was performed on a Biotage SNAP™ ultra 340 g HP-sphere 25 μm. Analytical HPLC was performed on a Varian ProStar 210™ solvent delivery system configured with a Varian ProStar 330™ PDA detector. Samples were eluted over a C12 Phenomenex Synergi™ 2.0×150 mm, 4 μm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass™ mass spectrometer interfaced to an HP Agilent 1100™ HPLC instrument equipped with a C12 Phenomenex Synergi 2.0×150 mm, 4 m, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2™ Tof mass spectrometer interfaced to a Waters 2695 Separations Module™ with a Waters 2996 Photodiode Array Detecto™; the column, mobile phases, gradient, and flow rate were same as for LC-MS system 1. UPLC-MS was performed by a Waters Xevo G2 ToF mass spectrometer interfaced to a Waters Acquity H-Class Ultra Performance LC™ equipped with an Acquity UPLC BEH™ C18 2.1×50 mm, 1.7 am reverse phase column (Milford, Mass.). The acidic mobile phase (0.1% formic acid) consisted of a gradient of 3% acetonitrile/97% water to 100% acetonitrile (flow rate=0.7 mL/min). Preparative HPLC was carried out on a Waters 2545 Binary Gradient Module with a Waters 2998 Photodiode Array Detector. Products were purified over a C12 Phenomenex Synergi 250×10.0 mm, 4 m, 80 Å reverse phase column (Column 1) or a C12 Phenomenex Synergi 250×50 mm, 10 μm, 80 Å reverse phase column (Column 2) eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was 4.6 mL/min with monitoring at 254 nm.

Method 1: Preparation of PEGylated Auristatin Drug Linker Compounds: Non-Convergent Synthesis of MDPr-PEG$_{12}$-GlucC-MMAE with Global Deprotection of the Glucuronide Unit Synthesis of PEGylated glucuronide-auristatin drug-linker compounds, as well as intermediates thereof, having 15-20 wt. % or more impurities from β-elimination within the Glucuronide Unit are exemplified by the following reaction schemes, which has MMAE as the model auristatin Drug Unit.

Scheme 1.
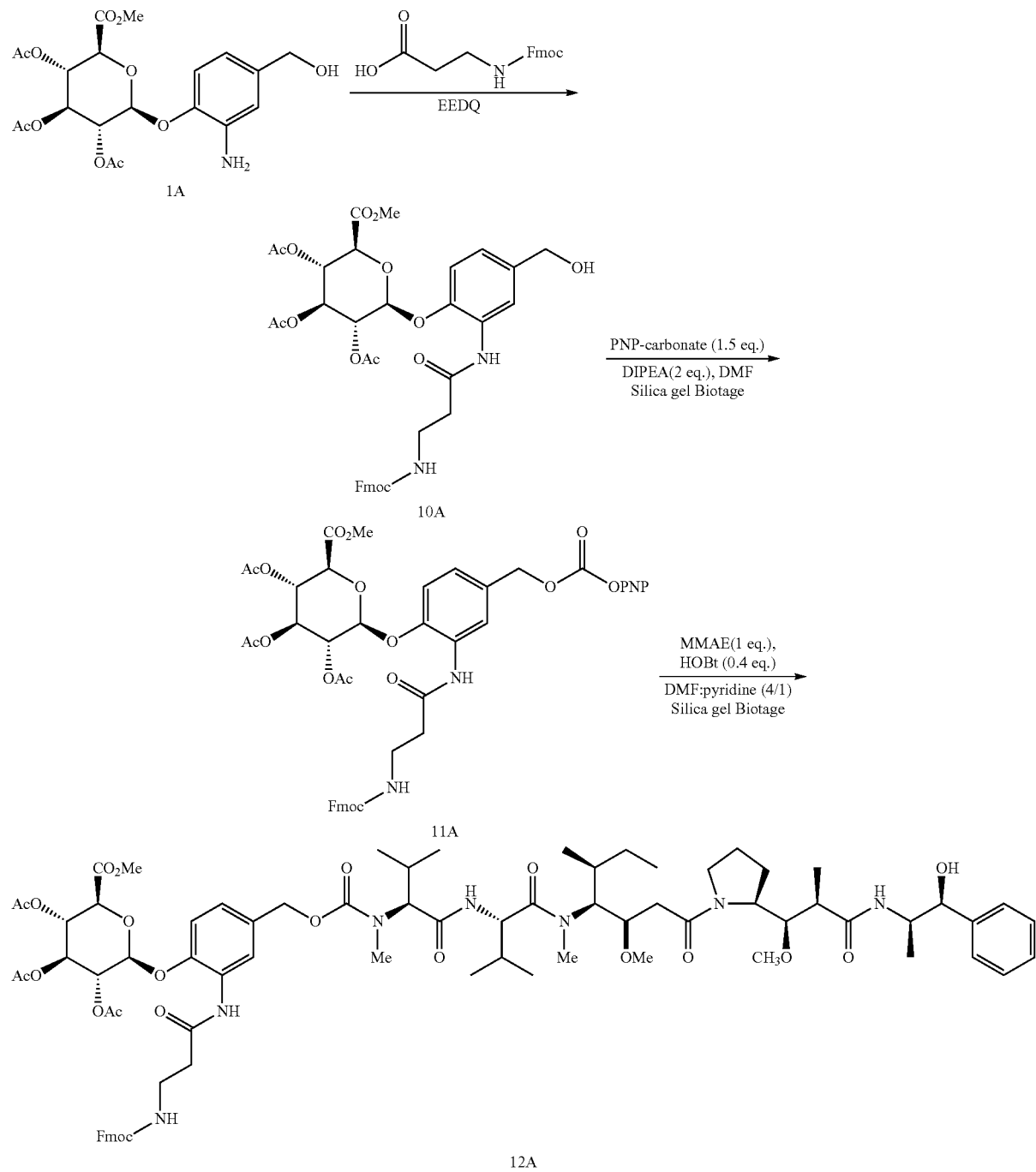

Scheme 2.
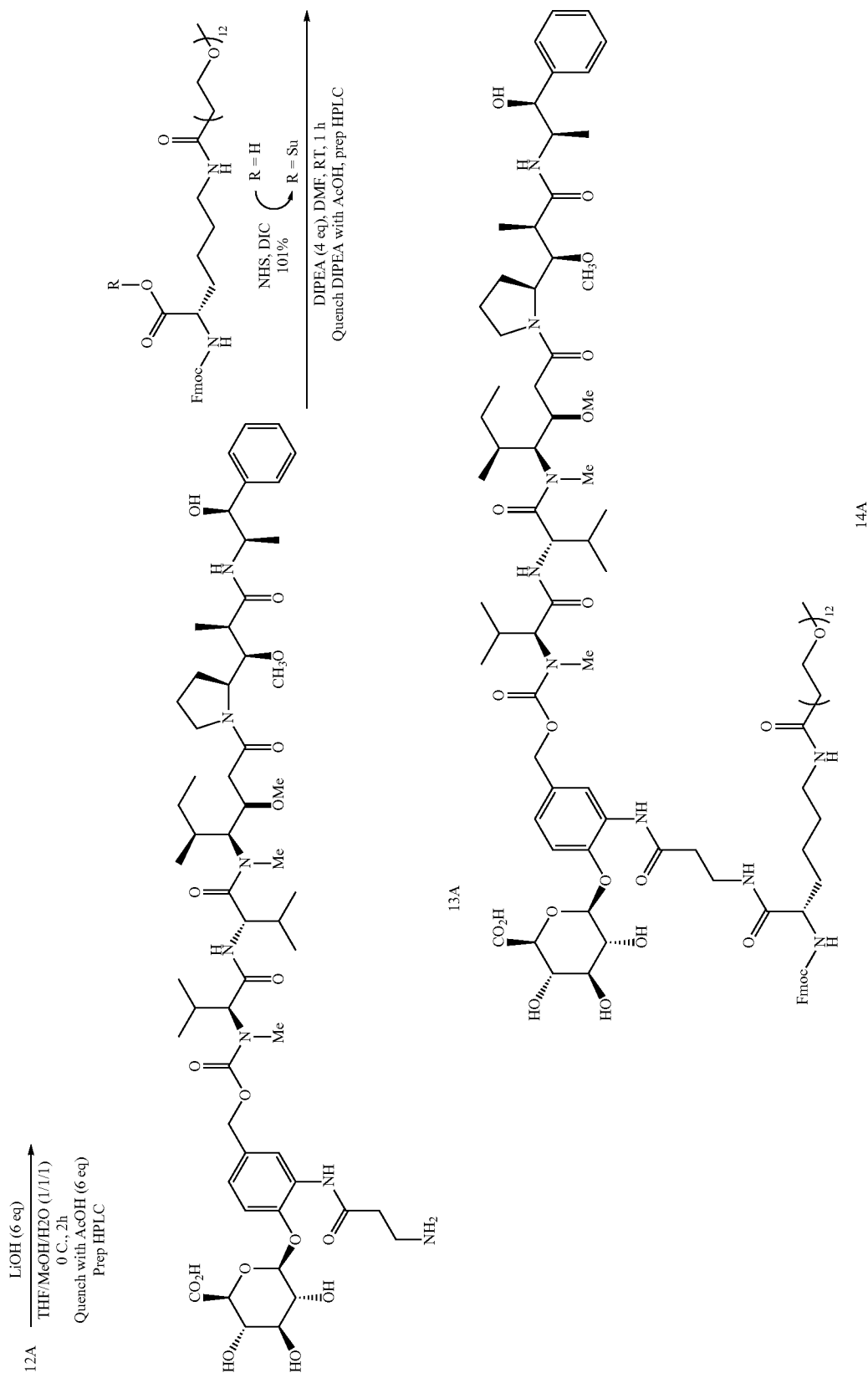

Scheme 3.
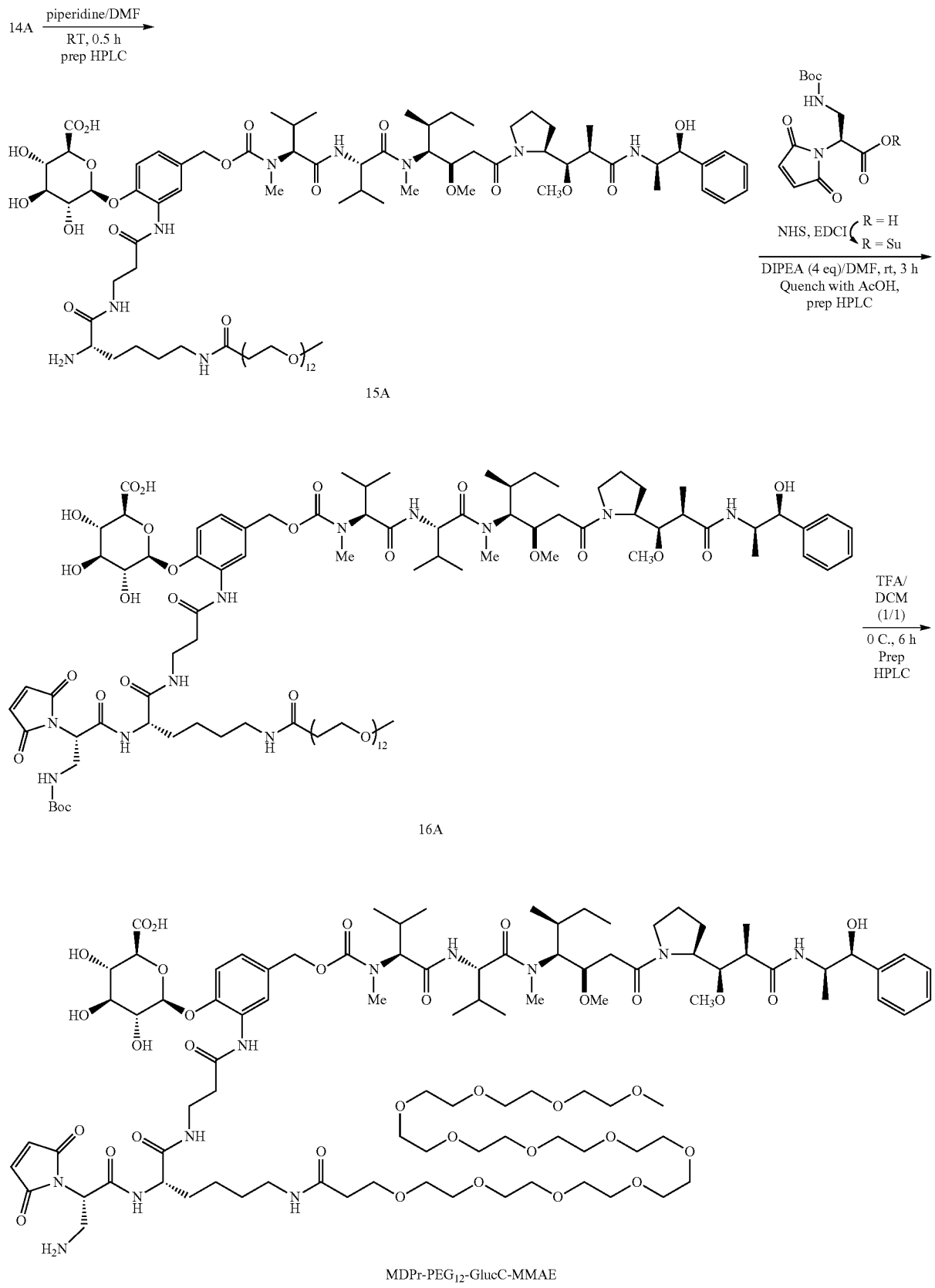
MDPr-PEG$_{12}$-GlucC-MMAE

Method 2: Preparation of PEGylated Auristatin Drug Linker Compounds: Convergent Synthesis of MDPr-PEG$_{12}$-GlucC-MMAE with Two Step Deprotection of the Glucuronide Unit Synthesis of PEGylated glucuronide-auristatin drug-linker compounds, as well as intermediates thereof, that substantially reduces β-elimination impurities are exemplified, in accordance with the present invention, by the following reaction schemes, which has MMAE as the model auristatin Drug Unit (Compound 10A, a representative compound of Formula 10, Formula I, and/or Formula IIF).

Scheme 1.

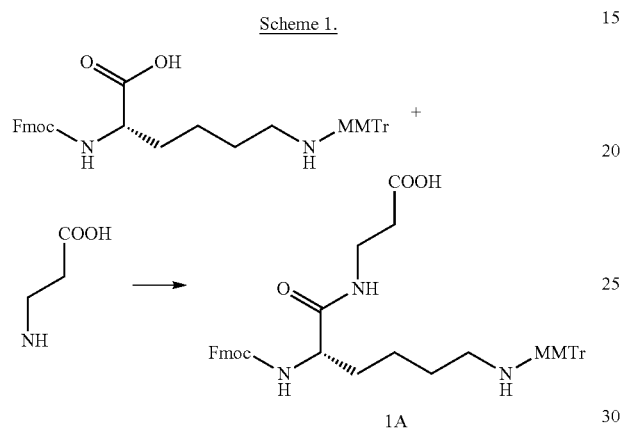

Scheme 2.

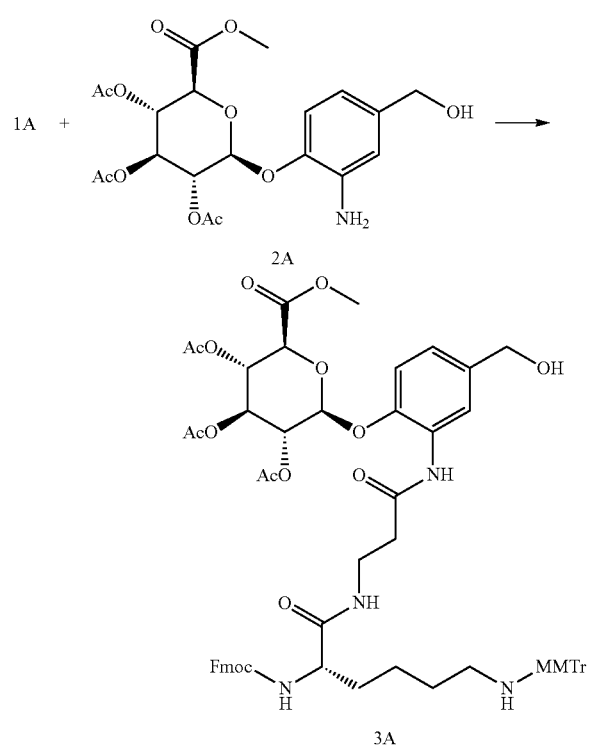

Scheme 3.

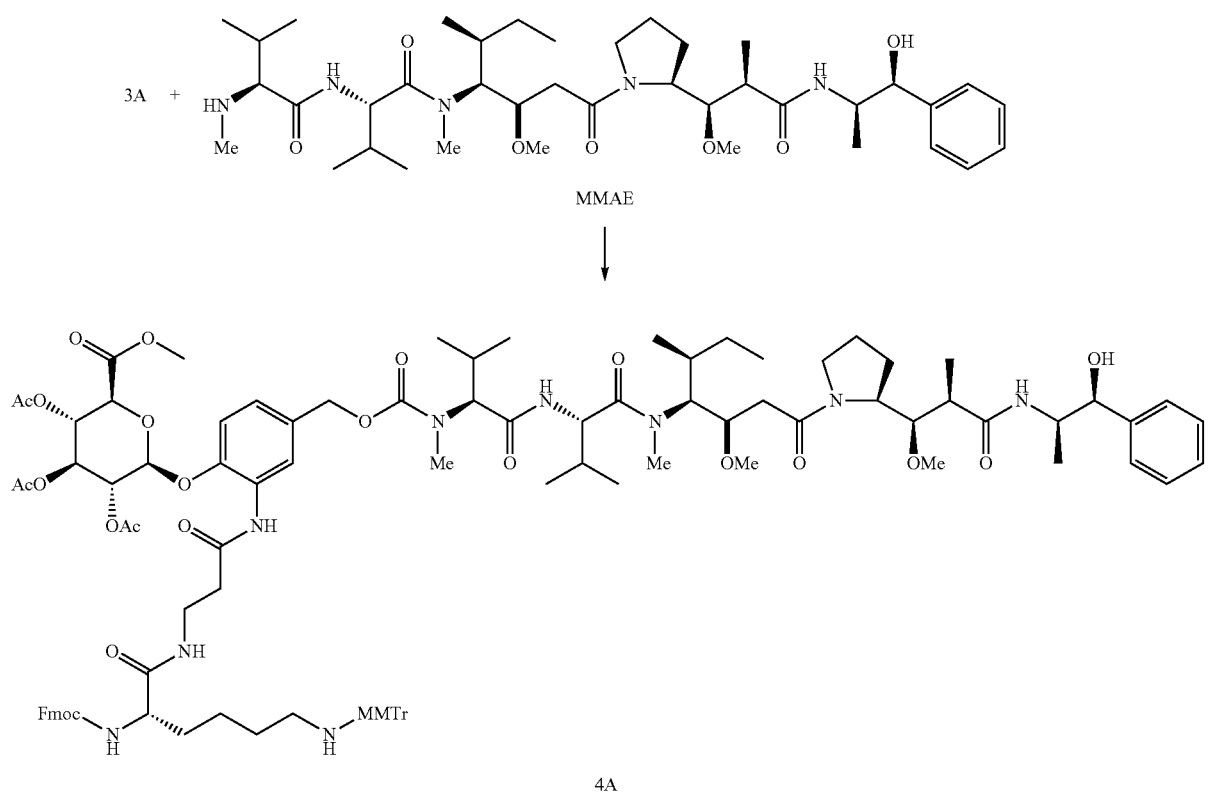

Scheme 4.
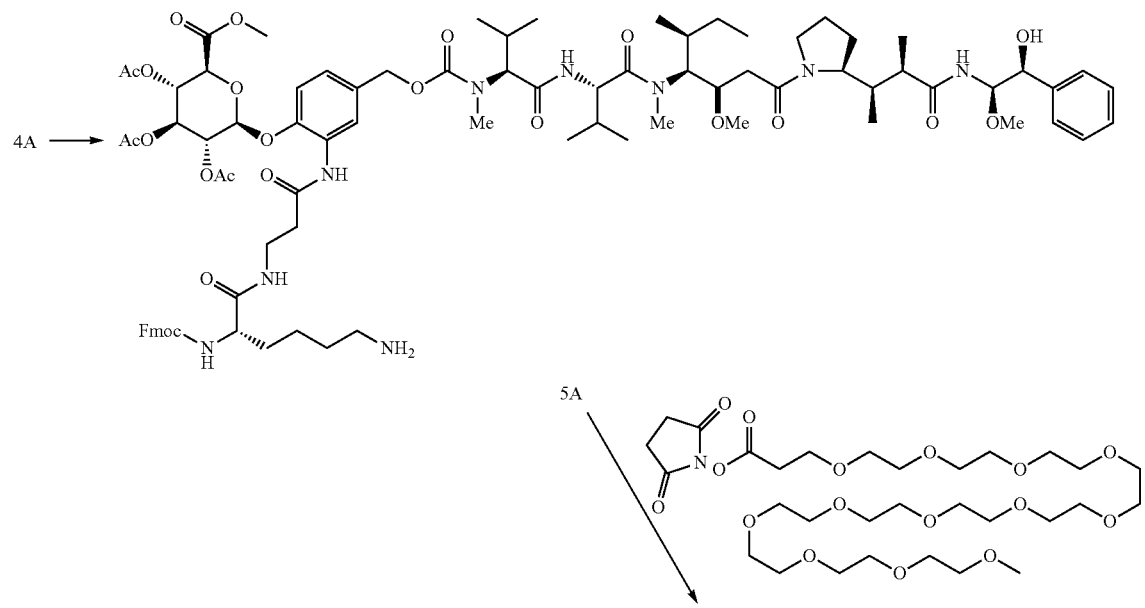
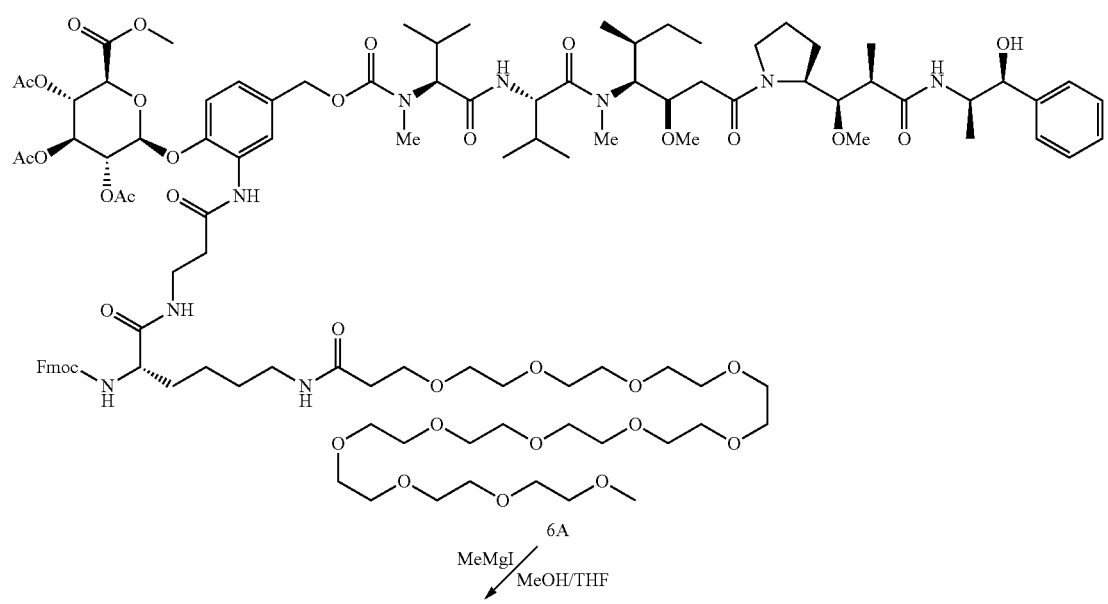

255 256
-continued
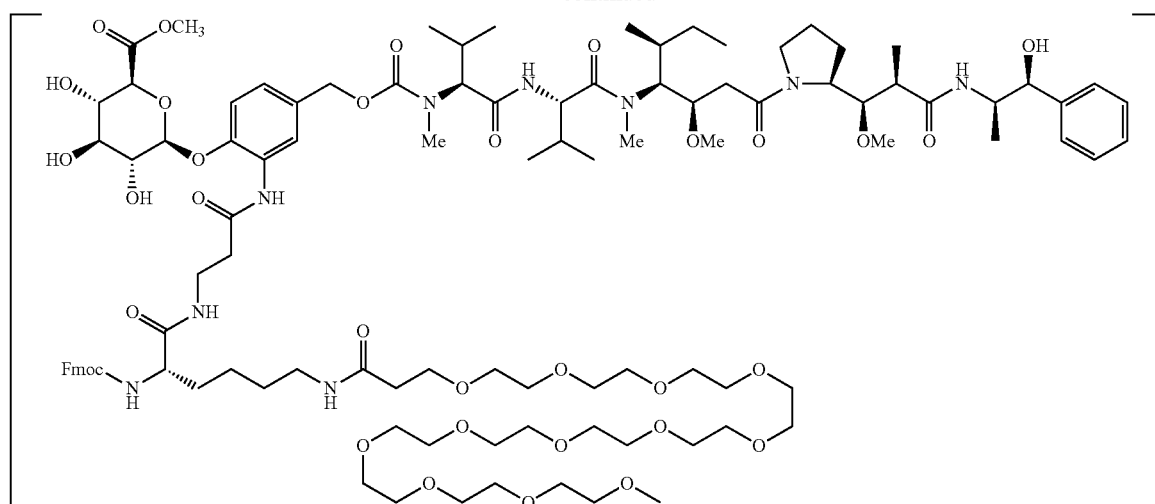
7A ↓ LiOH(aq.)
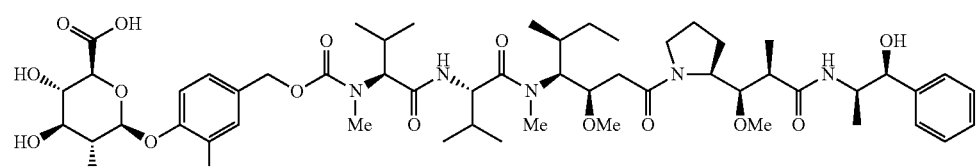
8A ↓
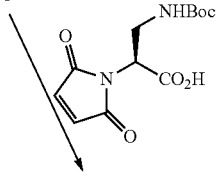

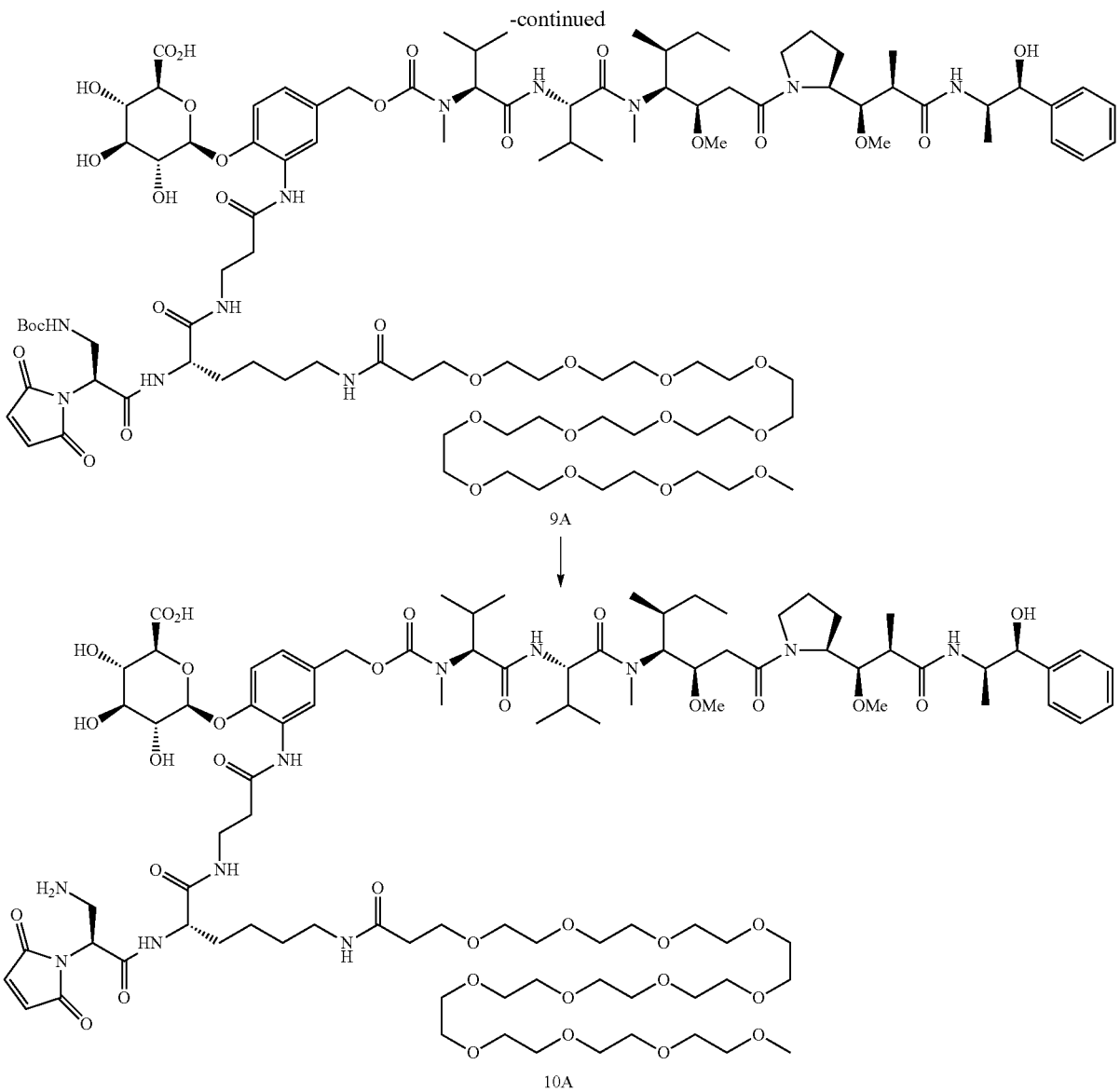

9A

10A

Example 1: Preparation of Compound 1A (Scheme 1)

Fluorenylmethyloxycarbonyl (FMOC) and Monomethoxytrityl (MMTr) protected L-lysine (15 g), N-hydroxysuccinimide (3.23 g, 1.2 eq)(Sigma-Aldrich, Cat #130672) and 1-hydroxybenzotriazole hydrate (HOBt) (~0.19 g, 0.05 eq))(Sigma-Aldrich, Cat #711489) were added to DCM (75 mL) at room temperature (rt). The reaction mixture was then cooled in an ice bath to ~5° C. followed by addition of N,N-Diisopropylethylamine (DIPEA) (0.30 mL, 0.075 eq.))(Sigma-Aldrich, Cat #387649) and N-(3-Dimethylaminopropyl)-N'-ethylcarbodiimide hydrochloride (5.83 g, 1.3 eq.)) (Sigma-Aldrich, Cat #03450) then stirring of the resulting reaction mixture at room temperature overnight. The reaction mixture was then washed with water (45 mL×2), dried over anhydrous sodium sulfate and evaporated in vacuo. Dioxane (45 mL), 0-alanine (2.29 g, 1.1 eq.) (Sigma-Aldrich, Cat #146064), N,N-Diisopropylethylamine (DIPEA) (4.5 mL, 1.1 eq.))(Sigma-Aldrich, Cat #387649) and deionized water (22.5 mL) were then added to the resulting residue. After stirring at rt overnight, DCM (225 mL) was added and then washed with HCl/water (0.4%, 225 mL) and then water (225 mL). The organic solution was dried over anhydrous sodium sulfate and concentrated to provide crude Compound 1A. Analytical LC-MS: $t_R$=1.93 min, m/z (ES+) found 712.5.

Example 2: Preparation of Compound 3A (Scheme 2)

The synthesis of glucuronide-based prodrugs including synthesis of Compound 2A is disclosed in, for example, *Anticancer Drug Design* (1998), 13(8), 955-68, the method for which is specifically incorporated by reference herein.

The crude Compound 1A (1.05 eq.) was dissolved in DCM (75 mL) to which was then added 2-ethoxy-1-ethoxy-carbonyl-1,2-dihydroquinoline (EEDQ))(Sigma-Aldrich, Cat #149837) (2.84 g, 1.30 eq) at rt. After stirring 10 min, Compound 2A (10.15 g, 1.0 eq) was added and to the reaction mixture, which was stirred at rt overnight. After the reaction was complete, the reaction mixture was loaded on to 150 g of silica gel in a filter funnel. EtOAc/heptane=1/1 was used to elute the less polar impurities and pure EtOAc was used to collect the desired product. A white solid was obtained after concentration and solvent exchange to heptane. The solid was collected by vacuum filtration and dried in vacuo for 1 day at room temperature to obtain 21.68 g Compound 3A (84.6% overall yield from lysine). Analytical LC-MS: $t_R$=1.95 min, m/z (ES+) found 1149.3.

Example 3: Preparation of Compound 4A (Scheme 3)

To Compound 3A (4.86 g) in 2-MeTHF (194 mL) was added 1,1'-Carbonyl-di-(1,2,4-triazole) (CDT) (Sigma-Aldrich, Cat #21861) 2.084 g (3 eq.). The reaction mixture was stirred at room temperature for 5 hrs with LC-MS showing completeness of the reaction. The reaction mixture was then washed with water (49 mL×3) (a little NaCl is needed for phase separation), (note: the wet solution is stable overnight) dried over anhydrous sodium sulfate. Evaporated of the solvent yielded a solid (5.833 g). That solid and MMAE 3.646 g (1.3 eq.) were dissolved in 2-MeTHF (29 mL). 1-Hydroxybenzotriazole hydrate (HOBt) (0.15 g, 0.2 eq.) (Sigma-Aldrich, Cat #711489) in 4 mL 2-MeTHF was evaporated to reduce the volume by about ½. The concentrated HOBt solution was then added to the reaction mixture, which was stirred at 55° C. for 60 hours. The reaction was washed with water (29 mL×4) to remove excess MMAE and HOBt. MMAE can also be removed by slurrying with polymer-bound isatoic anhydride, (Aldrich product #514373) in 2-MeTHF solution at rt overnight. MMAE reacts with polymer-bound isatoic anhydride, which is then filtered off.

Reaction mixture was dried over anhydrous sodium sulfate and solvent was exchanged with EtOAc and the resulting solution was loaded on Biotage column. 5% MeOH in EtOAc was used to elute the product to provide 4.914 g (62% yield) of Compound 4A. Analytical LC-MS: tr=2.22 min, m/z (ES+) found 1894.1.

Example 4: Preparation of Compound 5A (Scheme 4)

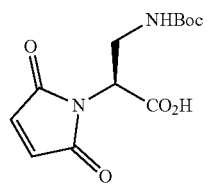 [SMILES: CC(C)(C)OC(=O)NC[C@@H](C(=O)O)N1C(=O)C=CC1=O]

Boc-protected maleimide (above) was prepared as described in PCT Publication No. WO2015057699, the method of which is specifically incorporated by reference herein.

Compound 4A (4.40 g) was dissolved in DCM 44 mL; and trichloroacetic acid (TCA) (8.8 g) (Sigma-Aldrich, Cat #T6399) was dissolved in 440 mL DCM. The TCA solution is cooled in ice bath to ~5° C. and then the Compound 4A solution was added in 5 minutes. Upon addition the reaction mixture immediately turned orange. The ice bath was removed and the temperature increased slowly to 15° C. The reaction was complete in 1 h, and was then cooled again in ice bath to −10° C. whereupon 6.0 g of $KHCO_3$ in 100 mL water is added in 5 min to quench the reaction mixture, which resulted in disappearance of the color. The organic phase was separated and washed with brine and dried over anhydrous sodium sulfate. The solvent was evaporated with addition of heptane to form a white solid. The white solid was collected by vacuum filtration to obtain crude Compound 5A. Analytical LC-MS: $t_R$=1.94 min, m/z (ES+) found 1621.0.

Example 5: Preparation of Compound 6A (Scheme 4)

The crude Compound 5A was then dissolved in DCM (17.6 mL) and subsequently $PEG_{12}$-OSu (1.756 g, 1.1 eq.) (Quanta BioDesign, cat #10262) and then N,N-Diisopropylethylamine (DIPEA) (0.24 mL, 0.60 eq.) (Sigma-Aldrich, Cat #387649) was added. The reaction mixture was stirred at room temperature for 4 h, then was loaded on to silica gel (88 g) and eluted with 1) 5% MeOH/EtOAc to remove excess amount of PEG-OSu, MMTr related by-product and N-hydroxysuccimide, followed by elution with 2) 5% MeOH/DCM to obtain Compound 6A (3.335 g, 66% yield). Analytical UPLC-MS: $t_R$=1.53 min, m/z (ES+) found 2191.3.

Example 6: Preparation of Compound 8A (Scheme 4)

Compound 6A (2.73 g) was added to a round bottle flask and then 9 mL THF and 9 mL MeOH were added. The solid dissolved and the solution so obtained was cooled in ice bath. Methylmagnesium iodide solution (3 M in $Et_2O$)(2.08 mL, 5 eq.)(Sigma-Aldrich, cat #254363) was added dropwise with control of the internal temperature to below 5° C. Afterwards, the reaction mixture was stirred at room temperature overnight to effect the transesterification reaction for selective removal of the acetate protecting groups by (MeO)MgI formed in situ, resulting in intermediate Compound 7A, which is then further deprotected with LiOH (aq.) as follows without requiring its purification.

The reaction mixture was again cooled in ice bath and lithium hydroxide (358 mg, 12 eq.)(Sigma-Aldrich, cat #545856) in water (9 mL) was added slowly. The temperature increased gradually to room temperature. After 3 hours removal of the FMOC protecting group was complete. The reaction mixture was then filtered through celite to remove FMOC related by-product. The pH of the filtrate, which contained the desired product, was adjusted to 7 by acetic acid. Purified Compound 8A (~1.8 g, 78% yield), as assessed by analytical HPLC, was obtained by reverse phase chromatography of the filtrate. Analytical LC-MS: $t_R$=1.53 min, m/z (ES+) found 1828.8.

Example 7: Preparation of Compound 9A (Scheme 4)

A 4 mL vial was charged with Boc-protected maleimide (46.6 mg, 0.16 mmol), COMU (46.8 mg, 0.11 mmol) (Sigma-Aldrich, cat #712191) and DMF (0.5 mL). The mixture was cooled to 0° C. and 2,6-lutidine (38.2 µL, 0.33 mmol))(Sigma-Aldrich, cat #336106) was added slowly and the reaction was stirred for 30 min. In a separate vial, Compound 7A (100.0 mg, 0.06 mmol) was dissolved in DMF (1.0 mL) and cooled to 0° C. The solution of Boc-protected maleimide was added to the solution of Compound 7A and stirred for 30 min.

DMSO (0.5 mL) was added to the reaction, then 0.1% TFA in water (2.0 mL) was slowly added to the reaction keeping the temperature at 0° C. The crude material was purified by preparative HPLC and the fractions were lyophilized to afford Compound 8A (28.0 mg, 24% yield). Analytical UPLC-MS: $t_R$=1.32 min, m/z (ES+) found 2096.44.

Example 8: Preparation of Compound 10A (Scheme 4)

A 4 mL vial was charged with Compound 9A (28 mg, 0.013 mmol) and a solution of 20% trifluoroacetic acid (TFA)(Sigma-Aldrich, cat #T6508) in DCM (1.5 mL). The reaction was stirred for 30 min, then the solvent was removed in vacuo. The crude was taken up in DMSO (1.0 mL) and 0.1% TFA in water (3 mL). The material was left to stand for 3 h then the product was purified by HPLC. The product fractions were collected and lyophilized to afford Compound 9A (24 mg, 90% yield). Analytical UPLC-MS: $t_R$=1.17 min, m/z (ES+) found 1996.42.

Example 9: Comparison of Various Conditions for Deprotection of Compound 6A

As shown in Table 1, conventional methods of removing acyl protecting groups from a carbohydrate moiety, as in a acetate-protected Glucuronide Unit, using aqueous base (Method 1) for global deprotection of an auristatin Drug Linker intermediate resulted in a deprotected product containing 15-20% wt. % or more of an impurity, which exemplified by the structure of dehydro-7A (see Scheme 5 below):

The impurity dehydro-7A originates as the result of a competing 3-elimination process within the Glucuronide Unit, which significantly decreases the yield of the desired product Compound 7A. That problem was unexpectedly solved by contacting compound 6A, which is the precursor to Compound 7A, in 1:1 (v/v) mixture of methanol and THF with a solution of MeMgI (Method 2). The reagent MeOMgI formed in situ surprisingly removes the acetate protecting groups by transesterification without disturbing the other base sensitive protecting group FMOC. The methyl ester protecting group is also unchanged since any transesterification by the methanol solvent regenerates that ester group. As in the Method 1, the FMOC and methyl ester groups of Method 2 are removed with aqueous LiOH The amount of the impurity dehydro-7A from that two-step process, which can be conveniently conducted in a single pot, decreased significantly to less than about 4%.

Scheme 5. Glucuronide Deprotection Methods

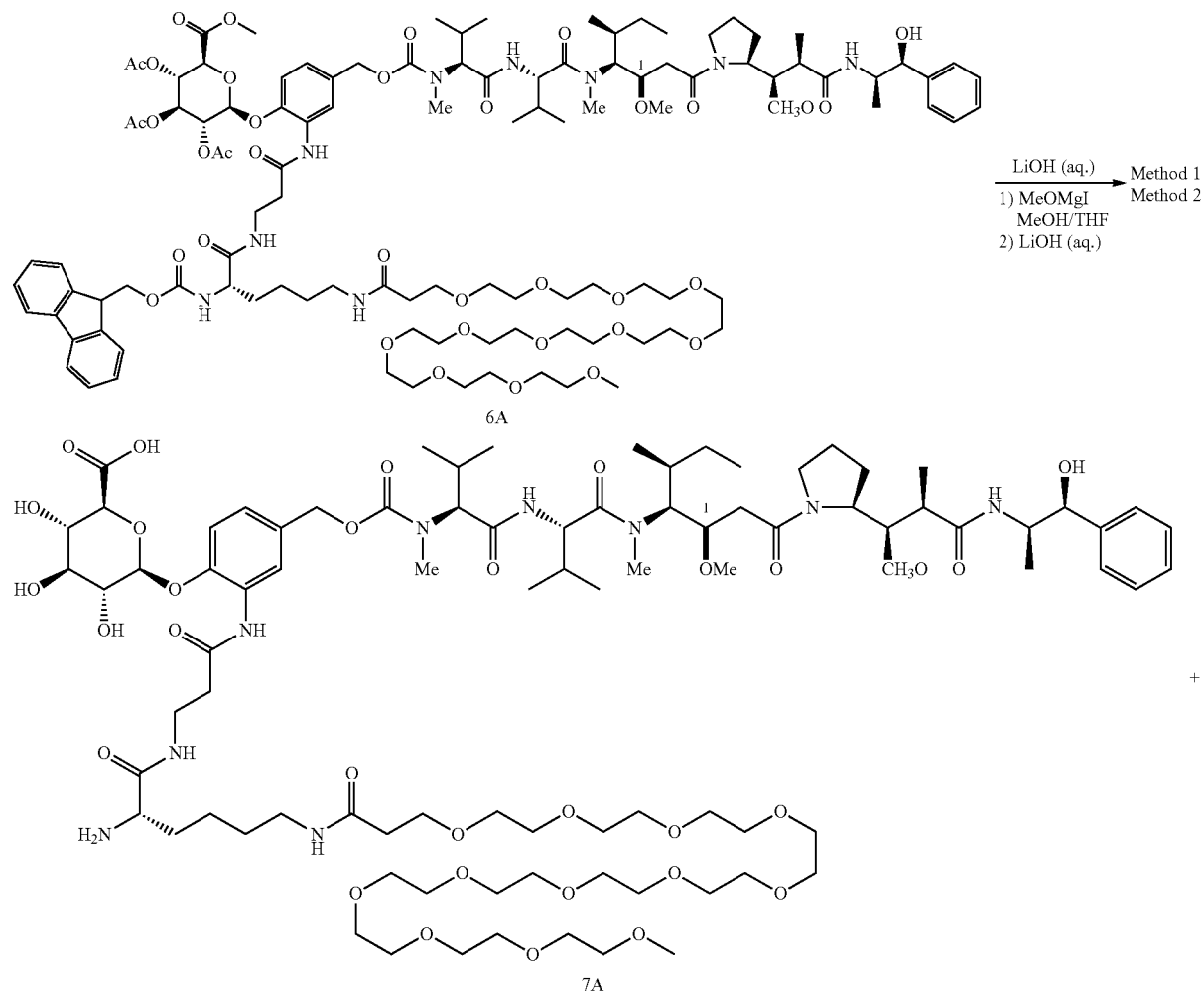

-continued

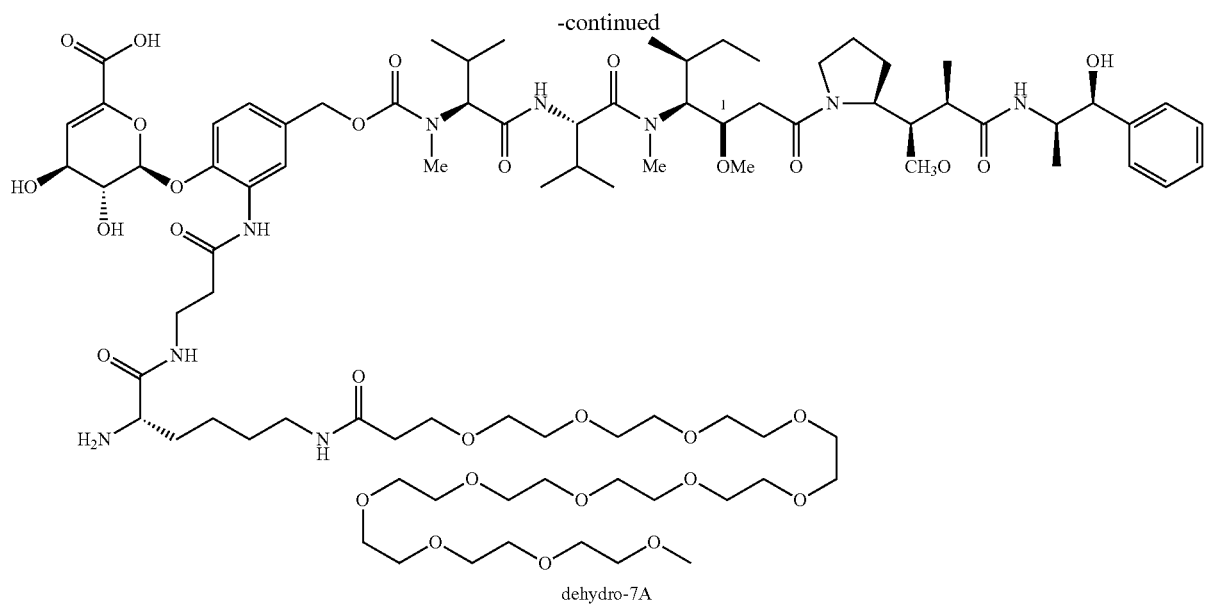

dehydro-7A

TABLE 1

Deprotection of compound 6A using conventional base method (5 mg in 300 μL solvent, stir at room temperature for 2 hours).

| Base | Solvent | Product/Impurity |
|---|---|---|
| LiOH | THF/MeOH/Water = 1/1/1 | 3.5/1 |
| CsOH | THF/MeOH/Water = 1/1/1 | 3.5/1 |
| Li$_2$CO$_3$ | THF/MeOH/Water = 1/1/1 | 3.2/1 |
| K$_2$CO$_3$ | THF/MeOH/Water = 1/1/1 | 2.7/1 |
| Cs$_2$CO$_3$ | THF/MeOH/Water = 1/1/1 | 2.6/1 |
| LiOH | THF/water = 1/1 | 4.9/1 |
| KOH | THF/water = 1/1 | 1.8/1 |
| CsOH | THF/water = 1/1 | 4.3/1 |
| KHCO$_3$ | THF/water = 1/1 | No reaction |
| CsHCO$_3$ | THF/water = 1/1 | No reaction |

TABLE 2

Deprotection of compound 6A using a Grignard reagent or an alkoxy magnesium halide in an alcohol-containing solvent (total reaction time 2.5 hours).

| Base | Solvent | Product/Impurity (after treatment with aqueous LiOH) |
|---|---|---|
| LiOMe | THF/MeOH = 1/1 | 3.2/1 |
| NaOMe | THF/MeOH = 1/1 | 1.6/1 |
| Mg(OMe)2 | THF/MeOH = 1/1 | 2.9/1 |
| MeMgI | THF/MeOH = 1/1 | 21/1 |
| MeMgCl | THF/MeOH = 1/1 | 21/1 |
| MeMgI | THF/EtOH = 1/1 | 7.9/1 (transesterification with ethanol) |

What is claimed is:

1. A method for preparing a Drug Linker intermediate compound of Formula ID:

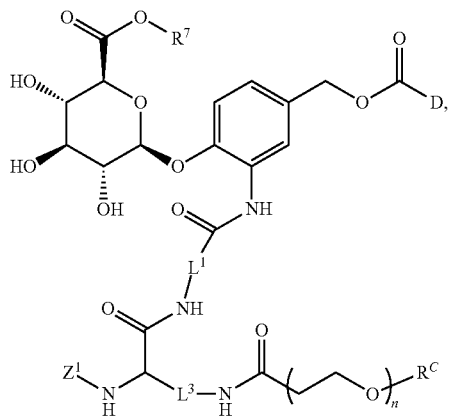

or a salt thereof,
wherein D is an auristatin Drug Unit,
each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_5$ heterocyclo;
$R^7$ is optionally substituted $C_1$-$C_8$ alkyl, optionally substituted $C_6$-$C_{10}$ arylene or optionally substituted $C_5$-$C_{10}$ heteroarylene so that —$OR^7$ provides an ester functional group that is a suitable carboxylic acid protecting group;
$Z^1$ is a first suitable amino protecting group;
$R^C$ is a PEG Capping Unit; and
subscript n ranges from 2 to 24,
the method comprising the step of:
contacting a Drug Linker intermediate compound of Formula IC with either a Grignard reagent or alkoxy magnesium halide in a suitable alcohol-containing solvent,
wherein the Formula IC Drug Linker intermediate compound has the structure of:

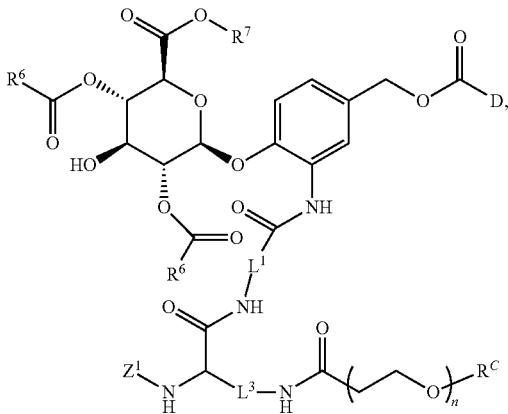

wherein each of $R^6$ is independently optionally substituted $C_1$-$C_8$ alkyl, optionally substituted $C_6$-$C_{10}$ arylene or optionally substituted $C_5$-$C_{10}$ heteroarylene so that $R^6C(=O)$-provides for an ester functional group that is a suitable hydroxyl protecting group; and the
the remaining variable groups are as previously described; and
wherein said Grignard reagent or an alkoxy magnesium halide contacting selectively removes the hydroxyl protecting groups to provide the Formula ID compound.

2. The method of claim 1, wherein the Formula IC and Formula ID Drug Linker intermediate compounds have the structures of Formula IIC and Formula IID:

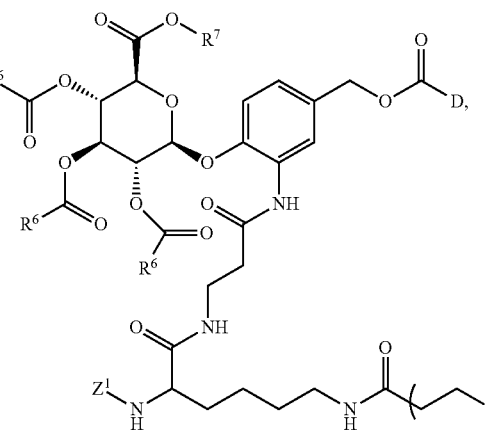

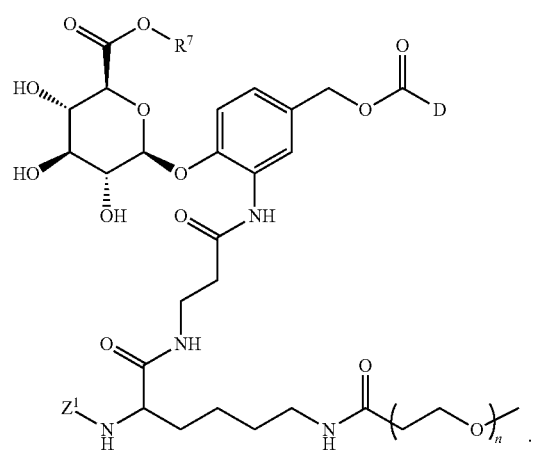

3. The method of claim 2, wherein the auristatin Drug Unit (D) has the structure of:

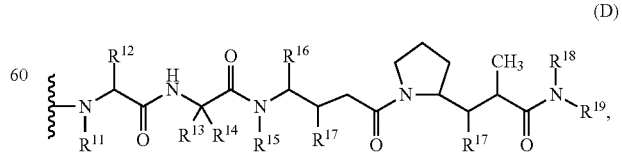

wherein the wavy line indicates covalent bonding of D to the remainder of the Drug Linker or Drug Linker intermediate compound;

$R^{11}$ is selected from the group consisting of H and $C_1$-$C_8$ alkyl, or $R^{11}$ is methyl, $R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{14}$ is selected from the group consisting of H and methyl, or $R^{13}$ and $R^{14}$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

each $R^{17}$ is independently selected from the group consisting of H, OH, $C_1$-$C_8$ alkyl, $C_3$-$C_8$ carbocycle, and O—($C_1$-$C_8$ alkyl);

$R^{18}$ is selected from the group consisting of H and $C_1$-$C_8$ alkyl;

$R^{19}$ is selected from the group consisting of —$C(R^{17})_2$—$C(R^{17})_2$-aryl, —$C(R^{17})_2$—$C(R^{17})_2$—($C_3$-$C_8$ heterocycle), —$C(R^{17})_2$—$C(O)$—$ZR^{20}$, and —$C(R^{17})_2$—$C(R^{17})_2$—($C_3$-$C_8$ carbocycle);

$R^{20}$ is selected from the group consisting of H, $C_1$-$C_8$ alkyl, optionally substituted $C_6$-$C_{10}$ aryl, optionally substituted $C_5$-$C_{10}$ heteroaryl, and $C_3$-$C_8$ heterocyclyl;

Z is —O— or —NH—, or

Z— is —O— and $R^{20}$ is $C_1$-$C_4$ alkyl or Z is —NH— and $R^{20}$ is optionally substituted phenyl or optionally substituted $C_5$-$C_6$ heteroaryl, or the auristatin Drug Unit (D) has the structure of Formula $D_{E-1}$, $D_{E-2}$, $D_{F-1}$ or $D_{F/E-3}$:

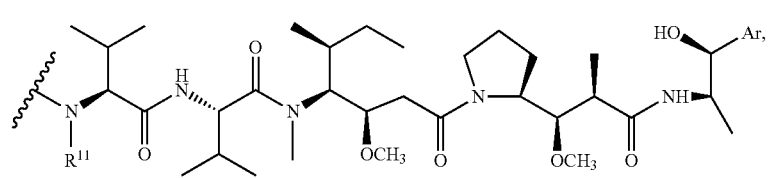

(D$_{E-1}$)

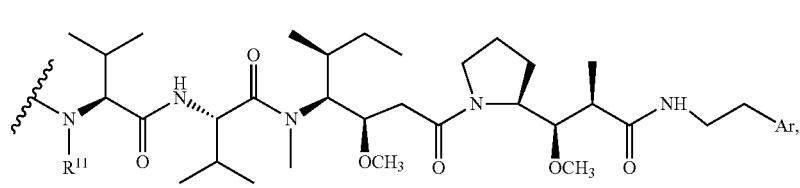

(D$_{E-2}$)

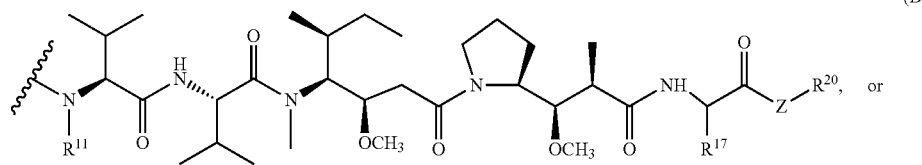

(D$_{F-1}$), or

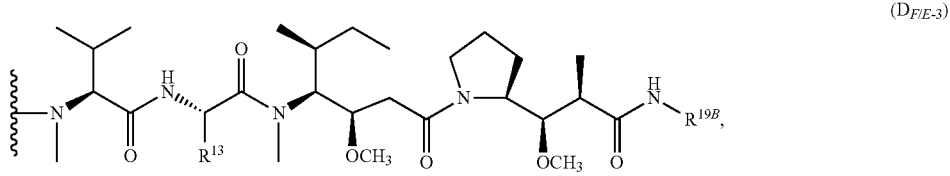

(D$_{F/E-3}$), wherein $R^{13}$ is isopropyl or —CH$_2$—CH(CH$_3$)$_2$; and
$R^{19B}$ is —CH(CH$_3$)—CH(OH)Ph, —CH(CO$_2$H)CH$_2$Ph, —CH(CH$_2$Ph)-2-thiazole, —CH(CH$_2$Ph)-2-pyridyl, —CH$_2$(CH$_2$-p-Cl-Ph), —CH(CO$_2$Me)-CH$_2$Ph, —CH(CO$_2$Me)-CH$_2$CH$_2$SCH$_3$, CH(CH$_2$CH$_2$SCH$_3$)C(=O)NH-3-quinolyl, or —CH(CH$_2$Ph)C(=O)NH-p-Cl-Ph;
Ar is optionally substituted C$_6$-C$_{10}$ aryl or optionally substituted C$_3$-C$_8$ heterocyclyl, or Ar is an optionally substituted phenyl or optionally substituted 2-pyridyl;
or D has the structure of:

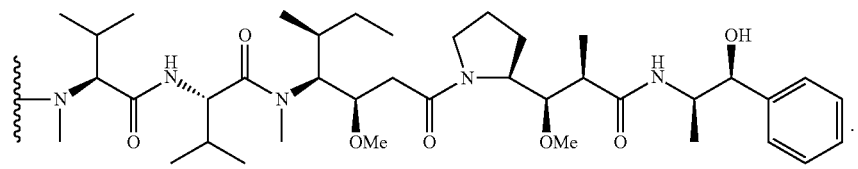 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

or a salt thereof, wherein
D is an auristatin Drug Unit with the structure of:

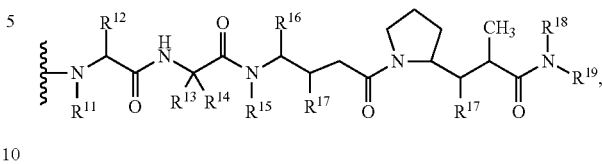

(D)

wherein the wavy line indicates covalent bonding of D to the remainder of the Drug Linker or Drug Linker intermediate compound;
$R^{11}$ is selected from the group consisting of H and C$_1$-C$_8$ alkyl, or $R^{11}$ is methyl,
$R^{12}$ is selected from the group consisting of H, C$_1$-C$_8$ alkyl, C$_3$-C$_8$ carbocycle, aryl, C$_1$-C$_8$ alkyl-aryl, C$_1$-C$_8$ alkyl-(C$_3$-C$_8$ carbocycle), C$_3$-C$_8$ heterocycle, and C$_1$-C$_8$ alkyl-(C$_3$-C$_8$ heterocycle);
$R^{13}$ is selected from the group consisting of H, C$_1$-C$_8$ alkyl, C$_3$-C$_8$ carbocycle, aryl, C$_1$-C$_8$ alkyl-aryl, C$_1$-C$_8$ alkyl-(C$_3$-C$_8$ carbocycle), C$_3$-C$_8$ heterocycle, and C$_1$-C$_8$ alkyl-(C$_3$-C$_8$ heterocycle); and
$R^{14}$ is selected from the group consisting of H and methyl or $R^{13}$ and $R^{14}$ jointly form a carbocyclic ring and have the formula —(CR$^a$R$^b$)$_n$— wherein R$^a$ and R$^b$ are independently selected from the group consisting of H, C$_1$-C$_8$ alkyl and C$_3$-C$_8$ carbocycle, and n is selected from the group consisting of 2, 3, 4, 5 and 6;
$R^{15}$ is selected from the group consisting of H and C$_1$-C$_8$ alkyl;
$R^{16}$ is selected from the group consisting of H, C$_1$-C$_8$ alkyl, C$_3$-C$_8$ carbocycle, aryl, C$_1$-C$_8$ alkyl-aryl, C$_1$-C$_8$ alkyl-(C$_3$-C$_8$ carbocycle), C$_3$-C$_8$ heterocycle, and C$_1$-C$_8$ alkyl-(C$_3$-C$_8$ heterocycle);
each $R^{17}$ is independently selected from the group consisting of H, OH, C$_1$-C$_8$ alkyl, C$_3$-C$_8$ carbocycle, and O—(C$_1$-C$_8$ alkyl);
$R^{18}$ is selected from the group consisting of H and C$_1$-C$_8$ alkyl;
$R^{19}$ is selected from the group consisting of —C(R$^{17}$)$_2$—C(R$^{17}$)$_2$-aryl, —C(R$^{17}$)$_2$—C(R$^{17}$)$_2$—(C$_3$-C$_8$ heterocycle), —C(R$^{17}$)$_2$—C(O)—ZR$^{20}$, and —C(R$^{17}$)$_2$—C(R$^{17}$)$_2$—(C$_3$-C$_8$ carbocycle);
$R^{20}$ is selected from the group consisting of H, C$_1$-C$_8$ alkyl, optionally substituted C$_6$-C$_{10}$ aryl, optionally substituted C$_5$-C$_{10}$ heteroaryl and C$_3$-C$_8$ heterocyclyl;
Z is —O— or —NH—, or
Z— is —O— and R$^{20}$ is C$_1$-C$_4$ alkyl or Z is —NH— and R$^{20}$ is optionally substituted phenyl or optionally substituted C$_5$-C$_6$ heteroaryl;

4. The method of claim 2, wherein $Z^1$ is fluorenylmethyloxycarbonyl (FMOC).
5. The method of claim 2, wherein the Grignard reagent in a suitable alcohol-containing solvent has the formula of R$^g$MgX and the alkoxy magnesium halide in a suitable alcohol-containing solvent has the formula of R$^g$OMgX, wherein R$^g$ is C$_1$-C$_4$ alkyl or phenyl; and X is I, Br, or Cl, or the Grignard reagent is MeMgI or MeMgCl, the alkoxy magnesium halide is MeOMgI or MeOMgCl and the alcohol-containing solvent comprises a C$_1$-C$_4$ alcohol, or
the Grignard reagent is MeMgI, the alkoxy magnesium halide is MeOMgI and the alcohol-containing solvent is a 1:1 (v/v) mixture of methanol and THF.
6. A Drug Linker intermediate compound, wherein the Drug Linker intermediate compound has the structure of Formula 6:

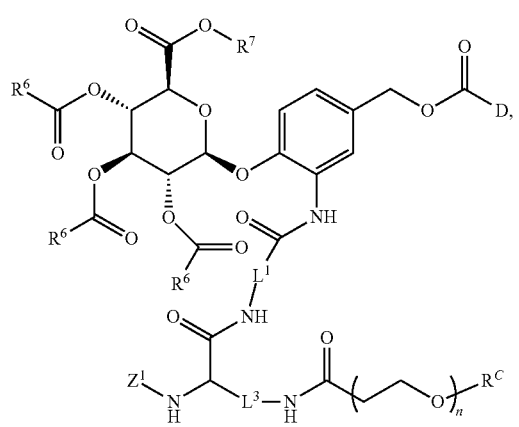

(6)

L¹ and L³ are independently selected from the group consisting of optionally substituted $C_1$-$C_{20}$ alkylene and optionally substituted $C_4$-$C_{20}$ heteroalkylene;

$R^6$ is optionally substituted $C_1$-$C_8$ alkyl or optionally substituted $C_6$-$C_{10}$ arylene so that $R^6C(=O)$— provides for an ester functional group that is a suitable hydroxyl protecting group;

$R^7$ is $C_1$-$C_8$ alkyl so that —$OR^7$ provides an ester functional group that is a suitable carboxylic acid protecting group;

$Z^1$ is a first suitable amino protecting group;

$R^C$ is a PEG Capping Unit; and subscript n ranges from 1 to 24.

7. The Drug Linker intermediate compound of claim 6, wherein the auristatin Drug Unit (D) has the structure of Formula $D_{F/E-3}$:

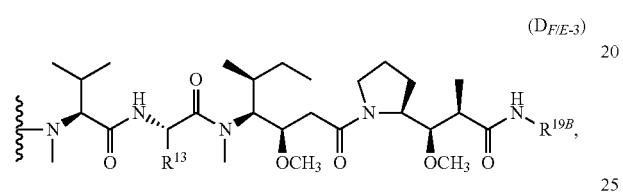

(D_{F/E-3})

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH_2(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph.

8. The Drug Linker intermediate compound of claim 6, wherein each of $R^6$ and $R^7$ is independently $C_1$-$C_4$ alkyl, or each of $R^6$ and $R^7$ is methyl or each of $R^6$ and $R^7$ is ethyl.

9. The Drug Linker intermediate compound of claim 6, wherein the Formula 6 compound has the structure of:

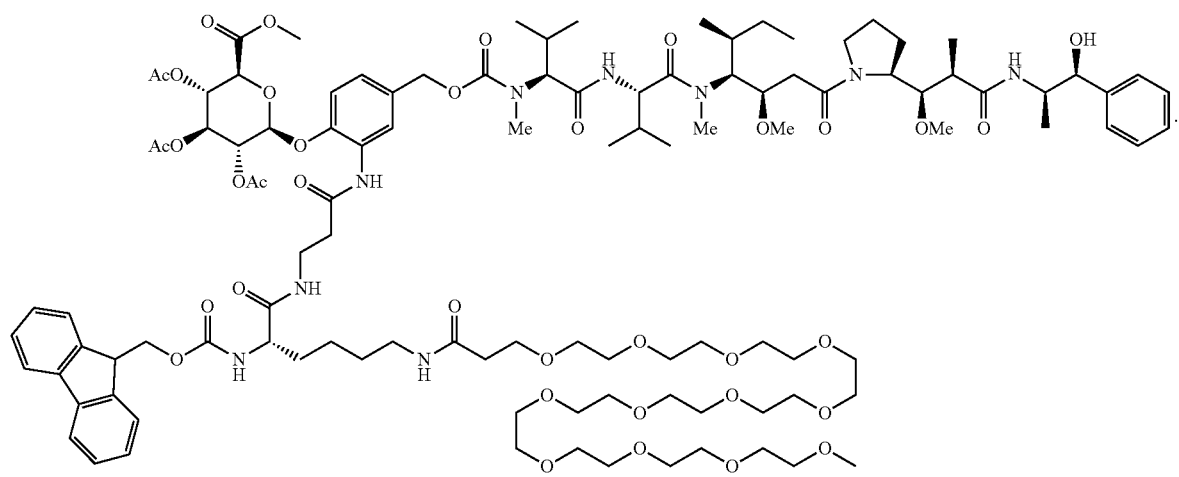 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)OC)[C@@H](OC(C)=O)[C@H](OC(C)=O)[C@H]2OC(C)=O)c(NC(=O)CCNC(=O)[C@H](CCCCNC(=O)CCOCCOCCOCCOCCOCCOCCOCCOCCOCCOCCOCCOC)NC(=O)OCC2c3ccccc3-c3ccccc32)c1)C(C)C]

or a salt thereof.

10. A composition comprising a Drug Linker intermediate of Formula 7 having the structure of:

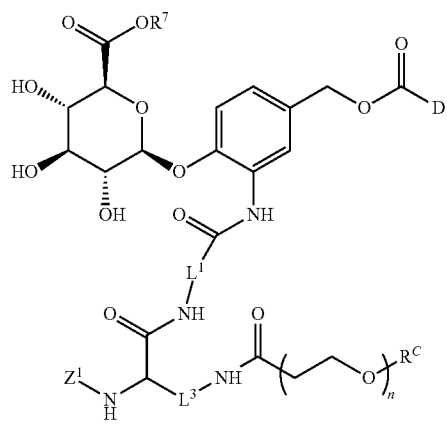

(7)

or a salt thereof, wherein D is an auristatin Drug Unit with the structure of:

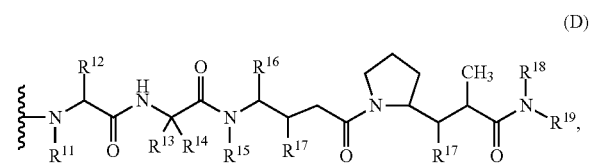

(D)

wherein the wavy line indicates covalent bonding of D to the remainder of the Drug Linker or Drug Linker intermediate compound;

$R^{11}$ is selected from the group consisting of H and $C_1$-$C_8$ alkyl, or $R^{11}$ is methyl, $R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); and $R^{14}$ is selected from the group consisting of H and methyl or $R^{13}$ and $R^{14}$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

each $R^{17}$ is independently selected from the group consisting of H, OH, $C_1$-$C_8$ alkyl, $C_3$-$C_8$ carbocycle, and O—($C_1$-$C_8$ alkyl);

$R^{18}$ is selected from the group consisting of H and $C_1$-$C_8$ alkyl;

$R^{19}$ is selected from the group consisting of —$C(R^{17})_2$—$C(R^{17})_2$-aryl, —$C(R^{17})_2$—$C(R^{17})_2$—($C_3$-$C_8$ heterocycle), —$C(R^{17})_2$—$C(O)$—$ZR^{20}$, and —$C(R^{17})_2$—$C(R^{17})_2$—($C_3$-$C_8$ carbocycle);

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl;

Z is —O— or —NH—, or

Z— is —O— and $R^{20}$ is $C_1$-$C_4$ alkyl or Z is —NH— and $R^{20}$ is optionally substituted phenyl or optionally substituted $C_5$-$C_6$ heteroaryl;

each of $L^1$ and $L^3$ is independently selected from the group consisting of optionally substituted $C_1$-$C_{20}$ alkylene and optionally substituted $C_4$-$C_{20}$ heteroalkylene;

$R^7$ is optionally substituted $C_1$-$C_8$ alkyl so that —$OR^7$ provides an ester functional group that is a suitable carboxylic acid protecting group, or $R^7$ is methyl;

$Z^1$ is a first suitable amino protecting group;

$R^C$ is a PEG Capping Unit; and subscript n ranges from 2 to 24, the composition further comprising no more than about 10 wt. %, or no more than about 5 wt. %, of a Drug Linker intermediate compound of Formula 7A having the structure of:

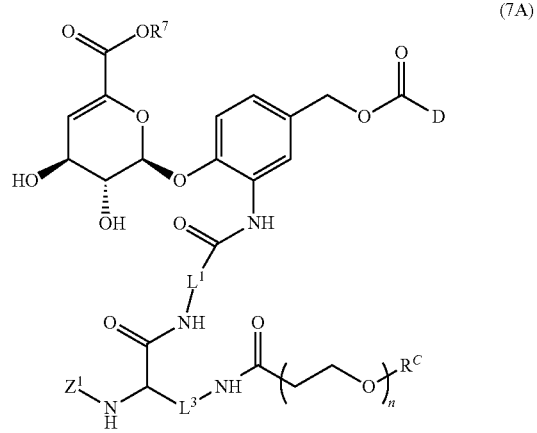

(7A)

or a salt thereof, wherein the variable groups retain their meanings from Formula 7.

11. The composition of claim 10, wherein the auristatin Drug Unit (D) has the structure of Formula $D_{F/E-3}$:

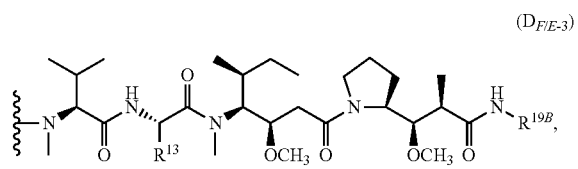

($D_{F/E-3}$)

wherein $R^{13}$ is isopropyl or —$CH_2$—$CH(CH_3)_2$; and $R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH_2(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)$NH-3-quinolyl, or —$CH(CH_2Ph)C(=O)$NH-p-Cl-Ph.

12. The composition of claim 10, wherein the Formula 7 and Formula 7A Drug Linker intermediate compounds, or a salt thereof, have the structures of:

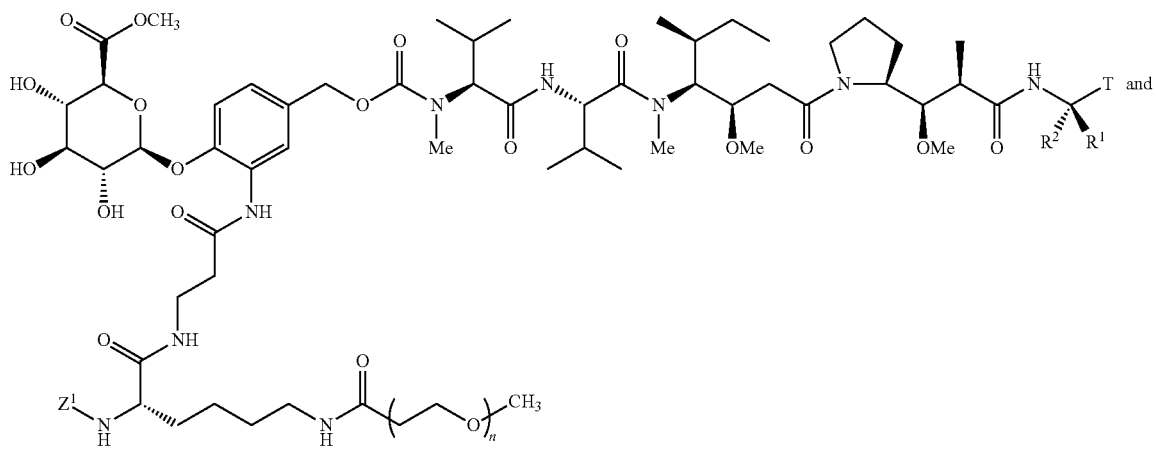

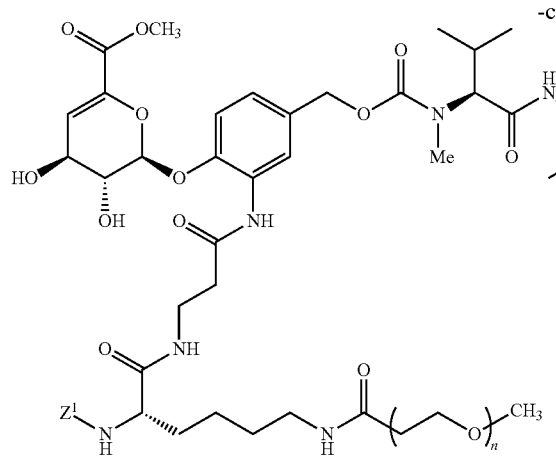
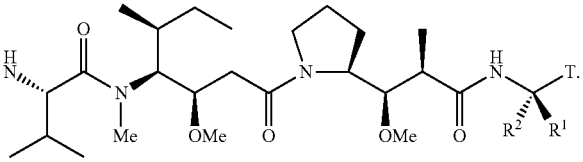

respectively, wherein $Z^1$ is fluorenylmethyloxycarbonyl (FMOC);

$R^1$ is H or $C_1$-$C_4$ alkyl; and $R^2$ is H, $C_1$-$C_4$ alkyl, or —$CH_2$—$R^3$;

$R^3$ is $C_6$-$C_{10}$ aryl or $C_3$-$C_8$ heterocyclyl; and

T is selected from the group consisting of —CH(OR$^4$)—R$^5$ and —C(=O)—OR$^4$, wherein $R^4$ is H or $C_1$-$C_4$ alkyl and $R^5$ is $C_6$-$C_{10}$ aryl or $C_3$-$C_6$ heteroaryl, or $R^2$ is hydrogen; and T is —CH(OR$^4$)—R$^5$; wherein $R^4$ is hydrogen or methyl and $R^5$ is $C_6$-$C_{10}$ aryl, or $R^2$ is H, and T is —CH(OH)-Ph;

and subscript n is 8 or 12.

13. A Drug Linker intermediate compound, wherein the Drug Linker intermediate compound, has the structure of:

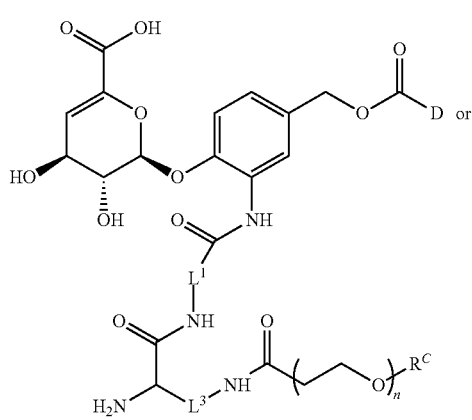

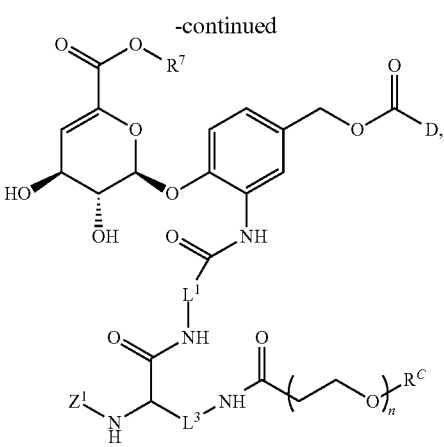

or a salt thereof, wherein

D is an auristatin Drug Unit with the structure of:

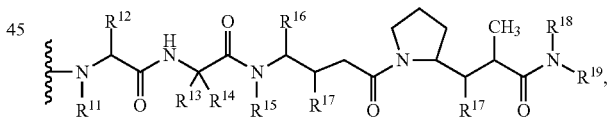

wherein the wavy line indicates covalent bonding of D to the remainder of the Drug Linker or Drug Linker intermediate compound;

$R^{11}$ is selected from the group consisting of H and $C_1$-$C_8$ alkyl, or $R^{11}$ is methyl, $R^{12}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

$R^{13}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle); and $R^{14}$ is selected from the group consisting of H and methyl or $R^{13}$ and $R^{14}$ jointly form a carbocyclic ring and have the formula —(CR$^a$R$^b$)$_n$— wherein R$^a$ and R$^b$ are independently selected from the group consisting of H, $C_1$-$C_8$ alkyl and $C_3$-$C_8$ carbocycle, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, and $C_1$-$C_8$ alkyl-($C_3$-$C_8$ heterocycle);

each $R^{17}$ is independently selected from the group consisting of H, OH, $C_1$-$C_8$ alkyl, $C_3$-$C_8$ carbocycle, and O—($C_1$-$C_8$ alkyl);

$R^{18}$ is selected from the group consisting of H and $C_1$-$C_8$ alkyl;

$R^{19}$ is selected from the group consisting of —C($R^{17}$)$_2$—C($R^{17}$)$_2$-aryl, —C($R^{17}$)$_2$—C($R^{17}$)$_2$—($C_3$-$C_8$ heterocycle), —C($R^{17}$)$_2$—C(O)—Z$R^{20}$, and —C($R^{17}$)$_2$—C($R^{17}$)$_2$—($C_3$-$C_8$ carbocycle);

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl;

Z is —O— or —NH—, or

Z— is —O— and $R^{20}$ is $C_1$-$C_4$ alkyl or Z is —NH— and $R^{20}$ is optionally substituted phenyl or optionally substituted $C_5$-$C_6$ heteroaryl;

$L^1$ and $L^3$, independently are selected from the group consisting of optionally substituted $C_1$-$C_{20}$ alkylene and optionally substituted $C_4$-$C_{20}$ heteroalkylene;

$Z^1$ is a first suitable amino protecting group;

$R^7$ is optionally substituted $C_1$-$C_8$ alkyl;

$R^C$ is a PEG Capping Unit; and subscript n ranges from 2 to 24.

14. The Drug Linker intermediate compound of claim 13, wherein the Drug Linker intermediate compound has the structure selected from the group consisting of:

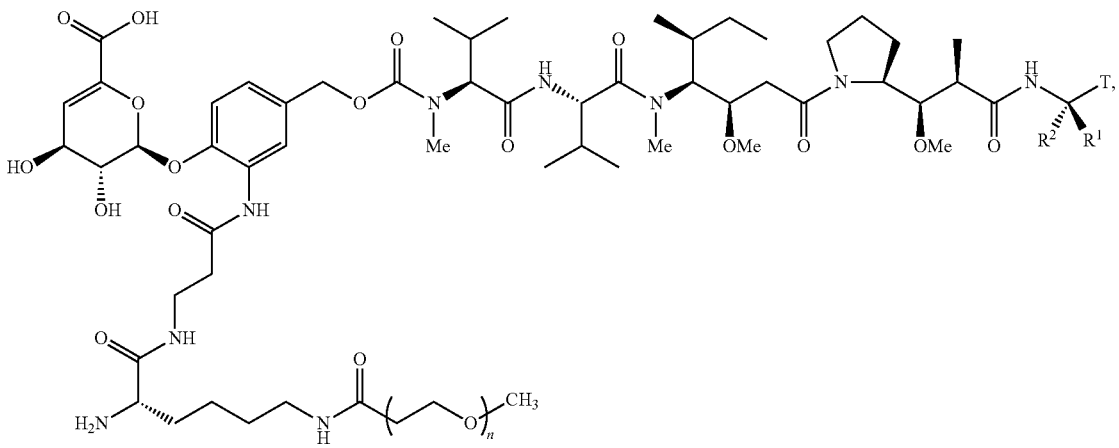

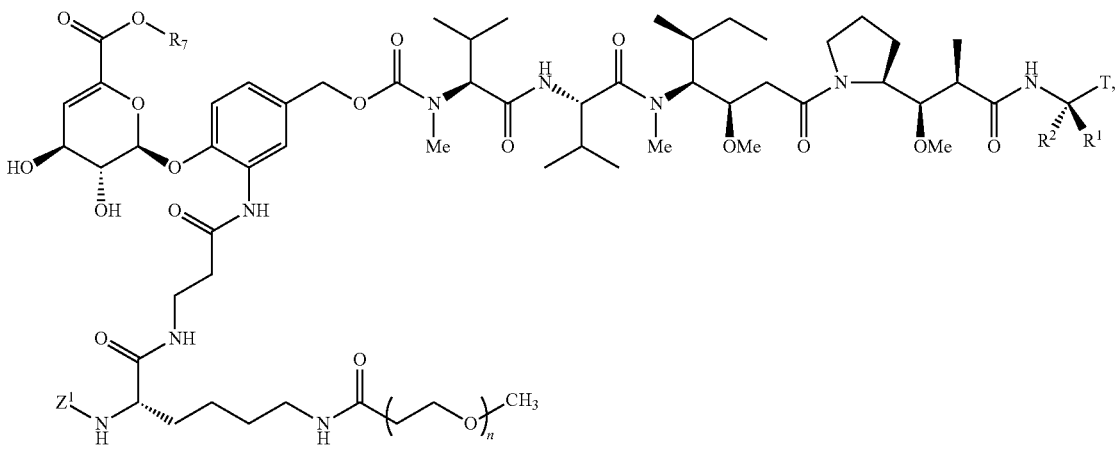

and salts thereof, wherein
R⁷ is methyl;
Z¹ is fluorenylmethyloxycarbonyl (FMOC);
R¹ is H or $C_1$-$C_4$ alkyl;
R² is H, $C_1$-$C_4$ alkyl, or —$CH_2$—R³;
R³ is $C_6$-$C_{10}$ aryl or $C_3$-$C_8$ heterocyclyl; and
T is selected from the group consisting of —CH(OR⁴)—R⁵ and —C(=O)—OR⁴, wherein R⁴ is H or $C_1$-$C_4$ alkyl and R⁵ is $C_6$-$C_{10}$ aryl or $C_3$-$C_6$ heteroaryl.

15. The Drug Linker intermediate compound of claim 13, wherein L¹ and L³ are independently $C_1$-$C_4$ alkyl.

16. The Drug Linker intermediate compound of claim 6, wherein the compound has the structure:

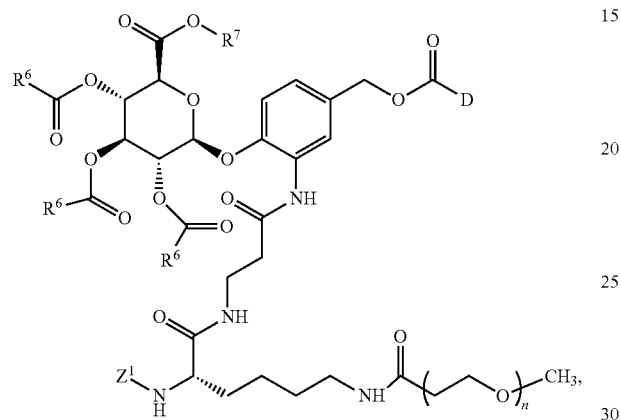

or a salt thereof, wherein subscript n is 8 or 12.

17. The Drug Linker intermediate compound of claim wherein the compound has the structure:

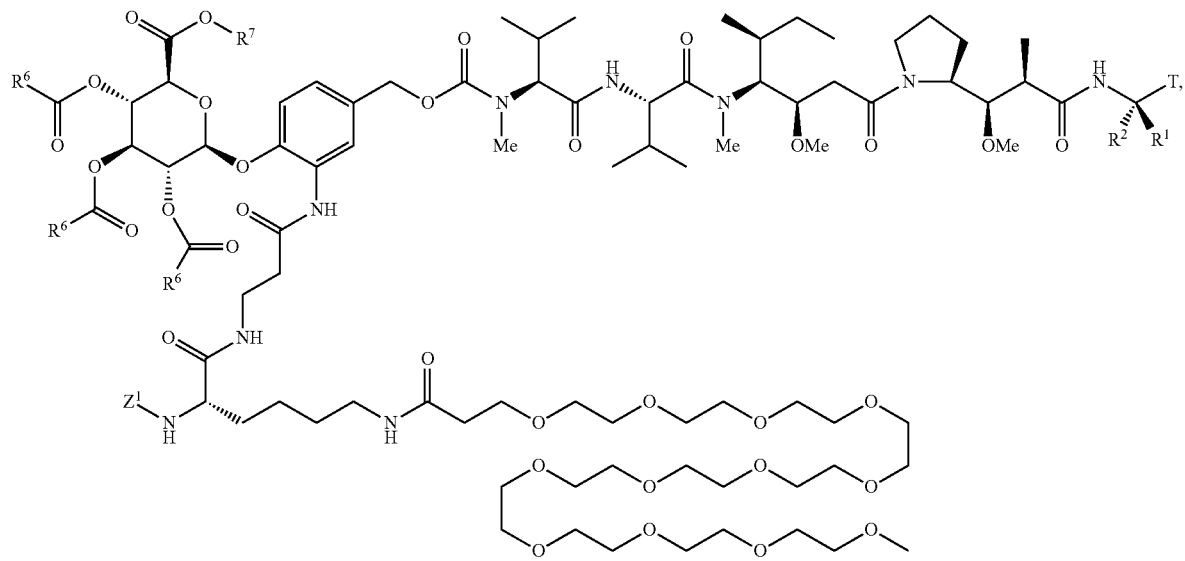

or a salt thereof, wherein
R$^1$ is H or C$_1$-C$_4$ alkyl;
R$^2$ is H, C$_1$-C$_4$ alkyl, or —CH$_2$—R$^3$;
R$^3$ is C$_6$-C$_{10}$ aryl or C$_3$-C$_8$ heterocyclyl; and
T is selected from the group consisting of —CH(OR$^4$)—R$^5$ and —C(=O)—OR$^4$, wherein R$^4$ is H, C$_1$-C$_4$ alkyl and R$^5$ is C$_6$-C$_{10}$ aryl or C$_3$-C$_6$ heteroaryl.

18. The Drug Linker intermediate compound of claim 7, or a salt thereof, wherein D has the structure of:

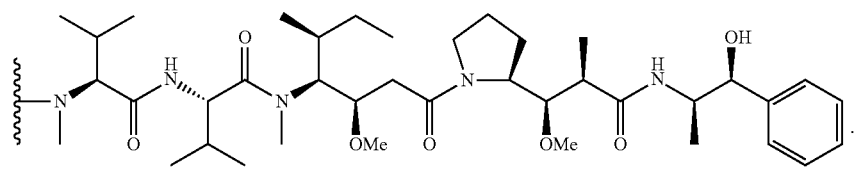 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

19. The composition of claim 10, wherein the Formula 7 and Formula 7A Drug linker intermediate compounds, or salts thereof, have the structures of:

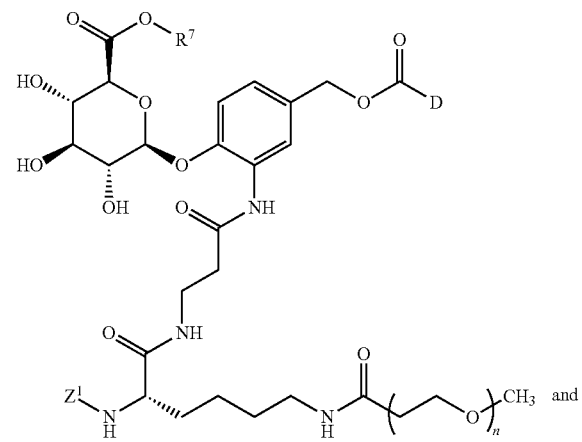

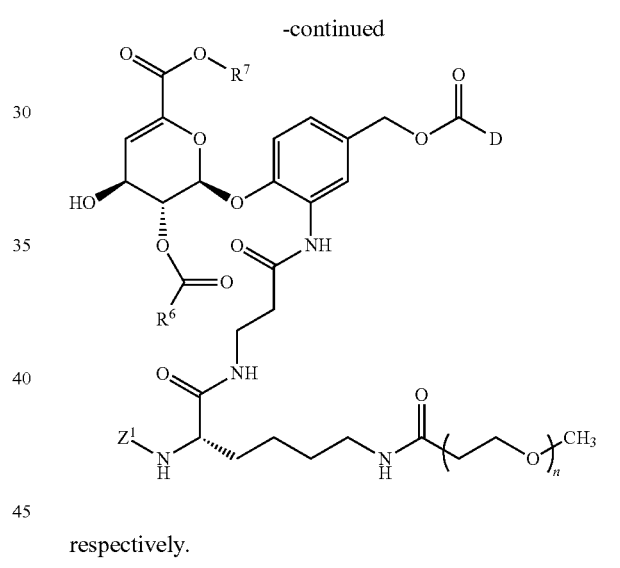

respectively.

20. The composition of claim 11, wherein D has the structure of:

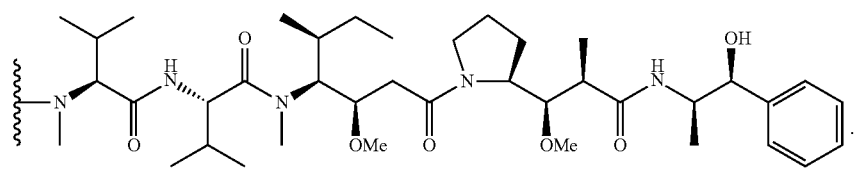 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

21. The composition of claim 12, wherein the Formula 7 and Formula 7A Drug linker intermediate compounds, or salts thereof, have the structures of:

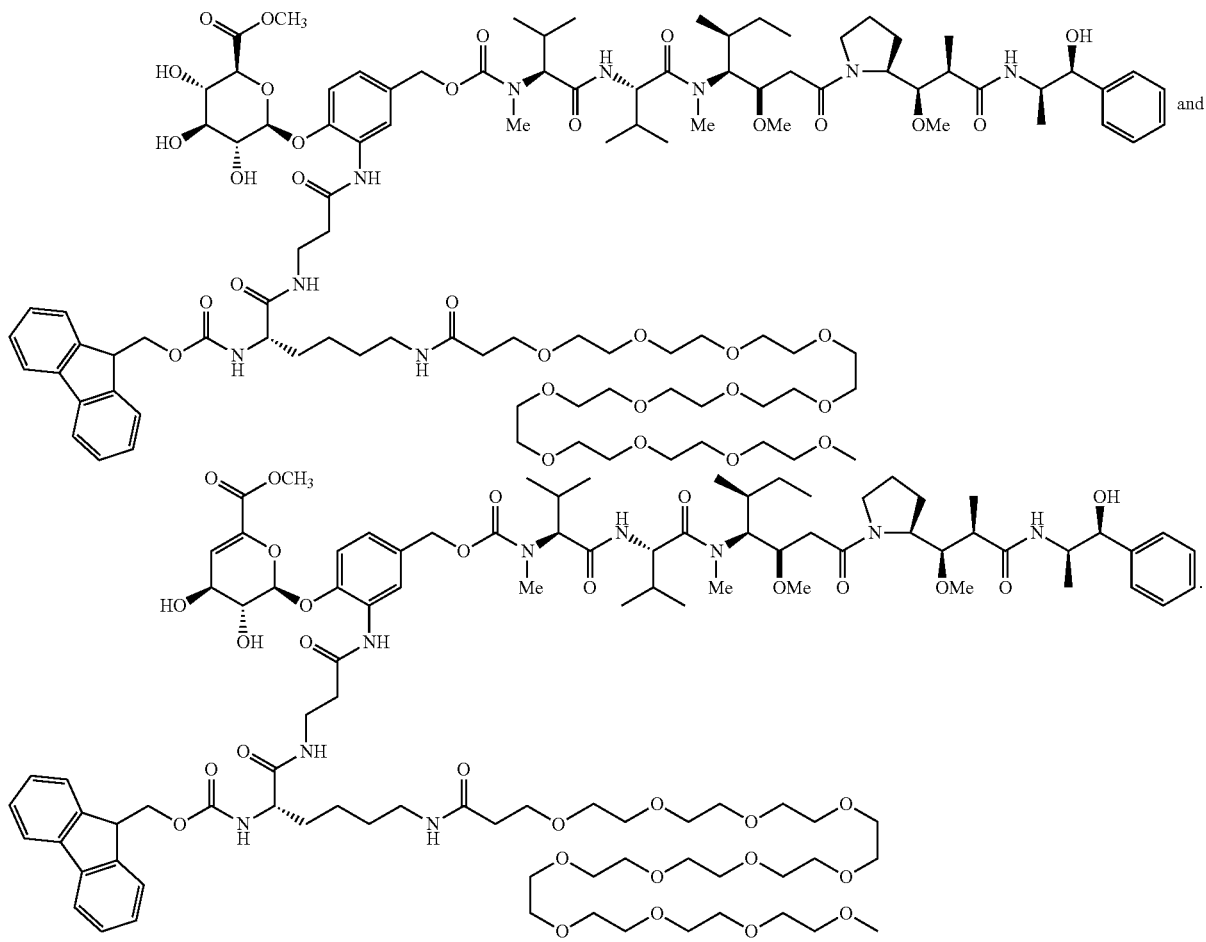

22. The Drug Linker intermediate compound of claim 13, wherein the Drug Linker intermediate compound has the structure selected from the group consisting of:

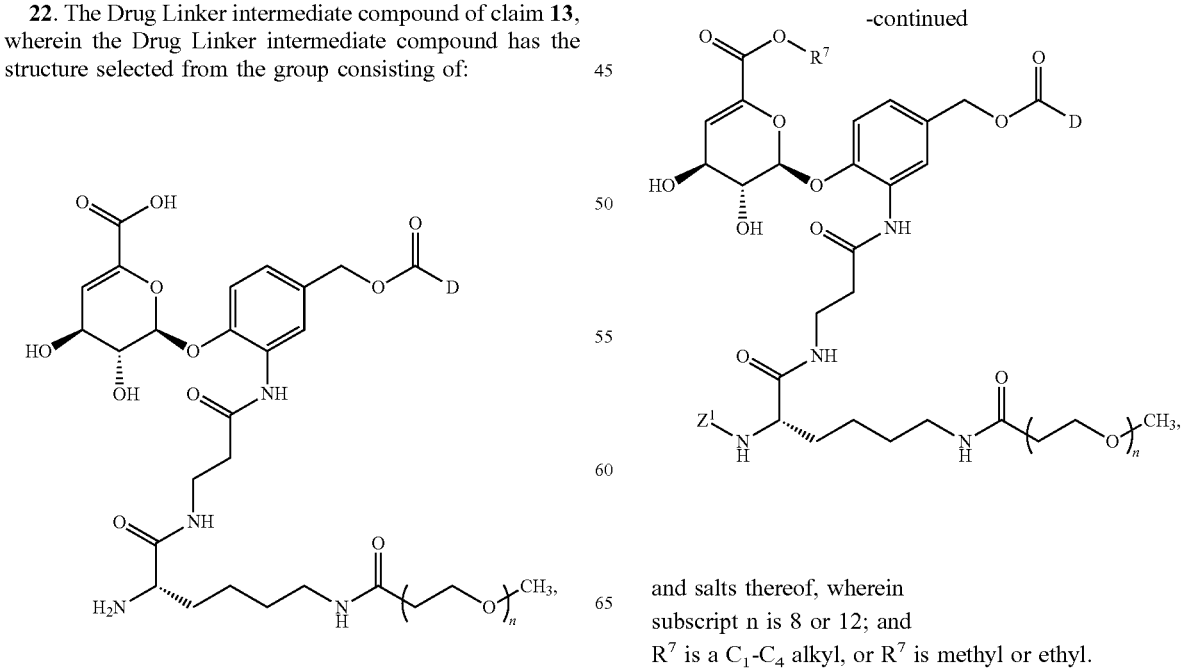

and salts thereof, wherein
subscript n is 8 or 12; and
$R^7$ is a $C_1$-$C_4$ alkyl, or $R^7$ is methyl or ethyl.

23. The Drug Linker intermediate compound of claim 14, or a salt thereof, wherein
$R^1$ is methyl;
$R^2$ is H;
T is —CH(OH)-Ph,
and subscript n is 8 or 12.

24. The Drug Linker intermediate compound of claim 14, wherein the Drug Linker intermediate compound has the structure selected from the group consisting of:

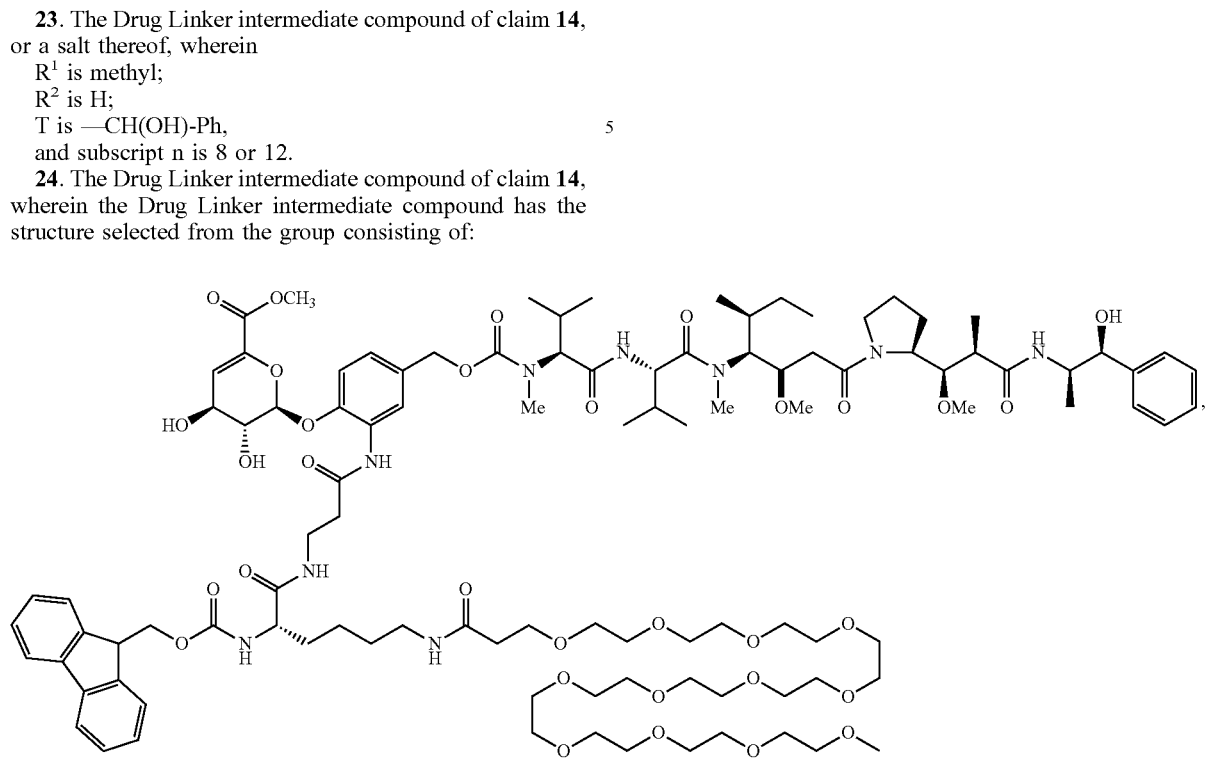

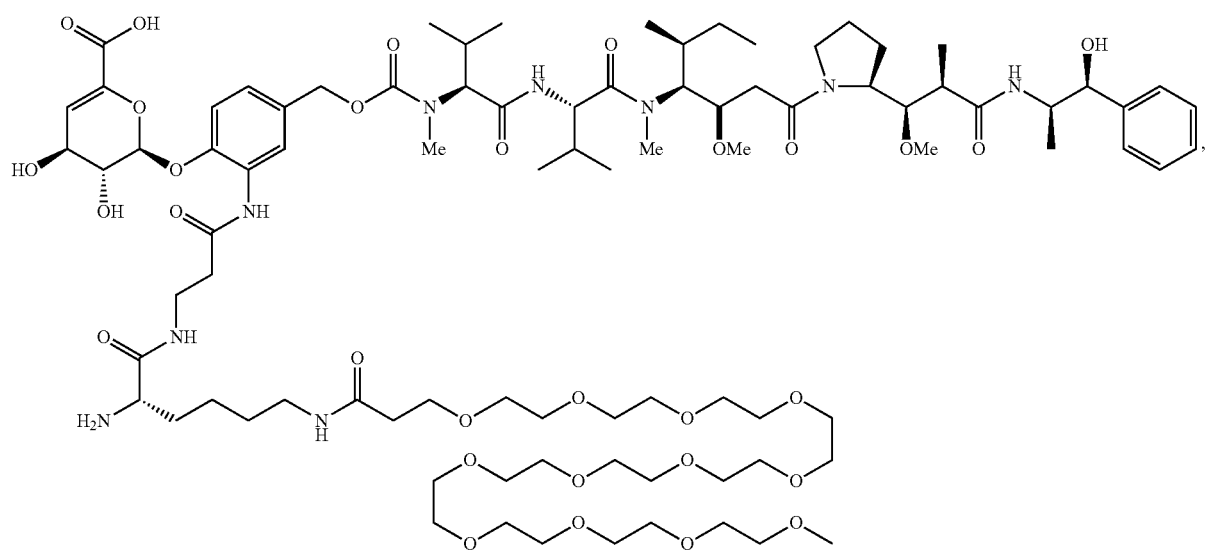

and salts thereof.

25. The Drug Linker intermediate compound of claim 17, wherein
$R^1$ is hydrogen or methyl; $R^2$ is hydrogen; and T is —CH(OR$^4$)—R$^5$; wherein $R^4$ is hydrogen or methyl and $R^5$ is $C_6$-$C_{10}$ aryl, or
$R^1$ is methyl, $R^2$ is H, and T is —CH(OH)-Ph,
and $Z^1$ is fluorenylmethyloxycarbonyl (FMOC).

26. The composition of claim 10, wherein $Z^1$ is fluorenylmethyloxycarbonyl (FMOC).

* * * * *

UNITED STATES PATENT AND TRADEMARK OFFICE
CERTIFICATE OF CORRECTION

| | |
|---|---|
| PATENT NO. | : 11,844,839 B2 |
| APPLICATION NO. | : 16/088235 |
| DATED | : December 19, 2023 |
| INVENTOR(S) | : Mao et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
Twelfth Day of November, 2024

Katherine Kelly Vidal
*Director of the United States Patent and Trademark Office*